US008513253B2

(12) United States Patent  
Parker et al.

(10) Patent No.: US 8,513,253 B2
(45) Date of Patent: *Aug. 20, 2013

(54) α-(N-SULFONAMIDO)ACETAMIDE DERIVATIVES AS β-AMYLOID INHIBITORS

(75) Inventors: Michael F. Parker, Higganum, CT (US); Katharine E. McElhone, San Diego, CA (US); Robert A. Mate, Waterbury, CT (US); Joanne J. Bronson, Durham, CT (US); Yonghua Gai, Killingworth, CT (US); Carl P. Bergstrom, Madison, CT (US); Lawrence R. Marcin, Bethany, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 352 days.

This patent is subject to a terminal disclaimer.

(21) Appl. No.: 12/840,612

(22) Filed: Jul. 21, 2010

(65) Prior Publication Data

US 2011/0105485 A1    May 5, 2011

Related U.S. Application Data

(63) Continuation of application No. 11/870,595, filed on Oct. 11, 2007, now Pat. No. 7,786,122, which is a continuation of application No. 10/326,365, filed on Dec. 20, 2002, now Pat. No. 7,300,936.

(60) Provisional application No. 60/344,322, filed on Dec. 20, 2001.

(51) Int. Cl.
*A01N 43/58* (2006.01)
*A61K 31/495* (2006.01)
*C07D 403/00* (2006.01)

(52) U.S. Cl.
USPC ............ 514/252.12; 514/254.09; 514/254.12; 544/359; 544/392; 544/393

(58) Field of Classification Search
USPC ............ 514/252.12, 254.03, 254.09, 254.12, 514/359; 544/392, 393, 359
See application file for complete search history.

(56) References Cited

U.S. PATENT DOCUMENTS

| 5,274,094 | A | 12/1993 | Whittaker et al. |
| 5,516,783 | A | 5/1996 | Whittaker et al. |
| 6,153,612 | A | 11/2000 | Ortwine et al. |
| 6,313,123 | B1 | 11/2001 | Levin et al. |
| 7,300,936 | B2 * | 11/2007 | Parker et al. ............ 514/252.12 |
| 7,300,951 | B2 | 11/2007 | Kreft et al. |
| 7,687,666 | B2 | 3/2010 | Chan et al. |
| 7,786,122 | B2 * | 8/2010 | Parker et al. ............ 514/252.12 |
| 7,838,550 | B2 | 11/2010 | Chan et al. |

FOREIGN PATENT DOCUMENTS

| JP | 11-343279 | 12/1999 |
| WO | WO 98/03166 | 1/1998 |
| WO | WO 00/44716 | 8/2000 |
| WO | WO 00/50391 | 8/2000 |
| WO | WO 03/053912 | 7/2003 |
| WO | WO 2005/042489 | 5/2005 |
| WO | WO 2005/095334 | 10/2005 |
| WO | WO 2006/005486 | 1/2006 |
| WO | WO 2006/034480 | 3/2006 |
| WO | WO 2007/098030 | 8/2007 |
| WO | WO 2008/112249 | 9/2008 |
| WO | WO 2009/005688 | 1/2009 |
| WO | WO 2009/058552 | 5/2009 |
| WO | WO 2009/137657 | 11/2009 |
| WO | WO 2010/107435 | 9/2010 |
| WO | WO 2010/107984 | 9/2010 |
| WO | WO 2010/107997 | 9/2010 |
| WO | WO 2010/108067 | 9/2010 |
| WO | WO 2010/120662 | 10/2010 |
| WO | WO 2010/120755 | 10/2010 |

OTHER PUBLICATIONS

Chapman, P.F. et al., "Impaired synaptic plasticity and learning in aged amyloid precursor protein transgenic mice", Nature Neuroscience, vol. 2, No. 3, pp. 271-276 (1999).

Clarke, W.J. et al., "Gender Differences in Oral Drug Exposure in the Rat with the Gamma-Secretase Inhibitor BMS-708163", Drug Metab. Rev., Abstract No. 126, vol. 41, pp. 58-59 (2009).

Dahlgren, K.N. et al., "Oligomeric and Fibrillar Species of Amyloid-β Peptides Differentially Affect Neuronal Viability", The Journal of Biological Chemistry, vol. 277, No. 35, pp. 32046-32053 (2002).

Freebern, W.J. et al., "From Phenotyping to Host Resistance Models: A Comprehensive Immunotoxicologic Investigation of a Gamma Secretase Inhibitor in Rats", International Journal of Toxicology, Abstract No. P12, vol. 29, No. 1, pp. 91-92 (2010).

Gillman, K.W. et al., "Discovery and Evaluation of BMS-708163, a Potent, Selective and Orally Bioavailable γ-Secretase Inhibitor", ACS Medicinal Chemistry Letters, vol. 1, pp. 120-124 (2010).

Golde, T.E., "Alzheimer's disease therapy: Can the amyloid cascade be halted?", The Journal of Clinical Investigation, vol. 111, No. 1, pp. 11-18 (2003).

(Continued)

*Primary Examiner* — Paul V. Ward
(74) *Attorney, Agent, or Firm* — Pamela A. Mingo

(57) ABSTRACT

There is provided a series of novel α-(N-sulfonamido)acetamide compounds of the Formula (I)

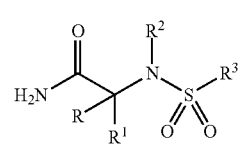

wherein R, $R^1$, $R^2$ and $R^3$ are defined herein, which are inhibitors of β-amyloid peptide (β-AP) production and are useful in the treatment of Alzheimer's Disease and other conditions affected by anti-amyloid activity.

3 Claims, No Drawings

(56) References Cited

OTHER PUBLICATIONS

Götz, J. et al., "Formation of Neurofibrillary Tangles in P301L Tau Transgenic Mice Induced by Aβ42 Fibrils", Science, vol. 293, pp. 1491-1495 (2001).
Leil, T.A. et al. "Model-Based Trial Simulation for Optimal Collection of CSF Aβ Samples in Clinical Studies: Application for BMS-708163", Clin. Pharmacol. Ther., Abstract No. OII-B-2, vol. 87, Suppl. 1, p. S38 (2010).
Lewis, J. et al., "Enhanced Neurofibrillary Degeneration in Transgenic Mice Expressing Mutant Tau and APP", Science, vol. 293, pp. 1487-1491 (2001).
Loane, D.J. et al., "Amyloid precursor protein secretases as therapeutic targets for traumatic brain injury", Nature Medicine, Advance Online Publication, pp. 1-3 (Mar. 15, 2009).
Maharvi, G.M. et al., "A synthesis of the γ-secretase inhibitor BMS-708163", Tetrahedron Letters, online Oct. 14, 2010.
Mayer, S.C. et al., Discovery of Begacestat, a Notch-1-Sparing γ-Secretase Inhibitor for the Treatment of Alzheimer's Disease, Journal of Medicinal Chemistry, vol. 51, No. 23, pp. 7348-7351 (2008).
McLean, C.A. et al., "Soluble Pool of Aβ Amyloid as a Determinant of Severity of Neurodegeneration in Alzheimer's Disease", Annals of Neurology, vol. 46, No. 6, pp. 860-866 (1999).
Seiffert, D. et al., "Presenilin-1 and -2 are Molecular Targets for γ-Secretase Inhibitors", The Journal of Biological Chemistry, vol. 275, No. 44, pp. 34086-34091 (2000).
Selkoe, D.J., "Alzheimer's Disease: Genes, Proteins, and Therapy", Physiological Reviews, vol. 81, No. 2, pp. 741-766 (2001).
Selkoe, D.J., "Cell Biology of the Amyloid β-Protein Precursor and the Mechanism of Alzheimer's Disease", Annu. Rev. Cell Biol., vol. 10, pp. 373-403 (1994).
Siemers, E.R. et al., "Effects of a γ-secretase inhibitor in a randomized study of patients with Alzheimer disease", Neurology, vol. 66, pp. 602-604 (2006).
Thal, D.R. et al., "Two Types of Sporadic Cerebral Amyloid Angiopathy", Journal of Neuropathology and Experimental Neurology, vol. 61, No. 3, pp. 282-293 (2002).
Walsh, D.M. et al., "Naturally secreted oligomers of amyloid β protein potently inhibit hippocampal long-term potentiation in vivo", Nature, vol. 416, pp. 535-539 (2002).
Watkins, T.A. et al., "Distinct Stages of Myelination Regulated by γ-Secretase and Astrocytes in a Rapidly Myelinating CNS Coculture System", Neuron, vol. 60, pp. 555-569 (2008).
Wolfe, M.S., "Secretase Targets for Alzheimer's Disease: Identification and Therapeutic Potential", Journal of Medicinal Chemistry, vol. 44, No. 13, pp. 2039-2060 (2001).
Zhang D. et al., "Disposition of a Gamma-Secretase Inhibitor 14C-Labeled BMS-708163 in Mice, Rats, Rabbits, Dogs, and Humans. Applications of Bile Collection in Differentiating Oxidative Versus Reductive Metabolic Pathways", Drug Metab. Rev., Abstract No. 127, vol. 41, pp. 59-60 (2009).
2008 CSHL Meeting on Neurodegenerative Diseases, Oral Presentation: "BMS-708163, A Potent and Selective Gamma-Secretase Inhibitor, Decreases CSF A-Beta at Safe and Tolerable Doses in Animals and Humans", Dec. 5, 2008.
2009 BMS URG Symposium, Oral Presentation: "The Discovery of BMS-708163: A Potent and Selective Gamma-Secretase Inhibitor for the Treatment of Alzheimer's Disease", May 1, 2009.
237th National American Chemical Society Meeting, Salt Lake City, UT, Oral Presentation: "The Discovery of BMS-708163: A Potent and Selective Gamma-Secretase Inhibitor Which Lowers CSF Beta-Amyloid in Humans", Mar. 22, 2009.
Alzheimer's Association International Conference on Alzheimer's Disease, Chicago, IL, Abstract, Jul. 26, 2008.
Alzheimer's Association International Conference on Alzheimer's Disease, Chicago, IL, Oral Presentation: "BMS-708163, A Potent and Selective Gamma-Secretase Inhibitor, Decreases CSF A-Beta at Safe and Tolerable Doses in Animals and Humans", Jul. 30, 2008.
Alzheimer's Association International Conference on Alzheimer's Disease, Honolulu, HI, Poster: "A Comprehensive Immunotoxicologic Investigation of a Gamma Secretase Inhibitor in Rats", Jul. 10-15, 2010.
Alzheimer's Association International Conference on Alzheimer's Disease, Honolulu, HI, Poster: "A Placebo-Controlled Ascending Multiple-Dose Study to Evaluate the Safety, Pharmacokinetics, and Pharmacodynamics of BMS-708163 in Healthy Young and Elderly Subjects", Jul. 10-15, 2010.
Alzheimer's Association International Conference on Alzheimer's Disease, Honolulu, HI, Poster: "A Study to Evaluate the Effects of Single Oral Doses of BMS-708163 on the Cerebrospinal Fluid A-Beta Level in Healthy Young Men", Jul. 10-15, 2010.
Alzheimer's Association International Conference on Alzheimer's Disease, Honolulu, HI, Poster: "Effect of Concomitant Administration of Multiple Doses of BMS-708163 on Safety and Tolerability and the Pharmacokinetics of Midazolam, Warfarin, Caffeine, Omeprazole, and Dextromethorphan in Healthy Male Subjects by Administration of a Modified Cooperstown Cocktail", Jul. 10-15, 2010.
Alzheimer's Association International Conference on Alzheimer's Disease, Honolulu, HI, Poster: "Gamma-Secretase Inhibitors Have Intrinsically Different Inhibitory Potencies Against A-Beta Production and Notch Signaling", Jul. 10-15, 2010.
Alzheimer's Association International Conference on Alzheimer's Disease, Honolulu, HI, Poster: "Separation of A-Beta Reduction from Notch Toxicity with Gamma-Secretase Inhibitors in Rats", Jul. 10-15, 2010.
Alzheimer's Association International Conference on Alzheimer's Disease, Honolulu, HI, Poster: "The Safety, Tolerability, Pharmacokinetics, and Pharmacodynamics of Single and Multiple Doses of BMS-708163 in Young and Elderly Japanese Subjects", Jul. 10-15, 2010.
Alzheimer's Association International Conference on Alzheimer's Disease, Honolulu, HI, Poster: "The Safety, Tolerability, Pharmacokinetics, and Pharmacodynamics of Single Doses of BMS-708163 in Young and Elderly Subjects", Jul. 10-15, 2010.
American Association of Pharmaceutical Sciences, New Orleans, LA, Oral Presentation: "Simple Allometric Scaling Predicts the Human Dose of BMS-708163, a Gamma Secretase Inhibitor Intended for the Treatment of Alzheimer's Disease", Nov. 14-18, 2010.
AMRI 2010 Integrated Drug Discovery Symposium, Oral Presentation: "Selection and Optimization of a Series of Gamma-Secretase Inhibitors: The Discovery of BMS-708163", Oct. 12-14, 2010.
Bristol-Myers Squibb Symposium, University of California, Irvine, CA, Oral Presentation: "Testing the Amyloid Hypothesis: The Discovery of Brain Penetrant Gamma-Secretase Inhibitors for the Treatment of Alzheimer's Disease", Jun. 2, 2010.
Gordon Research Conference, Newport, RI, Oral Presentation: "Heterocyclic Gamma-Secretase Inhibitors for the Treatment of Alzheimer's Disease", Jun. 30, 2009.
International Society for the Study of Xenobiotics Meeting, Baltimore, MD, Poster: "Gender Differences in Oral Drug Exposure of the Gamma Secretase Inhibitor, BMS-708163, in the Rat", Oct. 18-22, 2009.
Presentation to Department of Chemistry at the University of Arkansas, Fayetteville, AK, Oral Presentation: "Neuroscience Drug Discovery at Bristol-Myers Squibb", Apr. 15, 2010.

* cited by examiner

α-(N-SULFONAMIDO)ACETAMIDE DERIVATIVES AS β-AMYLOID INHIBITORS

CROSS-REFERENCE TO RELATED APPLICATIONS

This application is a continuation of U.S. Ser. No. 11/870,595 filed Oct. 11, 2007, now allowed, which claims the benefit of U.S. Ser. No. 10/326,365 filed Dec. 20, 2002, now U.S. Pat. No. 7,300,936, which in turn claims the benefit of U.S. Provisional Application Ser. No. 60/344,322 filed Dec. 20, 2001, now expired.

FIELD OF THE INVENTION

This invention provides novel α-(N-sulfonamido)acetamide compounds having drug and bio-affecting properties, their pharmaceutical compositions and method of use. In particular, the invention is concerned with α-(N-arylsulfonamido)acetamides. These compounds possess unique inhibition of the β-amyloid peptide (β-AP) production, thereby acting to prevent the accumulation of amyloid protein deposits in the brain. More particularly, the present invention relates to the treatment of Alzheimer's Disease (AD).

BACKGROUND OF THE INVENTION

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J., *Ann. Rev. Cell Biol.,* 10:373-403 (1994)).

There have been many theories relating to the etiology and pathogenesis of AD. These theories were either based on analogies with other diseases and conditions (e.g., slow virus and aluminum theories), or based on pathologic observations (e.g., cholinergic, amyloid, or tangle theories). Genetic analysis can potentially differentiate between competing theories. The identification of mutations in the β-amyloid precursor protein (β-APP) of individuals prone to early onset forms of AD and related disorders strongly supports the amyloidogenic theories.

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D., *Physiol. Rev.,* 81:741-766 (2001); Wolfe, M., *J. Med. Chem.,* 44:2039-2060 (2001)). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D. et al., *J. Biol. Chem.,* 275:34086-34091 (2000)).

Multiple lines of evidence together strongly suggest that a reduction in brain Aβ levels will prevent the onset and progression of AD. First, Aβ is a major constituent of the parenchemyal plaques observed in all AD patients and the cerebral vasculature amyloid deposits observed in 90% AD patients (reviewed in Selkoe, D., *Physiol. Rev.,* 81:741-766 (2001); Wolfe, M., *J. Med. Chem.,* 44:2039-2060 (2001)). These plaques are formed from the aggregation of soluble Aβ whose brain levels are highly correlated with the severity of AD neurodegeneration (McLean, C. et al., *Ann. Neural.,* 46:860-866 (1999)). Second, mutations in three genes (APP, PS-1, or PS-2) that increase Aβ cause familial AD (FAD), where AD onset is accelerated by at least a decade. Included in the mutations that increase Aβ are chromosome 21 Trisomy that causes Down's syndrome. Third, transgenic mice that express one or more of the mutant FAD genes have increased Aβ levels, form parenchymal plaques and cerebral vascular deposits containing Aβ, exhibit memory deficits (Chapman, P. et al., *Nature Neurosci,* 2:271-276 (1999)) and enhance neurofibrillary degeneration in mice that also over-express mutant tau (Lewis, J. et al., *Science,* 293:1487-1491 (2001)). Fourth, Aβ is toxic to cultured cells (Dahlgren, K. et al., *J. Biol. Chem.,* 277:32046-32053 (2002)), induces neurofibrillary tangles in mice with mutant tau (Gotz, J. et al., *Science,* 293:1491-1495 (2001)) and interferes with long-term potentiation, a likely component of memory (Walsh, D. et al., *Nature,* 416:535-539 (2002) and references therein). Taken together, these data lead one skilled in the art to conclude that excess Aβ production and/or reduced Aβ clearance cause AD. From this it follows that reducing brain Aβ levels by inhibition of γ-secretase will prevent the onset and progression of AD.

In addition to AD, excess production and/or reduced clearance of Aβ causes cerebral amyloid angiopathy (CAA) (reviewed in Thal, D. et al., *J. Neuropath. Exp. Neuro.,* 61:282-293 (2002)). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

It is hypothesized that inhibiting the production of Aβ will prevent and reduce neurological degeneration, reducing neurotoxicity and, generally, mediating the pathology associated with Aβ production. Methods of treatment could target the formation of Aβ through the enzymes involved in the proteolytic processing of β-amyloid precursor protein. Compounds that inhibit β- or γ-secretase activity, either directly or indirectly, could control the production of Aβ. Advantageously, compounds that specifically target γ-secretases, could control the production of Aβ. Such inhibition of β- or γ-secretases could thereby reduce production of Aβ which, could reduce or prevent the neurological disorders associated with Aβ protein.

Smith et al. in International Application WO 00/50391, published Aug. 31, 2000, discloses a series of sulfonamide compounds that can act to modulate production of amyloid β protein as a means of treating a variety of diseases, especially Alzheimer's Disease and other diseases relating to the deposition of amyloid. Japanese Patent No. 11343279, published Dec. 14, 1999 discloses a series of sulfonamide derivatives which are TNF-alpha inhibitors useful for treating autoimmune diseases.

Nothing in these references can be construed to disclose or suggest the novel compounds of this invention and their use to inhibit β-AP production.

SUMMARY OF THE INVENTION

A series of α-(N-sulfonamido)acetamide derivatives have been synthesized. These compounds specifically inhibit the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds to patients suffering from, or susceptible to, these conditions involves reducing β-AP available for accumulation and deposition in brains of these patients.

DETAILED DESCRIPTION OF THE INVENTION

The present invention comprises compounds of Formula I, their pharmaceutical formulations, and their use in inhibiting β-AP production in patients suffering from or susceptible to AD or other disorders resulting from β-AP accumulation in brain tissue. The compounds of Formula I which include nontoxic pharmaceutically acceptable salts and/or hydrates thereof have the following formula and meanings:

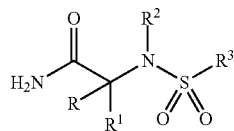

I wherein:
R$^1$ is selected from the group consisting of
(a) a straight or branched-chain C$_{1-6}$ alkyl or C$_{2-6}$alkenyl optionally substituted with substituents selected from the group consisting of hydroxy, C$_{3-7}$ cycloalkyl, C$_{1-4}$alkoxy, C$_{1-4}$alkylthio, and halogen;
(b) C$_{3-7}$ cycloalkyl optionally substituted with hydroxy or halogen;
R is hydrogen or R$^1$ and R taken together is C$_{2-5}$alkylene;

R$^2$ is selected from the group consisting of
(a) a straight or branched-chain C$_{1-6}$alkyl or C$_{3-6}$alkenyl optionally substituted with substituents selected from the group consisting of halogen, C$_{1-4}$alkoxy, and NR$^4$R$^5$;
(b) C$_{3-7}$ cycloalkylmethyl optionally substituted with substituents selected from the group consisting of amino, (C$_{1-4}$alkyl)NH—, di(C$_{1-4}$alkyl)N—, C$_{1-4}$alkylC(=O)NH—, and C$_{1-4}$alkylOC(=O)NH—;
(c) a straight or branched-chain C$_{1-6}$alkyl-C(=O)-A;
(d) —B-naphthyl;
(e)

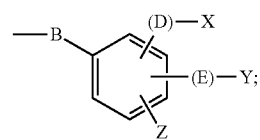

D and E are each independently a direct bond, a straight or branched-chain C$_{1-6}$alkyl, C$_{2-6}$ alkenyl, or C$_{3-7}$ cycloalkyl;
Z is selected from the group consisting of hydrogen, C$_{1-4}$alkyl, C$_{1-4}$alkoxy, halogen, cyano, hydroxy, —OCHF$_2$, —OCF$_3$, —CF$_3$, and —CHF$_2$;
X and Y are each independently selected from the group consisting of hydrogen, hydroxy, halogen, (halogen)$_3$C—, (halogen)$_2$CH—, C$_{1-4}$alkylS—, C$_{1-4}$alkylS(O)—, C$_{1-4}$alkylSO$_2$—, nitro, F$_3$S—, and cyano; —OR$^6$; —NR$^4$R$^5$; —NR$^7$C(=O)R$^8$; —NR$^7$C(=O)OR$^8$; —NHSO$_2$C$_{1-4}$alkyl; —N(SO$_2$C$_{1-4}$alkyl)$_2$; —C(=O)W wherein W is selected from the group consisting of hydroxy, C$_{1-4}$alkyl, C$_{1-4}$alkoxy, phenoxy, and —NR$^4$R$^5$; —OC(=O)C$_{1-4}$alkyl; -phenyl in which said phenyl is optionally substituted with cyano, halogen, C$_{1-4}$alkoxy, C$_{1-4}$alkylS—, CH$_3$C(=O), C$_{1-4}$alkylS(O)—, or C$_{1-4}$alkylSO$_2$—; and heterocyclic group, in which said heterocyclic group is selected from the group consisting of furanyl, thiofuranyl, pyrrolyl, imidazolyl, pyrazolyl, triazolyl, tetrazolyl, pyridinyl, pyrimidinyl, oxadiazolyl, oxazolyl, isoxazolyl, thiadiazolyl, and thiazolyl, wherein said heterocyclic group is optionally substituted with substituents selected from the group consisting of cyano, halogen, C$_{1-4}$alkyl, (halogen)C$_{1-4}$alkyl, and CO$_2$C$_{1-4}$alkyl;
(f) —B-(heterocycle), in which said heterocycle is selected from the group consisting of furanyl, thiofuranyl, pyrrolyl, imidazolyl, pyrazolyl, triazolyl, tetrazolyl, pyridinyl, pyrimidinyl, oxadiazolyl, oxazolyl, isoxazolyl, thiadiazolyl and thiazolyl wherein said heterocycle is optionally substituted with substituents selected from the group consisting of cyano, halogen, C$_{1-4}$alkyl, CO$_2$C$_{1-4}$alkyl, amino, (C$_{1-4}$alkyl)NH—, di(C$_{1-4}$alkyl)N—, morpholin-4-yl, thiomorpholin-4-yl, pyrrolidin-1-yl, piperidin-1-yl, piperazin-1-yl, and 4-(C$_{1-6}$alkyl)piperazin-1-yl;
(g) —B-(piperidin-4-yl), in which said piperidin-4-yl is optionally substituted with substituents selected from the group consisting of a straight or branched-chain C$_{1-6}$alkyl, CH$_2$C(=O)phenyl, phenyl and phenylmethyl in which said C$_{1-6}$alkyl and said phenyl are optionally substituted with substituents selected from the group consisting of cyano, halogen, benzimidazol-2-yl, pyridyl and tetrahydrofuran-2-yl; and —C(=O)W' wherein W' is selected from the group consisting of $C_{1-4}$alkoxy, $R^9$, and —$NR^4R^5$;

A is hydroxy, $C_{1-4}$alkoxy or $NR^4R^5$;

B is a straight or branched-chain $C_{1-6}$alkyl or $C_{3-6}$alkenyl;

$R^3$ is phenyl or pyridyl optionally substituted with substituents selected from the group consisting of halogen, hydroxy, $C_{1-4}$alkoxy, $C_{1-4}$alkyl, (halogen)$_3$C—, (halogen)$_2$CH—, and halogenCH$_2$—;

$R^4$ and $R^5$ each are independently hydrogen, a straight or branched-chain $C_{1-6}$ alkyl, $C_{3-6}$ alkenyl, $C_{3-6}$ alkynyl, $C_{3-7}$ cycloalkyl, $C_{3-7}$ cycloalkylmethyl, $C_{1-4}$alkoxy, phenyl, benzyl, pyridyl, piperidin-4-yl, indan-1-yl, indan-2-yl, tetrahydrofuran-3-yl, or pyrrolidin-3-yl; in which each is optionally substituted with substituents selected from the group consisting of hydroxy, cyano, halogen, (halogen)$_3$C—, (halogen)$_2$CH—, halogenCH$_2$—, hydroxymethyl, benzyloxymethyl, phenyl, pyridyl, $C_{1-4}$alkyl, $C_{1-4}$alkoxy, (halogen)$_3$C—O—, (halogen)$_2$CH—O—, $C_{1-4}$alkylthio, amino, ($C_{1-4}$alkyl)NH—, di($C_{1-4}$alkyl)N—, morpholin-4-yl, thiomorpholin-4-yl, pyrrolidin-1-yl, piperidin-1-yl, piperazin-1-yl, 4-($C_{1-6}$alkyl)piperazin-1-yl, 4-phenylpiperazin-1-yl, 4-benzylpiperazin-1-yl, 4-pyridylpiperazin-1-yl, CO$_2$H, CO$_2$$C_{1-4}$alkyl, C(=O)NHC$_{1-4}$alkyl, and C(=O)N(C$_{1-4}$alkyl)$_2$;

$R^4$ and $R^5$ taken together may be morpholin-4-yl, thiomorpholin-4-yl, pyrrolidin-1-yl, 1,2,3,4-tetrahydroisoquinolin-2-yl, decahydroquinolin-1-yl, piperidin-1-yl, piperazin-1-yl, [1,4]-oxazepan-4-yl, azetidin-1-yl, 2,3-dihydro-1H-isoindol-2-yl, or 2,3-dihydro-1H-indol-1-yl; in which each is optionally substituted with substituents selected from the group consisting of hydroxy, cyano, halogen, (halogen)$_3$C—, (halogen)$_2$CH—, halogenCH$_2$—, phenyl, pyridyl, benzyl, $C_{1-6}$alkyl, $C_{3-7}$ cycloalkyl, $C_{1-4}$alkoxy, $C_{1-4}$alkylthio, amino, ($C_{1-4}$alkyl)NH—, di($C_{1-4}$alkyl)N—, CO$_2$H, CO$_2$$C_{1-4}$alkyl, C(=O)NHC$_{1-4}$alkyl, and C(=O)N(C$_{1-4}$alkyl)$_2$;

$R^6$ is a straight or branched-chain $C_{1-6}$alkyl, $C_{3-6}$ alkenyl, benzyl, or phenyl in which each is optionally substituted with substituents selected from the group consisting of halogen, $C_{1-4}$alkyl, $C_{1-4}$alkoxy, amino, ($C_{1-4}$alkyl)NH—, di($C_{1-4}$alkyl)N—, ($C_{1-4}$alkyl)(phenyl)N—, morpholin-4-yl, thiomorpholin-4-yl, pyrrolidin-1-yl, piperidin-1-yl, piperazin-1-yl, and 4-($C_{1-6}$alkyl)piperazin-1-yl;

$R^7$ is hydrogen, a straight or branched-chain $C_{1-6}$ alkyl;

$R^8$ is a straight or branched-chain $C_{1-6}$alkyl, $C_{3-7}$ cycloalkyl, phenyl, pyridyl, or furanyl; in which each is optionally substituted with substituents selected from the group consisting of halogen, $C_{1-4}$alkyl, $C_{1-4}$alkoxy, ($C_{1-4}$alkyl)NH—, di($C_{1-4}$alkyl)N—, morpholin-4-yl, thiomorpholin-4-yl, pyrrolidin-1-yl, piperidin-1-yl, piperazin-1-yl, and 4-($C_{1-6}$alkyl)piperazin-1-yl;

$R^9$ is a straight or branched-chain $C_{1-6}$alkyl, $C_{3-6}$ alkenyl, benzyl, phenyl, oxazolyl or pyridyl; in which each is optionally substituted with substituents selected from the group consisting of halogen, (halogen)$_3$C—, (halogen)$_2$CH—, halogenCH$_2$—, $C_{1-4}$alkyl, $C_{1-4}$alkoxy, amino, ($C_{1-4}$alkyl)NH—, di($C_{1-4}$alkyl)N—, morpholin-4-yl, thiomorpholin-4-yl, pyrrolidin-1-yl, piperidin-1-yl, piperazin-1-yl, and 4-($C_{1-6}$alkyl)piperazin-1-yl;

or a non-toxic pharmaceutically acceptable salt thereof.

The present invention also provides a method for the treatment or alleviation of disorders associated with β-amyloid peptide, especially Alzheimer's Disease, which comprises administering together with a conventional adjuvant, carrier or diluent a therapeutically effective amount of a compound of formula I or a nontoxic pharmaceutically acceptable salt, solvate or hydrate thereof.

The term "$C_{1-6}$ alkyl" as used herein and in the claims (unless the context indicates otherwise) means straight or branched chain alkyl groups such as methyl, ethyl, propyl, isopropyl, butyl, isobutyl, t-butyl, pentyl, 3-methylbutyl, hexyl and the like. The term "$C_{2-6}$ alkenyl" used herein and in the claims (unless the context indicates otherwise) means straight or branched chain alkenyl groups such as ethenyl (i.e., vinyl), propenyl, allyl, butenyl, 3-methylbutenyl, pentenyl, hexenyl and the like. Unless otherwise specified, the term "halogen" as used herein and in the claims is intended to include bromine, chlorine, iodine and fluorine while the term "halide" is intended to include bromide, chloride and iodide anion.

The term "$C_{3-7}$ cycloalkyl" means a carbon cyclic ring system such as cyclopropyl, cyclobutyl, cyclopentyl, cyclohexyl and cycloheptyl.

The term "$C_{1-4}$ haloalkyl" means a straight or branched chain $C_{1-4}$ alkyl group containing from 1 to 3 halogen atoms such as trifluoromethyl, fluoroethyl, 1,2-dichloroethyl, trichloroethyl and the like.

The term "$C_{2-5}$ alkylene" means a straight or branched chain alkylene group such as methylene, ethylene, propylene, methylethylene, butylene, methylpropylene, pentylene, methylbutylene and ethylpropylene.

As the compounds of the present invention possess an asymmetric carbon atom, the present invention includes the racemate as well as the individual enantiomeric forms of the compounds of Formula I as described herein and in the claims. The use of a single designation such as (R) or (S) is intended to include mostly one stereoisomer. Mixtures of isomers can be separated into individual isomers according to methods which are known per se, e.g., fractional crystallization, adsorption chromatography or other suitable separation processes. Resulting racemates can be separated into antipodes in the usual manner after introduction of suitable salt-forming groupings, e.g., by forming a mixture of diastereoisomeric salts with optically active salt-forming agents, separating the mixture into diastereomeric salts and converting the separated salts into the free compounds. The possible enantiomeric forms may also be separated by fractionation through chiral high pressure liquid chromatography columns.

The term "nontoxic pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like.

In the method of the present invention, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

GENERAL REACTION SCHEMES

The general procedures used to synthesize the compounds of Formula I are described in Reaction Schemes 1 to 23. Reasonable variations of the described procedures, which Reaction Scheme 1

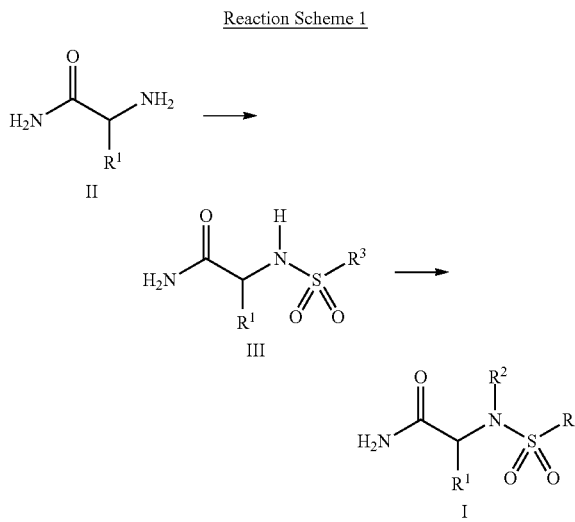

The starting (α-amino)acetamides of Formula II are used in racemic or in enantiomerically pure form and are commercially available or are prepared by well-known literature procedures from commercially available (α-amino)acids (general reference for amide preparation: Larock, R. C., *Comprehensive Organic Transformations*, pp. 972-976, VCH Publishers, New York (1989)); see also Reaction Scheme 18 for the conversion of the acid of Formula XLVIII to the amide of Formula XLIX). The compound of Formula II is treated with a suitable base and a sulfonylating reagent such as a sulfonyl chloride in an aprotic solvent such as $CH_2Cl_2$ at room temperature to generate the (α-sulfonamido)acetamide of Formula III. Suitable bases include triethylamine and pyridine.

In one method for conversion of the compound of Formula III to the sulfonamide of Formula I, the compound of Formula III is treated with a suitable base and an alkylating agent in an aprotic solvent with or without heating. Suitable bases for this reaction include potassium carbonate and cesium carbonate. Alkylating agents include alkyl halides (e.g., alkyl chloride, alkyl bromide, or alkyl iodide) and alkyl sulfonates (tosylates, mesylates, trifluoromethanesulfonates). Preferred solvents include DMF and acetonitrile. The temperature range for the reaction is typically 20° C. to 100° C.

An alternative method for conversion of the compound of Formula III to the compound of Formula I involves treatment of the compound of Formula III with triphenyl phosphine, a dialkyl azodicarboxylate, and an alcohol in an inert solvent with or without heating.

Reaction Scheme 1-Solid Support

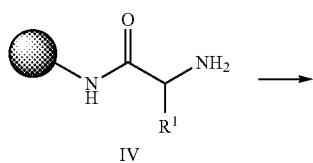

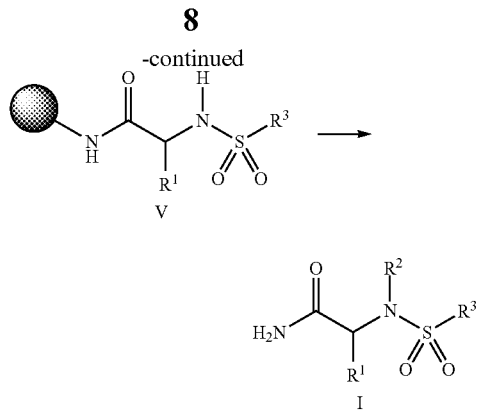

The compounds of Formula I can also be prepared using solid phase methodology. For example, FMOC-protected Rink amide resin is treated with piperidine in DMF to effect removal of the FMOC group. The resin is then coupled with an amino-protected (α-amino)acid in the presence of a coupling agent such as 1-hydroxybenzotriazole and a dialkyl carbodiimide in an inert solvent such as DMF with or without heating. Deprotection of the α-amino group affords the polymer-bound amide of Formula IV. In the case of an FMOC-protected amino acid, the deprotection can be accomplished by treatment with piperidine in DMF.

Reaction of the compound of Formula IV with an appropriate base such as pyridine and a sulfonylating agent such as a sulfonyl chloride in an inert solvent provides the resin-linked sulfonamide of Formula V. Alkylation of the compound of Formula V with an alkyl halide (e.g., alkyl chloride, alkyl bromide, or alkyl iodide) or alkyl sulfonate (e.g., mesylate, tosylate, or trifluoromethanesulfonate) is carried out in the presence of a base in an inert solvent at room temperature. A preferred base is 2-t-butylimino-2-diethylamino-1,3-dimethylperhydro-1,3,2-diasaphorine. Cleavage from the resin provides the sulfonamide of Formula I. In the case of the Rink amide resin, the cleavage is preferably carried out using trifluoroacetic acid in an inert solvent such as $CH_2Cl_2$.

Reaction Scheme 2

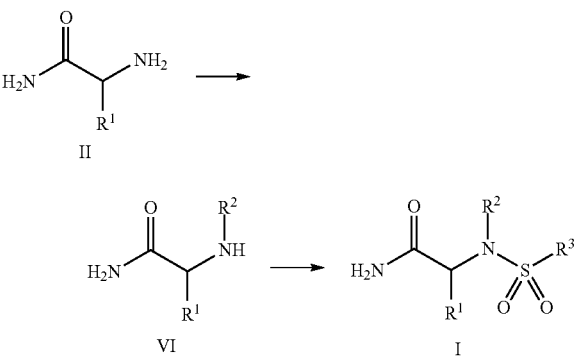

The compounds of Formula I can also be prepared as shown in Reaction Scheme 2. Reductive alkylation of the amine of Formula I to provide the amine of Formula VI is effected by treatment with an aldehyde and a hydride reducing agent in the presence of an acid catalyst with or without heating. A preferred reducing agent is sodium cyanoborohydride. A preferred acid catalyst is a Lewis acid such as ZnCl$_2$. The reaction solvent is preferably methanol. The amine of Formula VI is then treated with a sulfonylating agent such as a sulfonyl chloride in the presence of an amine such as triethylamine. This reaction is carried out in an inert solvent such as CH$_2$Cl$_2$ with or without heating to afford the product of Formula I. The reaction is typically carried out at room temperature.

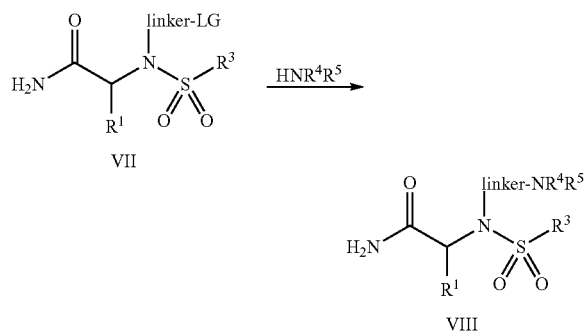

wherein linker = straight-chain or branched C$_{1-6}$alkyl or C$_{3-6}$alkenyl;
LG - leaving group Preparation of compounds of Formula VIII is accomplished as shown in Reaction Scheme 3 by reaction of the compound of Formula VII with an amine in the presence of an acid scavenger such as triethylamine in an inert solvent such as CH$_2$Cl$_2$ with or without heating. The compound of Formula VII is prepared by the sequence shown in Reaction Scheme 1 or Reaction Scheme 2.

The compounds of Formula XI and XII are prepared as shown in Reaction Scheme 4. Reduction of the nitro group of the compound of Formula IX (prepared by the sequence shown in Reaction Scheme 1 or 2) with hydrogen gas under pressure in the presence of a palladium catalyst, acid, and in a solvent such as methanol provided the aniline derivative of Formula X. Monomethylation of the compound of Formula X to provide the compound of Formula XI is accomplished by reaction with 1.1 equivalents of a methyl halide or a methyl sulfonate, for example dimethylsulfate, in the presence of a base such as triethylamine and in an inert solvent such as DMF. The monomethylation reaction is typically carried out between 20° C. and 40° C. Preparation of the dimethylaniline of Formula XII is effected by treatment of the aniline of Formula X with an excess of a methyl halide such as methyl iodide or a methyl sulfonate in the presence of a base, for example cesium carbonate, in a solvent such as DMF, with or without heating.

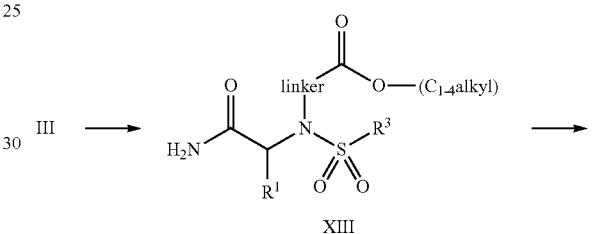

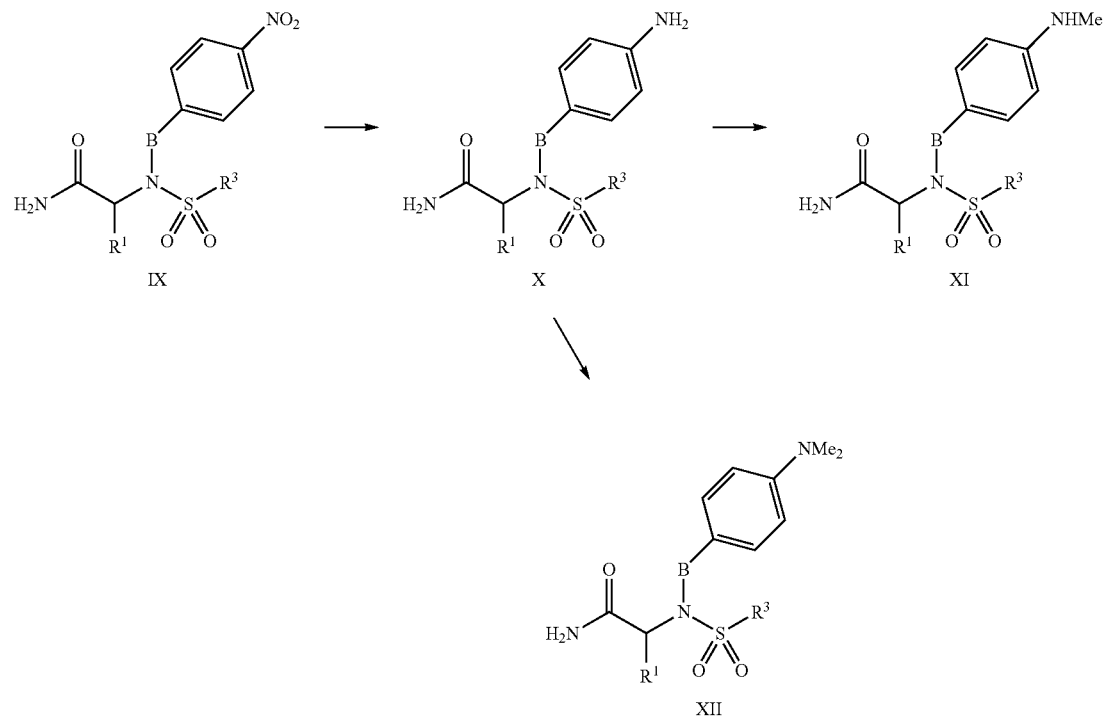

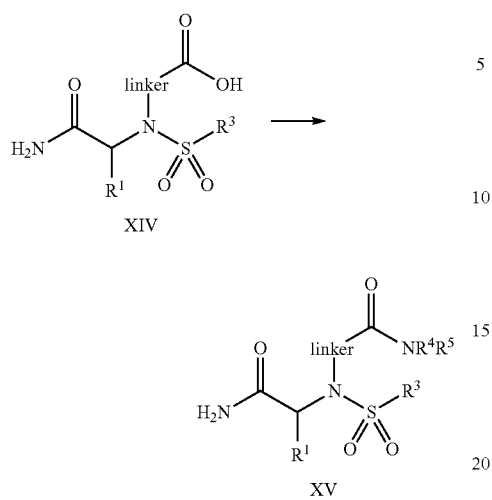

wherein linker = straight-chain or branched C$_{1-6}$alkyl

Reaction Scheme 5 outlines the synthesis of esters of Formula XIII, acids of Formula XIV, and amides of Formula XV. Reaction of a compound of Formula III with a haloalkylcarboxylate ester, for example t-butyl bromoacetate, in the presence of a base such as potassium carbonate and in an inert solvent such as DMF affords the ester of Formula XIII. Deprotection of the ester is effected by methods known to those skilled in the art (ref: Greene, T. W. et al., *Protecting Groups in Organic Synthesis*, pp. 373-442, Wiley Interscience, New York (1999)). For example, for t-butyl esters, cleavage to the acid of Formula XIV is accomplished by treatment with trifluoroacetic acid in a solvent such as CH$_2$Cl$_2$. Conversion of the acid to the amide of Formula XV is carried out using common amide coupling procedures well known to those skilled in the art (ref: Larock, R. C., *Comprehensive Organic Transformations*, pp. 972-976, VCH Publishers, New York (1989)). In a preferred procedure, the acid of Formula XIV is treated with a primary or secondary amine in the presence of 1-hydroxybenzotriazole and 1,3-dicyclohexylcarbodiimide in an aprotic solvent such as CH$_2$Cl$_2$ or DMF.

Reaction Scheme 6

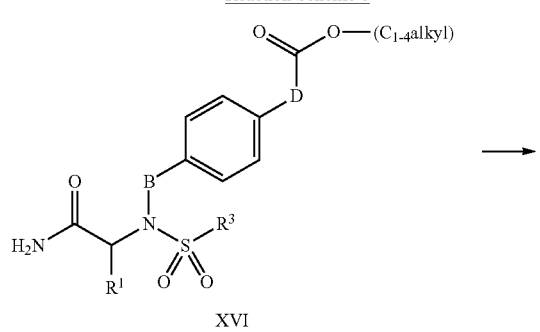

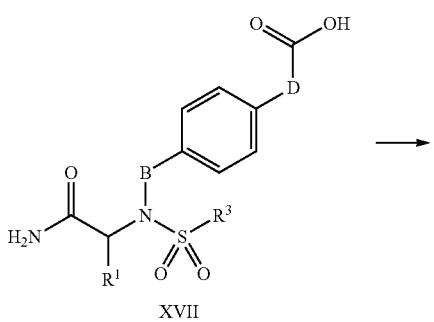

The preparation of acids of Formula XVII and amides of Formula XVIII is shown in Reaction Scheme 6. Conversion of an ester of Formula XVI (prepared as shown in Reaction Schemes 1 or 2) to an acid of Formula XVII is accomplished using standard ester cleavage conditions well known to those skilled in the art (ref: Greene, T. W. et al., *Protecting Groups in Organic Synthesis*, pp. 373-442, Wiley Interscience, New York (1999)). In the case of a methyl ester of Formula XVI, treatment with aqueous sodium hydroxide in a solvent such a methanol or a methanol/THF mixture at 20° C. to 40° C. provides the acid of Formula XVII. Conversion of the acid of Formula XVII to the amide of Formula XVIII is achieved using common amide coupling procedures well known to those skilled in the art (ref: Larock, R. C., *Comprehensive Organic Transformations*, pp. 972-976, VCH Publishers, New York (1989)). In a preferred procedure, the acid of Formula XVII is treated with a primary or secondary amine in the presence of 1-hydroxybenzotriazole and a carbodiimide, for example 1-(3-dimethylaminopropyl)-3-ethylcarbodiimide, in a solvent such as DMF or CH$_2$Cl$_2$. A base such a diisopropylethylamine can be added as an acid scavenger.

Reaction Scheme 7

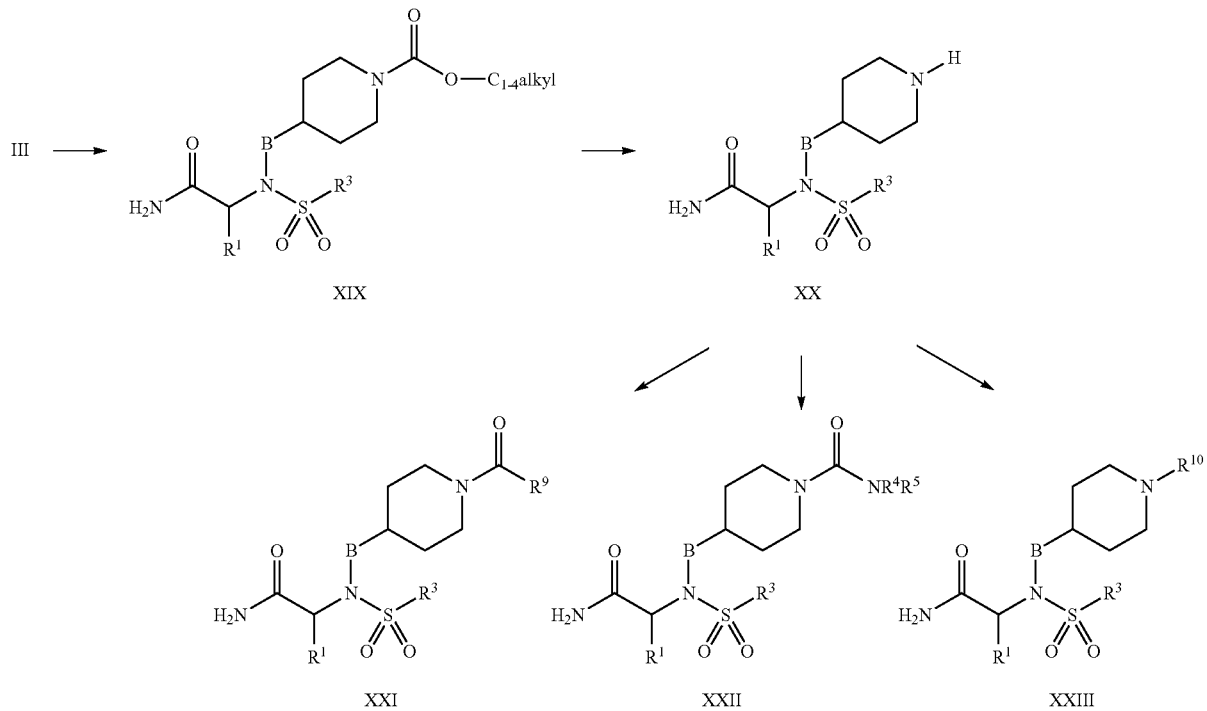

The synthesis of piperidine derivatives of Formula XIX, XX, XXI, XXII, and XXIII is described in Reaction Scheme 7. Reaction of a compound of Formula III with an N-protected piperidine substituted with a 4-haloalkyl or 4-sulfonyloxyalkyl group, such as 4-(toluenesulfonyloxymethyl)-1-(t-butoxycarbonyl)piperidine, in the presence of a base such as cesium carbonate in a solvent such as DMF, with or without heating, provides the carbamate of Formula XIX. Cleavage of the carbamate group in the compound of Formula XIX is carried out under standard conditions well known to those skilled in the art (ref: Greene, T. W. et al., *Protecting Groups in Organic Synthesis*, pp. 503-550, Wiley Interscience, New York (1999)) to provide the piperidine of Formula XX. In the case of a (t-butoxycarbonyl)piperidine derivative, the cleavage is effected by treatment with trifluoroacetic acid in $CH_2Cl_2$.

Conversion of the piperidine of Formula XX to an amide of Formula XXI is carried out using amide-coupling procedures well known to those skilled in the art (ref: Larock, R. C., *Comprehensive Organic Transformations*, pp. 972-976, VCH Publishers, New York (1989)). In a preferred method, the piperidine of Formula XX is treated with an acyl chloride in the presence of an amine such as triethylamine and in an inert solvent such as $CH_2Cl_2$ with or without heating. Alternatively, the piperidine of Formula XX may be coupled with an acid in the presence of coupling agents such as hydroxybenzotriazole and a carbodiimide to provide an amide of Formula XXI. Preparation of the urea of Formula XXII is achieved by treatment of the amine of Formula XX with an isocyanate and a base such as triethylamine in a solvent such as $CH_2Cl_2$ with or without heating. Alkylation of the piperidine of Formula XX provides N-substituted piperidines of Formula XXIII. In a typical procedure, the piperidine is treated with an alkyl halide or an alkyl sulfonate in the presence of a base such as triethylamine and in a solvent such as $CH_2Cl_2$.

Reaction Scheme 8

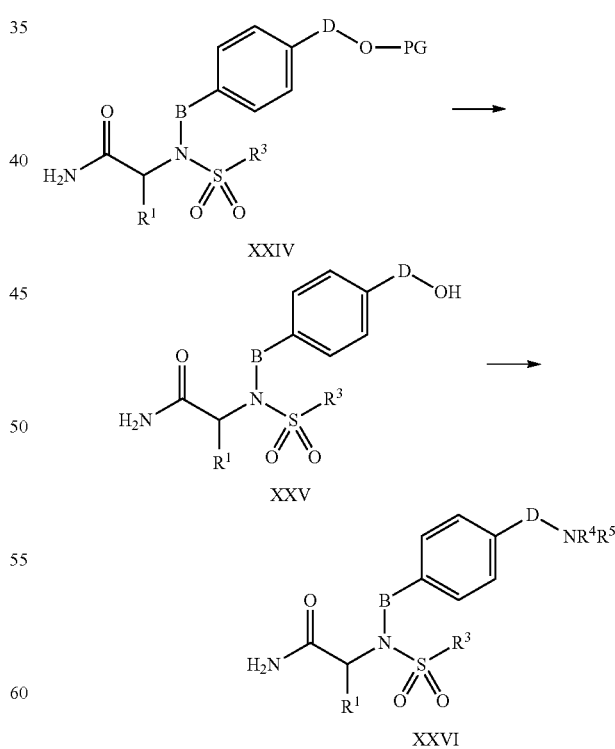

PG = an alcohol protecting group
D is other than a bond

Alcohols of Formula XXV and amines of Formula XXVI are synthesized by the sequence shown in Reaction Scheme 8.

A protected alcohol of Formula XXIV is prepared by the procedure shown in Reaction Schemes 1 or 2. Deprotection of the alcohol under the appropriate conditions for the chosen protecting group (ref: Greene, T. W. et al., *Protecting Groups in Organic Synthesis*, Chapter 2) provides the alcohol of Formula XXV. For example, when the protecting group is a tetrahydropyranyl moiety, the alcohol is liberated by treatment of the compound of Formula XXIV with p-toluenesulfonic acid in a solvent such as methanol. The alcohol of Formula XXV is converted to a leaving group (e.g., a halide or sulfonate) and then treated with a primary or secondary amine to afford an amine of Formula XXVI. For example, the alcohol may be converted to a mesylate derivative by reaction with methanesulfonyl chloride and a base such as triethylamine in $CH_2Cl_2$. Subsequent reaction of the mesylate with a primary or secondary amine in the presence of a base such as triethylamine in a solvent such as $CH_2Cl_2$ provides the amine of Formula XXVI.

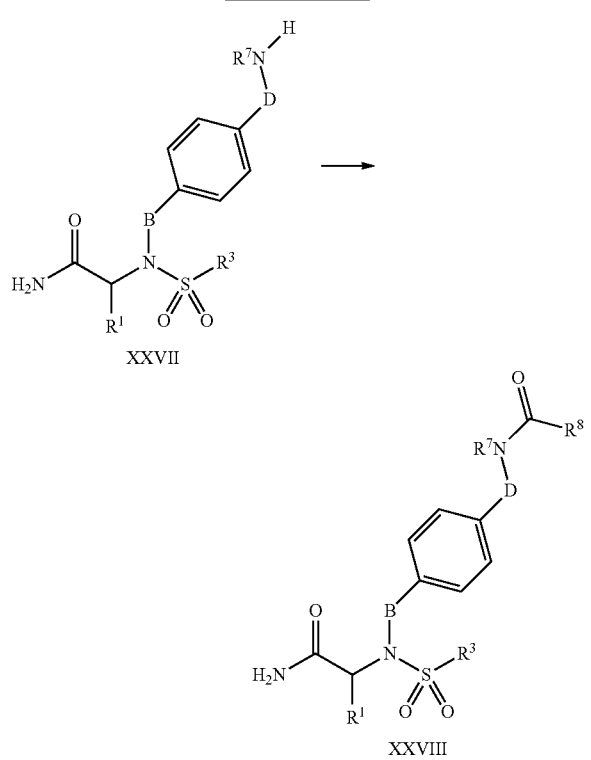

Amides of Formula XXVIII are prepared from amines of Formula XXVII as shown in Reaction Scheme 9 Amines of Formula XXVII wherein D is a direct bond are prepared as in Reaction Scheme 1 or 4 Amines of Formula XXVII wherein D is other than a direct bond are prepared as in Reaction Scheme 8. Conversion of the amines of Formula XXVII to the amides of Formula XXVIII is carried out using amide-coupling conditions well known to those skilled in the art (ref: Larock, R. C., *Comprehensive Organic Transformations*, pp. 972-976, VCH Publishers, New York (1989)). For example, reaction of the amine of Formula XXVII with an acid chloride in the presence of a base such as triethylamine in a solvent such as $CH_2Cl_2$ provides the amide of Formula XXVIII. Conversion of the amines of Formula XXVII to carbamate derivatives can be carried out using conditions well known to those skilled in the art. (ref: Greene, T. W. et al., *Protecting Groups in Organic Synthesis*, pp. 503-550). Preparation of sulfonamide derivatives from an amine of Formula XXVII can also be achieved using methods such as that described for the conversion of the intermediate of Formula II to the sulfonamide of Formula III.

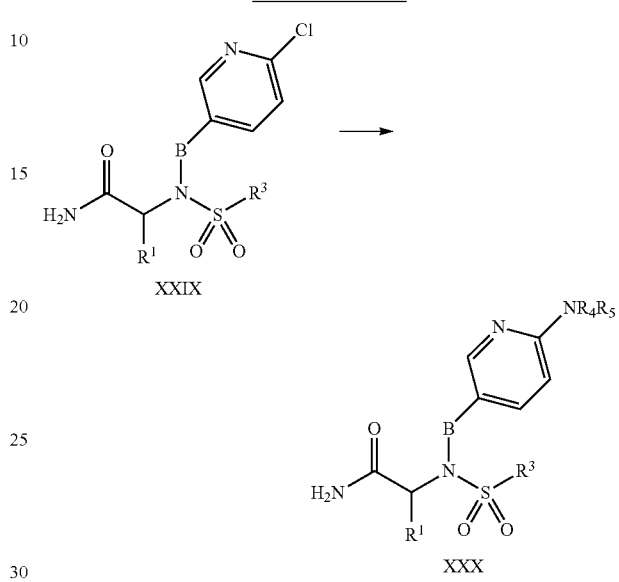

The synthesis of pyridine derivatives of Formula XXX is accomplished as shown in Reaction Scheme 10. The chloropyridine derivative of Formula XXIX is prepared using the chemistry described in Reaction Schemes 1 or 2. Treatment of the compound of Formula XXIX with a primary or secondary amine in a solvent such as THF at temperatures from 20° C. to 100° C., using sealed, pressurized vessel as appropriate, provides the aminopyridine of Formula XXX.

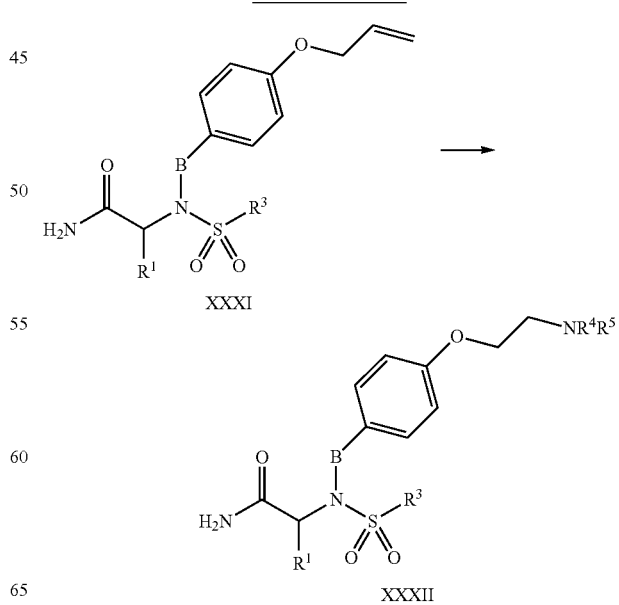

Amine-substituted phenol ethers of Formula XXXII are prepared from (O-allyl)phenols as indicated in Reaction Scheme 11. The starting allyl ethers of Formula XXXI are prepared as shown in Reaction Schemes 1 or 2. Treatment of the compound of Formula XXXI with osmium tetroxide and trimethylamine N-oxide in a solvent such as acetone followed by treatment with sodium periodate gives an intermediate aldehyde that is typically used without purification. Reaction of the unpurified aldehyde with a primary or secondary amine and a reducing agent such as sodium triacetoxyborohydride in a solvent such as ethanol with or without heating affords the amine of Formula XXXII.

Reaction Scheme 12

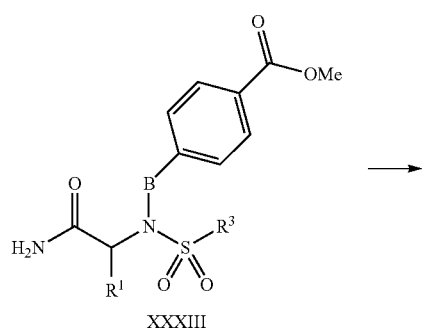

XXXIII

Conversion of the ester of Formula XXXIII to the tertiary alcohol of Formula XXXIV is carried out as shown in Reaction Scheme 12. Reaction of the ester of Formula XXXIII with an excess of a methyl organometallic reagent such as methyl magnesium bromide in a solvent such as THF at a temperature ranging from 0° C. to 25° C. yields the alcohol of Formula XXXIV.

Reaction Scheme 13

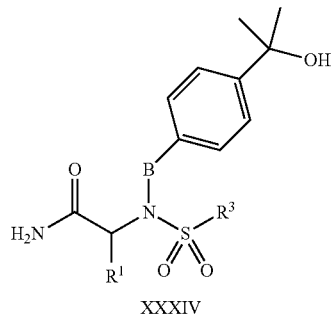

XXXV

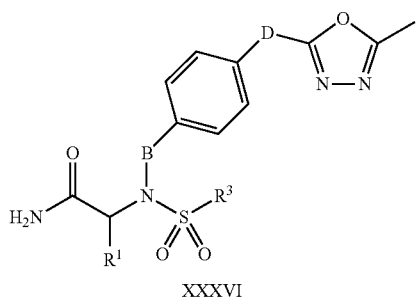

XXXVI

Preparation of the 1,3,4-oxadiazole of Formula XXXVI is carried out as shown in Reaction Scheme 13 using methods well known to those skilled in the art (ref: Joule, J. A. et al., *Heterocyclic Chemistry*, 3rd Edition, pp. 452-456, Chapman & Hall, London (1995) and references cited therein). For example, the ester of Formula XXXV is treated with hydrazine in methanol with heating up to the reflux point. The resulting acyl hydrazide intermediate is used without purification in a subsequent reaction with an alkyl acetimidate in pyridine with heating at reflux to provide the oxadiazole of Formula XXXVI.

Reaction Scheme 14

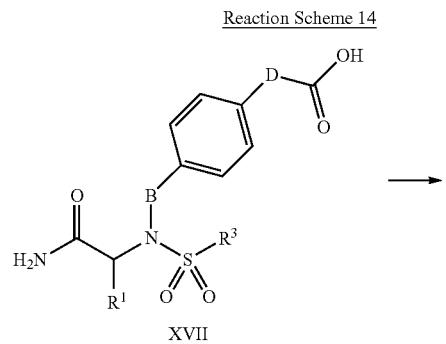

XVII

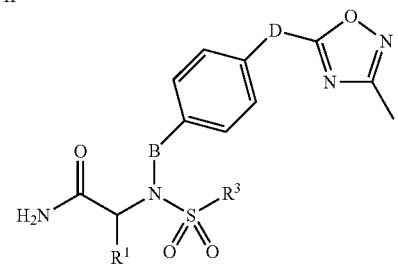

XXXVII

Synthesis of the 1,2,4-oxadiazole of Formula XXXVII is achieved as shown in Reaction Scheme 14 using methods well known to those skilled in the art (ref: Joule, J. A. et al., *Heterocyclic Chemistry*, 3rd Edition, pp. 452-456, Chapman & Hall, London (1995) and references cited therein). For example, treatment of the acid of Formula XVII with hydroxbenzotriazole, a carbodiimide, and acetamidoxime (N-hydroxy ethanimidamide) in the presence of a base such as triethylamine provides an intermediate that is heated in refluxing pyridine to provide the oxadiazole of Formula XXXVII.

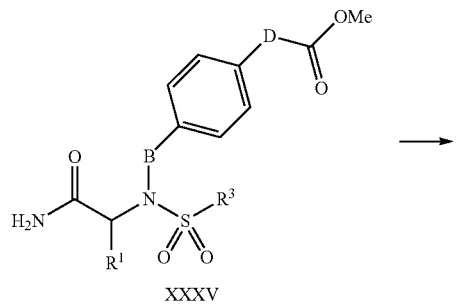

Reaction Scheme 15

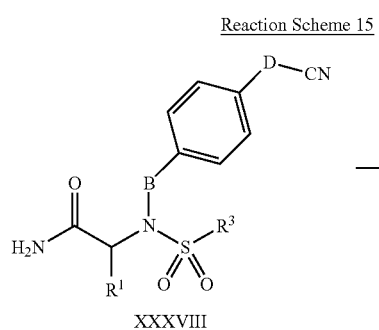

The 1,2,4-oxadiazole of Formula XXXIX is prepared from the nitrile of Formula XXXV111 (Reaction Scheme 15) using methods well-known to those skilled in the art (ref: Joule, J. A. et al., *Heterocyclic Chemistry*, 3rd Edition, pp. 452-456, Chapman & Hall, London (1995) and references cited therein). For example, reaction of the nitrile of Formula XXXVIII with hydroxylamine in a solvent such as ethanol at temperatures up to reflux provides an intermediate N-hydroxyamidine that is subsequently treated with acetyl chloride in the presence of a base such as triethylamine in a solvent such as $CH_2Cl_2$ to provide the 1,2,4-oxadiazole of Formula XXXIX.

Reaction Scheme 16

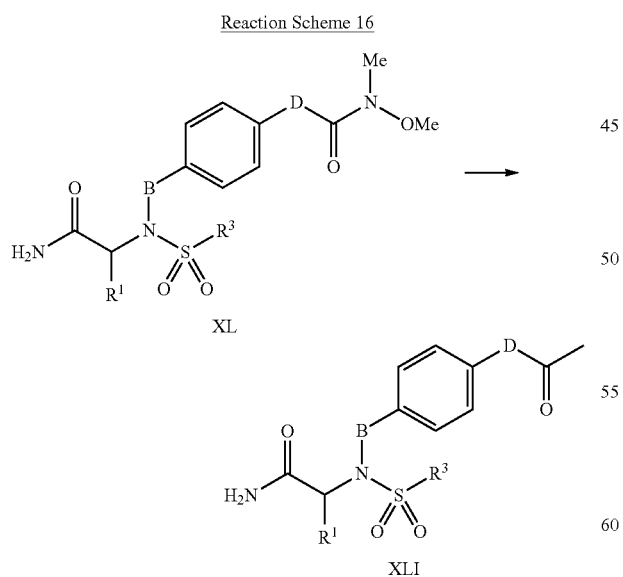

Reaction Scheme 16 shows the transformation of the amide of Formula XL to the ketone of Formula XLI. The amide of Formula XL, which is prepared as described in Reaction Scheme 6, is treated with a methyl organometallic reagent such as methyl magnesium bromide in a solvent such as THF to provide the ketone of Formula XLI. The range of the reaction temperature is from −20° C. to 25° C.

Reaction Scheme 17

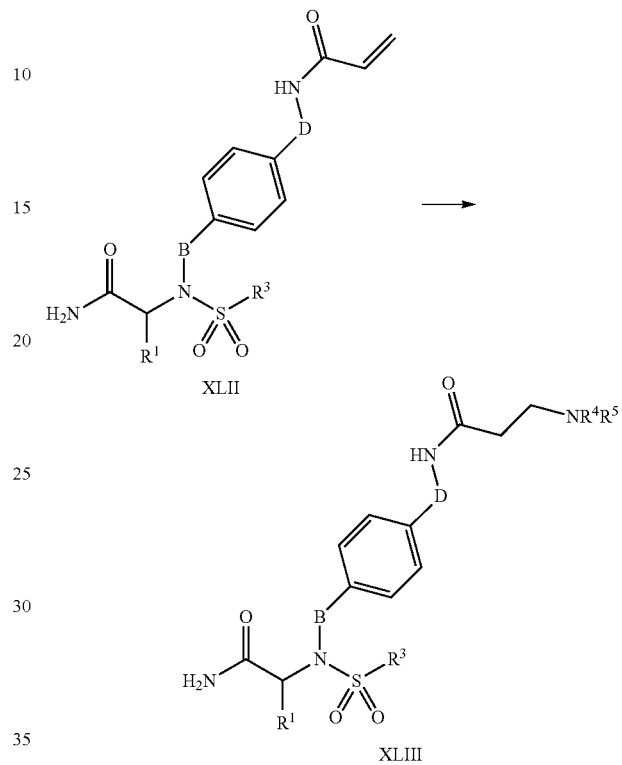

β-Amino amides of Formula XLIII are prepared from acrylamides of Formula XLII as shown in Reaction Scheme 17. For example, an acrylamide of Formula XLII, which is prepared as described in Reaction Scheme 9, is treated with a primary or secondary amine in a solvent such as toluene to provide the β-amino amide of Formula XLIII.

Reaction Scheme 18

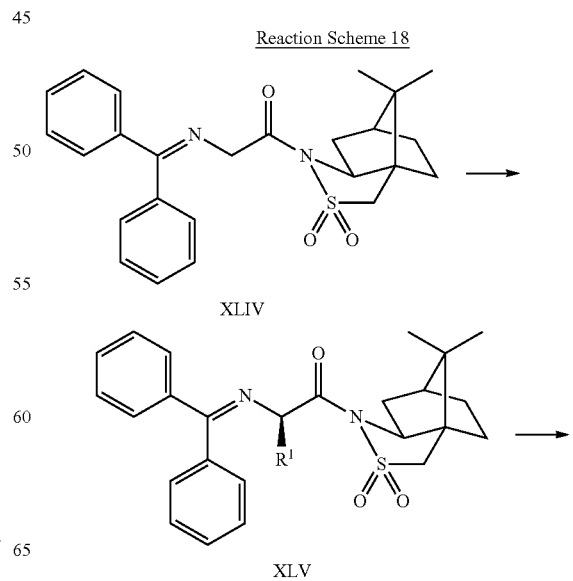

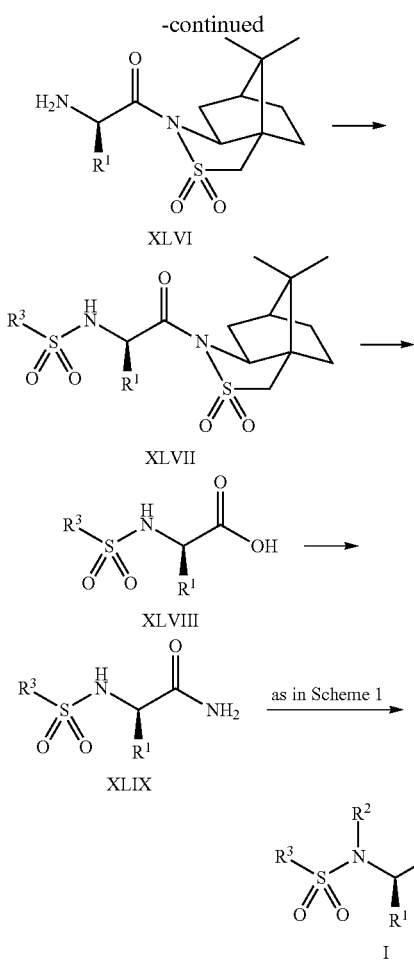

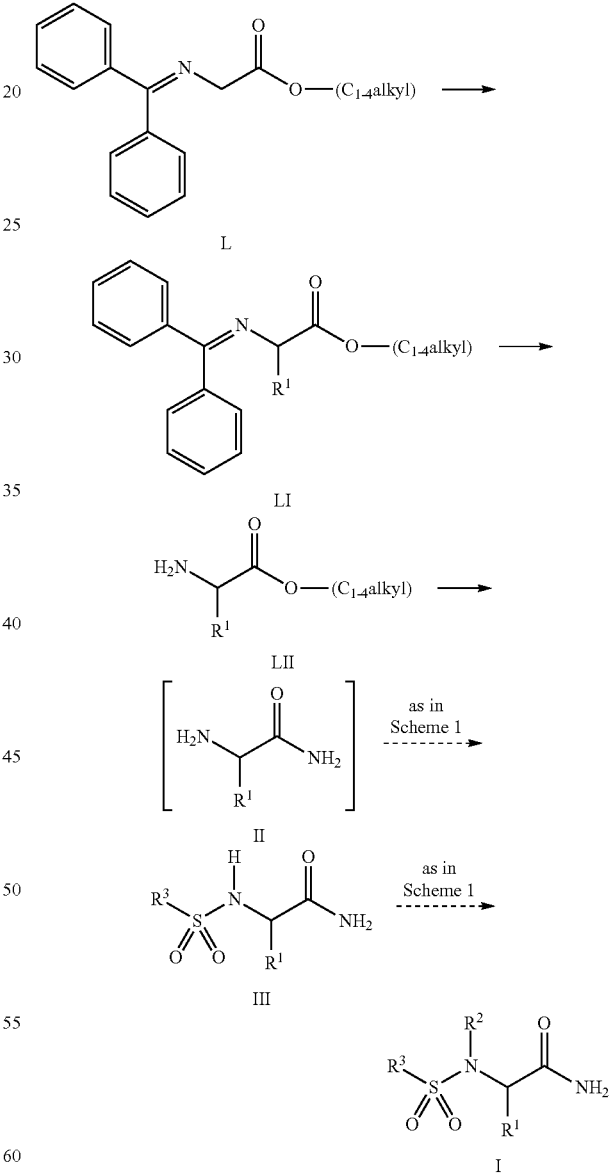

Reaction Scheme 19

Preparation of the sulfonamide intermediate of Formula XLIX (a single enantiomer of the compound of Formula III) is outlined in Reaction Scheme 18. Reaction of the α-anion of the intermediate of Formula XLIV (ref: Josien, H. et al., Tetrahedron Lett., 32:6547 (1991)) with an alkylating agent such as an alkyl halide (e.g., an alkyl chloride, alkyl bromide, or alkyl iodide) or an alkyl sulfonate (e.g., an alkyl mesylate, alkyl tosylate, or alkyl trifluoromethanesulfonate) provides the intermediate of Formula XLV. The α-anion of the compound of Formula XLIV is formed by treatment with a strong base such as an alkyl lithium (e.g., n-BuLi) or a dialkylamide (e.g., lithium diisopropylamide) in a solvent such as THF with or without a co-solvent such as HMPA. The reaction temperature is typically between −78° C. and 25° C. Removal of the benzhydrylidene protecting group of the compound of Formula XLV is carried out under conditions well known to those skilled in the art (ref.: Greene, T. W. et al., *Protecting Groups in Organic Synthesis*, pp. 587-588, Wiley Interscience, New York (1999)). For example, the compound of Formula XLV is treated with an acid such as HCl in water in a solvent such as THF to effect hydrolysis of the benzhydrylidene protecting group. The resulting amine of Formula XLVI is treated with a sulfonylating agent as described for Reaction Scheme 1 to provide the sulfonamide of Formula XLVII. Hydrolysis of the acylsulfonamide of Formula XLVII to afford the acid of Formula XLVIII is carried out by treatment with hydroxide ion, for example in the form of lithium hydroxide, in the presence of additives such as lithium bromide and tetrabutylammonium bromide. The acid of Formula XLVIII is converted to the amide of formula XLIX under conditions that are well known to those skilled in the art (general ref for amide preparation: Larock, R. C., *Comprehensive Organic Transformations*, pp. 972-976, VCH Publishers, New York (1989)). For example, reaction of the compound of Formula XLVIII with ammonium chloride in the presence of 1-hydroxybenzotriazole, a carbodiimide reagent, and an amine base such as diisopropylethylamine provides the amide of Formula XLIX. This reaction is typically run in a polar solvent such as DMF and at a reaction temperature from 0° C. to 40° C. The amide of Formula XLIX is converted to the compounds of Formula I by the method described in Reaction Scheme 1.

Reaction Scheme 19 illustrates one method for synthesis of an α-substituted (N-sulfonamido)acetamide intermediate of Formula III starting with an activated glycine derivative of Formula L. Reaction of the compound of Formula L (ref.: Haufe, G. et al., *Tetrahedron*, 54:5929-5938 (1998); Kroger, S. et al., *Amino Acids*, 12:363-372 (1997)) with an alkylating agent such as an alkyl halide (e.g., an alkyl chloride, alkyl bromide, or alkyl iodide) or an alkyl sulfonate (e.g., an alkyl mesylate, an alkyl tosylate, or an alkyl trifluoromethanesulfonate) in the presence of a base such as potassium carbonate and an additive such as tetrabutylammonium bromide and in an inert solvent such as acetonitrile at a reaction temperature of between 25° C. and 70° C. provides the compound of Formula LI. Removal of the benzhydrylidene protecting group is carried out under conditions well known to those skilled in the art (ref: Greene, T. W. et al., *Protecting Groups in Organic Synthesis*, pp. 587-588, Wiley Interscience, New York (1999)). For example, a solution of the compound of Formula LI in a solvent such as diethyl ether is treated with aqueous acid (e.g., aqueous HCl), typically at a reaction temperature of between 0° C. and 30° C., to provide the amine ester of Formula LII. Conversion of the ester of Formula LII to the amide of Formula II is carried out using procedures well known to those skilled in the art. For example, when the compound of Formula LII is an ethyl ester, hydrolysis of the ester is achieved by treatment of an ethereal solution with an acid such as HCl, typically with heating of the reaction mixture in refluxing solvent. The resulting acid intermediate is then converted to a methyl ester of Formula LII by transformation to the acid chloride under standard conditions, (e.g., treatment with thionyl chloride and methanol), followed by reaction with aqueous ammonia in a solvent such as toluene (ref: Larock, R. C., *Comprehensive Organic Transformations*, pp. 972-976, VCH Publishers, New York (1989)). The amine of Formula II is converted to the compound of Formula I as described in Reaction Scheme 1.

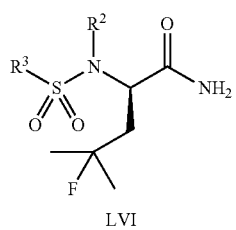

Preparation of the compound of Formula LVII is shown in Reaction Scheme 20. Alkene LIII is prepared as described in Reaction Scheme 18 from an intermediate of Formula XLIV and 1-bromo-2-methyl-2-propene). Treatment of the alkene of Formula LIII with HF.pyridine in a solvent such as THF at a reaction temperature between 0° C. and 25° C. affords the fluoroalkyl compound of Formula LIV. Conversion of the compound of Formula LIV to the amide of Formula LV is accomplished as described in Reaction Scheme 18. Transformation of the amide of Formula LV to the compound of Formula LVI is carried out as described in Reaction Scheme 1.

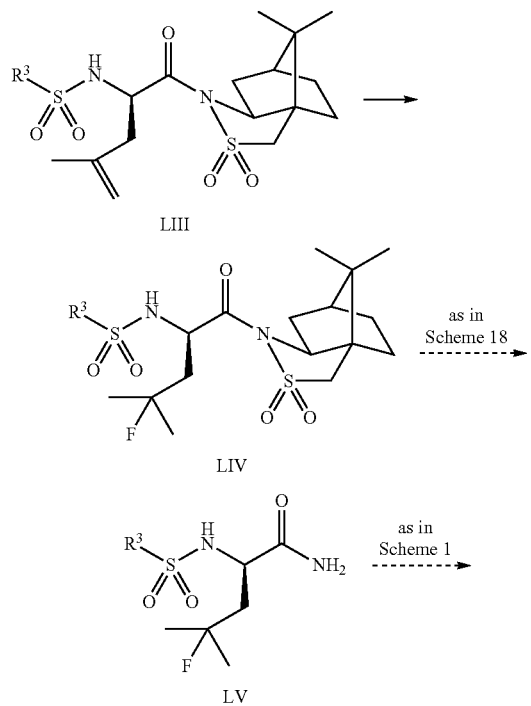

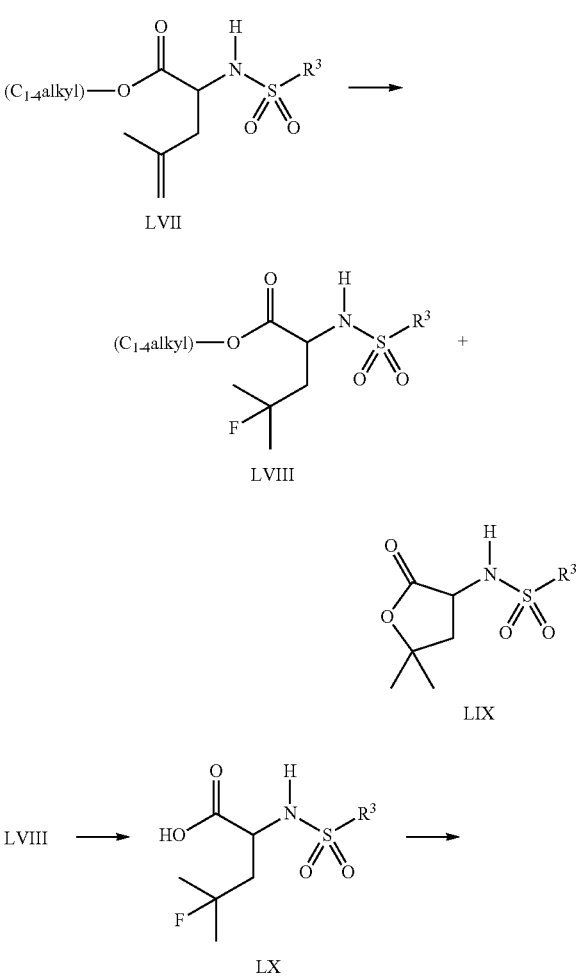

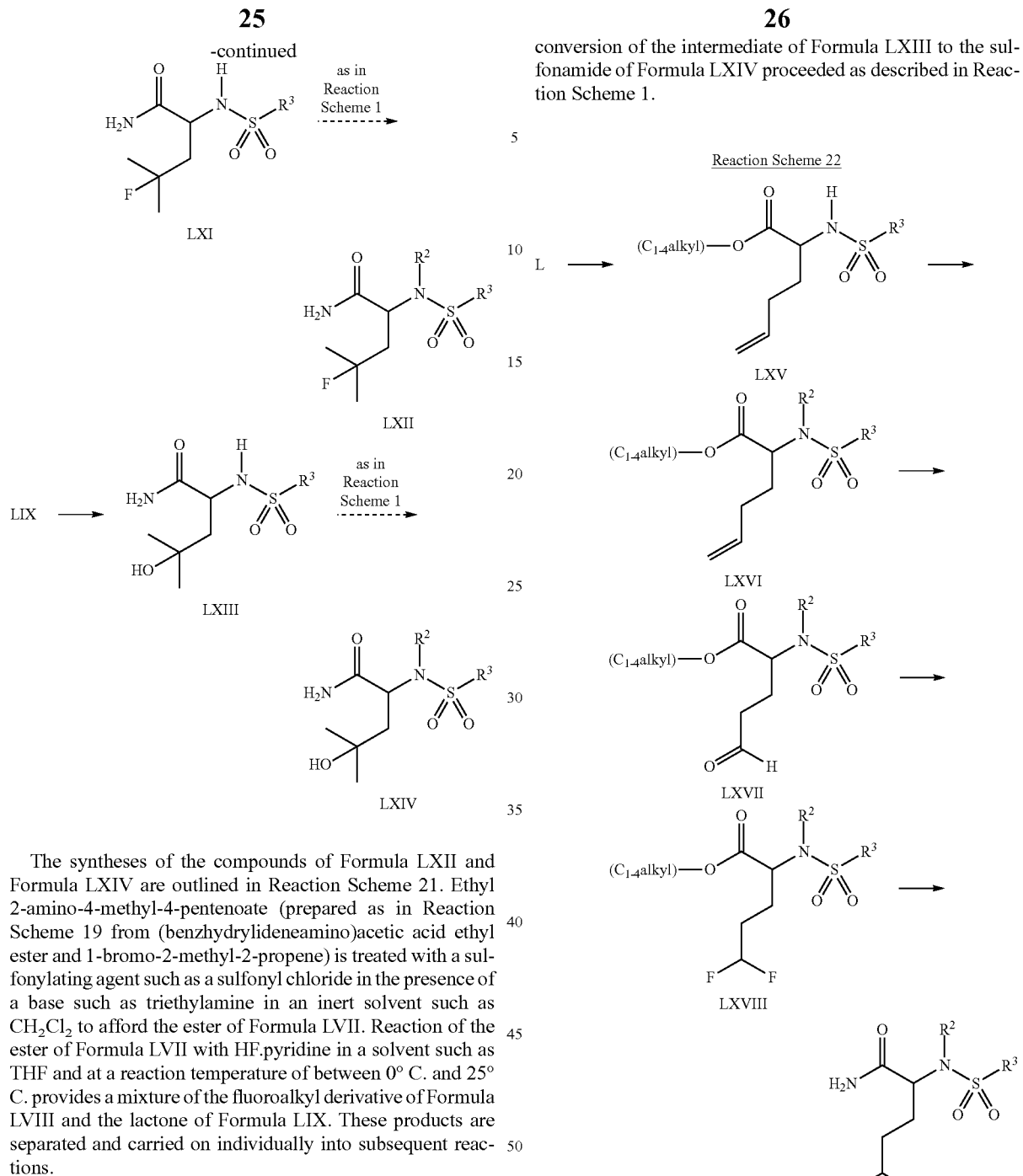

The syntheses of the compounds of Formula LXII and Formula LXIV are outlined in Reaction Scheme 21. Ethyl 2-amino-4-methyl-4-pentenoate (prepared as in Reaction Scheme 19 from (benzhydrylideneamino)acetic acid ethyl ester and 1-bromo-2-methyl-2-propene) is treated with a sulfonylating agent such as a sulfonyl chloride in the presence of a base such as triethylamine in an inert solvent such as $CH_2Cl_2$ to afford the ester of Formula LVII. Reaction of the ester of Formula LVII with HF.pyridine in a solvent such as THF and at a reaction temperature of between 0° C. and 25° C. provides a mixture of the fluoroalkyl derivative of Formula LVIII and the lactone of Formula LIX. These products are separated and carried on individually into subsequent reactions.

The ester of Formula LVIII is hydrolyzed to the acid of Formula LX using methods well known to those skilled in the art (ref.: Greene, T. W. et al., *Protecting Groups in Organic Synthesis*, pp. 373-442, Wiley Interscience, New York (1999)). For example, treatment of the ester of Formula LVIII with aqueous sodium hydroxide in a solvent such as methanol affords the acid of Formula LX. The acid of Formula LX is converted to the amide of Formula LXI using the procedure described in Reaction Scheme 18 for the preparation of the amide of Formula XLIX. Preparation of the amide of Formula LXII from the compound of Formula LXI is achieved as described in Reaction Scheme 1.

For the lactone of Formula LIX, treatment with aqueous ammonia provides the amide of Formula LXIII. This reaction is typically carried out with heating in a sealed tube. The reaction temperature is between 40° C. and 80° C. Further conversion of the intermediate of Formula LXIII to the sulfonamide of Formula LXIV proceeded as described in Reaction Scheme 1.

The synthetic sequence for preparation of a difluoroalkyl amide of Formula LXIX is shown in Reaction Scheme 22. The compound of Formula L is treated with 4-bromo-1-butene in the presence of a base such potassium carbonate in the presence of a tetraalkylammonium halide salt such as tetrabutylammonium bromide in a solvent such as $CH_3CN$ at a temperature from 20° C. to 70° C. Removal of the benzhydrylidene protecting group as described in Reaction Scheme 19 provides an intermediate amine that is then treated with a sulfonylating reagent such as a sulfonyl chloride to provide the ester of Formula LXV. Alkylation of the sulfonamide nitrogen is accomplished using the procedure described in Reaction Scheme 1 to afford the compound of Formula LXVI. Conversion of the alkene of Formula LXVI to the aldehyde of Formula LXVII is achieved by reaction of the alkene with osmium tetroxide and trimethylamine N-oxide in a solvent such as acetone, followed by treatment with sodium periodate. The reaction temperature is typically 20° C. to 40° C. Reaction of the aldehyde of Formula LXVII with a fluorinating agent such as DAST in a solvent such as CH$_2$Cl$_2$ yields the difluoroalkyl derivative of Formula LXVIII. The compound of Formula LXVIII is converted to the amide of Formula LXIX by hydrolysis of the ester to an acid using an base such as sodium hydroxide in a solvent such as methanol. The intermediate acid was converted to the amide using conditions well known to those skilled in the art (ref: Larock, R. C., *Comprehensive Organic Transformations*, pp. 972-976, VCH Publishers, New York (1989)). For example, reaction of the acid with ammonium chloride in the presence of hydroxybenzotriazole and a carbodiimide reagent and an amine base such as diisopropylethylamine provided the amide of Formula LXIX. This reaction is typically run in a polar solvent such as DMF and at a reaction temperature from 0° C. to 40° C.

Reaction Scheme 23

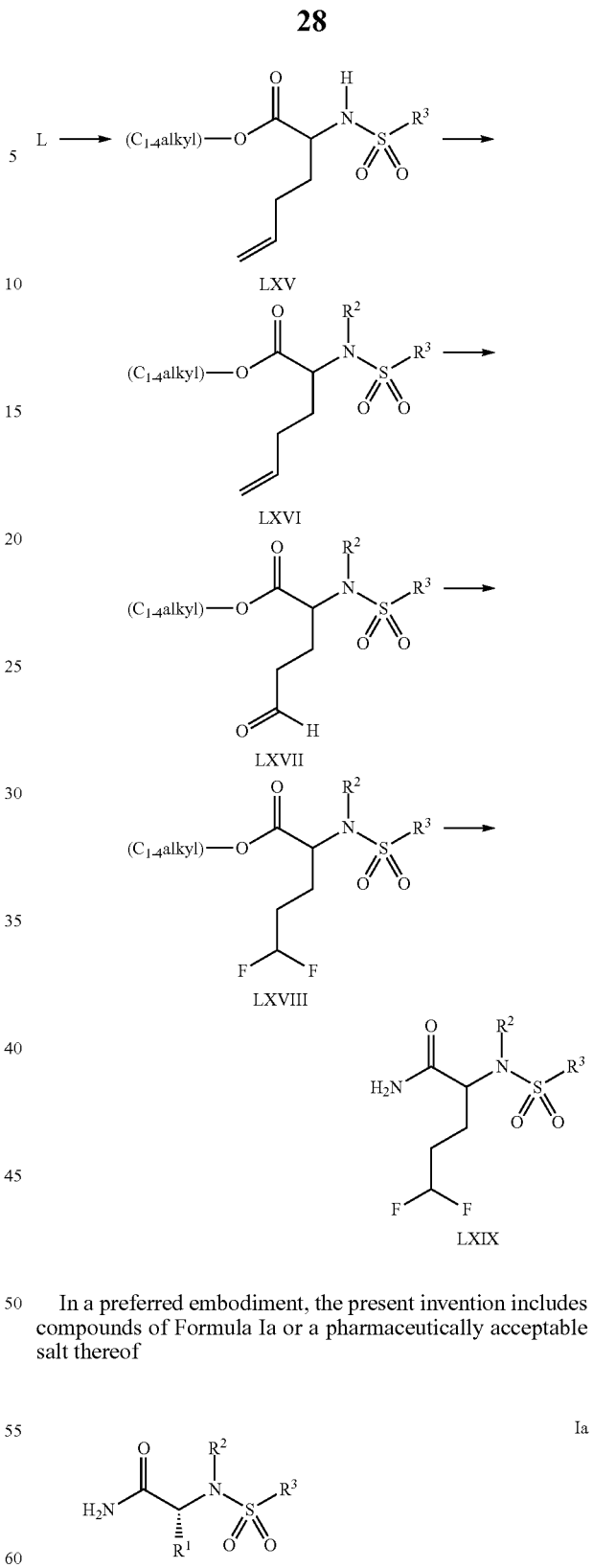

The α-amino amide of Formula LXXI is prepared using the reaction showed in Reaction Scheme 23. The amide of Formula LXX is prepared as described in Reaction Scheme 9. Treatment of the compound of Formula LXX with a secondary or tertiary amine in a solvent such as THF at a reaction temperature between 20° C. and 40° C. affords the amine of Formula LXXI.

In a preferred embodiment, the present invention includes compounds of Formula Ia or a pharmaceutically acceptable salt thereof

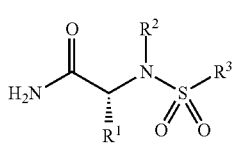

Ia wherein:
R$^1$ is selected from the group consisting of
(a) a straight or branched-chain C$_{1-6}$ alkyl or C$_{2-6}$alkenyl optionally substituted with substituents selected from the group consisting of hydroxy, C$_{3-7}$ cycloalkyl, C$_{1-4}$alkoxy, C$_{1-4}$alkylthio, and halogen;

(b) $C_{3-7}$ cycloalkyl optionally substituted with hydroxy or halogen;

$R^2$ is selected from the group consisting of
(a) a straight or branched-chain $C_{1-6}$alkyl or $C_{3-6}$alkenyl optionally substituted with substituents selected from the group consisting of halogen, $C_{1-4}$alkoxy, and $NR^4R^5$;
(b) $C_{3-7}$ cycloalkylmethyl optionally substituted with substituents selected from the group consisting of amino, $(C_{1-4}alkyl)NH—$, $di(C_{1-4}alkyl)N—$, $C_{1-4}alkylC(=O)NH—$, and $C_{1-4}alkylOC(=O)NH—$;
(c) a straight or branched-chain $C_{1-6}$alkyl-C(=O)-A;
(d) —B-naphthyl;
(e)

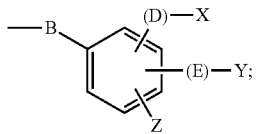

D and E are each independently a direct bond, a straight or branched-chain $C_{1-6}$alkyl, $C_{2-6}$ alkenyl, or $C_{3-7}$ cycloalkyl;
Z is selected from the group consisting of hydrogen, $C_{1-4}$alkyl, $C_{1-4}$alkoxy, halogen, cyano, hydroxy, —OCHF$_2$, —OCF$_3$, —CF$_3$, and —CHF$_2$;
X and Y are each independently selected from the group consisting of hydrogen, hydroxy, halogen, (halogen)$_3$C—, (halogen)$_2$CH—, $C_{1-4}$alkylS—, $C_{1-4}$alkylS(O)—, $C_{1-4}$alkylSO$_2$—, nitro, F$_3$S—, and cyano;
—OR$^6$;
—NR$^4$R$^5$;
—NR$^7$C(=O)R$^8$;
—NR$^7$C(=O)OR$^8$;
—NHSO$_2$C$_{1-4}$alkyl;
—N(SO$_2$C$_{1-4}$alkyl)$_2$;
—C(=O)W wherein W is selected from the group consisting of hydroxy, $C_{1-4}$alkyl, $C_{1-4}$alkoxy, phenoxy, and —NR$^4$R$^5$;
—OC(=O)C$_{1-4}$alkyl;
-phenyl in which said phenyl is optionally substituted with cyano, halogen, $C_{1-4}$alkoxy, $C_{1-4}$alkylS—, CH$_3$C(=O), $C_{1-4}$alkylS(O)—, or $C_{1-4}$-alkylSO$_2$—; and
heterocyclic group, in which said heterocyclic group is selected from the group consisting of furanyl, thiofuranyl, pyrrolyl, imidazolyl, pyrazolyl, triazolyl, tetrazolyl, pyridinyl, pyrimidinyl, oxadiazolyl, oxazolyl, isoxazolyl, thiadiazolyl, and thiazolyl, wherein said heterocyclic group is optionally substituted with substituents selected from the group consisting of cyano, halogen, $C_{1-4}$alkyl, (halogen)$C_{1-4}$alkyl, and CO$_2$C$_{1-4}$alkyl;
(f) —B-(heterocycle), in which said heterocycle is selected from the group consisting of furanyl, thiofuranyl, pyrrolyl, imidazolyl, pyrazolyl, triazolyl, tetrazolyl, pyridinyl, pyrimidinyl, oxadiazolyl, oxazolyl, isoxazolyl, thiadiazolyl and thiazolyl wherein said heterocycle is optionally substituted with substituents selected from the group consisting of cyano, halogen, $C_{1-4}$alkyl, CO$_2$C$_{1-4}$alkyl, amino, $(C_{1-4}alkyl)NH—$, $di(C_{1-4}alkyl)N—$, morpholin-4-yl, thiomorpholin-4-yl, pyrrolidin-1-yl, piperidin-1-yl, piperazin-1-yl, and 4-($C_{1-6}$alkyl)piperazin-1-yl;

(g) —B-(piperidin-4-yl), in which said piperidin-4-Y1 is optionally substituted with substituents selected from the group consisting of a straight or branched-chain $C_{1-6}$alkyl, CH$_2$C(=O)phenyl, phenyl and phenylmethyl in which said $C_{1-6}$alkyl and said phenyl are optionally substituted with substituents selected from the group consisting of cyano, halogen, benzimidazol-2-yl, pyridyl and tetrahydrofuran-2-yl; and —C(=O)W' wherein W' is selected from the group consisting of $C_{1-4}$alkoxy, R$^9$, and —NR$^4$R$^5$;

A is hydroxy, $C_{1-4}$alkoxy or NR$^4$R$^5$;
B is a straight or branched-chain $C_{1-6}$alkyl or $C_{3-6}$alkenyl;
$R^3$ is phenyl or pyridyl optionally substituted with substituents selected from the group consisting of halogen, hydroxy, $C_{1-4}$alkoxy, $C_{1-4}$alkyl, (halogen)$_3$C—, (halogen)$_2$CH—, and halogenCH$_2$—;
$R^4$ and $R^5$ each are independently hydrogen, a straight or branched-chain $C_{1-6}$ alkyl, $C_{3-6}$ alkenyl, $C_{3-6}$ alkynyl, $C_{3-7}$ cycloalkyl, $C_{3-7}$ cycloalkylmethyl, $C_{1-4}$alkoxy, phenyl, benzyl, pyridyl, piperidin-4-yl, indan-1-yl, indan-2-yl, tetrahydrofuran-3-yl, or pyrrolidin-3-yl; in which each is optionally substituted with substituents selected from the group consisting of hydroxy, cyano, halogen, (halogen)$_3$C—, (halogen)$_2$CH—, halogenCH$_2$—, hydroxymethyl, benzyloxymethyl, phenyl, pyridyl, $C_{1-4}$alkyl, $C_{1-4}$alkoxy, (halogen)$_3$C—O—, (halogen)$_2$CH—O—, $C_{1-4}$alkylthio, amino, $(C_{1-4}alkyl)NH—$, $di(C_{1-4}alkyl)N—$, morpholin-4-yl, thiomorpholin-4-yl, pyrrolidin-1-yl, piperidin-1-yl, piperazin-1-yl, 4-($C_{1-6}$alkyl)piperazin-1-yl, 4-phenylpiperazin-1-yl, 4-benzylpiperazin-1-yl, 4-pyridylpiperazin-1-yl, CO$_2$H, CO$_2$C$_{1-4}$alkyl, C(=O)NHC$_{1-4}$alkyl, and C(=O)N(C$_{1-4}$alkyl)$_2$;

$R^4$ and $R^5$ taken together may be morpholin-4-yl, thiomorpholin-4-yl, pyrrolidin-1-yl, 1,2,3,4-tetrahydroisoquinolin-2-yl, decahydroquinolin-1-yl, piperidin-1-yl, piperazin-1-yl, [1,4]-oxazepan-4-yl, azetidin-1-yl, 2,3-dihydro-1H-isoindol-2-yl, or 2,3-dihydro-1H-indol-1-yl; in which each is optionally substituted with substituents selected from the group consisting of hydroxy, cyano, halogen, (halogen)$_3$C—, (halogen)$_2$CH—, halogenCH$_2$—, phenyl, pyridyl, benzyl, $C_{1-6}$alkyl, $C_{3-7}$ cycloalkyl, $C_{1-4}$alkoxy, $C_{1-4}$alkylthio, amino, $(C_{1-4}alkyl)NH—$, $di(C_{1-4}alkyl)N—$, CO$_2$H, CO$_2$C$_{1-4}$alkyl, C(=O)NHC$_{1-4}$alkyl, and C(=O)N(C$_{1-4}$alkyl)$_2$;

$R^6$ is a straight or branched-chain $C_{1-6}$alkyl, $C_{3-6}$ alkenyl, benzyl, or phenyl in which each is optionally substituted with substituents selected from the group consisting of halogen, $C_{1-4}$alkyl, $C_{1-4}$alkoxy, amino, $(C_{1-4}alkyl)NH—$, $di(C_{1-4}alkyl)N—$, $(C_{1-4}alkyl)(phenyl)N—$, morpholin-4-yl, thiomorpholin-4-yl, pyrrolidin-1-yl, piperidin-1-yl, piperazin-1-yl, and 4-($C_{1-6}$alkyl)piperazin-1-yl;

$R^7$ is hydrogen, a straight or branched-chain $C_{1-6}$ alkyl;
$R^8$ is a straight or branched-chain $C_{1-6}$alkyl, $C_{3-7}$ cycloalkyl, phenyl, pyridyl, or furanyl; in which each is optionally substituted with substituents selected from the group consisting of halogen, $C_{1-4}$alkyl, $C_{1-4}$alkoxy, $(C_{1-4}alkyl)NH—$, $di(C_{1-4}alkyl)N—$, morpholin-4-yl, thiomorpholin-4-yl, pyrrolidin-1-yl, piperidin-1-yl, piperazin-1-yl, and 4-($C_{1-6}$alkyl)piperazin-1-yl;

$R^9$ is a straight or branched-chain $C_{1-6}$alkyl, $C_{3-6}$ alkenyl, benzyl, phenyl, oxazolyl or pyridyl; in which each is optionally substituted with substituents selected from the group consisting of halogen, (halogen)$_3$C—, (halogen)$_2$CH—, halogenCH$_2$—, $C_{1-4}$alkyl, $C_{1-4}$alkoxy, amino, $(C_{1-4}alkyl)NH—$, $di(C_{1-4}alkyl)N—$, morpholin-4-yl, thiomorpholin-4-yl, pyrrolidin-1-yl, piperidin-1-yl, piperazin-1-yl, and 4-($C_{1-6}$alkyl)piperazin-1-yl;

or a non-toxic pharmaceutically acceptable salt thereof.

In another preferred embodiment, the invention includes compounds of Formula Ia or a pharmaceutically acceptable salt thereof wherein $R^3$ is phenyl optionally substituted with substituents selected from the group consisting of halogen, hydroxy, $C_{1-4}$alkoxy, $C_{1-4}$alkyl, (halogen)$_3$C—, (halogen)$_2$CH—, and halogenCH$_2$—.

In yet another preferred embodiment, the invention includes compounds of Formula Ia or a pharmaceutically acceptable salt thereof wherein $R^2$ is

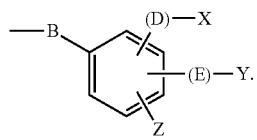

BIOLOGICAL TESTING METHODS

Compounds of Formula (I) are expected to possess γ-secretase inhibitory activity. The detection of γ-secretase activity requires assays capable of reliable, accurate and expedient detection of γ-secretase cleavage products, particularly Aβ. The γ-secretase inhibitory activity of the compounds of the present invention is demonstrated using assays for such activity, for example, using the assays described below. Compounds within the scope of the present invention have been shown to inhibit the activity of γ-secretase, as determined using assays for such activity.

Compounds provided by this invention should also be useful as standards and reagents in determining the ability of a potential pharmaceutical to inhibit Aβ production. These would be provided in commercial kits comprising a compound of this invention.

In Vitro Binding Assay to Identify γ-Secretase Inhibitors

Competitive binding assays can be used to identify molecules that inhibit the binding of a radiolabeled γ-secretase inhibitor and therefore inhibit γ-secretase activity. For example, [$^3$H]-Compound A can be used for binding assays with membranes from THP-1 cells (Seiffert, D. et al., *J. Biol. Chem.*, 275:34086-34091 (2000)). Compound A is (2R,3S) N1-[(3S)-hexahydro-1-(3-phenoxybenzyl)-2-oxo-1H-azepin-3-yl]-2-(2-methylpropyl)-3-(propyl)-butanediamide, the synthesis of which is described in U.S. Pat. No. 6,331,408 (Dec. 18, 2001); PCT Publication Nos. WO 00/28331 and WO 00/07995; and Seiffert, D. et al., *J. Biol. Chem.*, 275: 34086-34091 (2000).

Compound A

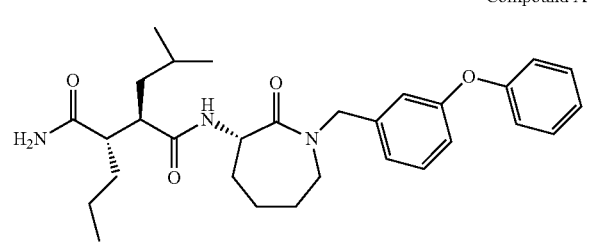

For these assays, THP-1 cells were grown in spinner cultures in RPMI 1640 containing L-glutamine and 10 μM β-mercaptoethanol to a density of 5×10$^5$ cells/ml. Cells were harvested by centrifugation and cell pellets were quick frozen in dry ice/ethanol and stored at −70° C. prior to use. The pellets of approximately 2×10$^4$ THP-1 cells were homogenized using a Brinkman Polytron at setting 6 for 10 sec. The homogenate was centrifuged at 48,000×g for 12 min, and the resulting pellet was washed by repeating the homogenization and centrifugation. The final cell pellet was resuspended in buffer to yield a protein concentration of approximately 0.5 mg/ml. Assays were initiated by the addition of 150 μl of membrane suspension to 150 μl of assay buffer containing 0.064 μCi of radioligand and various concentrations of unlabeled compounds. Binding assays were performed in duplicate in polypropylene 96-well plates in a final volume of 0.3 ml containing 50 mM Hepes, pH 7.0, and 5% dimethyl sulfoxide. Nonspecific binding was defined using incubations with 300 nM compound A (Seiffert, D. et al., *J. Biol. Chem.*, 275:34086-34091 (2000)). After incubating at 23° C. for 1.3 hr, bound ligand was separated from free radioligand by filtration over GFF glass fiber filters presoaked in 0.3% ethyleneimine polymer solution. Filters were washed three times with 0.3 ml of ice cold phosphate-buffered saline, pH 7.0, containing 0.1% Triton X-100. Filter-bound radioactivity was measured by scintillation counting. IC$_{50}$ values were then determined and used to calculate K$_i$ values using the Cheng-Prusoft correction for IC$_{50}$ values. Compounds were scored as active γ-secretase inhibitors if K$_i$ values were less than 10 μM.

Examples of the results obtained when the invention compounds are subjected to the above described assay are shown in Table 1. In the table, an inhibitory concentration (IC$_{50}$) of less than or equal to 50 nM is represented by +++; between 50 nM and 500 nM by ++; between 500 nM and 10000 nM by +.

TABLE 1

Examples of Activity in the In Vitro Binding Assay

| Example No. | Activity Rating[a] |
|---|---|
| 96 | +++ |
| 123 | +++ |
| 159 | +++ |
| 315 | ++ |
| 341 | ++ |
| 357 | ++ |
| 362 | +++ |
| 365 | +++ |
| 366 | +++ |
| 367 | + |
| 376 | ++ |
| 379 | +++ |
| 385 | +++ |
| 389 | +++ |
| 394 | +++ |
| 403 | ++ |
| 405 | +++ |
| 408 | + |
| 409 | ++ |
| 437 | +++ |
| 441 | +++ |
| 443 | ++ |
| 445 | +++ |
| 447 | +++ |
| 450 | ++ |
| 451 | + |
| 452 | ++ |
| 457 | ++ |
| 464 | + |
| 474 | +++ |
| 476 | +++ |
| 479 | ++ |
| 486 | +++ |

[a]Activity based on IC$_{50}$ values:
+++ <50 nM
++ = 50-500 nM
+ = >500 nM and <10,000 nM In Vitro Assay to Identify γ-Secretase Inhibitor Based on the Inhibition of Aβ Formation from Membrane Preparations An isolated membrane fraction which contains functionally active γ-secretase and β-APP substrates can generate γ-secretase cleavage products including Aβ (Roberts, S. B. et al., PCT Publication No. WO 01/0175435; Fechteler, K. et al., Patent Application No. DE 99-19941039; Shearman, M. et al., *Biochemistry*, 39:8698-8704 (2000); Zhang, L. et al., *Biochemistry*, 40:5049-5055 (2001)). An isolated membrane fraction can be prepared from human derived cell lines such as HeLa and H4 which have been transfected with wild type or mutant forms of β-APP or a human alkaline phosphatase β-APP fusion construct, and stably express high levels of γ-secretase substrates. The endogenous γ-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M. et al., *Proc. Natl. Acad. Sci. USA*, 93:13170-13175 (1996)), western blot (Klafki, H.-W. et al., *J. Biol. Chem.*, 271:28655-28659 (1996)), enzyme linked immunosorbent assay (ELISA) as demonstrated by Seubert, P. et al., *Nature*, 359:325-327 (1992), or by a preferred method using time-resolved fluorescence of the homogeneous sample containing membranes and Aβ (Roberts, S. B. et al., PCT Publication No. WO 01/0175435; Shearman, M. et al., *Biochemistry*, 39:8698-8704 (2000)). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the γ-secretase cleavage. The second antibody binds to any other epitope present on Aβ. For example, antibodies that bind the N-terminal region (e.g., 26D6-B2-B3, SIBIA Neurosciences, La Jolla, Calif.) or bind the C-terminal end (e.g., 9S3.2 antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of γ-secretase. The isolated membrane assay can be used to identify candidate agents that inhibit the activity of γ-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B. et al., PCT Publication No. WO 01/0175435; Shearman, M. et al., *Biochemistry*, 39:8698-8704 (2000)). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. If a compound is found to be active then a dose response experiment is performed to determine the lowest dose of compound necessary to elicit the inhibition of the production of Aβ. Compounds were scored as active γ-secretase inhibitors if $K_i$ values were less than 10 μM.

Examples of the results obtained when the invention compounds are subjected to the above described assay are shown in Table 2. In the table, an inhibitory concentration ($IC_{50}$) of less than or equal to 50 nM is represented by +++; between 50 nM and 500 nM by ++; between 500 nM and 10000 nM by +.

TABLE 2

Examples of Activity in the In Vitro Assay Based on the Inhibition of Aβ Formation from Membrane Preparations

| Example No. | Activity Rating[a] |
| --- | --- |
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | ++ |
| 19 | ++ |
| 20 | ++ |
| 21 | +++ |
| 22 | +++ |
| 23 | +++ |
| 24 | +++ |
| 25 | +++ |
| 26 | +++ |
| 27 | ++ |
| 28 | ++ |
| 29 | +++ |
| 30 | ++ |
| 31 | ++ |
| 32 | +++ |
| 33 | +++ |
| 34 | +++ |
| 35 | ++ |
| 36 | ++ |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | +++ |
| 48 | +++ |
| 49 | ++ |
| 50 | +++ |
| 51 | +++ |
| 52 | +++ |
| 59 | ++ |
| 61 | +++ |
| 83 | + |
| 85 | + |
| 87 | +++ |
| 89 | +++ |
| 95 | +++ |
| 103 | +++ |
| 113 | ++ |

TABLE 2-continued

Examples of Activity in the In Vitro Assay Based on the
Inhibition of Aβ Formation from Membrane Preparations

| Example No. | Activity Rating[a] |
|---|---|
| 122 | + |
| 133 | +++ |
| 153 | ++ |

[a]Activity based on $IC_{50}$ values:
+++ = <50 nM
++ = 50-500 nM
+ = >500 nM and <10,000 nM In Vitro Assays to Identify γ-Secretase Inhibitor Based on the Inhibition of Aβ Formation in Cultured Cells Cultured human cell lines, such as HEK293 and H4 cells, which express APP and γ-secretase activity or transfected derivative cell lines that overexpress wild-type APP, mutant APP, or APP fusion proteins will secrete Aβ peptides into the culture media that can be quantified as previously outlined (Dovey, H. et al., *J. Neurochem.*, 76:173-181 (2001)). The incubation of these cultured cells with γ-secretase inhibitors decreases the production of Aβ peptides. For instance, H4 cells stably transfected to overexpress the HPLAP-APP fusion protein described above were grown as above, detached, and adjusted to 2×10⁵ cells/ml. 100 μl of the resulting suspension was then added to each well of a 96-well plate. After 4 hrs, the media was removed and replaced with 100 μl serum-free media containing various dilutions of the test compound. Plates were then incubated for 18 hrs at 37° C. and a 100 μl aliquot of the tissue culture supernatant was removed for determination of Aβ levels using time-resolved fluorescence of the homogenous sample as outlined above. Alternately, the other methods described above for Aβ determination could be used. The extent of Aβ inhibition was used to calculate the $IC_{50}$ value for the test compound. Compounds of the present invention are considered active when tested in the above assay if the $IC_{50}$ value for the test compound is less than 50 μM.

Examples of the results obtained when the invention compounds are subjected to the above described assay are shown in Table 3. In the table, an inhibitory concentration ($IC_{50}$) of less than or equal to 50 nM is represented by +++; between 50 nM and 500 nM by ++; between 500 nM and 50000 nM by +.

TABLE 3

Examples of Activity in the In Vitro Assay Based on the Inhibition of Aβ Formation in Cultured Cells

| Example No. | Activity Rating[a] |
|---|---|
| 1 | +++ |
| 5 | +++ |
| 19 | ++ |
| 26 | +++ |
| 38 | +++ |
| 41 | +++ |
| 51 | +++ |
| 55 | +++ |
| 61 | +++ |
| 72 | +++ |
| 80 | +++ |
| 89 | +++ |
| 96 | +++ |
| 101 | +++ |
| 123 | +++ |
| 127 | ++ |
| 143 | +++ |
| 147 | ++ |
| 158 | +++ |
| 171 | ++ |
| 193 | +++ |
| 203 | +++ |
| 205 | ++ |
| 207 | +++ |
| 245 | +++ |
| 246 | +++ |
| 249 | ++ |
| 254 | +++ |
| 256 | +++ |
| 260 | +++ |
| 272 | +++ |
| 280 | ++ |
| 282 | +++ |
| 288 | ++ |
| 301 | ++ |
| 302 | +++ |
| 321 | ++ |
| 322 | +++ |
| 329 | +++ |
| 330 | ++ |
| 331 | + |
| 340 | +++ |
| 341 | ++ |
| 342 | +++ |
| 349 | +++ |
| 352 | ++ |
| 358 | ++ |
| 359 | +++ |
| 366 | +++ |
| 367 | + |
| 378 | +++ |
| 383 | +++ |
| 394 | +++ |
| 403 | ++ |
| 416 | +++ |
| 418 | +++ |
| 424 | +++ |
| 433 | +++ |
| 434 | +++ |
| 439 | +++ |
| 442 | +++ |
| 472 | +++ |
| 481 | + |
| 492 | ++ |
| 495 | +++ |
| 497 | +++ |

[a]Activity based on $IC_{50}$ values:
+++ = <50 nM
++ = 50-500 nM
+ = >500 nM and <10,000 nM Compounds of the present invention have been demonstrated to have an $IC_{50}$ value less than 10 μM in one or all of the above assays. Therefore, the compounds of Formula I or pharmaceutical compositions thereof are useful in the treatment, alleviation or elimination of disorders or other disorders associated with the inhibition of β-amyloid peptide.

In addition to cleaving APP, γ-secretase cleaves other substrates, including: the Notch family of transmembrane receptors (reviewed in: Selkoe, D., *Physiol. Rev.*, 81:741-766 (2001); Wolfe, M., *J. Med. Chem.*, 44:2039-2060 (2001)); LDL receptor-related protein (May, P. et al., *J. Biol. Chem.*, 277:18736-18743 (2002)); ErbB-4 (Ni, C. Y. et al., *Science*, 294:2179-2181 (2001)); E-cadherin (Marambaud, P. et al., *EMBO J.*, 21:1948-1956 (2002)); and CD44 (Okamoto, I. et al., *J. Cell Biol.*, 155:755-762 (2001)). If inhibition of cleavage of non-APP substrates causes undesirable effects in humans, then desired γ-secretase inhibitors would preferentially inhibit APP cleavage relative to unwanted substrates.

Notch cleavage can be monitored directly by measuring the amount of cleavage product or indirectly by measuring the effect of the cleavage product on transcription (Mizutani, T. et al., *Proc. Natl. Acad. Sci. USA,* 98:9026-9031 (2001)).

In Vivo Assays for the Determination of Aβ Reduction by γ-Secretase Inhibitors

In vivo assays are available to demonstrate the inhibition of γ-secretase activity. In these assays, animals, such as mice, that express normal levels of APP and γ-secretase or are engineered to express higher levels of APP and hence Aβ can be used to demonstrate the utility of γ-secretase inhibitors (Dovey, H. et al., *J. Neurochem.,* 76:173-181 (2001)). In these assays, γ-secretase inhibitors were administered to animals and Aβ levels in multiple compartments, such as plasma, cerebral spinal fluid, and brain extracts, were monitored for Aβ levels using methods previously outlined. For instance, Tg2576 mice, which overexpress human APP, was administered γ-secretase inhibitors by oral gavage at doses that will cause measurable Aβ lowering, typically less than 100 mg/kg. Three hours after dosing plasma, brain, and CSF were collected, frozen in liquid nitrogen, and stored at −80° C. until analysis. For Aβ detection, plasma was diluted 15-fold in PBS with 0.1% Chaps while CSF was diluted 15-fold in 1% Chaps with protease inhibitors (5 µg/ml leupeptin, 30 µg/ml aprotinin, 1 mM phenylmethylsulfonylfluoride, 1 µM pepstatin). Brains were homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate were measured using time-resolved fluorescence of the homogenous sample or one of the other methods previously described.

A γ-secretase inhibitor is considered active in one of the above in vivo assays if it reduces Aβ by at least 50% at a dosage of 100 mg/kg.

Therefore, the compounds of Formula I or pharmaceutical compositions thereof are useful in the treatment, alleviation or elimination of disorders or other disorders associated with the inhibition of β-amyloid peptide.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to the inhibition of β-amyloid peptide in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating Alzheimer's Disease and Down's Syndrome in a mammal in need thereof, which comprises administering to said mammal a therapeutically effective amount of a compound of Formula I or a non-toxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences,* 17th Edition, Mack Publishing Company, Easton, Pa. (1985).

The dosage of the compounds of Formula I to achieve a therapeutic effect will depend not only on such factors as the age, weight and sex of the patient and mode of administration, but also on the degree of β-AP inhibition desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to β-AP production as described herein, generally the daily dose will be from about 0.05 mg/kg to about 10 mg/kg and preferably, about 0.1 to 2 mg/kg when administered parenterally. For oral administration, the dose may be in the range from about 1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF THE SPECIFIC EMBODIMENTS

In the following examples, all temperatures are given in degrees Centigrade. Melting points were recorded on a Thomas Scientific Uni-melt capillary melting point apparatus and are uncorrected. Proton magnetic resonance ($^1$H NMR) spectra were recorded on a Bruker Avance 300, a Bruker Avance 400, or a Bruker Avance 500 spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; br d, broad doublet; dt, doublet of triplet; br s, broad singlet; dq, doublet of quartet. Infrared (IR) spectra using potassium bromide (KBr) or sodium chloride film were determined on a Jasco FT/IR-410 or a Perkin Elmer 2000 FT-IR spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations [α]$_D$ were determined on a Rudolph Scientific AUTOPOL® IV polarimeter in the solvents indicated; concentrations are given in mg/mL. Low resolution mass spectra (MS) and the apparent molecular (MH$^+$) or (M–H)$^+$ was determined on a Finnegan SSQ7000. High resolution mass spectra were determined on a Finnegan MAT900. Liquid chromatography (LC)/mass spectra were run on a Shimadzu LC coupled to a Water MICROMASS® ZQ.

The following abbreviations are used: DMF (dimethylformamide); THF (tetrahydrofuran); DMSO (dimethylsulfoxide), Leu (leucine); TFA (trifluoroacetic acid); DAST [(diethylamino)sulfur trifluoride], HPLC (high pressure liquid chromatography); rt (room temperature); aq. (aqueous).

Exemplification of Reaction Scheme 1

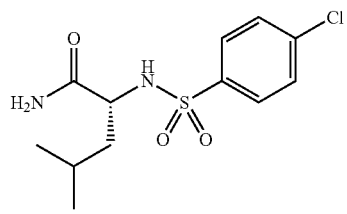 [SMILES: CC(C)C[C@@H](NS(=O)(=O)c1ccc(Cl)cc1)C(N)=O]

(2R)-2-(4-Chlorobenzenesulfonylamino)-4-methylpentanoic acid amide

To a solution of (D)-leucinamide hydrochloride (0.25 g, 1.5 mmol), and Et$_3$N (0.43 mL, 3.0 mmol) in CH$_2$Cl$_2$ (150 mL) was added 4-chlorobenzene-sulfonyl chloride (380 mg, 1.8 mmol). The resulting solution was stirred at rt for 18 h. The reaction was then diluted with CH$_2$Cl$_2$ (200 mL) and washed with H$_2$O, 0.5 N HCl, brine, and dried over MgSO$_4$, to afford the titled compound (410 mg) as a white solid in 90% yield. MS (ESI), (M+H)$^+$305.2; $^1$H NMR (DMSO-d$_6$) δ 7.77 (d, 2H, J=8.7), 7.62 (d, 2H, J=8.7), 6.90 (br s, 1H), 3.67 (m, 1H), 1.54 (m, 1H), 1.31 (m, 2H), 0.81 (d, 3H, J=7.0), 0.71 (d, 3H, J=7.0).

Method A for Conversion of III to I

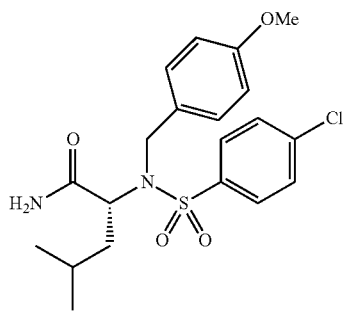 [SMILES: COc1ccc(CN([C@H](CC(C)C)C(N)=O)S(=O)(=O)c2ccc(Cl)cc2)cc1]

(2R)-2-[N-(4-Chlorobenzenesulfonyl)-N-(4-methoxybenzyl)amino]-4-methylpentanoic acid amide (Example 1)

(2R)-2-(4-Chlorobenzenesulfonylamino)-4-methylpentanoic acid amide (300 mg, 1 mmol), K$_2$CO$_3$ (170 mg, 1.2 mmol), and 4-methoxybenzyl chloride (170 mg, 1.1 mmol) in DMF (25 mL) was heated to 60° C. for 18 h. The reaction was then diluted with EtOAc (150 mL) and washed with H$_2$O, brine, dried over MgSO$_4$ and concentrated to give a crude white wax. Further purification by flash chromatography (SiO$_2$, 25% EtOAc/hexanes) afforded the titled compound (297 mg) as a white solid in 70% yield. [α]$_D$=+44.2 (c 1.00, MeOH); MS (ESI), (M–H)$^-$422.9; $^1$H NMR (CDCl$_3$) δ 7.63 (d, 2H, J=7.0), 7.42 (d, 2H, J=7.0), 7.25 (d, 2H, J=8.0), 6.79 (d, 2H, J=8.0), 6.25 (br s, 1H), 5.35 (br s, 1H), 4.36 (dd, 2H, J=50, 15), 4.26 (t, 1H, J=7.2), 3.78 (s, 3H), 1.83 (m, 1H), 1.18-1.34 (m, 2H), 0.75 (d, 3H, J=7.0), 0.67 (d, 3H, J=7.0); IR (KBr) 3480, 2959, 1693, 1674, 1514, 1333, 1158 cm$^{-1}$.

Method B for Conversion of III to I

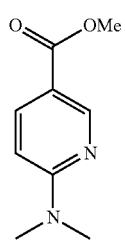

Methyl 6-dimethylaminonicotinate

A solution of methyl 6-chloronicotinate (4.0 g, 23 mmol) in dimethylamine/MeOH (2 M, 80 mL, 160 mmol) in a pressure vessel was stirred at 95° C. for 2 h, cooled to rt and concentrated. The residue was dissolved in EtOAc (250 mL), washed with water (2×150 mL), dried over Na$_2$SO$_4$, and concentrated to afford the title compound as a tan solid (4.1 g, 98%). MS (ESI), (M+H)$^+$181.24; $^1$H NMR (CDCl$_3$) δ 8.79 (s, 1H), 7.99 (d, 1H, J=9.2), 6.45 (d, 1H, J=9.2), 3.85 (s, 3H), 3.15 (s, 6H).

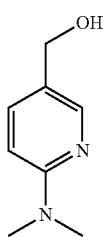

2-Dimethylamino-5-hydroxymethylpyridine

A solution of methyl 6-dimethylamino-nicotinate (4.14 g, 23.0 mmol) in anhydrous ether (80 mL) at 0° C. was treated with lithium aluminum hydride (1 M in ether, 20 mL, 20 mmol). The mixture was stirred at rt for 0.5 h, cooled again to 0° C. and quenched slowly with sat. aq. NaHCO$_3$ (10 mL). The resulting mixture was stirred at rt for 0.5 h, filtered, and washed with ether. The combined filtrates were dried over Na$_2$SO$_4$ and concentrated to give the title compound as a beige waxy solid (3.5 g, 100%). MS (ESI), (M+H)$^+$153.4; $^1$H NMR (CDCl$_3$) δ 8.06 (d, 1H, J=2.4), 7.47 (dd, 1H, J=2.4, 8.8), 6.45 (d, 1H, J=8.8), 4.50 (s, 2H), 3.06 (s, 6H), 1.98 (br s, 1H).

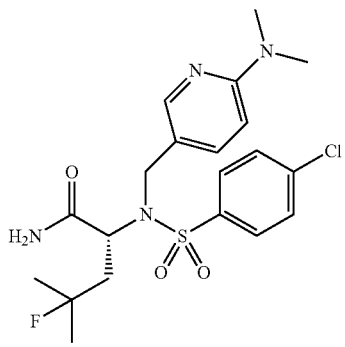 [SMILES: CN(C)c1ccc(CN([C@H](CC(C)(C)F)C(N)=O)S(=O)(=O)c2ccc(Cl)cc2)cn1]

(2R)-2-[N-(4-Chlorobenzenesulfonyl)-N-(2-dimethylaminopyridin-5-yl)amino]-4-fluoro-4-methylpentanoic acid amide TFA salt (Example 459)

To a cloudy solution of (2R)-2-[(4-chlorobenzenesulfonylamino)-4-fluoro-4-methylpentanoic acid amide (prepared as in Reaction Scheme 20 or from γ-fluoro-D-Leu-OH methyl ester, Papageorgiou et al., *Bioorg. & Med. Chem. Lett.*, 4:267-272 (1994); 0.060 g, 0.18 mmol), 2-dimethylamino-5-hydroxymethylpyridine (71 mg, 0.46 mmol), triphenylphosphine (122 mg, 0.464 mmol) in CH$_2$Cl$_2$ (9.5 mL) at rt was added dropwise diisopropyl azodicarboxylate (75 mL, 0.46 mmol). The resulting pale yellow solution was stirred at rt for 2 h and concentrated under vacuum. The residue was dissolved in methanol an purified by reverse phase preparative HPLC (YMC S5, ODS, MeOH-water-TFA) to afford the title compound as a white foam (90 mg, 85%). MS (ESI), (M+H)$^+$ 457.2; $^1$H NMR (CDCl$_3$) δ 8.11 (s, 1H), 7.95 (d, 1H, J=9.6), 7.77 (d, 2H, J=6.8), 7.51 (d, 2H, J=6.8), 6.76 (d, 2H, J=9.6), 6.34 (s, 1H), 6.02 (s, 1H), 4.58 (br d, 1H, J=8.4), 4.46 (d, 1H, J=16.0), 4.06 (d, 1H, J=16), 3.29 (s, 6H), 2.50 (m, 1H), 1.39 (m, 1H), 1.25 (d, 3H, J=22.0), 1.17 (d, 3H, J=22.0).

Exemplification of Reaction Scheme 1

Solid Support

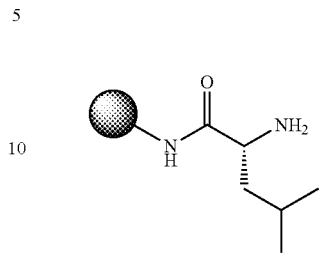

Polymer-bound D-Leu-NH$_2$

FMOC-protected Rink amide resin (30 g, 0.61 mmol/g, 18 mmol) was treated with piperidine/DMF solution (250 mL). The mixture was shaken at rt for 24 h, drained, washed with DMF (5×200 mL), CH$_2$Cl$_2$ (5×200 mL) and dried under vacuum. The resin was then treated with FMOC-D-Leu-OH (22 g, 62 mmol), 1-hydroxybenzotriazole hydrate (2.5 g, 18 mmol), 1,3-diisopropylcarbodiimide (9.8 mL, 62 mmol), and DMF (250 mL). The mixture was shaken for 20 h, drained, washed with DMF (4×200 mL), DMF-water (1:1, 3×200 mL), DMF (3×200 mL), MeOH (3×200 mL), CH$_2$Cl$_2$ (3×200 mL) and dried. The completion of reaction and the loading of the resin-bound FMOC-D-Leu-NH$_2$ (0.56 mmol/g) were determined by the treatment of 52 mg of the resin with 10% (v/v) TFA/CH$_2$Cl$_2$ (2 mL) to give 11 mg of FMOC-D-Leu-NH$_2$. The resin-bound FMOC-D-Leu-NH$_2$ was deprotected with 20% (v/v) piperidine/DMF solution (250 mL) to give polymer-bound D-Leu-NH$_2$ (20 g).

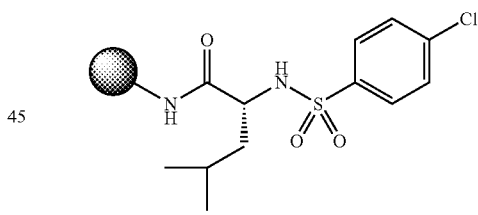

Polymer-bound (R)-2-(4-chlorobenzenesulfonylamino)-4-methylpentanoic acid amide

The above polymer-bound D-Leu-NH$_2$ (20 g) was treated with CH$_2$Cl$_2$ (150 mL), pyridine (100 mL) and 4-chlorophenylsulfonyl chloride (20.0 g, 94.8 mmol). The mixture was shaken for 24 h, drained, washed with DMF (4×200 mL), CH$_2$Cl$_2$ (4×200 mL) and concentrated to give polymer-bound (R)-2-(4-chlorobenzenesulfonylamino)-4-methylpentanoic acid amide as a yellow resin (22 g). The completion of the reaction and the loading of the resin (0.57 mmol/g) were determined by the treatment of 50 mg of the resin with 10% (v/v) TFA/CH$_2$Cl$_2$ (2 mL) to give 8.7 mg of (R)-2-(4-chlorobenzenesulfonylamino)-4-methylpentanoic acid amide.

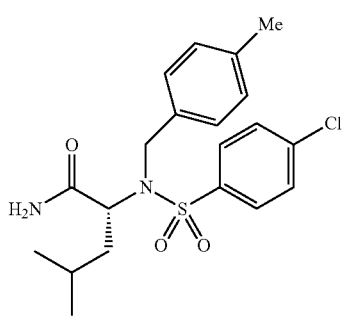 [SMILES: Cc1ccc(CN([C@H](CC(C)C)C(N)=O)S(=O)(=O)c2ccc(Cl)cc2)cc1]

(2R)-2-[N-(4-Chlorobenzenesulfonyl)-N-(4-methyl-benzyl)amino]-4-methylpentanoic acid amide (Example 60)

To a mixture of polymer-bound (2R)-2-[N-(4-chlorobenzenesulfonyl)amino]-4-methylpentanoic acid amide (loading 0.45 mmol/g, 50.0 mg, 0.0225 mmol), 4-methylbenzyl bromide (44 mg, 0.24 mmol) and DMF (1.5 mL) was added 2-tert-butylimino-2-diethylamino-1,3-dimethylperhydro-1,3,2-diaza-phosphorine (0.10 mL, 0.34 mmol). The resulting mixture was shaken at rt for 2 days, then was drained and washed with DMF (4×2 mL), MeOH (4×2 mL) and $CH_2Cl_2$ (4×2 mL).

The resin was then treated with 10% (v/v) $TFA/CH_2Cl_2$. The mixture was shaken for 1 h, filtered and washed with $CH_2Cl_2$ (2×0.5 mL). The combined filtrates were concentrated under vacuum to afford the title compound as a beige solid (7.7 mg, 100%, HPLC purity >95%). HRMS (ESI), $(M-H)^-$ for $C_{20}H_{24}SClN_2O_3$ calcd: 407.1206, found: 407.1201; $^1$H NMR ($CDCl_3$) δ 7.64 (d, 2H, J=8.0), 7.44 (d, 2H, J=8.0), 7.22 (d, 2H, J=8.0), 7.08 (d, 2H, J=8.0), 6.29 (br s, 1H), 5.34 (br s, 1H), 4.53 (d, 1H, J=15.2), 4.34 (d, 1H, J=15.2), 4.27 (t, 1H, J=7.2), 2.32 (s, 3H), 1.84 (m, 1H), 1.30 (m, 1H), 1.21 (m, 1H), 0.75 (d, 3H, J=6.8), 0.67 (d, 3H, J=6.8); IR (KBr) 3467, 3367, 2956, 2869, 1694, 1670, 1340, 1160 cm$^{-1}$.

Exemplification of Reaction Scheme 2

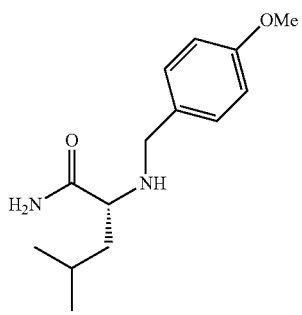 [SMILES: COc1ccc(CN[C@H](CC(C)C)C(N)=O)cc1]

(2R)-2-(4-Methoxybenzylamino)-4-methylpentanoic acid amide

A solution of D-leucinamide hydrochloride (2.8 g, 16.8 mmol), and p-anisaldehyde (2.29 g, 16.8 mmol) in methanol (150 mL) was treated with anhydrous $ZnCl_2$ (538 mg, 5 mmol). The resulting suspension was then treated with NaCNBH$_3$ (1.05 g, 16.8 mmol) portion wise and heated at reflux for 3 h. The reaction was cooled to rt, quenched with saturated $NaHCO_3$ (3 mL), diluted with EtOAc (500 mL), and washed with brine. Concentration afforded the crude benzyl amine as a white wax, which was carried on without further purification (3.57 g, 84%). MS (ESI), $(M+H)^+$251.4; $^1$H NMR ($CDCl_3$) δ 7.20 (d, 2H, J=6.6), 7.10 (br s, 2H), 6.88 (d, 2H, J=8.4), 5.30 (br s, 1H), 3.80 (s, 3H), 3.63 (dd, 2H, J=4.5, 12), 1.44-1.65 (m, 3H), 0.95 (d, 3H, J=6.3), 0.80 (d, 3H, J=6.3).

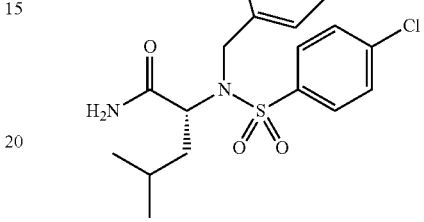

(2R)-2-[N-(4-Chlorobenzenesulfonyl)-N-(4-methoxybenzyl)amino]-4-methylpentanoic acid amide (Example 1)

(2R)-2-[N-(4-Methoxybenzyl)amino]-4-methylpentanoic acid amide (3.57 g, 14.3 mmol) was dissolved in $CH_2Cl_2$ (100 mL) and treated with $Et_3N$ (4.2 mL, 29 mmol) and 4-chlorobenzenesulfonyl chloride (3.6 g, 17 mmol) at rt for 18 h. The solvents were removed and the residue was taken into EtOAc (500 mL). The organic solution was washed with $H_2O$, brine, dried over $MgSO_4$, and concentrated. The resulting material was then further purified by flash chromatography ($SiO_2$, 1% $MeOH/CH_2Cl_2$) to afford the title compound (2.4 g) as a slightly colored solid in 40% yield. MS (ESI), $(M-H)^-$422.9; $^1$H NMR ($CDCl_3$) δ 7.63 (d, 2H, J=7.0), 7.42 (d, 2H, J=7.0), 7.25 (d, 2H, J=8.0), 6.79 (d, 2H, J=8.0), 6.25 (br s, 1H), 5.35 (br s, 1H), 4.36 (dd, 2H, J=5.0, 15), 4.26 (t, 1H, J=7.2), 3.78 (s, 3H), 1.83 (m, 1H), 1.18-1.34 (m, 2H), 0.75 (d, 3H, J=7.0), 0.67 (d, 3H, J=7.0); IR (KBr) 3480, 2959, 1693, 1674, 1514, 1333, 1158 cm$^{-1}$.

Exemplification of Reaction Scheme 3

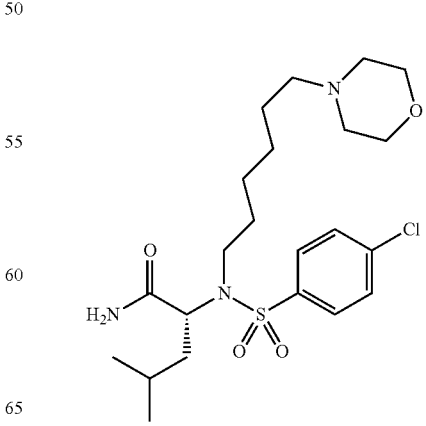

(2R)-2-[N-(4-Morpholinohexyl)-N-(4-chlorobenzenesulfonyl)amino]-4-methylpentanoic acid amide (Example 25)

A solution of (2R)-2-[N-(4-bromohexyl)-N-(4-chlorobenzenesulfonyl)amino]-4-methylpentanoic acid amide (Example 24; prepared as described in Reaction Scheme 1; 0.20 g, 0.44 mmol), Et$_3$N (0.25 mL, 1.7 mmol), and morpholine (150 mg, 1.7 mmol) in CH$_2$Cl$_2$ (2 mL) was stirred at rt for 18 h. The reaction was then concentrated to give a crude white wax which was purified by flash chromatography (SiO$_2$, 85% EtOAc/5% hexanes/10% MeOH) to afford the title compound (112 mg) as a white solid in 54% yield. MS (ESI), (M+H)$^+$474.4; $^1$H NMR (DMSO-d$_6$) δ 7.82 (d, 2H, J=8.0), 7.64 (d, 2H, J=8.0), 7.42 (br s, 1H) 6.99 (s, 1H), 4.25 (m, 1H), 3.51-3.60 (br s, 4H), 3.18-3.41 (m, 2H), 2.25-2.35 (br s, 4H), 2.27 (m, 2H) 1.15-1.62 (m, 9H), 0.80 (d, 6H, J=6.0).

Exemplification of Reaction Scheme 4

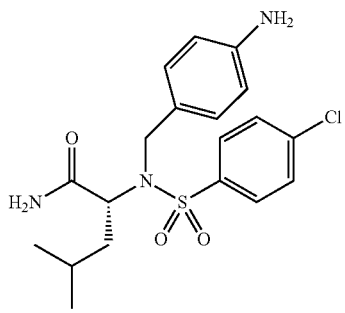 [SMILES: CC(C)C[C@H](C(N)=O)N(Cc1ccc(N)cc1)S(=O)(=O)c1ccc(Cl)cc1]

(2R)-2-[N-(4-Chlorobenzenesulfonyl)-N-(4-aminobenzyl)amino]-4-methylpentanoic acid amide (Example 48)

(2R)-(2-[N-(4-Chlorobenzenesulfonyl)-N-(4-nitrobenzyl)amino]-4-methylpentanoic acid amide (Compound of Example 24; prepared as described in Reaction Scheme 1; 2.8 g, 6.6 mmol) was suspended with 10% Pd/C (1 g) and conc. HCl (1 mL) in MeOH (100 mL) and placed under a hydrogen atmosphere at 40 psi for 1 h. The suspension was filtered through CELITE® and then concentrated to give the title compound as a tan solid (2.4 g, 88% yield). MS (ESI), (M+H)$^+$410.1; $^1$H NMR (CDCl$_3$) δ 7.80 (d, 2H, J=8.5), 7.63 (d, 2H, J=8.5), 7.52 (br s, 1H), 7.46 (d, 1H, J=8.0), 7.26 (d, 1H, J=8.0), 7.02 (br s, 1H), 4.70 (dd, 2H, J=50, 18), 4.30-4.41 (m, 1H), 3.67 (br s, 2H), 1.28-1.33 (m, 3H), 0.86 (d, 3H, J=7.0), 0.57 (d, 3H, J=7.0).

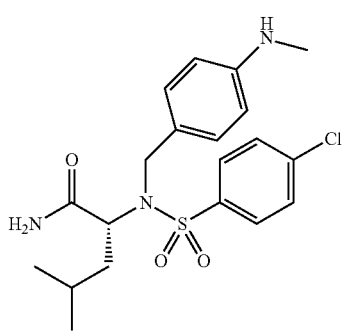 [SMILES: CNc1ccc(CN([C@H](CC(C)C)C(N)=O)S(=O)(=O)c2ccc(Cl)cc2)cc1]

(2R)-2-[N-(4-Chlorobenzenesulfonyl)-N-(4-methylaminobenzyl)amino]-4-methylpentanoic acid amide (Example 51)

A solution of (2R)-2-[N-(4-chlorobenzenesulfonyl)-N-(4-aminobenzyl)amino]-4-methyl-pentanoic acid amide (Example 48, 400 mg, 1 mmol), Et$_3$N (0.16 mL, 1.1 mmol), dimethylsulfate (139 mg, 1.1 mmol) in 25 mL of toluene was stirred at rt for 18 h. The reaction was concentrated, then taken into EtOAc and washed with H$_2$O, brine, dried over K$_2$CO$_3$ and concentrated to give a crude mixture of starting material and product. The material was further purified by flash chromatography (SiO$_2$, 35% EtOAc/hexanes) to afford the title compound, 195 mg, in 46% yield. MS (ESI), (M+H)$^+$424.1; $^1$H NMR (CDCl$_3$) δ 7.65 (d, 2H, J=8.0), 7.58 (d, 2H, J=8.2), 7.47 (d, 2H, J=8.0), 7.31 (d, 2H, J=8.5), 6.24 (br s, 1H), 5.16 (br s, 1H), 4.50 (dd, 2H, J=50, 17), 4.27 (t, 1H, J=10), 2.44 (s, 3H), 1.74-1.83 (m, 1H), 1.25-1.33 (m, 1H), 0.93-1.01 (m, 1H), 0.74 (d, 3H, J=7.0), 0.63 (d, 3H, J=7.0).

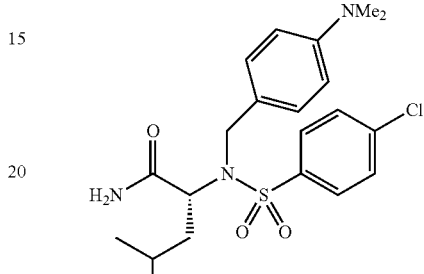

(2R)-2-[N-(4-Chlorobenzenesulfonyl)-N-(4-dimethylaminobenzyl)amino]-4-methylpentanoic acid amide (Example 65)

(2R)-2-[N-(4-Chlorobenzene-sulfonyl)-N-(4-aminobenzyl)amino]-4-methyl-pentanoic acid amide (Example 48, 0.10 g, 0.22 mmol) was dissolved in DMF (5 mL). To this solution was added iodomethane (62 mg, 0.44 mmol), and cesium carbonate (220 mg, 0.66 mmol). The reaction was then stirred at 40° C. for 18 h. The reaction was poured into EtOAc and water. The organic was collected, dried over MgSO$_4$, and concentrated to an oily residue. The residue was further purified (BIOTAGE® 40S, loaded in CH$_2$Cl$_2$, eluted in 25% EtOAc/hexanes) to yield a yellow powder (15 mg, 16%). MS (ESI), (M+H)$^+$438.1; $^1$H NMR (DMSO-d$_6$, 500 MHz) δ 7.74 (dd, 2H, J=1.9, 6.7), 7.54 (dd, 2H, J=1.9, 6.8), 7.43 (s, 1H), 7.16 (d, 2H, J=8.6), 7.01 (s, 1H), 6.61 (d, 2H, J=8.8), 4.59 (q, 2H, J=16, 25), 4.34 (dd, 1H, J=5.0, 9.3), 2.85 (s, 6H), 1.27-1.47 (m, 3H), 0.80 (d, 3H, J=5.9), 0.52 (d, 3H, J=6.1).

Exemplification of Reaction Scheme 5

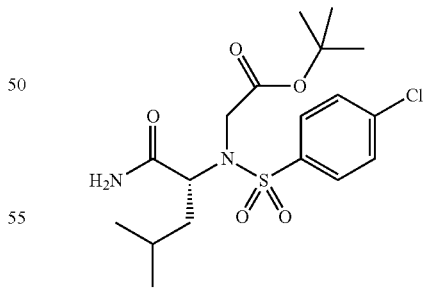

{N-[(1R)-1-Carbamoyl-3-methyl-butyl]-N-(4-chlorobenzenesulfonyl)amino}acetic acid tert-butyl ester (Example 46)

(2R)-2-(4-Chlorobenzenesulfonylamino)-4-methylpentanoic acid amide (3.00 g, 9.87 mmol) was dissolved in DMF (50 mL). To the solution was added potassium carbonate (6.0 g, 39 mmol) and bromoacetic acid tert-butyl ester (6.0 mL, 39 mmol). The solution was heated to 70° C. for 3 h. The reaction was quenched with EtOAc and saturated NaHCO₃. The organic layer was washed with brine, dried over MgSO₄, and concentrated. The crude oil was further purified on a BIOTAGE® 40M (loaded in CH₂Cl₂, eluted in 30% EtOAc/hexanes) to afford a white powder (1.2 g, 35%). MS (ESI), (M+H)⁺446.3; ¹H NMR (CDCl₃) δ 7.76 (d, 2H, J=8.0), 7.52 (d, 2H, J=8.0), 6.61 (br s, 1H) 5.45 (s, 1H), 4.15-4.18 (m, 1H), 3.09-3.24 (m, 2H), 2.50-2.58 (m, 4H), 2.31-2.39 (m, 2H), 1.92-1.99 (m, 1H), 1.15-1.59 (m, 8H), 1.00-1.04 (m, 7H), 0.71-0.74 (m, 6H).

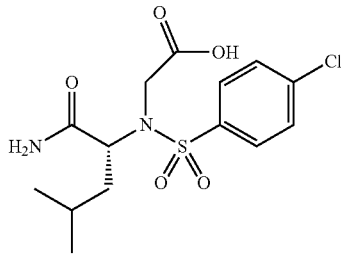 [SMILES: CC(C)C[C@H](C(N)=O)N(CC(=O)O)S(=O)(=O)c1ccc(Cl)cc1]

{N-[(1R)-1-Carbamoyl-3-methyl-butyl]-N-(4-chlorobenzenesulfonyl)amino}acetic acid (Example 59)

Trifluoroacetic acid (15 mL) was added to a solution of {N-[(1R)-1-carbamoyl-3-methyl-butyl]-N-(4-chlorobenzenesulfonyl)amino}acetic acid tert-butyl ester (0.50 g, 1.2 mmol) in CH₂Cl₂ (15 mL). The reaction was stirred at rt for 4 h. The reaction was then concentrated to a white solid (0.40 g, 92%), which was used without further purification. MS (ESI), (M+H)⁺363.1; ¹H NMR (DMSO-d₆, 500 MHz) δ 7.90 (dd, 2H, J=2.0, 6.8), 7.65 (dd, 2H, J=2.0, 6.8), 7.60 (s, 1H), 7.06 (s, 1H), 4.32 (d, 1H, J=18), 4.12 (t, 1H, J=8.0), 4.02 (d, 1H, J=18), 1.55-1.65 (m, 1H), 1.35-1.45 (m, 2H), 0.78 (d, 3H, J=6.1), 0.73 (d, 3H, J=6.1).

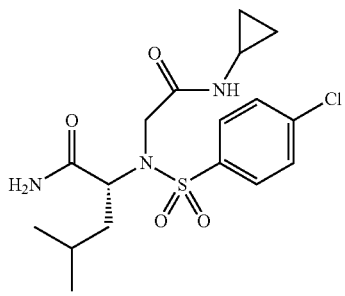 [SMILES: CC(C)C[C@H](C(N)=O)N(CC(=O)NC1CC1)S(=O)(=O)c1ccc(Cl)cc1]

(2R)-2-[N-(4-Chlorobenzenesulfonyl)-N-(cyclopropylcarbamoylmethyl)amino]-4-methyl-pentanoic acid amide (Example 88)

To a solution of {N-[(1R)-1-carbamoyl-3-methyl-butyl]-N-(4-chlorobenzenesulfonyl)amino}acetic acid (Example 59, 175 mg, 0.480 mmol), cyclopropylamine (41 mL, 0.58 mmol) in CH₂Cl₂ (3 mL) was added 1-hydroxybenzotriazole (47 mg, 0.72 mmol), and 1,3-dicyclohexylcarbodiimide (144 mg, 0.720 mmol). The reaction was stirred for 18 h at rt, and then was poured into an EtOAc/water mixture. The organic layer was separated, dried over MgSO₄, and concentrated to a clear oil residue. The residue was further purified by BIOTAGE® 40S (eluted in 40% EtOAc in hexanes) to afford a white solid (54 mg, 29%). MS (ESI), (M+H)⁺402.2; ¹H NMR (CDCl₃, 500 MHz) δ 7.85 (dd, 2H, J=1.9, 8.9), 7.50 (dd, 2H, J=2.0, 8.7), 7.40 (br s, 1H), 6.55 (br s, 1H), 6.30 (br s, 1H), 4.23 (dd, 1H, J=2.9, 8.9), 3.92 (d, 1H, J=17), 3.83 (d, 1H, J=17), 2.68-2.73 (m, 1H), 1.75-1.83 (m, 1H), 1.50-1.57 (m, 1H), 1.40-1.49 (m, 1H), 0.88 (d, 3H, J=6.4), 0.87 (d, 3H, J=6.7), 0.80 (d, 2H, J=7.0), 0.51 (t, 2H, J=4.0).

Exemplification of Reaction Scheme 6

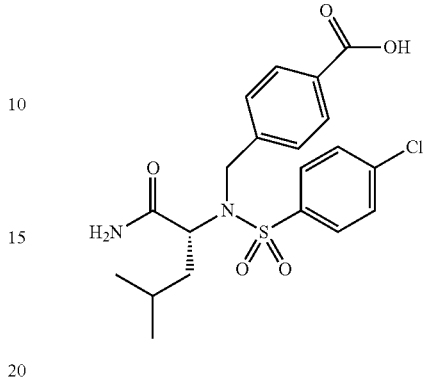

4-{[N-((1R)-1-Carbamoyl-3-methyl-butyl)-N-(4-chlorobenzenesulfonyl)amino]-methyl}-benzoic acid (Example 89)

A solution of the compound of Example 61 [4-{[N-((1R)-1-carbamoyl-3-methyl-butyl)-N-(4-chlorobenzenesulfonyl)amino]-methyl}-benzoic acid methyl ester, 354 mg, 0.782 mmol] was dissolved in methanol (4 mL). A solution of 5 N NaOH (1 mL) was added, followed by enough THF (1 mL) to achieve homogeneity. After 1 h, an additional aliquot of 5 N NaOH (1 mL) was added, and stirring was continued for 2.5 h. The solution was acidified to pH 2 with 1 N HCl and extracted with CHCl₃ (2×). The combined organic layers were dried (Na₂SO₄) and concentrated to give a white solid (343 mg, 100%). MS (ESI), (M+H)⁺439.17; ¹H NMR (CDCl₃, 300 MHz) δ 7.91 (d, 2H, J=8.2), 7.81-7.84 (m, 3H), 7.56 (d, 2H, J=8.6), 7.49 (d, 2H, J=8.2), 6.55 (br s, 1H), 5.10 (d, 1H, J=15.4), 4.23 (dd, 1H, J=4.6, 9.7), 4.05 (d, 1H, J=15.4), 2.04-2.14 (m, 1H), 1.20-1.31 (m, 1H), 0.80-0.89 (m, 1H), 0.74 (d, 3H, J=6.6), 0.68 (d, 3H, J=6.6).

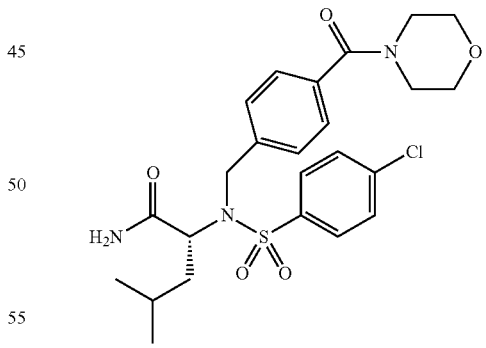

(2R)-2-{N-(4-Chlorobenzenesulfonyl)-N-[4-(morpholine-4-carbonyl)-benzyl]amino}-4-methyl-pentanoic acid amide (Example 101)

To a 0° C. solution of 4-{[N-((1R)-1-carbamoyl-3-methyl-butyl)-N-(4-chlorobenzenesulfonyl)amino}-methyl]benzoic acid (50.0 mg, 0.114 mmol) in DMF (0.3 mL) was added morpholine (12.9 mg, 0.148 mmol), followed by 1-hydroxybenzotriazole (18.5 mg, 0.137 mmol), 1-(3-dimethylaminopropyl)-3-ethylcarbodiimide hydrochloride (26.2 mg, 0.137 mmol), and iPr$_2$NEt (26 μL, 0.15 mmol). After 2 h, the solution was warmed to rt. After 4 h, the solution was poured into 10% aq. citric acid and extracted with EtOAc (2×). The combined organic layers were washed sequentially with water and sat. aq. NaHCO$_3$, then dried (MgSO$_4$) and concentrated. Flash column chromatography (SiO$_2$, 40 to 100% EtOAc/hexanes) gave the title compound as a white solid (46.0 mg, 79%). MS (ESI), (M+H)$^+$508.22; $^1$H NMR (CDCl$_3$, 300 MHz) δ 7.68 (d, 2H, J=8.6), 7.29-7.47 (m, 6H), 6.38 (br s, 1H), 5.75 (br s, 1H), 4.65 (d, 1H, J=16.0), 4.42 (d, 1H, J=16.0), 4.32 (t, 1H, J=7.5), 3.30-3.85 (br m, 8H), 1.69-1.78 (m, 1H), 1.28-1.37 (m, 1H), 1.08-1.14 (m, 1H), 0.76 (d, 3H, J=6.5), 0.63 (d, 3H, J=6.6).

Exemplification of Reaction Scheme 7

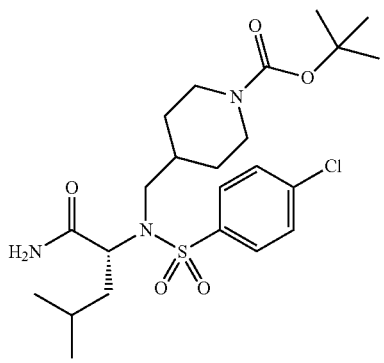 [SMILES: CC(C)C[C@H](C(N)=O)N(CC1CCN(C(=O)OC(C)(C)C)CC1)S(=O)(=O)c1ccc(Cl)cc1]

4-{[N-((1R)-1-Carbamoyl-3-methyl-butyl)-N-(4-chlorobenzenesulfonyl)amino]-methyl}-piperidine-1-carboxylic acid tert-butyl ester (Example 92)

To a solution of (2R)-2-(4-chlorobenzenesulfonylamino)-4-methylpentanoic acid amide (4.2 grams, 14 mmol) in DMF (50 mL) was added cesium carbonate (13.6 grams, 417 mmol). To this reaction was added 4-(toluene-4-sulfonyloxymethyl)-piperidine 1-carboxylic acid tert-butyl ester (ref.: Gilissen, C. et al., *J. Labeled Cmpd. Radiopharm.*, 42:1289 (1999); 10.4 g, 282 mmol). The reaction was stirred at 70° C. for 18 h. The reaction was then quenched with sat. aq. NaHCO$_3$ and extracted with EtOAc. The organic layer was collected, washed with brine, dried over MgSO$_4$, and concentrated to a clear oil. The oil was then purified on a BIOTAGE® 40S (eluted with 30% EtOAc in hexanes) to afford a white solid (3.0 g, 44%). MS (ESI), (M+H)$^+$502.1; $^1$H NMR (DMSO-d$_6$, 500 MHz) δ 7.86 (dd, 2H, J=2.0, 6.8), 7.65 (dd, 2H, J=2.0, 6.8) 7.37 (br s, 1H), 7.07 (br s, 1H), 4.19 (t, 1H, J=7.6), 3.92 (br s, 2H), 3.35 (dd, 1H, J=15, 6.8), 3.05 (dd, 1H, J=15, 8.1), 1.85 (br s, 1H), 1.50-1.70 (m, 4H), 1.38 (s, 9H), 1.10-1.20 (m, 1H), 0.80-1.00 (m, 3H), 0.82 (d, 6H, J=7.6).

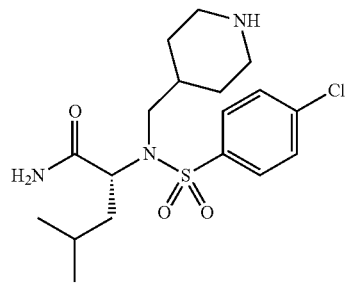 [SMILES: CC(C)C[C@H](C(N)=O)N(CC1CCNCC1)S(=O)(=O)c1ccc(Cl)cc1]

(2R)-2-[N-(4-Chlorobenzenesulfonyl)-N-(piperidin-4-ylmethyl)amino]-4-methyl-pentanoic acid amide (Example 126)

To a solution of 4-{[N-((1R)-1-carbamoyl-3-methyl-butyl)-N-(4-chlorobenzenesulfonyl)amino]-methyl}-piperidine-1-carboxylic acid tert-butyl ester (Example 92, 2.6 grams, 5.2 mmol) in CH$_2$Cl$_2$ (25 mL) was added trifluoroacetic acid (10 mL). The reaction was stirred at rt for 1 h and then was concentrated to give a white solid (1.6 grams, 84%). MS (ESI), (M+H)$^+$402.15; $^1$H NMR (DMSO-d$_6$, 500 MHz), δ 7.87 (d, 2H, J=8.5), 7.66 (d, 2H, J=8.6), 7.41 (s, 1H), 7.04 (s, 1H), 4.17 (t, 1H, J=7.3), 3.40-3.50 (m, 1H), 3.20-3.25 (m, 1H), 3.03-3.10 (m, 1H), 2.65-2.80 (m, 2H), 1.85-2.00 (m, 1H), 1.20-1.85 (m, 2H), 1.45-1.60 (m, 1H), 1.30-1.40 (m, 1H), 1.10-1.30 (m, 4H), 0.75-0.90 (m, 1H), 0.82 (d, 3H, J=7.3), 0.80 (d, 3H, J=7.0).

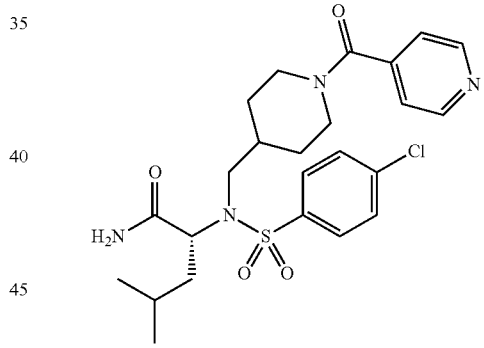

(2R)-2-{N-(4-Chlorobenzenesulfonyl)-N-[1-(pyridine-4-carbonyl)-piperidin-4-ylmethyl]-amino}-4-methyl-pentanoic acid amide (Example 278)

To a solution of (2R)-2-[N-(4-chlorobenzenesulfonyl)-N-(piperidin-4-ylmethyl)amino]-4-methyl-pentanoic acid amide (Example 126, 0.10 g, 0.22 mmol) and Et$_3$N (0.06 mL, 0.5 mmol) in CH$_2$Cl$_2$ (3.0 mL) was added isonicotinoyl chloride hydrochloride (56 mg, 0.32 mmol). The reaction was stirred at rt for 18 h and then was poured into a mixture of EtOAc and sat. aq. NaHCO$_3$. The organic solution was separated and washed with brine, dried over MgSO$_4$, and concentrated to an oily residue. The residue was purified on a BIOTAGE® 10M (eluted with 80% EtOAc/hexanes) to give a white solid (36 mg, 30%). MS (ESI), (M+H)$^+$509.20; $^1$H NMR (CDCl$_3$, 500 MHz) δ 8.66 (br s, 2H), 7.80 (d, 1H, J=8.6), 7.73 (d, 2H, J=8.5), 7.51 (d, 2H, J=7.6), 7.41 (br s, 1H), 6.64 (br s, 1H), 5.35 (br s, 1H), 4.70 (br s, 1H), 4.10 (br s, 1H), 3.71 (br s, 1H), 3.33 (br s, 1H), 3.02 (dd, 2H, J=4.8, 16), 2.70-2.85 (br s, 1H), 1.50-2.09 (m, 5H), 1.18-1.33 (m, 4H), 0.73 (d, 3H, J=6.7), 0.68 (d, 3H, J=6.5).

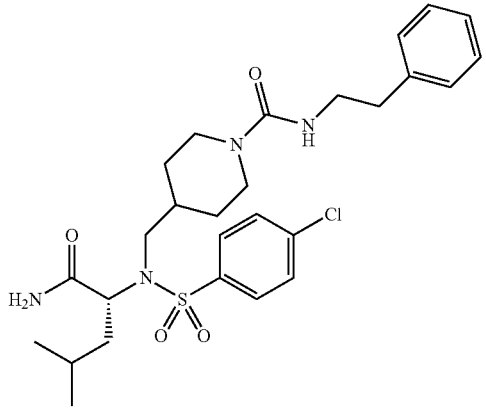 [SMILES: CC(C)C[C@H](C(N)=O)N(CC1CCN(C(=O)NCCc2ccccc2)CC1)S(=O)(=O)c1ccc(Cl)cc1]

4-{[N-((1R)-1-Carbamoyl-3 methyl-butyl)-N-(4-chlorobenzenesulfonyl)amino]-methyl}-piperidine-1-carboxylic acid phenethylamide (Example 256)

To a solution of (2R)-2-[N-(4-chlorobenzenesulfonyl)-N-(piperidin-4-ylmethyl)amino]-4-methyl-pentanoic acid amide (Example 126, 0.10 g, 0.22 mmol) and Et$_3$N (32 µL, 0.25 mmol) in CH$_2$Cl$_2$ (3.0 mL) was added (2-isocyanato-ethyl)-benzene (0.040 mL, 0.30 mmol). The reaction was stirred at rt for 18 h and then was poured into sat. aq. NaHCO$_3$ and extracted with EtOAc. The organic layer was washed with brine, dried over MgSO$_4$, and concentrated to an oily residue. The residue was further purified on a BIOTAGE® system (eluted with 75% EtOAc/hexanes) to afford the desired product as a white solid (67 mg, 52%). MS (ESI), (M+H)$^+$549.00; $^1$H NMR (CDCl$_3$, 500 MHz) δ 7.71 (d, 2H, J=8.6), 7.71 (d, 2H, J=8.9), 7.15-7.35 (m, 5H), 6.64 (s, 1H), 5.86 (s, 1H), 4.15 (dd, 1H, J=5.2, 9.5), 3.88 (d, 1H, J=13), 3.76 (d, 1H, J=13), 3.46 (t, 2H, J=6.7), 3.21-3.29 (m, 1H), 2.97 (dd, 1H, J=4.6, 14), 2.65-2.85 (m, 4H), 1.75-1.95 (m, 3H), 1.00-1.30 (m, 5H), 0.75-0.80 (m, 1H), 0.72 (d, 3H, J=6.7), 0.67 (d, 3H, J=6.7).

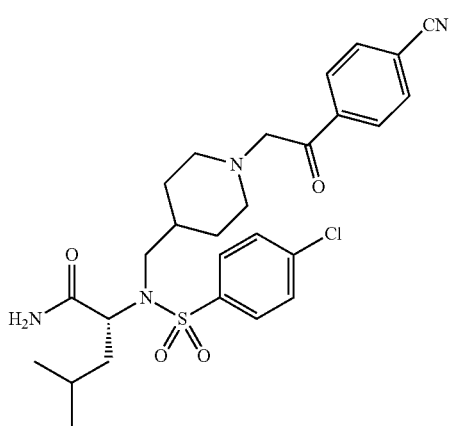 [SMILES: CC(C)C[C@H](C(N)=O)N(CC1CCN(CC(=O)c2ccc(C#N)cc2)CC1)S(=O)(=O)c1ccc(Cl)cc1]

(2R)-2-(N-(4-Chlorobenzenesulfonyl)-N-{1-[2-(4-cyanophenyl)-2-oxo-ethyl]-piperidin-4-ylmethyl}-amino)-4-methyl-pentanoic acid amide (Example 286)

To a solution of (2R)-2-[N-(4-chlorobenzenesulfonyl)-N-(piperidin-4-ylmethyl)amino]-4-methyl-pentanoic acid amide (Example 126, 0.050 g, 0.12 mmol) and Et$_3$N (0.040 mL, 0.30 mmol) in CH$_2$Cl$_2$ (2.0 mL) was added 4-(2-chloro-acetyl)-benzonitrile (55 mg, 0.30 mmol). The reaction was stirred at rt for 18 h and then was concentrated to residue. The residue was purified on a BIOTAGE® system (eluted with 80% EtOAc/hexanes) to produce 29 mg (48%) of the desired product as a white solid. MS (ESI), (M+H)$^+$545.16; $^1$H NMR (CDCl$_3$, 500 MHz) δ 7.72 (d, 2H, J=8.5), 7.50-7.65 (m, 2H), 7.50 (d, 2H, J=7.0), 7.35-7.45 (m, 2H), 6.67 (s, 1H), 5.32 (s, 1H), 4.14 (dd, 1H, J=5.0, 9.0), 3.52 (br s, 1H), 3.28 (t, 1H, J=14), 2.97 (dd, 1H, J=3.5, 14), 2.82 (br s, 1H), 1.00-2.00 (m, 10H), 0.71 (d, 3H, J=6.5), 0.66 (d, 3H, J=6.5).

Exemplification of Reaction Scheme 8

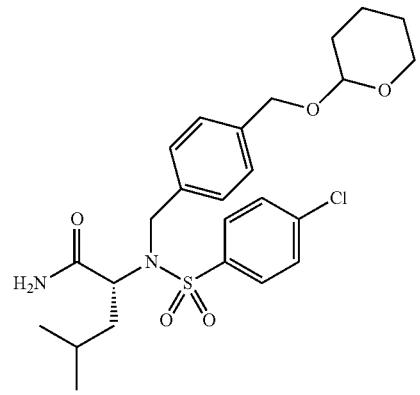 [SMILES: CC(C)C[C@H](C(N)=O)N(Cc1ccc(COC2CCCCO2)cc1)S(=O)(=O)c1ccc(Cl)cc1]

(2R)-2-{N-(4-Chlorobenzenesulfonyl)-N-[4-(tetrahydro-pyran-2-yloxymethyl)-benzyl]-amino}-4-methyl-pentanoic acid amide (2R)-2-(4-Chlorobenzenesulfonylamino)-4-methylpentanoic acid amide (6.35 g, 196 mmol), Cs$_2$CO$_3$ (5.62 g, 196 mmol), and 2-[(4-bromomethyl)benzyl]oxy) tetrahydropyran (5.62 g, 196 mmol) in acetonitrile (200 mL) were heated to reflux for 1 h. The reaction was filtered hot with suction through CELITE®. The filtrate was reduced in vacuo to a white foam (9.5 g, 96%). The foam was used as is in the next reaction. MS (ESI), (M+H)$^+$510.9, $^1$H NMR (CDCl$_3$) δ 7.83 (d, 2H, J=8.0), 7.75 (d, 2H, J=8.0), 7.39 (d, 2H, J=8.0), 7.24 (d, 2H, J=8.0), 6.25 (br s, 1H), 5.35 (br s, 1H), 4.82 (d, 1H, J$_{ab}$=12), 4.65 (m, 1H), 4.52 (d, 1H, J$_{ab}$=12), 4.30 (d, 1H, J$_{ab}$=16), 4.20 (d, 1H, J$_{ab}$=16), 3.74 (m, 2H), 3.46 (m, 1H), 1.89 (m, 1H), 1.66 (m, 6H), 0.97 (d, 3H, J=7.0), 0.94 (d, 3H, J=7.0).

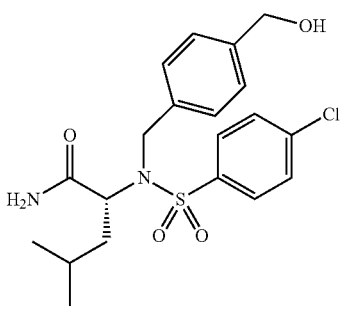 [SMILES: CC(C)C[C@H](C(N)=O)N(Cc1ccc(CO)cc1)S(=O)(=O)c1ccc(Cl)cc1]

(2R)-2-[N-(4-Chlorobenzenesulfonyl)-N-(4-hydroxymethyl)benzylamino]-4-methyl-pentanoic acid amide (Example 95)

To a solution of (2R)-2-N-(4-chlorobenzenesulfonyl)-N-[4-(tetrahydropyran-2-yloxymethyl)benzylamino]-4-methyl-pentanoic acid amide (9.5 g, 186 mmol) in methanol (200 mL) was added a catalytic amount of p-toluenesulfonic acid. The mixture was stirred overnight at rt. The solvent was removed in vacuo. The resulting foam was dissolved in $CH_2Cl_2$ (100 mL) washed with 1 N NaOH, $H_2O$, brine, and dried over $MgSO_4$. The filtrate solvent was removed in vacuo. The resulting foam was crystallized from hot hexane affording the product as a white solid (7.7 g) in 92% yield. MS (ESI), $(M+H)^+$425.17, $^1H$ NMR (CDCl$_3$) δ 7.68 (d, 2H, J=7.0), 7.46 (d, 2H, J=7.0), 7.33 (d, 2H, J=8.0), 7.28 (d, 2H, J=8.0), 6.26 (br s, 1H), 5.35 (br s, 1H), 4.67 (br s, 2H), 4.59 (d, 1H, $J_{ab}$=16), 4.37 (d, 1H, $J_{ab}$=16), 4.26 (t, 1H, 7.0), 1.86-1.80 (m, 2H), 1.34-1.28 (m, 1H), 1.16-1.10 (m, 1H), 0.96 (d, 3H, J=7.0), 0.93 (d, 3H, J=7.0).

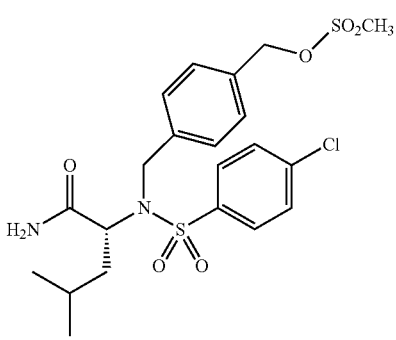 [SMILES: CC(C)C[C@H](C(N)=O)N(Cc1ccc(COS(C)(=O)=O)cc1)S(=O)(=O)c1ccc(Cl)cc1]

Methanesulfonic acid 4-{[N-((1R)-1-carbamoyl-3-methyl-butyl)-N-(4-chlorobenzene-sulfonyl)-amino]methyl}benzyl ester To a stirred solution of (2R)-2-[N-(4-chloro-benzenesulfonyl)-N-(4-hydroxymethyl-benzyl)amino]-4-methyl-pentanoic acid amide (1.5 g, 3.5 mmol) in $CH_2Cl_2$ (15 mL) cooled to 0° C. was added $Et_3N$ (0.74 mL, 5.3 mmol). A solution of methanesulfonyl chloride (0.29 mL, 3.5 mmol) in 5 mL $CH_2Cl_2$ was added dropwise and the reaction was allowed to stir at 0° C. for 1 h. The reaction mixture was diluted with 25 mL $CH_2Cl_2$, quickly washed with 1 N HCl, brine, and dried by passing the organic phase through a cotton plug. The solvent was removed in vacuo affording the title compound in quantitative yield. The resulting foam was used as is in subsequent reactions. MS (ESI), $(M+95)^+$, 409.15 $^1H$ NMR (CDCl$_3$) δ 7.70 (d, 2H, J=8.0), 7.48 (d, 2H, J=8.0), 7.41 (d, 2H, J=8.0), 7.38 (d, 2H, J=8.0), 6.27 (br s, 1H), 5.32 (br s, 1H), 5.24 (s, 2H), 4.64 (d, 1H, $J_{ab}$=16), 4.43 (d, 1H, $J_{ab}$=16), 4.33 (t, 1H, J=6), 2.90 (s, 3H), 1.90 (m, 1H), 1.60 (m, 2H), 0.96 (d, 3H, J=7.0), 0.91 (d, 3H, J=7.0)

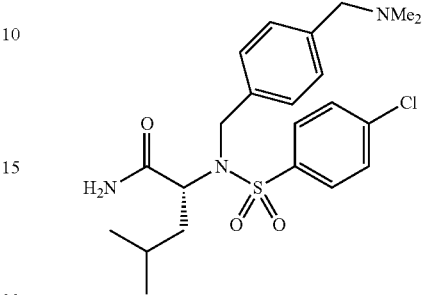

(2R)-2-[N-(4-Chlorobenzenesulfonyl)-N-(4-dimethylaminomethyl-benzyl)amino]-4-methyl-pentanoic acid amide (Example 110)

To a stirred solution of methanesulfonic acid 4-{[N-((1R)-1-carbamoyl-3-methyl-butyl)-N-(4-chlorobenzenesulfonyl)amino]-methyl}-benzyl ester (150 mg, 0.298 mmol) in (3 mL) $CH_2Cl_2$ at 0° C. was added 1 equivalent of $Et_3N$, followed by dimethylamine (0.3 mL, 2 M in THF). The reaction was stirred overnight at rt. The mixture was diluted with $CH_2Cl_2$, washed with $H_2O$, brine, dried over $MgSO_4$, and concentrated to give an amber glass. Purification by flash chromatography (SiO$_2$, 10% MeOH/$CH_2Cl_2$) afforded the title compound (95 mg) in 71% yield. MS (ESI), $(M+H)^+$ 452.23, $^1H$ NMR (CDCl$_3$) δ 7.94 (d, 2H, J=8.0), 7.74 (d, 2H, J=8.0), 7.63 (d, 2H, J=8.0) 7.38 (d, 2H, J=8.0), 6.23 (br s, 1H), 5.35 (br s, 1H), 4.22 (d, 1H, $J_{ab}$=16), 4.14 (d, 1H, $J_{ab}$=16), 3.28-3.23 (m, 3H), 2.17 (br s, 6H), 1.95 (m, 1H), 1.55 (m, 2H), 0.96 (d, 3H, J=7.0), 0.93 (d, 3H, J=7.0).

Exemplification of Reaction Scheme 9

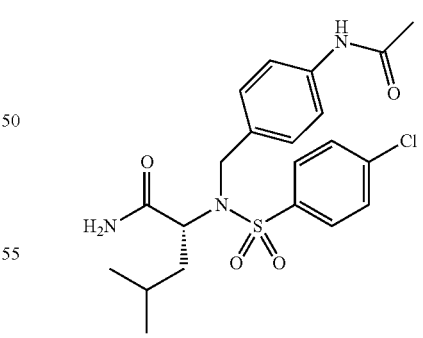

(2R)-2-[N-(4-Acetylaminobenzyl)-N-(4-chlorobenzenesulfonyl)amino]-4-methyl-pentanoic acid amide (Example 163)

A solution of the compound of Example 48 [(2R)-24N-(4-chlorobenzenesulfonyl)-N-(4-aminobenzyl)amino]-4-methyl-pentanoic acid amide (250 mg, 0.60 mmol) and $Et_3N$ (120 mg, 1.2 mmol) in CH$_2$Cl$_2$ (20 mL) was treated with acetyl chloride (56 mg, 0.72 mmol). After stirring for 18 h, the reaction was concentrated, chromatographed using silica gel flash chromatography (1% methanol/CH$_2$Cl$_2$) to afford the titled compound (110 mg, 41%). MS (ESI), (M–H)⁻422.9; $^1$H NMR (CDCl$_3$) δ 7.67 (d, 2H, J=8.0), 7.28-7.46 (m, 6H), 7.12 (br s, 1H), 6.24 (br s, 1H), 5.19 (br s, 1H), 4.48 (dd, 2H, J=50, 15), 4.27 (t, 1H, J=7.0), 2.18 (s, 3H), 1.80-2.01 (m, 1H), 1.12-1.32 (m, 2H), 0.75 (d, 3H, J=7.0), 0.67 (d, 3H, J=7.0).

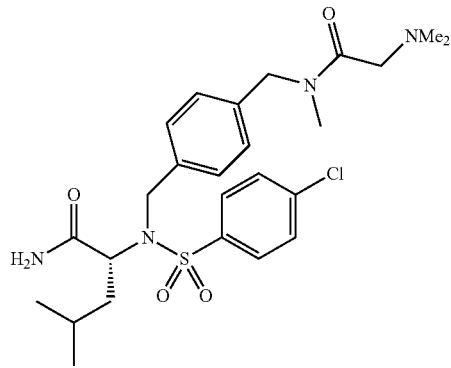 [SMILES: CC(C)C[C@H](C(N)=O)N(Cc1ccc(CN(C)C(=O)CN(C)C)cc1)S(=O)(=O)c1ccc(Cl)cc1]

(2R)-2-[N-(4-Chlorobenzenesulfonyl)-N-(4-{[(2-dimethylamino-acetyl)-methyl-amino]-methyl}-benzyl)-amino]-4-methyl-pentanoic acid amide (Example 272)

(2R)-2-[N-(4-Chlorobenzenesulfonyl)-N-(4-methylaminomethyl-benzyl)-amino]-4-methyl-pentanoic acid amide (75 mg, 0.17 mmol), (α-dimethylamino)acetic acid (18 mg, 0.17 mmol), 1-hydroxybenzotriazole (24 mg, 0.17 mmol), and 1-[3-(dimethylamino)propyl]-3-ethylcarbodiimide hydrochloride (33 mg, 0.17 mmol) were combined in 3 mL CH$_2$Cl$_2$ and stirred overnight. The reaction mixture was diluted with 5 mL CH$_2$Cl$_2$ and washed with 1 N NaOH and brine. The organic phase was dried by filtering through cotton and the solvent was removed in vacuo. Purification via preparative HPLC afforded the title compound (61 mg) in 68% yield. MS (ESI), 523.4 (M+H)⁺$^1$H NMR (CDCl$_3$) δ 8.02 (d, 2H, J=8.0), 7.71 (d, 2H, J=8.0), 7.37 (d, 2H, J=8.0), 7.28 (d, 2H, J=8.0), 6.23 (br s, 1H), 5.51 (br s, 1H), 4.46 (s, 2H), 4.70 (d, 1H, J$_{ab}$=16), 4.33 (d, 1H, J$_{ab}$=16), 3.25 (t, 1H, J=6.0), 2.69 (s, 3H), 2.63 (s, 2H), 2.20 (s, 6H), 1.95 (m, 1H), 1.60 (m, 2H), 0.98 (d, 3H, J=7.0), 0.94 (d, 3H, J=7.0).

Exemplification of Reaction Scheme 10

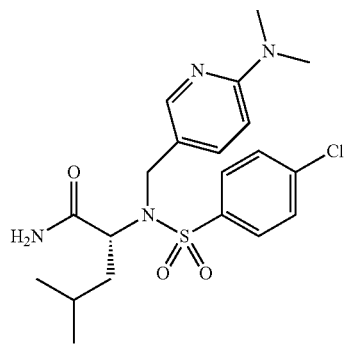 [SMILES: CC(C)C[C@H](C(N)=O)N(Cc1ccc(N(C)C)nc1)S(=O)(=O)c1ccc(Cl)cc1]

(2R)-2-[N-(4-Chlorobenzenesulfonyl)-N-(2-dimethylaminopyridin-5-ylmethyl)amino]-4-methylpentanoic acid amide TFA salt (Example 254)

A solution of (2R)-2-[N-(4-chlorobenzenesulfonyl)-N-(2-chloropyridin-5-ylmethyl)amino]-4-methylpentanoic acid amide (prepared via Reaction Scheme 1, 18 mg, 41 mmol) in dimethylamine/THF (2 M, 20 mL, 40 mmol) was stirred at 95° C. for 30 h in a pressure vessel. Five mL of reaction mixture (25% of total reaction volume) was purified by reverse phase preparative HPLC (YMC S5, ODS, MeOH-water-TFA) to afford the title compound as a white foam (17 mg, 30% yield). HRMS (ESI), (M–H)⁻ for C$_{20}$H$_{26}$SClN$_4$O$_3$ calcd: 437.1426, found: 437.1420; $^1$H NMR (CDCl$_3$): δ 8.04 (s, 1H), 8.03 (d, 1H, J=9.8), 7.76 (d, 2H, J=7.6), 7.54 (d, 2H, J=7.6), 6.83 (d, 1H, J=9.8), 6.62 (br s, 1H), 6.40 (br s, 1H), 4.64 (d, 1H, J=15.9), 4.29 (m, 1H), 4.18 (d, 1H, J=15.9), 3.30 (s, 6H), 1.84 (m, 1H), 1.29 (m, 1H), 0.93 (m, 1H), 0.77 (d, 3H, J=6.5), 0.72 (d, 3H, J=6.5).

Exemplification of Reaction Scheme 11

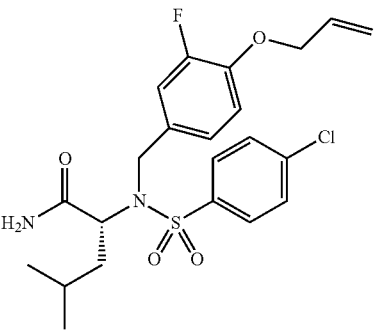 [SMILES: C=CCOc1ccc(CN([C@H](CC(C)C)C(N)=O)S(=O)(=O)c2ccc(Cl)cc2)cc1F]

(2R)-2-[N-(4-Allyloxy-3-fluorobenzyl)-N-(4-chlorobenzenesulfonyl)amino]-4-methyl-pentanoic acid amide To a solution of (2R)-2-(4-chlorobenzenesulfonylamino)-4-methyl-pentanoic acid amide (1.00 g, 3.29 mmol), and Cs$_2$CO$_3$ (1.29 g, 3.95 mmol) in DMF (25 mL) was added 1-allyloxy-4-bromomethyl-2-fluorobenzene (ref.: Graham, S. L. et al., EP Patent Application No. EP 487270 (1992): 0.88 g, 3.67 mmol). The resulting solution was stirred at rt for 18 h. The reaction was then diluted with 9:1 EtOAc:hexanes (350 mL) and washed with H$_2$O (4×200 mL), brine, and dried over Na$_2$SO$_4$, to afford the titled compound (393 mg) as a white solid in 26% yield. MS (ESI), (M+H)⁺469.1; $^1$H NMR (CDCl$_3$) δ 7.66 (d, 2H, J=8.1), 7.45 (d, 2H, J=8.1), 7.11 (d, 1H, J=12.0), 6.98 (m, 1H), 6.84 (t, 1H, J=8.0), 6.22 (br s, 1H), 6.04 (m, 2H), 5.42 (m, 1H), 5.16 (br s, 1H), 4.59 (m, 2H), 4.40 (m, 3H), 1.83 (m, 1H), 1.32 (m, 1H), 1.14 (m, 1H), 0.76 (d, 3H, J=7.0), 0.68 (d, 3H, J=7.0).

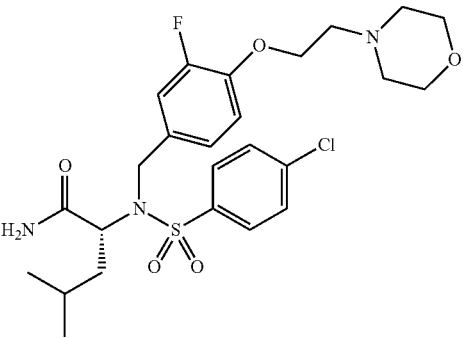 [SMILES: CC(C)C[C@H](C(N)=O)N(Cc1ccc(OCCN2CCOCC2)c(F)c1)S(=O)(=O)c1ccc(Cl)cc1]

(2R)-2-{N-(4-Chlorobenzenesulfonyl)-N-[3-fluoro-4-(2-morpholin-4-yl-ethoxy)-benzyl]-amino}-4-methyl-pentanoic acid amide (Example 427)

A mixture of the allyloxy intermediate (0.39 g, 0.84 mmol) from above, osmium tetraoxide (0.01 g, 0.04 mmol), and trimethylamine N-oxide (0.140 g, 1.81 mmol) was dissolved in acetone (10 mL) and stirred for 4 h at rt. The solution was concentrated in vacuo and redissolved in 1.5:1 dioxane:$H_2O$ (15 mL). Sodium periodate (0.22 g, 1.0 mmol) was added and the solution was stirred at rt for 18 h. The reaction was then diluted with EtOAc (200 mL) and washed with $H_2O$, brine, dried over $Na_2SO_4$ and concentrated to give (2R)-{N-(4-chloro-benzenesulfonyl)-N-[3-fluoro-4-(2-oxo-ethoxy)-benzyl]-amino}-4-methyl-pentanoic acid amide as a crude beige solid. This crude material was taken onto the next step without further purification. (2R)-2-{N-(4-Chlorobenzenesulfonyl)-N-[3-fluoro-4-(2-oxo-ethoxy)-benzyl]-amino}-4-methyl-pentanoic acid amide (0.16 g, 0.34 mmol) and morpholine (0.090 g, 1.0 mmol) was dissolved in EtOH (5 mL) and heated to 80° C. for approximately 15 min. The oil bath was removed and sodium triacetoxyborohydride (0.290 g, 1.36 mmol) was added and the slurry was stirred at rt for 16 h. The solution was concentrated to dryness, taken up in brine, extracted with EtOAc (2×100 mL), dried over $Na_2SO_4$, and concentrated in vacuo to give a crude orange residue. Further purification by Prep HPLC (20×100 mm YMC S5 ODS C-18 column, 25 mL/min, 0-100% MeOH/$H_2O$ 0.1% TFA 15 min) afforded as a TFA salt the titled compound (69.5 mg) as a pale yellow solid in 31% yield. $[\alpha]_D$+23 (c 6.4, $CH_2Cl_2$); LCMS $(M+H)^+$542.25; $^1H$ NMR ($CDCl_3$) δ 7.71 (d, 2H, J=8.0), 7.50 (d, 2H, J=8.0), 7.16 (d, 1H, J=12.0), 7.05 (d, 1H, J=8.0), 6.87 (t, 1H, J=8.0), 6.38 (br s, 1H), 5.91 (br s, 1H), 4.41 (ABq, 2H, J=16, $J_{ab}$=176), 4.45 (m, 2H), 4.27 (t, 1H, J=8.0), 4.03 (m, 4H), 3.70 (m, 2H), 3.51 (m, 2H), 3.10 (m, 2H), 1.83 (m, 1H), 1.29 (m, 1H), 1.05 (m, 1H), 0.75 (d, 3H, J=8.0), 0.68 (d, 3H, J=8.0).

Exemplification of Reaction Scheme 12

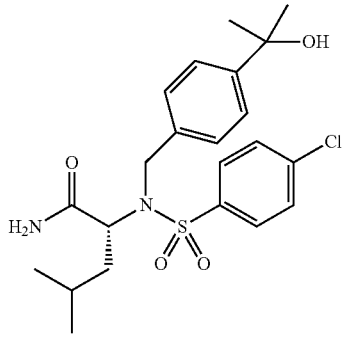 [SMILES: CC(C)C[C@H](C(N)=O)N(Cc1ccc(C(C)(C)O)cc1)S(=O)(=O)c1ccc(Cl)cc1]

(2R)-2-{N-(4-Chlorobenzenesulfonyl)-N-[4-(1-hydroxy-1-methyl-ethyl)-benzyl]-amino}-methyl-pentanoic acid amide (Example 287)

A solution of the compound of Example 61 [4-{[N-((1R)-1-carbamoyl-3-methyl-butyl)-N-(4-chlorobenzenesulfonyl)amino]-methyl}-benzoic acid methyl ester, 101 mg, 0.221 mmol] was cooled to 0° C. in THF (2 mL). A solution of methyl magnesium bromide (1.4 M in toluene/THF, 0.50 mL, 0.71 mmol) was added dropwise. The dark yellow solution was stirred at 0° C., and after 30 min, additional methyl magnesium bromide solution (0.25 mL, 0.353 mmol) was added. After 1 h, the solution was allowed to warm to rt. After 3.5 h, the reaction was quenched by the addition of sat. aq. $NH_4Cl$, and the mixture was extracted with EtOAc (2×). The combined organic layers were dried ($Na_2SO_4$) and concentrated. Flash column chromatography ($SiO_2$, 20 to 100% EtOAc/hexanes) provided the title compound as a white foam (62 mg, 62%). MS (ESI), $(M+H)^+$453.16; $^1H$ NMR ($CDCl_3$, 300 MHz) δ 7.61 (d, 2H, J=8.7), 7.40 (d, 2H, J=8.7), 7.37 (d, 2H, J=8.4), 7.26 (d, 2H, J=8.4), 6.28 (br s, 1H), 5.25 (br s, 1H), 4.49 (d, 1H, J=15.9), 4.41 (d, 1H, J=15.9), 4.33 (t, 1H, J=6.6), 1.73-1.80 (m, 1H), 1.55 (s, 6H), 1.28-1.35 (m, 1H), 1.20-1.25 (m, 1H), 0.77 (d, 3H, J=6.5), 0.66 (d, 3H, J=6.6).

Exemplification of Reaction Scheme 13

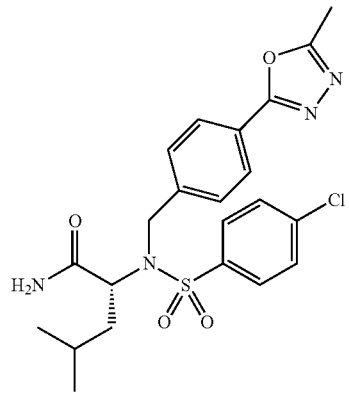 [SMILES: Cc1nnc(-c2ccc(CN([C@H](CC(C)C)C(N)=O)S(=O)(=O)c3ccc(Cl)cc3)cc2)o1]

(2R)-2-{N-(4-Chlorobenzenesulfonyl)-[4-(5-methyl-[1,3,4]oxadiazol-2-yl)-benzyl]-amino}-4-methyl-pentanoic acid amide (Example 436)

Step 1: A solution of the compound of Example 61 [4-{[N-((1R)-1-carbamoyl-3-methyl-butyl)-N-(4-chlorobenzenesulfonyl)amino]-methyl}-benzoic acid methyl ester, 0.500 g, 1.10 mmol] was diluted with methanol (10 mL) and hydrazine (2 mL) was added. The starting material slowly dissolved over 5 min. After 30 min, the solution was heated at reflux. After 22 h, the solution was cooled to rt. water (15 mL) was added, and a white precipitate formed. The mixture was extracted with EtOAc (2×). The combined organic layers were washed with brine, dried ($Na_2SO_4$), and concentrated to give the corresponding acyl hydrazide as a white foam, which was carried directly on to the cyclization step without purification.

Step 2: The crude acyl hydrazide (0.150 g, 0.331 mmol) was dissolved in pyridine (2.2 mL) and ethyl acetimidate hydrochloride (60.0 mg, 0.364 mmol) was added. The mixture was heated at reflux for 1.25 h. The solution was cooled to rt and concentrated to remove pyridine. The residue was taken up in EtOAc, and was washed sequentially with water, 1 N HCl (2×), sat. aq. $NaHCO_3$, and brine. The solution was dried ($MgSO_4$) and concentrated. Flash column chromatography ($SiO_2$, 50 to 100% EtOAc/hexanes) provided the listed compound as a white solid (138 mg, 88% for 2 steps). $[\alpha]_D$+ 11.1 (c 7.0 mg/ml, $CHCl_3$); MS (ESI), $(M+H)^+$477.22; $^1H$ NMR ($CDCl_3$, 300 MHz) δ 7.94 (dd, 2H, J=1.8, 8.4), 7.69 (dd, 2H, J=1.8, 8.7), 7.45-7.50 (m, 4H), 6.23 (br s, 1H), 5.19 (br s, 1H), 4.65 (d, 1H, J=15.9), 4.46 (d, 1H, J=15.9), 4.31 (dd, 1H, J=6.6, 7.8), 2.61 (s, 3H), 1.75-1.85 (m, 1H), 1.28-1.35 (m, 1H), 1.08-1.15 (m, 1H), 0.76 (d, 3H, J=6.6), 0.64 (d, 3H, J=6.6).

Exemplification of Reaction Scheme 14

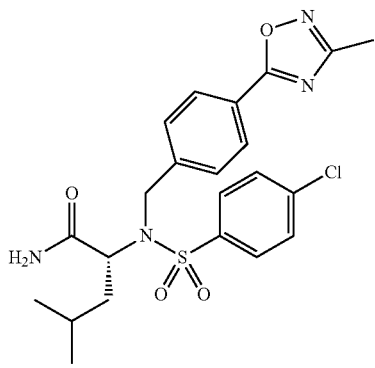 [SMILES: Cc1noc(-c2ccc(CN([C@H](CC(C)C)C(N)=O)S(=O)(=O)c3ccc(Cl)cc3)cc2)n1]

(2R)-2-{N-(4-Chlorobenzenesulfonyl)-N-[4-(3-methyl-[1,2,4]oxadiazol-5-yl)-benzyl]-amino}-4-methyl-pentanoic acid amide (Example 437)

Step 1: To a rt solution of the compound of Example 89 [4-{[N-((1R)-1-carbamoyl-3-methyl-butyl)-N-(4-chlorobenzene-sulfonyl)-amino]-methyl}-benzoic acid, 520 mg, 1.2 mmol] in DMF (2.4 mL) and CH$_2$Cl$_2$ (7.1 mL) was added 1-hydroxybenzotriazole (192 mg, 1.42 mmol), 1-(3-dimethylaminopropyl)-3-ethylcarbodiimide hydrochloride (272 mg, 1.42 mmol), and iPr$_2$NEt (0.31 mL, 1.8 mmol). N-Hydroxyacetamide (105 mg, 1.42 mmol) was also added. After 21 h, starting material was evident, so additional portions of all reagents were added periodically to push the reaction forward. After 3 d, the mixture was concentrated and partitioned between sat. aq. NaHCO$_3$ and EtOAc (2×). The combined organic layers were washed with brine, dried (MgSO$_4$), and concentrated to a yellow oil, which was carried on to the next step without purification.

Step 2: The crude acetamidoxime was dissolved in toluene (10 mL) and the solution was heated at reflux. After 1 h, pyridine (2 mL) was added and heating was continued for another 15 h. The mixture was concentrated and diluted with EtOAc. The organic phase was washed sequentially with water, 1 N HCl (2×), sat. aq. NaHCO$_3$, and brine, then was dried (MgSO$_4$) and concentrated. Flash column chromatography (SiO$_2$, to 40% EtOAc/hexanes) gave the title compound as a pale yellow solid (238 mg, 42% for two steps). $[\alpha]^{23}_D$+9.30 (c 5.93, CHCl$_3$); MS (ESI), (M+H)$^+$477.18; $^1$H NMR (CDCl$_3$, 300 MHz) δ 8.04 (d, 2H, J=8.4), 7.70 (dd, 2H, J=1.8, 8.4), 7.45-7.52 (m, 4H), 6.23 (br s, 1H), 5.19 (br s, 1H), 4.67 (d, 1H, J=16.2), 4.47 (d, 1H, J=15.9), 4.31 (t, 1H, J=7.2), 2.47 (s, 3H), 1.75-1.85 (m, 1H), 1.28-1.35 (m, 1H), 1.08-1.15 (m, 1H), 0.76 (d, 3H, J=6.6), 0.64 (d, 3H, J=6.6).

Exemplification of Reaction Scheme 15

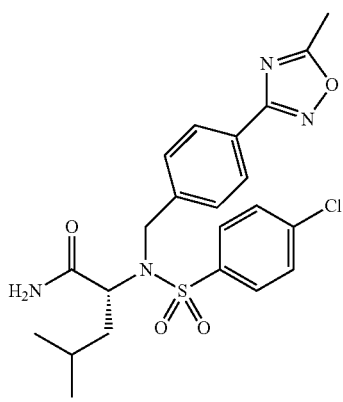 [SMILES: Cc1nc(-c2ccc(CN([C@H](CC(C)C)C(N)=O)S(=O)(=O)c3ccc(Cl)cc3)cc2)no1]

(2R)-2-{N-(4-Chlorobenzenesulfonyl)-N-[4-(5-methyl-[1,2,4]oxadiazol-3-yl)-benzyl]-amino}-4-methyl-pentanoic acid amide (Example 465)

A solution of the compound of Example 6 [(2R)-2-[N-(4-chlorobenzenesulfonyl)-N-(4-cyanobenzyl)amino]-4-methyl-pentanoic acid amide (0.20 g, 0.47 mmol) in ethanol (6 mL) was treated with hydroxylamine (50% solution in water, 0.050 mL, 0.71 mmol). The reaction was heated to 80° C. for 18 h. The reaction was concentrated to a residue and recrystallized from EtOAc/hexanes to produce a white solid (136 mg, 51%). This solid (0.18 mmol) was then dissolved in chloroform and treated with Et$_3$N (0.030 mL, 0.24 mmol) and acetyl chloride (0.020 mL, 0.18 mmol). The reaction was stirred at rt for 2 h and then was poured into EtOAc and brine. The organic layer was separated, dried over MgSO$_4$, and concentrated to residue. The residue was taken up in toluene and heated at reflux for 24 h. The reaction was concentrated to a residue and purified on a BIOTAGE® system (eluted in 1:1 EtOAc/hexanes) to afford the desired product as a white solid (35 mg, 39% yield). MS (ESI), (M+H)$^+$477.13; $^1$H NMR (CDCl$_3$, 500 MHz) δ 7.98 (d, 2H, J=8.2), 7.68 (d, 2H, J=8.9), 7.45 (d, 4H, J=8.5), 6.21 (s, 1H), 5.19 (s, 1H), 4.62 (d, 1H, J=15), 4.48 (d, 1H, J=16), 4.31 (t, 1H, J=7.0), 2.65 (s, 3H), 1.75-1.85 (m, 1H), 1.20-1.35 (m, 4H), 1.10-1.17 (m, 1H), 0.85-0.90 (m, 1H), 0.75 (d, 3H, J=6.7), 0.64 (d, 3H, J=6.4).

Exemplification of Reaction Scheme 16

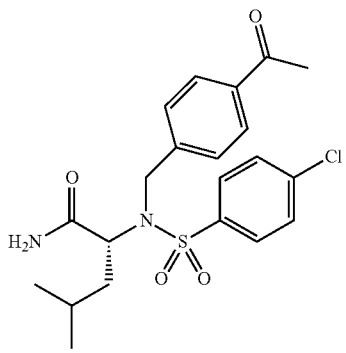 [SMILES: CC(=O)c1ccc(CN([C@H](CC(C)C)C(N)=O)S(=O)(=O)c2ccc(Cl)cc2)cc1]

(2R)-2-[N-(4-Acetylbenzyl)-N-(4-chlorobenzenesulfonyl)amino]-4-methyl-pentanoic acid amide (Example 273)

A solution of the compound of Example 251 [4-{[N-((1S)-1-carbamoyl-3-methyl-butyl)-N-(4-chlorobenzenesulfonyl)-amino]-methyl}-N-methoxy-N-methyl-benzamide, 0.100 g, 0.207 mmol] was cooled to 0° C. in THF (2.1 mL). A solution of methyl magnesium bromide (1.4 M in toluene/THF, 0.178 mL, 0.249 mmol) was added dropwise. The resulting solution was stirred at 0° C. for 3 h, at which time additional methyl magnesium bromide solution (0.178 mL, 0.249 mmol) was added. After another 30 min, a final portion of MeMgBr solution (0.3 mL) was added. After a final 15 min, the reaction was quenched by the addition of sat. aq. NH$_4$Cl and 1 N HCl, and the mixture was extracted with EtOAc (2×). The combined organic layers were washed with sat. aq. NaHCO$_3$ and brine, dried (Na$_2$SO$_4$) and concentrated. Flash column chromatography (SiO$_2$, 20 to 60% EtOAc/hexanes) gave the desired compound as an off-white foam (79 mg, 87%).

[α]²³_D +20.4 (c 7.57, CHCl₃); MS (ESI), (M+H)⁺437.13; ¹H NMR (CDCl₃, 300 MHz) δ 7.87 (d, 2H, J=8.4), 7.67 (dd, 2H, J=1.8, 8.7), 7.42-7.46 (m, 4H), 6.21 (br s, 1H), 5.28 (br s, 1H), 4.64 (d, 1H, J=15.9), 4.45 (d, 1H, J=15.9), 4.31 (t, 1H, J=6.6), 2.58 (s, 3H), 1.73-1.80 (m, 1H), 1.25-1.35 (m, 1H), 1.05-1.14 (m, 1H), 0.74 (d, 3H, J=6.5), 0.65 (d, 3H, J=6.6).

Exemplification of Reaction Scheme 17

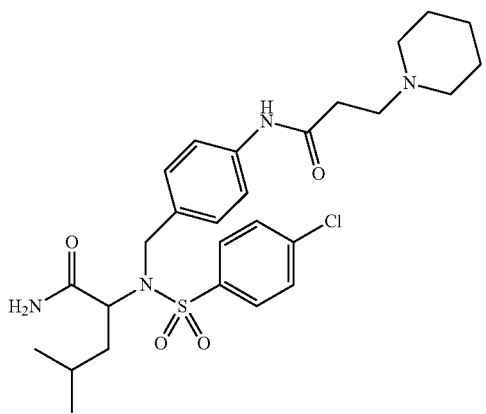 [SMILES: CC(C)CC(C(N)=O)N(Cc1ccc(NC(=O)CCN2CCCCC2)cc1)S(=O)(=O)c1ccc(Cl)cc1]

(2R)-2-{N-(4-Chlorobenzenesulfonyl)-N-[4-(3-piperidin-1-yl-propionylamino)-benzyl]-amino}-4-methyl-pentanoic acid amide (Example 274)

To a solution of N-(4-{[N-((1S)-1-carbamoyl-3-methyl-butyl)-N-(4-chlorobenzenesulfonyl)amino]-methyl}-phenyl)-acrylamide (0.10 g, 0.22 mmol) in toluene (5 mL) was added piperidine (20 mg, 0.24 mmol). The mixture was heated at a gentle reflux for 1 h and then the solvent was removed in vacuo. Purification by flash chromatography (SiO₂, 10% MeOH/CH₂Cl₂) afforded the title compound (105 mg) in 86% yield. MS (ESI), (M+H)⁺449.16, ¹H NMR (CDCl₃, 400 MHz) δ 7.69 (d, 2H, J=8.0), 7.63 (d, 2H, J=8.0), 7.38 (d, 2H, J=8.0), 7.23 (d, 2H, J=8.0), 6.25 (br s, 1H), 5.35 (br s, 1H), 4.75 (d, 1H, J_ab=16), 4.38 (d, 1H, J_ab=16), 3.25 (t, 1H, J=6.0), 2.65 (t, 2H, J=6.0), 2.56-2.44 (m, 6H), 1.95 (m, 1H), 1.68-1.45 (m, 8H), 0.98 (d, 3H, J=7.0), 0.94 (d, 3H, J=7.0).

Exemplification of Reaction Scheme 18

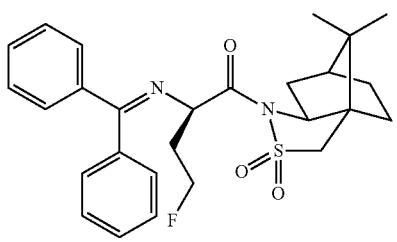 [SMILES: CC1(C)C2CCC13CS(=O)(=O)N(C(=O)[C@@H](CCF)N=C(c1ccccc1)c1ccccc1)C3C2]

(2R)-2-(Benzhydrylidene-amino)-1-{(1'S),(5'S)-10',10'-dimethyl-3',3'-dioxo-3'λ⁶-thia-4'-aza-tricyclo-[5.2.1.0¹,⁵]dec-4'-yl}-4-fluorobutan-1-one To a −78° C. solution of N-2-(benzhydrylidene-amino)-1-{(1'S),(5'S)-10',10'-dimethyl-3',3'-dioxo-3'λ⁶-thia-4'-aza-tricyclo-[5.2.1.0¹,⁵] dec-4'-yl}ethanone (ref: Josien, H. et al., Tetrahedron Let., 32:6547 (1991); 30.0 g, 68 mmol) in HMPA (60 mL) and THF (300 mL) was added n-BuLi (1.6 M in hexane, 42.4 mL, 68 mmol) dropwise, maintaining the temperature below −65° C. The reaction was allowed to come to rt, at which time a solution of 1-bromo-3-fluoroethane (17.4 g, 137 mmol) in THF (30 mL) was added dropwise at rt. After 18 h the reaction was poured over H₂O/HOAc (200 mL/2 mL), diluted with EtOAc, and the organic layers were washed with saturated NH₄Cl, brine, dried over MgSO₄, and concentrated. The resulting orange oil was then further purified by silica gel chromatography (25% EtOAc/hexanes) to afford a white solid which was recrystallized from 15% EtOAc/hexanes to give the desired material (24.3 g, 70%). MS (ESI) (M+H⁺) 483.27; ¹H NMR (CDCl₃) δ 7.66 (d, 2H, J=7.2), 7.13-7.44 (m, 8H), 4.82-4.83 (m, 2H), 4.39-4.81 (m, 2H), 3.84-3.87 (m, 1H), 3.28 (ABq, 2H, J=18, 10) 2.33-2.41 (m, 2H), 2.02-2.04 (m, 2H), 1.84-1.87 (m, 2H), 1.32-1.39 (m, 2H), 1.10 (s, 3H), 0.91 (s, 3H).

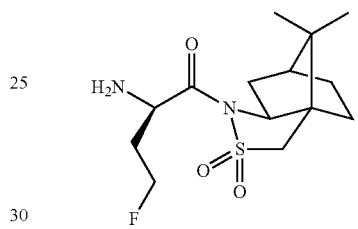

(2R)-2-Amino-1-{(1'S),(5'S)-10',10'-dimethyl-3',3'-dioxo-3'λ⁶-thia-4'-aza-tricyclo-[5.2.1.0¹,⁵]dec-4'-yl}-4-fluorobutan-1-one A solution of (2R)-2-(benzhydrylidene-amino)-1-{(1'S),(5'S)-10',10'-dimethyl-3',3'-dioxo-3'λ⁶-thia-4'-aza-tricyclo-[5.2.1.0¹,⁵]dec-4'-yl}-4-fluorobutan-1-one (20.0 g, 41.0 mmol) in THF (400 mL) was treated with 1 N HCl (200 mL). After 3 h, the reaction was diluted with H₂O and extracted with Et₂O. The aqueous phase was then neutralized by the addition of 0.5 N NaOH. The basic phase was then extracted with CH₂Cl₂, dried over MgSO₄, and concentrated to give a white solid (11.9 g, 90%). ¹H NMR (CDCl₃) δ 4.56-4.71 (m, 2H), 4.23-4.31 (m, 1H), 3.40-3.49 (m, 3H), 3.11 (d, 2H, J=4.4), 1.17-2.23 (m, 8H), 1.13 (s, 3H), 0.93-1.12 (m, 3H).

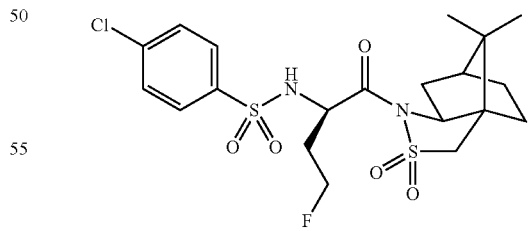

(2R)-2-(4-Chlorobenzensulfonylamino)-1-{(1'S),(5'S)-10',10'-dimethyl-3',3'-dioxo-3'λ⁶-thia-4'-aza-tricyclo-[5.2.1.0¹,⁵]dec-4'-yl}-4-fluorobutan-1-one To a solution of (2R)-2-amino-1-{(1'S),(5'S)-10',10'-dimethyl-3',3'-dioxo-3'λ⁶-thia-4'-aza-tricyclo-[5.2.1.0¹,⁵]dec-4'-yl}-4-fluorobutan-1-one: (12 g, 36 mmol) and Et₃N (10.4 mL, 72.0 mmol) in CH$_2$Cl$_2$ (350 mL) was added 4-chlorobenzenesulfonyl chloride (9.1 g, 43 mmol) in one portion. After 18 h the reaction was concentrated and the resulting residue was taken into EtOAc and washed with H$_2$O, brine, dried over MgSO$_4$, and concentrated. The material was then further purified by silica gel chromatography (30% EtOAc/hexanes) to afford the titled compound (16.0 g, 92%) as a white wax. $^1$H NMR (CDCl$_3$) δ 7.79 (d, 2H, J=8.0), 7.43 (d, 2H, J=8.0), 5.69 (br d, 8.0), 4.42-4.77 (m, 4H), 3.71-3.72 (m, 1H), 3.10 (ABq, 2H, J=9, 4.4) 2.11-2.29 (m, 2H), 1.33-1.99 (m, 6H), 1.04 (s, 3H), 0.91 (s, 3H).

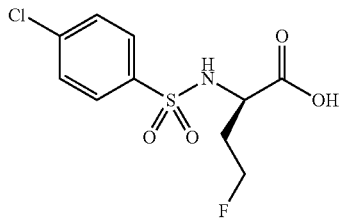 [SMILES: O=C(O)[C@@H](CCF)NS(=O)(=O)c1ccc(Cl)cc1]

(2R)-2-(4-Chlorobenzenesulfonylamino)-4-fluorobutanoic acid

To a rapidly stirred solution of (2R)-2-(4-chlorobenzensulfononylamino)-1-{(1'S),(5'S)-10',10'-dimethyl-3',3'-dioxo-3'λ$^6$-thia-4'-aza-tricyclo-[5.2.1.0$^{1,5}$]dec-4'-yl}-4-fluorobutan-1-one: (16 g, 32 mmol) in acetonitrile (200 mL) was added LiBr (13.9 g, 16 mmol), tetrabutylammonium bromide (4.13 g, 12.8 mmol), and LiOH (5.45 g, 0.130 mol). After 4.5 h the reaction was concentrated to half volume then diluted with H$_2$O and extracted with CH$_2$Cl$_2$. The aqueous layer was acidified with 1 N HCl and extracted with EtOAc. The EtOAc extracts were combined, dried over MgSO$_4$, and concentrated to give a white solid of which 9.4 g was taken directly towards the next step. $^1$H NMR (DMSO-d$_6$) δ 8.39 (d, 1H, J=9.0), 7.76 (d, 2H, J=6.8), 7.64 (d, 2H, J=6.8), 7.00 (br s, 1H), 4.29-4.48 (m, 2H), 3.80-3.88 (m, 1H), 1.66-1.96 (m, 2H).

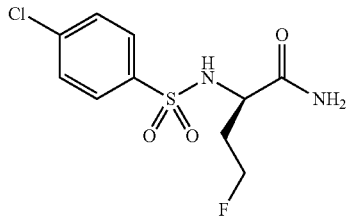 [SMILES: NC(=O)[C@@H](CCF)NS(=O)(=O)c1ccc(Cl)cc1]

(2R)-2-(4-Chlorobenzenesulfonylamino)-4-fluorobutanoic acid amide

To a solution of (2R)-2-(4-chlorobenzenesulfonylamino)-4-fluorobutanoic acid (9.0 g, 31 mmol) in DMF (250 mL) was added consecutively 1-hydroxybenzotriazole hydrate (6.2 g, 46 mmol), N,N-diisopropylethylamine (23 mL, 124 mmol), ammonium chloride (3.34 g, 62 mmol), and 1-[3-(dimethylamino)propyl]-3-ethylcarbodiimide hydrochloride (8.8 g, 46 mmol) under N$_2$. The resulting solution was stirred at rt for 18 h. The solution was poured over ice water (500 mL) and the solid was filtered off and dried. The material was then precipitated from 10% EtOAc/hexanes to afford a clean white solid (4.5 g) in 50% yield. [α]$_D$=−21.0 (c 1.00, DMF); MS (ESI) (M−H$^-$) 293.01; $^1$H NMR (DMSO-d$_6$) δ 8.12 (d, 1H, J=8.8), 7.77 (d, 2H, J=7.0), 7.62 (d, 2H, J=7.0), 7.38 (br s, 1H), 7.03 (br s, 1H), 4.22-4.47 (m, 2H), 3.71-3.85 (m, 1H), 1.65-1.92 (m, 2H).

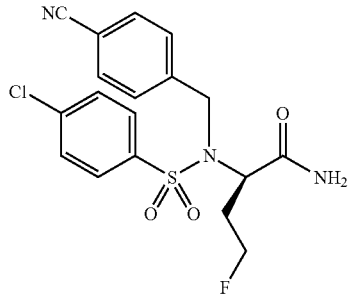 [SMILES: N#Cc1ccc(CN([C@H](CCF)C(N)=O)S(=O)(=O)c2ccc(Cl)cc2)cc1]

(2R)-2-[(4-Chlorobenzenesulfonyl)-(4-cyanobenzyl)-amino]-4-fluorobutyramide (Example 360)

(2R)-2-(4-Chlorobenzenesulfonylamino)-4-fluorobutyramide (20 mg, 0.7 mmol) was converted to the title compound as in Reaction Scheme 1, method A to afford the titled compound (208 mg) in 73% yield. MS (ESI) (M−H)$^-$407.99; [α]$_D$=+39.13 (c 1.00, MeOH); $^1$H NMR (CDCl$_3$) δ 7.72 (d, 2H, J=8.4) 7.58 (d, 2H, J=8.4), 7.50 (d, 2H, J=8.4), 7.45 (d, 2H, J=8.4), 6.29 (br s, 1H), 5.21 (br s, 1H), 4.19-4.67 (m, 5H), 2.17-2.28 (m, 1H), 1.49-1.61 (m, 1H).

Exemplification of Reaction Scheme 19

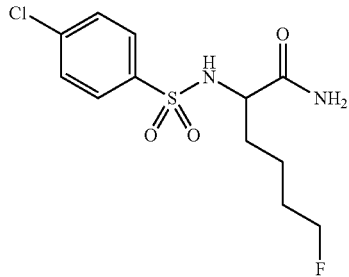 [SMILES: NC(=O)C(CCCCF)NS(=O)(=O)c1ccc(Cl)cc1]

2-(4-Chlorobenzenesulfonylamino)-6-fluoro-hexanoic acid amide (III)

A mixture of (benzhydrylidene-amino)acetic acid ethyl ester (8.6 g, 32 mmol), 4-bromo-1-fluorobutane (10.0 g, 64.5 mmol), K$_2$CO$_3$ (13.4 g, 96.9 mmol), tetrabutylammonium bromide (2.1 g, 6.5 mmol), and acetonitrile (300 mL) was heated at reflux for 72 h. The reaction was cooled to rt and filtered through a sintered glass funnel The filtrate was concentrated in vacuo. The residue was dissolved in diethyl ether (250 mL) and a white solid precipitated. The solid was removed by vacuum filtration. A solution of 1 N HCl (100 mL) was added to the filtrate, which contained the crude product (2-(benzhydrylideneamino)-6-fluoro-hexanoic acid ethyl ester). The resulting biphasic mixture was stirred vigorously for 3 h. The mixture was transferred to a separatory funnel. The aqueous layer was collected. The organic layer was extracted with 1 N HCl (30 mL). The combined aqueous layers were washed with 200 mL of diethyl ether. Concentrated HCl (10.8 mL) was added to the aqueous portion and the resulting solution was heated at reflux for 6 h. The reaction mixture was cooled to rt and concentrated in vacuo. Toluene was added to the residue and the mixture was reconcentrated in vacuo to afford 2-amino-6-fluoro-hexanoic acid hydrochloride as a white solid. The crude amino acid salt was used without purification or characterization. 2-Amino-6-fluoro-hexanoic acid hydrochloride (32.3 mmol, theoretically) was suspended in anhydrous methanol (300 mL) and cooled to 0° C. Thionyl chloride (10.3 mL, 129 mmol) was slowly was over 5 min. The resulting solution was allowed to warm to rt and stir for 18 h. The reaction mixture was concentrated in vacuo to afford methyl 2-amino-6-fluoro-hexanoic acid hydrochloride. Toluene (100 mL) and 28% ammonia in water (75 mL) were added to the crude amino ester. The resulting biphasic mixture was stirred vigorously at rt for 24 h. The reaction mixture was concentrated in vacuo. The residual solid was suspended in toluene (200 mL) and reconcentrated in vacuo to afford 6-fluorohexanoic acid amide (II) as a white solid. The crude amino acid amide was dissolved in anhydrous DMF (50 mL) and $CH_2Cl_2$ (350 mL) and reacted with 4-chlorobenzenesulfonylchloride (82 g, 32.3 mmol) and $Et_3N$ (13.5 mL, 96.9 mmol). After 2 h, a second portion of 4-chlorobenzenesulfonylchloride (1.70 g, 8.1 mmol) was added. After an additional 18 h, the resulting mixture was poured into 1 N HCl (500 mL). The organic layer was collected and washed with water (2×500 mL). Hexane (600 mL) was added to the organic layer. A white precipitate formed. The solid was collected by vacuum filtration, rinsed with cold ethanol (50 mL), and dried in vacuo to afford 4.95 g (48% yield, 6 steps) of 2-(4-chlorobenzenesulfonylamino)-6-fluoro-hexanoic acid amide (III): LCMS (M+Na)⁺345.2; $^1$H NMR (400 MHz, DMSO-$d_6$) 7.99 (d, 1H, J=8.8), 7.77 (d, 2H, J=8.8), 7.62 (d, 2H, J=8.8), 7.29 (s, 1H), 6.95 (s, 1H), 4.34 (dt, 2H, $J_d$=47.5, $J_t$=6.1), 3.65 (dt, 1H, $J_d$=5.6, $J_t$=8.6), 1.60-1.39 (m, 4H), 1.36-1.15 (m, 2H); Anal. Calcd for $C_{12}H_{16}ClFN_2O_3S$: C, 44.65; H, 4.99; N, 8.67. Found: C, 44.61; H, 5.08; N, 8.75.

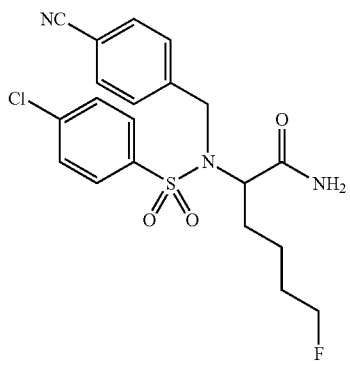 [SMILES: N#Cc1ccc(CN(C(CCCCF)C(N)=O)S(=O)(=O)c2ccc(Cl)cc2)cc1]

2-[(4-Chlorobenzenesulfonyl)-(4-cyanobenzyl)-amino]-6-fluoro-hexanoic acid amide (Example 333)

2-(4-Chlorobenzenesulfonylamino)-6-fluoro-hexanoic acid amide (0.500 g, 1.55 mmol) was converted to the title compound (360 mg, 50% yield) as in Reaction Scheme 1, method A. LCMS (M+Na)⁺459.9; $^1$H NMR (400 MHz, DMSO-$d_6$) δ 7.82 (d, 2H, J=8.8), 7.79 (d, 2H, J=8.5), 7.63 (d, 2H, J=8.8), 7.58 (d, 2H, J=8.3), 7.52 (s, 1H), 7.09 (s, 1H). 4.82 (ABq, 2H, Δv=37.2, $J_{ab}$=17.6), 4.34 (dd, 1H, J=8.0, 6.6), 4.25 (dt, 2H, $J_d$=47.2, $J_t$=5.7), 1.58 (m, 1H), 1.49-1.12 (m, 5H); Anal. Calcd for $C_{20}H_{21}ClFN_3O_3S$: C, 54.85; H, 4.83; N, 9.59. Found: C, 54.92; H, 4.76; N, 9.54.

Exemplification of Reaction Scheme 20

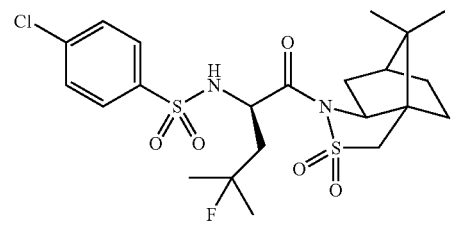 [SMILES: CC(C)(F)C[C@@H](NS(=O)(=O)c1ccc(Cl)cc1)C(=O)N1C2CC3CCC2(CS1(=O)=O)C3(C)C]

(2R)-2-(4-Chlorobenzensulfonylamino)-1-{(1'S),(5'S)-10',10'-dimethyl-3',3'-dioxo-3'λ⁶-thia-4'-aza-tricyclo-[5.2.1.0$^{1,5}$]dec-4'-yl}-4-fluoro-4-methyl-pentan-1-one To a solution of (2R)-2-(4-chlorobenzenesulfonylamino)-1-{(1'S),(5'S)-10',10'-dimethyl-3',3'-dioxo-3'λ⁶-thia-4'-aza-tricyclo-[5.2.1.0$^{1,5}$] dec-4'-yl}-4-methyl-4-penten-1-one [500 mg, 1 mmol, prepared as in Reaction Scheme 18 from N-2-(benzhydrylidene-amino)-1-{(1'S),(5'S)-10',10'-dimethyl-3', 3'-dioxo-3'λ⁶-thia-4'-aza-tricyclo-[5.2.1.0$^{1,5}$]dec-4'-yl}ethanone (ref: Josien, H. et al., *Tetrahedron Leu.*, 32:6547 (1991)) and 1-bromo-2-methyl-2-propene] in THF (5 mL) at 0° C. was added hydrofluoric acid.pyridine (10 mL). The reaction mixture was allowed to warm to rt and stir for 18 h. The reaction contents were carefully added to a saturated aqueous solution of $NaHCO_3$ (300 mL). The aqueous mixture was extracted with EtOAc (3×100 mL). The combined organic layers were sequentially washed with 1 N HCl (200 mL) and brine (100 mL). The organic layer was dried over $MgSO_4$, filtered, and concentrated in vacuo to afford 490 mg (94%) of the title compound as a white solid: $^1$H NMR (400 MHz, DMSO-$d_6$) δ 7.83 (d, 2H, J=8.8), 7.45 (d, 2H, J=8.8), 5.37 (d, 1H, J=8.1), 4.65 (m, 1 H), 3.64 (t, 1H, J=6.4), 3.43 (ABq, 2H, Δv=5.4, $J_{ab}$=13.7), 2.19-1.83 (m, 7H), 1.41-1.31 (m, 8H), 1.04 (s, 3H), 0.94 (s, 3H).

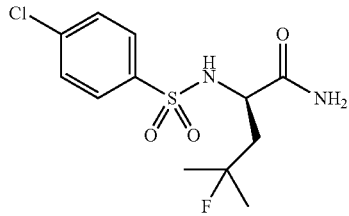 [SMILES: CC(C)(F)C[C@@H](NS(=O)(=O)c1ccc(Cl)cc1)C(N)=O]

(2R)-2-(4-Chlorobenzenesulfonylamino)-4-fluoro-4-methyl-pentanoic acid amide (2R)-2-(4-Chlorobenzensulfonylamino)-1-{(1'S),(5'S)-10',10'-dimethyl-3',3'-dioxo-3'λ⁶-thia-4'-aza-tricyclo-[5.2.1.0$^{1,5}$]dec-4'-yl}-4-fluoro-4-methyl-pentan-1-one was converted to the title compound in two steps as in Reaction Scheme 18 (165 mg, 55% yield): LCMS (M+Na)⁺345.1; $^1$H NMR (500 MHz, DMSO-$d_6$) δ 8.10 (d, 1H, J=9.2), 7.77 (d, 2H, J=8.5), 7.62 (d, 2H, J=8.9), 7.34 (s, 1H), 6.92 (s, 1H). 3.85 (m, 1H), 1.89 (m, 1H), 1.74 (m, 1H), 1.31 (d, 3H, J=21.7), 1.29 (d, 3H, J=21.9).

Exemplification of Reaction Scheme 21

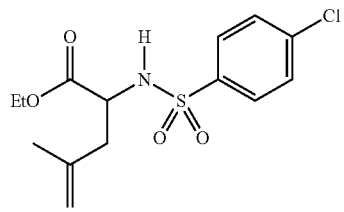 [SMILES: C=C(C)CC(NS(=O)(=O)c1ccc(Cl)cc1)C(=O)OCC]

Ethyl 2-(4-chlorobenzenesulfonylamino)-4-methyl-4-pentenoate

A solution of ethyl 2-amino-4-methyl-4-pentenoate (2.84 g, 18.1 mmol, prepared as in Reaction Scheme 19 from (benzhydrylideneamino)acetic acid ethyl ester and 1-bromo-2-methyl-2-propene) in CH$_2$Cl$_2$ (250 mL) was reacted with 4-chlorobenzenesulfonyl chloride (4.20 g, 19.9 mmol) and Et$_3$N (3.78 mL, 27.2 mmol). After 4 h, the resulting mixture was poured into 1 N aqueous HCl (500 mL) and extracted with EtOAc (3×150 mL). The organic layer was washed with brine (50 mL), dried (MgSO$_4$), filtered, and concentrated in vacuo. The crude concentrate was purified using silica gel column chromatography (10:1 to 5:1 gradient, hexanes/EtOAc) to afford 3.04 g (25% yield over 3 steps) of ethyl 2-(4-chlorobenzenesulfonylamino)-4-methyl-4-pentenoate: LCMS (M+Na)$^+$354.2; $^1$H NMR (400 MHz, CDCl$_3$) 7.77 (d, 2H, J=9.1), 7.46 (d, 2H, J=8.8), 5.07 (d, 1H, J=9.0), 4.84 (s, 1H), 4.73 (s, 1H), 4.05 (m, 1H), 3.95 (q, 2H, J=7.1), 2.40 (m, 2 H), 1.66 (s, 3H), 1.13 (t, 3H, J=7.1).

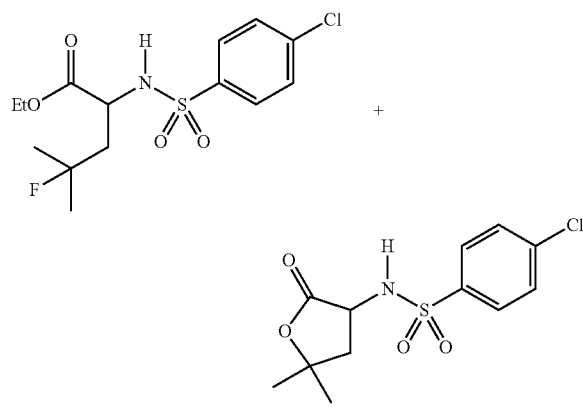

2-(4-Chlorobenzenesulfonylamino)-4-fluoro-4-methyl-pentanoic acid ethyl ester and 4-Chloro-N-(5,5-dimethyl-2-oxo-tetrahydro-furan-3-yl)-benzenesulfonamide Hydrogen fluoride.pyridine (10 mL) was added to a 0° C. solution of ethyl 2-(4-chloro-benzenesulfonylamino)-4-methyl-4-pentenoate (1.0 g, 3.0 mmol) in THF (15 mL). The reaction mixture was allowed to warm to rt. After 5 h, an additional portion (10 mL) of hydrogen fluoride.pyridine was added. The mixture was stirred for 24 h, then a third portion of hydrogen fluoride.pyridine (10 mL) was added. After a total of 53 h, the reaction was quenched with ice chips (20 mL). The crude mixture was poured into ice water (500 mL) and extracted with CH$_2$Cl$_2$ (2×200 mL). The combined organic layers were washed with sat. aq. NaHCO$_3$ (100 mL) and concentrated in vacuo. The crude concentrate was purified using silica gel column chromatography (10:1 to 5:1 gradient, hexanes/EtOAc) to afford 0.395 g (37% yield) of ethyl 2-(4-chlorobenzenesulfonylamino)-4-fluoro-4-methyl-pentanoate and 0.425 g (46% yield) of 4-chloro-N-(5,5-dimethyl-2-oxo-tetrahydro-furan-3-yl)-benzenesulfonamide.

Data for ethyl 2-(4-chlorobenzenesulfonylamino)-4-fluoro-4-methyl-pentanoate: LCMS (M+Na)$^+$374.1; $^1$H NMR (500 MHz, CDCl$_3$) 7.78 (d, 2H, J=8.9), 7.47 (d, 2H, J=8.5), 5.19 (d, 1H, J=7.9), 4.08 (m, 1H), 3.93 (m, 2H), 2.09-1.94 (m, 2H), 1.42 (d, 3H, J=21.6), 1.37 (d, 3H, J=21.6), 1.12 (t, 3H, J=7.0).

Data for 4-chloro-N-(5,5-dimethyl-2-oxo-tetrahydro-furan-3-yl)-benzenesulfonamide: LCMS (M+Na)$^+$326.0; $^1$H NMR (400 MHz, DMSO-d$_6$) 8.41 (d, 1H, J=9.1), 7.86 (d, 2H, J=8.6), 7.67 (d, 2H, J=8.8), 4.57 (m, 1H), 2.22 (dd, 1H, J=12.4, 9.0), 1.72 (t, 1H, J=12.0), 1.33 (s, 3H), 1.31 (s, 3H).

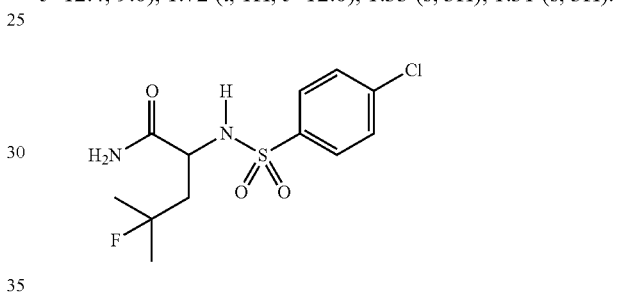

2-(4-Chlorobenzenesulfonylamino)-4-fluoro-4-methyl-pentanoic acid amide

A solution of 2-(4-chlorobenzenesulfonylamino)-4-fluoro-4-methyl-pentanoic acid ethyl ester (457 mg, 1.30 mmol) in MeOH (20 mL) was treated with 10 N NaOH (780 μL, 7.8 mmol) at rt for 18 h. The crude reaction mixture was concentrated in vacuo. The residue was treated with water (50 mL) and 1 N HCl (20 mL). The aqueous solution was extracted with EtOAc (3×100 mL). The combined organic layers were washed with brine (50 mL), dried over MgSO$_4$, filtered and concentrated in vacuo to afford a white solid containing 2-(4-chlorobenzenesulfonylamino)-4-fluoro-4-methyl-pentanoic acid. A mixture of the crude solid, 1-hydroxybenzotriazole (263 mg, 1.95 mmol), diisopropylethylamine (670 mg, 5.2 mmol), ammonium chloride (140 mg, 2.6 mmol), 1-(3-dimethylaminopropyl)-3-ethylcarbodiimide hydrochloride (373 mg, 1.95 mmol), and DMF (20 mL) was stirred at rt for 24 h. The crude mixture was poured into water (500 mL). The aqueous solution was extracted with EtOAc/hexane (90:10, 3×150 mL). The combined organic layers were washed with brine (50 mL), dried over MgSO$_4$, filtered and concentrated in vacuo. The crude concentrate was purified using silica gel column chromatography (95:5, chloroform/MeOH) to afford 0.426 g (100% yield) of the title compound: LCMS (M+Na)$^+$345.3; $^1$H NMR (400 MHz, DMSO-d$_6$) δ 8.10 (d, 1H, J=9.2), 7.77 (d, 2H, J=8.5), 7.62 (d, 2H, J=8.9), 7.34 (s, 1H), 6.92 (s, 1H). 3.85 (m, 1H), 1.89 (m, 1H), 1.74 (m, 1H), 1.31 (d, 3H, J=21.7), 1.29 (d, 3H, J=21.9).

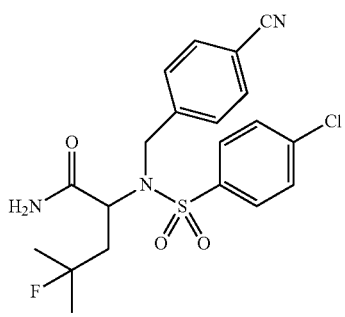 [SMILES: CC(C)(F)CC(C(N)=O)N(Cc1ccc(C#N)cc1)S(=O)(=O)c1ccc(Cl)cc1]

2-[(4-Chlorobenzenesulfonyl)-(4-cyanobenzyl)-amino]-4-fluoro-4-methyl-pentanoic acid amide (Example 357)

2-(4-Chlorobenzenesulfonylamino)-4-fluoro-4-methyl-pentanoic acid amide was converted to the title compound as in Reaction Scheme 1, method A. LCMS (M+Na)$^+$460.2; $^1$H NMR (400 MHz, DMSO-d$_6$) δ 7.83 (d, 2H, J=8.5), 7.75 (d, 2H, J=8.3), 7.68 (s, 1H), 7.64 (d, 2H, J=8.6), 7.49 (d, 2H, J=8.1), 7.20 (s, 1H), 4.67 (ABq, 2H, Δv=28.3, J$_{ab}$=17.3), 4.54 (dd, 1H, J=9.3, 3.2), 2.23 (m, 1H), 1.42 (m, 1H), 1.25 (d, 3H, J=21.6), 1.21 (d, 3H, J=21.7).

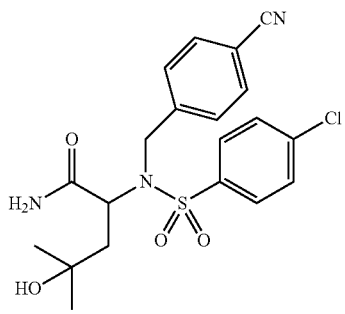 [SMILES: CC(C)(O)CC(C(N)=O)N(Cc1ccc(C#N)cc1)S(=O)(=O)c1ccc(Cl)cc1]

2-[(4-Chlorobenzenesulfonyl)-(4-cyanobenzyl)-amino]-4-hydroxy-4-methyl-pentanoic acid amide (Example 443)

A sealed vial containing a mixture of 4-chloro-N-(5,5-dimethyl-2-oxo-tetrahydro-furan-3-yl)-benzenesulfonamide (0.20 g, 0.66 mmol) and 28% ammonia in water (3 mL) was heated in a microwave reactor at 80° C. for 40 min. The reaction mixture was cooled to rt and concentrated to dryness in vacuo to afford a white solid containing 2-(4-chlorobenzenesulfonylamino)-4-hydroxy-4-methyl-pentanoic acid amide. The crude solid was converted to the title compound (98 mg, 34% yield) as in Reaction Scheme 1, method A: LCMS (M+Na)$^+$458.2; $^1$H NMR (400 MHz, DMSO-d$_6$) δ 7.84 (d, 2H, J=8.6), 7.76 (d, 2H, J=8.3), 7.62 (d, 2H, J=8.8), 7.51 (d, 2H, J=8.3), 7.40 (s, 1H), 7.11 (s, 1H), 4.63 (ABq, 2H, Δv=5.9, J$_{ab}$=17.6), 4.56 (dd, 1H, J=8.3, 2.5), 4.54 (s, 1H), 1.95 (dd, 1H, J=13.7, 8.6), 1.26 (dd, 1H, J=13.6, 2.4), 1.04 (s, 3H), 0.99 (s, 3H). Anal. Calcd for C$_{20}$H$_{22}$ClN$_3$O$_4$S: C, 55.10; H, 5.08; N, 9.64. Found: C, 54.96; H, 5.14; N, 9.58.

Exemplification of Reaction Scheme 22

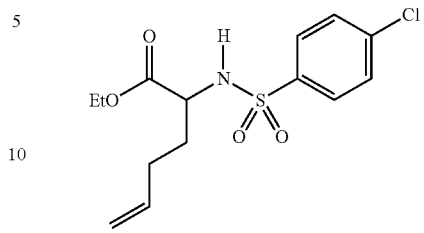

2-(4-Chlorobenzenesulfonylamino)-5-hexenoic acid ethyl ester

A mixture of (benzhydrylidene-amino)acetic acid ethyl ester (20 g, 74.8 mmol), 4-bromo-1-butene (10.1 g, 74.8 mmol), K$_2$CO$_3$ (31.0 g, 224 mmol), tetrabutylammonium bromide (2.41 g, 7.48 mmol), and acetonitrile (150 mL) was heated at reflux for 6 h. The reaction was cooled to rt and filtered through a sintered glass funnel. The filtrate was concentrated in vacuo. The residue was dissolved in diethyl ether (250 mL) and a white solid precipitated. The solid was removed by vacuum filtration. A solution of 1 N HCl (150 mL) was added to the filtrate, which contained the crude product (2-(benzhydrylidene-amino)-hex-5-enoic acid ethyl ester). The resulting biphasic mixture was stirred vigorously for 18 h. The mixture was transferred to a separatory funnel The aqueous layer was collected and concentrated in vacuo. The residue was dissolved in toluene (2×200 mL) and reconcentrated. The crude amino ester was dissolved in CH$_2$Cl$_2$ and reacted with 4-chlorobenzenesulfonyl chloride (15.8 g, 74.8 mmol) and Et$_3$N (31.2 mL, 224 mmol). After 18 h, the resulting mixture was poured into 1 N HCl (500 mL). The organic layer was collected and washed sequentially with 1 N HCl (500 mL) and brine (50 mL). The organic layer was dried over MgSO$_4$, filtered, and concentrated in vacuo. The crude concentrate was purified using silica gel column chromatography (5:1, hexanes/EtOAc) to afford 5.57 g (23% yield over 3 steps) of the title compound: LCMS (M+Na)$^+$354.0; $^1$H NMR (400 MHz, DMSO-d$_6$) δ 8.47 (d, 1H, J=8.8), 7.76 (d, 2H, J=8.8), 7.66 (d, 2H, J=8.8), 5.69 (m, 1H), 4.95-4.88 (m, 2H). 3.86 (q, 2H, J=7.1), 3.76 (m, 1H), 1.98 (m, 2H), 1.71-1.54 (m, 2H), 1.03 (t, 3H, J=7.1).

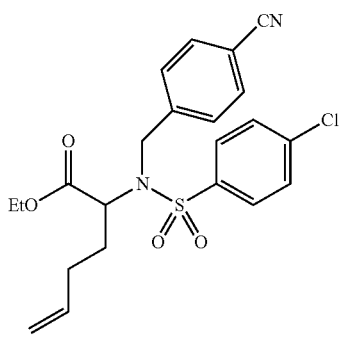 [SMILES: C=CCCC(C(=O)OCC)N(Cc1ccc(C#N)cc1)S(=O)(=O)c1ccc(Cl)cc1]

2-[(4-Chlorobenzenesulfonyl)-(4-cyanobenzyl)-amino]-hex-5-enoic acid ethyl ester 2-[(4-Chlorobenzenesulfonyl)-(4-cyanobenzyl)-amino]-hex-5-enoic acid ethyl ester was made in a similar manner to Reaction Scheme 1 starting from 2-(4-chloro-benzenesulfonylamino)-hex-5-enoic acid ethyl ester. 2-[(4-Chlorobenzenesulfonyl)-(4-cyanobenzyl)-amino]-hex-5-enoic acid ethyl ester was isolated as a crude yellow solid (1.14 g) and used in the next step without further purification. $^1$H NMR (CDCl$_3$) δ 7.71 (d, 2H, J=8.0), 7.61 (d, 2H, J=8.0), 7.53 (d, 2H, J=8.0), 7.46 (d, 2H, J=8.0), 5.54 (m, 2H), 4.90 (m, 2H), 4.74 (d, 1H, J=16.0), 4.48 (m, 2H), 3.90 (m, 1H), 1.95 (m, 2H), 1.81 (m, 1H), 1.48 (m, 1H), 1.11 (t, 3H, J=8.0).

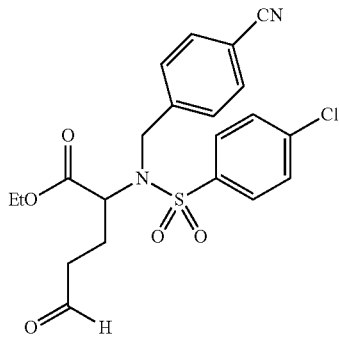 [SMILES: CCOC(=O)C(CCC=O)N(Cc1ccc(C#N)cc1)S(=O)(=O)c1ccc(Cl)cc1]

2-[(4-Chlorobenzenesulfonyl)-(4-cyanobenzyl)-amino]-5-oxo-pentanoic acid ethyl ester A mixture of (4-chlorobenzenesulfonyl)-(4-cyanobenzyl)-amino]-hex-5-enoic acid ethyl ester (1.14 g, 2.56 mmol), osmium tetraoxide (0.030 g, 0.13 mmol), and trimethylamine N-oxide (0.41 g, 5.5 mmol) was dissolved in acetone (50 mL) and stirred for 4 h at rt. Upon completion, the solution was concentrated in vacuo and redissolved in 1.5:1 dioxane:H$_2$O (50 mL). To this solution, sodium periodate (0.66 g, 3.07 mmol) was added and stirred at rt for 18 h. The reaction was then diluted with EtOAc (500 mL) and washed with H$_2$O, brine, dried over Na$_2$SO$_4$ and concentrated to give a crude colorless oil. Further purification by flash chromatography (SiO$_2$, 5 to 75% EtOAc/hexanes) afforded 2-[(4-chlorobenzenesulfonyl)-(4-cyanobenzyl)-amino]-5-oxo-pentanoic acid ethyl ester (0.26 g) as a colorless oil in 23% yield. $^1$H NMR (CDCl$_3$) δ 9.57 (s, 1H), 7.69 (d, 2H, J=8.0), 7.51 (m, 6H), 5.99 ABq, 2H, Δv=16, J$_{ab}$=168), 4.47 (m, 1H), 3.89 (m, 2H), 2.53 (m, 1H), 2.32 (m, 1H), 2.11 (m, 1H), 1.61 (m, 1H), 1.06 (t, 3H, J=8.0).

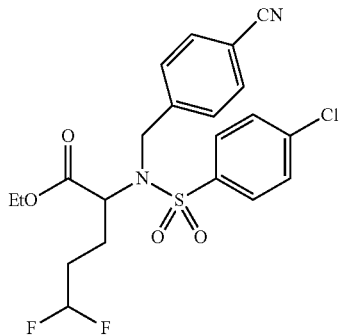 [SMILES: CCOC(=O)C(CCC(F)F)N(Cc1ccc(C#N)cc1)S(=O)(=O)c1ccc(Cl)cc1]

2-[(4-Chlorobenzenesulfonyl)-(4-cyanobenzyl)-amino]-5,5-difluoro-pentanoic acid ethyl ester 2-[(4-Chlorobenzenesulfonyl)-(4-cyanobenzyl)-amino]-5-oxo-pentanoic acid ethyl ester (0.05 g, 0.11 mmol) was slowly added to a solution of DAST (0.020 mL, 0.11 mmol) in CH$_2$Cl$_2$ (2 mL) at rt and stirred for 16 h. The reaction was diluted with CH$_2$Cl$_2$ (20 mL) and extracted with H$_2$O (2×25 mL). The combined organic layers were washed with H$_2$O, brine, dried over Na$_2$SO$_4$ and concentrated to give 2-[(4-Chloro-benzenesulfonyl)-(4-cyanobenzyl)-amino]-5,5-difluoro-pentanoic acid ethyl ester as a crude yellow residue (61 mg). This crude residue was taken onto the next step without further purification.

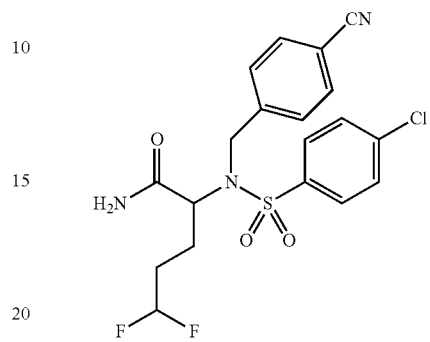

2-[(4-Chlorobenzenesulfonyl)-(4-cyanobenzyl)-amino]-5,5-difluoro-pentanoic acid amide (Example 377)

The crude 2-[(4-chlorobenzenesulfonyl)-(4-cyanobenzyl)-amino]-5,5-difluoro-pentanoic acid ethyl ester (0.061 g, 0.13 mmol) was dissolved in MeOH (2 mL). To this mixture was added 10 N NaOH (0.052 mL, 0.52 mmol) and the resulting solution was stirred at rt for 16 h. The reaction was diluted with H$_2$O (25 mL), acidified with 1 N HCl, and extracted with CH$_2$Cl$_2$ (4×100 mL). The combined organic layers were dried over Na$_2$SO$_4$ and concentrated in vacuo to give the carboxylic acid moiety as a crude colorless oil. The carboxylic acid intermediate was then dissolved in DMF (10 mL) and mixed with 1-hydroxybenzotriazole (0.030 g, 0.20 mmol), iPr$_2$NEt (0.090 mL, 0.52 mmol), NH$_4$Cl (0.01 g, 0.26 mmol), 1-(3-dimethylaminopropyl)-3-ethylcarbodiimide hydrochloride (0.04 g, 0.20 mmol) and stirred at rt for 72 h. The reaction was diluted with EtOAc (150 mL) and washed with H$_2$O (4×50 mL). The organic layer was dried over Na$_2$SO$_4$ and concentrated in vacuo to give a crude off-white solid. Further purification by flash chromatography (SiO$_2$, 5 to 85% EtOAc/hexanes) afforded the titled compound (10.7 mg) as a white solid in 19% yield. LCMS (M+Na)$^+$464.01; $^1$H NMR (CDCl$_3$) δ 7.69 (d, 2H, J=8.3), 7.60 (d, 2H, J=8.3), 7.49 (m, 4H), 6.18 (br s, 1H), 5.67 (tt, 1H, J=56, 4.0), 5.22 (br s, 1H), 4.52 (ABq, 2H, Δv=16, J$_{ab}$=100), 4.34 (m, 1H), 2.03 (m, 1H), 1.68 (m, 1H), 1.38 (m, 1H), 0.86 (m, 1H).

Exemplification of Reaction Scheme 23

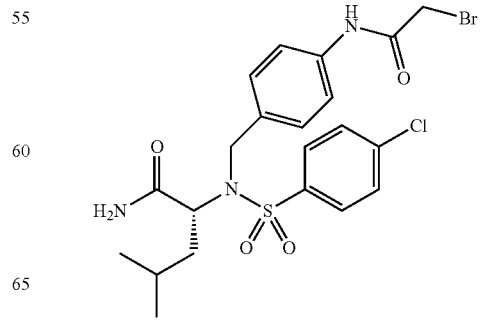

(2R)-2-[[4-(2-Bromo-acetylamino)-benzyl]-(4-chlorobenzenesulfonyl)-amino]-4-methyl-pentanoic acid amide To a solution of (2R)-2-[(4-aminobenzyl)-(4-chloro-benzenesulfonyl)amino]-4-methyl-pentanoic acid amide (248 mg, 0.56 mmol) and Et$_3$N (176 mg, 1.74 mmol) in CH$_2$Cl$_2$ (3 mL) was added bromoacetylchloride (105 mg, 0.67 mmol). The reaction mixture was stirred overnight at rt. The reaction mixture was diluted with CH$_2$Cl$_2$ (5 mL), washed with 1 N HCl, brine, and dried through a cotton plug. The solvent was removed in vacuo. Purification by flash chromatography (SiO$_2$, 10% acetone/CH$_2$Cl$_2$) afforded the title compound (124 mg) in 42% yield. MS (ESI), (M+H)$^+$531.86, $^1$H NMR (CDCl$_3$, 400 MHz) δ 8.78 (br s, NH), 7.95 (d, 2H, J=8.0), 7.82 (d, 2H, J=8.0), 7.42 (d, 2H, J=8.0), 7.33 (d, 2H, J=8.0), 6.20 (br s, 1H), 5.20 (br s, 1H), 4.30 (s, 2H), 4.22 (d, 1H, J$_{ab}$=16), 4.14 (d, 1H, J$_{ab}$=16), 3.25 (t, 1H, J=6.0), 1.95 (m, 1H), 1.60 (m, 2H), 0.98 (d, 3H, J=7.0), 0.94 (d, 3H, J=7.0)

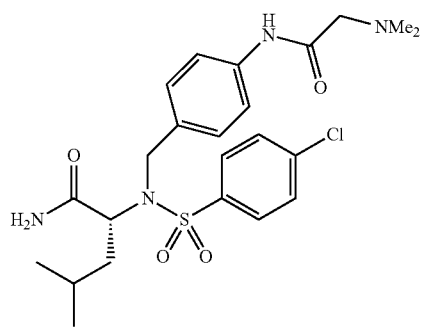 [SMILES: CC(C)C[C@H](C(N)=O)N(Cc1ccc(NC(=O)CN(C)C)cc1)S(=O)(=O)c1ccc(Cl)cc1]

(2R)-2-{(4-Chlorobenzenesulfonyl)-[4-(2-dimethylamino-acetylamino)-benzyl]-amino}-4-methyl-pentanoic acid amide (Example 308)

To a solution of (2R)-2-[[4-(2-bromo-acetylamino)-benzyl]-(4-chlorobenzenesulfonyl)-amino]-4-methyl-pentanoic acid amide (41 mg, 0.77 mmol) in CH$_2$Cl$_2$ (2 mL) was added excess 2.0 M dimethylamine in THF. The reaction mixture was stirred overnight. The solvent was removed in vacuo. Purification by flash chromatography (SiO$_2$, 10% MeOH/CH$_2$Cl$_2$) afforded the title compound (24 mg) in 63% yield. MS (ESI), (M+H)$^+$495.14, $^1$H NMR (CDCl$_3$, 400 MHz) δ 8.85 (s, 1H), 8.02 (d, 2H, J=8.0), 7.75 (d, 2H, J=8.0), 7.38 (d, 2H, J=8.0), 7.29 (d, 2H, J=8.0), 6.23 (br s, 1H), 5.39 (br s, 1H), 4.62 (m, 4H), 3.25 (t, 1H, J=6.0), 2.95 (s, 6H), 1.95 (m, 1H), 1.60 (m, 2H), 0.98 (d, 3H, J=7.0), 0.94 (d, 3H, J=7.0)

Starting Materials

The following α-amino amides were commercially available or obtained by standard methods from commercially available amino acids:

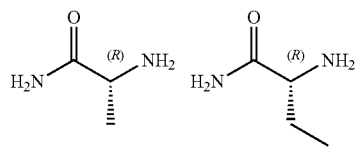

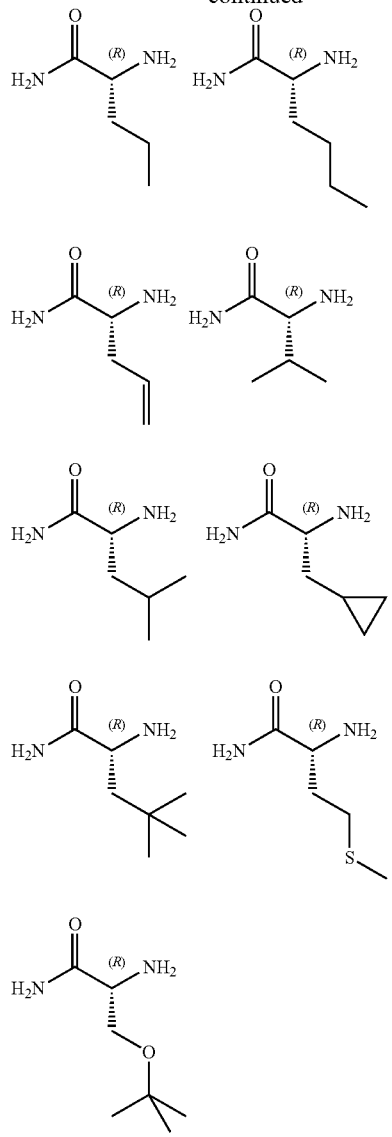

5,5,5-Trifluoro-2-aminopentanoic acid amide and 6,6,6-trifluoro-2-aminohexanoic acid were prepared according to: Ojima, I. et al., *J. Org. Chem.*, 54:4511 (1989).

The benzyl bromide used in the synthesis of the compounds of Examples 100 and 155 was prepared according to: Ishihara, Y. et al., PCT Publication No. WO 98/46590; Senanayake, C. H. et al., PCT Publication No. WO 98/33789.

The aldehydes required for the synthesis of the compounds of Examples 91, 248, 249, 289, 290, and 300 (see Reaction Scheme 2) were prepared as exemplified for 4-(piperidin-1-yl)benzaldehyde. A suspension of 4-fluorobenzaldehye (0.48 mL, 4 mmol), K$_2$CO$_3$ (522 mg, 4 mmol), piperidine (340 mg, 4 mmol) in DMSO (5 mL) was heated in a sealed tube at 150° C. for 18 h. after which time, the reaction was concentrated and purified by silica gel chromatography (CH$_2$Cl$_2$, then 2% MeOH/CH$_2$Cl$_2$) to afford 4-(piperidin-1-yl)benzaldehyde, 748 mg, 98% yield.

The aldehydes used in the synthesis of the compounds of Examples 317, 318, and 320 were prepared as exemplified for 4-(piperidin-1-yl)-3-fluorobenzaldehyde. A suspension of 4,3-difluorobenzaldehye (500 mg, 3.5 mmol), K$_2$CO$_3$ (483 mg, 3.5 mmol), piperidine (298 mg, 3.5 mmol) in DMSO (5 mL) was heated in a sealed tube at 130° C. for 18 h. The reaction mixture was allowed to cool to rt, concentrated and purified by silica gel chromatography ($CH_2Cl_2$, then 2% MeOH/$CH_2Cl_2$) to afford 4-(piperidin-1-yl)-3-fluorobenzaldehyde, 740 mg, 99% yield.

The benzyl chloride used in the preparation of the compounds of Examples 433, 474, 480, and 500 was prepared by the following method. To a solution of 2-[(4-chloromethyl)phenyl]propan-2-ol (769 mg, 4.16 mmol) (ref: Creary, X. et al., *J. Org. Chem.*, 52:3254 (1987)) in $CH_2Cl_2$ (14 mL) at −78° C. was added DAST (0.72 mL, 5.4 mmol). After 1.5 h, the solution was quenched with water and warmed to rt. The mixture was extracted with $CH_2Cl_2$ (3×). The combined organic layers were dried ($Na_2SO_4$) and concentrated. Flash column chromatography ($SiO_2$, 0 to 5% EtOAc/hexanes) provided the chloride as a pale yellow liquid (512 mg, 66%). $^1$H NMR ($CDCl_3$, 300 MHz) δ 7.30-7.48 (m, 4H), 4.58 (s, 2H), 1.70 (s, 3H), 1.63 (s, 3H).

The preparation of the 2-trimethylsilanyl ethyl ester of 4-bromomethyl benzoic acid, which is used in the synthesis of the compound of Example 470 is described by Graffner-Nordberg, M. et al., *Chem. Pharm. Bull.*, 46:591 (1998).

Conditions for Chromatographic Separation of Enantiomeric Mixtures

Condition 1: Example 345 was separated using the following method. 4.6×250 mm, 10 μM, Chiracel OJ column, 1.0 mL/min, 85% Hexane/EtOH 0.1% DEA, over 20 min.

Condition 2: Example 346 was separated using the following method. 4.6×250 mm, 10 μM, CHIRALPAK® AD column, 1.0 mL/min, 80% Hexane/EtOH 0.15% DEA, over 20 min.

Condition 3: Example 347 was separated using the following method. 4.6×250 mm, 10 μM, CHIRALPAK® AD column, 1.0 mL/min, 65% Hexane/IPA 0.1% DEA, over 18 min.

Condition 4: Examples 365 and 366 were separated using the following method. 4.6×250 mm, 10 μM, CHIRALPAK® AD column, 1.0 mL/min, 75% Hexane/EtOH 0.15% DEA, over 25 min.

Condition 5: Examples 408 and 409 were separated using the following method. 4.6×250 mm, 10 μM, Chiracel OD column, 1.0 mL/min, 90% Hexane/EtOH 0.15% DEA, over 36 min.

TABLE 4

![Structure: H2N-C(=O)-C(R1)(NR2)-S(=O)2-R3]

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 1 | isobutyl | 4-methoxybenzyl (OMe) | 4-chlorophenyl (Cl) | 1.2 | white solid | 424.95 | 1.76 Method B | 425.1 | ¹H NMR (CDCl₃) δ 7.63 (d, 2H, J = 7.0 Hz), 7.42 (d, 2H, J = 7.0 Hz), 7.25 (d, 2H, J = 8.0 Hz), 6.79 (d, 2H, J = 8.0 Hz), 6.25 (s, br, 1H), 5.35 (s, br, 1H), 4.36 (dd, 2H, J = 50 Hz, 15 Hz), 4.26 (t, 1H, J = 7.2 Hz), 3.78 (s, 3H), 1.83 (m, 1H), 1.18-1.34 (m, 3H), 0.75 (d, 3H, J = 7.0 Hz), 0.67 (d, 3H, J = 7.0 Hz) |
| 2 | isobutyl | benzyl | 4-chlorophenyl (Cl) | 1 | white solid | 394.92 | 1.71 Method B | 395.2 | ¹H NMR (DMSO-d₆) δ 7.81 (d, 2H, J = 7.0 Hz), 7.60 (d, 2H, J = 7.0 Hz), 7.50 (s, br, 1H), 7.41, (d, 2H, J = 8.0 Hz), 7.32 (m, 2H), 7.24 (m, 1H), 7.18 (s, br, 1H), 4.76 (dd, 2H, J = 50 Hz, 15 Hz), 4.36 (t, 1H, J = 7.0 Hz), 3.33 (s, 3H), 1.20-1.34 (m, 3H), 0.79 (d, 3H, J = 6.0 Hz), 0.46 (d, 3H, J = 6.0 Hz) |
| 3 | isobutyl | 4-trifluoromethylbenzyl (CF₃) | 4-chlorophenyl (Cl) | 1 | white solid | 462.92 | 1.71 Method A | 463.1 | ¹H NMR (DMSO-d₆) δ 7.83 (d, 2H, J = 7.0 Hz), 7.67 (d, 2H, J = 7.0 Hz), 7.57-7.62 (m, 4H), 7.06 (s, br, 1H), 4.79 (dd, 2H, J = 70 Hz, 17 Hz), 4.38 (t, 1H, J = 6.0 Hz), 3.32 (s, 3H), 1.23-1.35 (m, 3H), 0.81 (d, 3H, J = 6.0 Hz), 0.50 (d, 3H, J = 6.0 Hz) |

TABLE 4-continued

| Ex. No. | R¹ | R² | R³ | Reaction Scheme | Appearance | Calc. MW | Ret. Time/Method | M+H+ | NMR Data |
|---|---|---|---|---|---|---|---|---|---|
| 4 | isobutyl | 4-chlorobenzyl | 4-chlorophenyl | 1 | white solid | 429.37 | 1.69 Method A | 429.1 | $^1$H NMR (DMSO-$d_6$) δ 7.83 (d, 2H, J = 7.0 Hz), 7.61 (d, 2H, J = 7.0 Hz), 7.52 (s, br, 1H), 7.41 (d, 2H, J = 8.2 Hz), 7.37 (d, 2H, J = 8.2 Hz), 7.03 (s, br, 1H), 4.70 (dd, 2H, J = 50 Hz, 15 Hz), 4.35 (t, 1H, J = 7.0 Hz), 1.28-1.30 (m, 3H), 0.80 (d, 3H J = 6.0 Hz), 0.51 (d, 3H J = 6.0 Hz) |
| 5 | isobutyl | 4-phenylbutyl | 4-chlorophenyl | 1 | white solid | 422.98 | 1.71 Method A | 423.2 | $^1$H NMR (DMSO-$d_6$) δ 7.76 (d, 2H, J = 7.0 Hz), 7.61 (d, 2H J = 7.0 Hz), 7.42 (s, br, 1H), 7.16-7.20 (m, 5H), 6.99 (s, br, 1H), 4.24 (m, 1H), 3.45-3.51 (m, 1H), 3.10-3.18 (m, 1H), 2.52-2.59 (m, 2H), 1.95-2.05 (m, 1H), 1.69-1.80 (m, 1H), 1.55-1.34 (m,3H), 0.84 (m,6H) |
| 6 | isobutyl | 4-cyanobenzyl | 4-chlorophenyl | 1 | white solid | 419.93 | 1.45 Method A | 420.13 | $^1$H NMR (DMSO-$d_6$) δ 7.84 (d, 2H, J = 8.0 Hz), 7.79 (d, 2H, J = 8.0 Hz), 7.63 (d, 2H, J = 8.0 Hz), 7.58 (m, 3H), 7.03 (s, br, 1H), 4.87 (dd, 2H, J = 50 Hz, 15 Hz), 4.32 (t, 1H, J = 7.0 Hz), 1.28-1.30 (m, 3H), 0.81 (d, 3H J = 6.0 Hz), 0.53 (d, 3H, J = 6.0 Hz) |
| 7 | isobutyl | 4-fluorobenzyl | 4-chlorophenyl | 1 | white solid | 412.91 | 1.58 Method A | 413.4 | $^1$H NMR (DMSO-$d_6$) δ 7.81 (d, 2H, J = 7.0 Hz), 7.61 (d, 2H, J = 7.0 Hz), 7.51 (s, br, 1H), 7.43 (m, 1H), 7.11-7.14 (m, 2H), 7.03 (s, br, 1H), 4.77 (dd, 2H, J = 50 Hz,15 Hz),4.33 (t, 1H, J = 6.0 Hz), 1.21-1.31 (m, 3H), 0.80 (d, 3H, J = 6.0 Hz), 0.50 (d, 3H, J = 6.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 8 | isobutyl | 3-F-benzyl | 4-Cl-phenyl | 1 | white solid | 412.91 | 1.58 Method A | 413.2 | ¹H NMR (DMSO-d₆) δ 7.82 (d, 2H, J = 8.0 Hz), 7.61 (d, 2H, J = 8.0 Hz), 7.55 (s, br, 1H), 7.39 (m, 1H), 7.05-7.32 (m, 4H), 7.03 (s, br, 1H), 4.78 (dd, 2H, J = 50 Hz, 15 Hz), 4.38 (t, 1H, J = 6.0 Hz), 1.26-1.32 (m, 3H), 0.81 (d, 3H, J = 6.0 Hz), 0.54 (d, 3H, J = 6.0 Hz) |
| 9 | isobutyl | 4-tBu-benzyl | 4-Cl-phenyl | 1 | white solid | 451.03 | 2.99 Method C | 451.2 | ¹H NMR (DMSO-d₆) δ 7.75 (d, 2H, J = 8.5 Hz), 7.55 (d, 2H, J = 8.5 Hz), 7.51 (s, br, 1H), 7.25-7.29 (m, 4H), 7.03 (s, br, 1H), 4.69 (dd, 2H, J = 25 Hz, 14 Hz), 4.35 (m, 1H), 1.21-1.31 (m, 3H),1.25 (s, 9H) 0.81 (d, 3H, J = 6.0 Hz), 0.46 (d, 3H, J = 6.0 Hz) |
| 10 | isobutyl | 3-OMe-benzyl | 4-Cl-phenyl | 1 | white solid | 424.95 | 1.56 Method A | 425.2 | ¹H NMR (DMSO-d₆) δ 7.80 (d, 2H J = 8.0 Hz), 7.58 (d, 2H, J = 8.0 Hz), 7.50 (s, br, 1H), 7.21 (m, 1H), 7.04 (m, 1H), 6.80-6.95 (m, 3H), 4.70 (dd, 2H, J = 50 Hz, 15 Hz), 4.37 (m, 1H), 3.70 (s, 3H), 1.30-1.39 (m, 3H), 0.81 (d, 3H, J = 6.0 Hz), 0.52 (d, 3H, J = 6.0 Hz) |
| 11 | isobutyl | 3,4-diCl-benzyl | 4-Cl-phenyl | 1 | white solid | 463.81 | 1.76 Method A | 463 | ¹H NMR (DMSO-d₆) δ 7.80 (d, 2H, J = 8.0 Hz), 7.61 (d, 2H, J = 8.0 Hz), 7.55-7.60 (m, 2H), 7.40 (m, 1H), 7.10 (s, br, 1H), 4.72 (dd, 2H, J = 50 Hz, 15 Hz), 4.40 (m, 1H), 1.26-1.40 (m,3H), 0.83 (d, 3H, J = 6.0 Hz), 0.60 (d, 3H, J = 6.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 12 | isobutyl | 3-CF₃-benzyl (CH₂-C₆H₄-CF₃) | 4-Cl-phenyl | 1 | white solid | 462.92 | 1.68 Method A | 463.1 | ¹H NMR (DMSO-d₆) δ 7.80 (d, 2H, J = 8.0 Hz), 7.68-7.80 (m, 2H), 7.54-7.61 (m, 4H), 7.08 (s, br, 1H), 4.80 (dd, 2H, J = 50 Hz, 15 Hz), 4.38 (t, 1H, J = 6.0 Hz), 1.26-1.33 (m, 3H), 0.82 (d, 3H, J = 6.0 Hz), 0.52 (d, 3H, J = 6.0 Hz) |
| 13 | isobutyl | 3-F-4-OMe-benzyl | 4-Cl-phenyl | 1 | white solid | 442.94 | 1.55 Method A | 443.2 | ¹H NMR (DMSO-d₆) δ 7.78 (d, 2H, J = 8.0 Hz), 7.61 (d, 2H, J = 8.0 Hz), 7.56 (s, br, 1H), 7.05-7.24 (m, 4H), 4.65 (dd, 2H, J = 50 Hz, 15 Hz), 4.40 (t, 1H, J = 6.0 Hz), 3.81 (s, 3H) 1.28-1.35 (m, 3H), 0.81 (d, 3H, J = 6.0 Hz), 0.56 (d, 3H, J = 6.0 Hz) |
| 14 | isobutyl | 4-OH-benzyl | 4-Cl-phenyl | 1 | white solid | 410.92 | 1.51 Method B | 411.2 | ¹H NMR (CDCl₃) δ 7.69 (d, 2H, J = 8.0 Hz), 7.45 (d, 2H, J = 8.5 Hz), 7.26 (d, 2H, J = 8.5 Hz), 6.73 (d, 2H, J = 8.0 Hz), 6.33 (s, br, 1H), 5.24 (s, br, 1H), 4.28 (dd, 2H, J = 70 Hz, 20 Hz), 4.23 (m, 1H), 1.67-1.93 (m, 2H), 1.12-1.32 (m, 2H), 0.77 (d, 3H, J = 7.0 Hz), 0.68 (d, 3H, J = 7.0 Hz) |
| 15 | isobutyl | 3-F-4-OMe-benzyl | phenyl | 1 | sticky pale yellow foam | 408.5 | 1.58 Method B | 409.3 | ¹H NMR (CDCl₃) δ 7.77 (d, 2H, J = 8.0 Hz), 7.74-7.59 (m, 3H), 7.02-7.13 (m, 2H), 6.84 (t, 1H, J = 8.4 Hz), 6.32 (s, br, 1H), 5.31 (s, br, 1H), 4.48 (dd, 2H, J = 50 Hz, 17 Hz), 4.26 (m, 1H), 3.85 (s, 3H), 1.79-1.84 (m, 1H), 1.25-1.30 (m, 1H), 1.04-1.11 (m, 1H), 0.72 (d, 3H, J = 7.0 Hz), 0.63 |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 16 | isobutyl | 3-F-4-OMe-benzyl | 4-F-phenyl | 1 | white film | 426.49 | 1.63 Method B | 427.3 | ¹H NMR (CDCl₃) δ 7.73-7.77 (m, 2H), 6.81-7.18 (m, 5H), 6.29 (s, br, 1H), 5.37 (s, br, 1H), 4.45 (dd, 2H, J = 50 Hz, 17 Hz), 4.26 (m, 1H), 3.89 (s, 3H), 1.76-1.84 (m, 1H), 1.26-1.33 (m, 1H), 1.08-1.17 (m, 1H), 0.74 (d, 3H, J = 7.0 Hz), 0.66 (d, 3H, J = 7.0 Hz) |
| 17 | isobutyl | 3-F-4-OMe-benzyl | 4-CF₃-phenyl | 1 | pale yellow solid | 476.49 | 1.79 Method B | 477.2 | ¹H NMR (CDCl₃) δ 7.84 (d, 2H, J = 8.0 Hz), 7.72 (d, 1H, J = 8.0 Hz), 7.10 (d, 1H, J = 9.5 Hz), 6.99 (d, 2H, J = 8.5 Hz), 6.82 (t, 1H, J = 8.5 Hz), 6.21 (s, br, 1H), 5.35 (s, br, 1H), 4.46 (dd, 2H, J = 50 Hz,15 Hz), 4.31 (t, 1H, J = 7.5 Hz), 3.87 (s, 3H), 1.78-1.85 (m, 1H), 1.30-1.35 (m, 1H), 1.12-1.21 (m, 1H), 0.77 (d, 3H, J = 7.0 Hz), 0.68 (d, 3H, J = 7.0 Hz) |
| 18 | isobutyl | 3-F-4-OMe-benzyl | 3-CF₃-phenyl | 1 | pale yellow solid | 476.49 | 1.76 Method B | 477.2 | ¹H NMR (CDCl₃) δ 7.79-7.89 (m, 3H), 7.59-7.64 (m, 1H), 7.01-7.08 (m, 1H), 6.83 (t, 1H, J = 8.8 Hz), 6.25 (s, br, 1H), 5.42 (s, br, 1H), 4.45 (dd, 2H, J = 50 Hz, J = 7 Hz), 4.33 (m, 1H), 3.88 (s, 3H), 1.78-1.85 (m, 1H), 1.31-1.35 (m, 1H), 1.17-1.23 (m, 1H), 0.77 (d, 3H, J = 7.0 Hz), 0.70 (d, 3H, J = 7.0 Hz) |
| 19 | isobutyl | 3-F-4-OMe-benzyl | 3-Cl-phenyl | 1 | white solid | 442.94 | 1.73 Method B | 443.2 | ¹H NMR (CDCl₃) δ 7.42-7.63 (m, 4H), 7.02-7.10 (m, 2H), 6.86 (t, 1H, J = 8.5 Hz), 6.24 (s, br, 1H), 5.42 (s, br, 1H), 4.45 (dd, 2H, J = 50 Hz, 17 Hz), 4.27 (m, 1H), 3.87 (s, 3H), 1.79-1.87 (m, 1H), 1.27-1.33 (m, 1H), 1.14-1.22 (m, 1H), 0.78 (d, 3H, J = 7.0 Hz), 0.71 (d, 3H, J = 7.0 Hz) |

TABLE 4-continued

| Ex. No. | R¹ | R² | R³ | Reaction Scheme | Appearance | Calc. MW | Ret. Time/Method | M + H+ | NMR Data |
|---|---|---|---|---|---|---|---|---|---|
| 20 | isobutyl | 3-fluoro-4-methoxybenzyl | 3-methylphenyl | 1 | pale yellow oil | 422.52 | 1.68 Method B | 423.2 | $^1$H NMR (CDCl$_3$) δ 7.52-7.57 (m, 2H), 7.37-7.39 (m, 2H), 7.02-7.12 (m, 2H), 6.84 (t, 1H, J = 8.5 Hz), 6.34 (s, br, 1H), 5.35 (s, br, 1H), 4.45 (dd, 2H, J = 50 Hz, 17 Hz), 4.25 (m, 1H), 3.86 (s, 3H), 2.38 (s, 3H), 1.78-1.87 (m, 1H), 1.25-1.31 (m, 1H), 1.04-1.11 (m, 1H), 0.72 (d, 3H, J = 7.0 Hz), 0.65 (d, 3H, J = 7.0 Hz) |
| 21 | isobutyl | 3-fluoro-4-methoxybenzyl | 4-methylphenyl | 1 | pale yellow oil | 422.52 | 1.67 Method B | 423.2 | $^1$H NMR (CDCl$_3$) δ 7.64 (d, 2H, J = 8.0 Hz), 7.25-7.30 (m, 2H), 7.02-7.12 (m, 2H), 6.84 (t, 1H, J = 8.5 Hz), 6.34 (s, br, 1H), 5.32 (s, br, 1H), 4.45 (dd, 2H, J = 50 Hz, 17 Hz), 4.26 (t, 1H, J = 10 Hz), 3.86 (s, 3H), 2.42 (s, 3H), 1.76-1.85 (m, 1H), 1.25-1.31 (m, 1H), 1.05-1.12 (m, 1H), 0.72 (d, 3H, J = 7.0 Hz), 0.62 (d, 3H, J = 7.0 Hz) |
| 22 | isobutyl | imidazolyl-hexyl | 4-chlorophenyl | 3 | clear oil | 455.02 | 1.94 Method B | 455.2 | $^1$H NMR (DMSO-d$_6$) δ 7.82 (d, 2H, J = 8.0 Hz), 7.68 (d, 2H, J = 8.0 Hz), 7.56 (s, br, 1H), 7.45 (m, 1H), 7.16 (m, 1H), 7.04 (s, 1H), 6.86 (m, 1H), 4.25 (m, 1H), 3.94 (m, 1H), 3.40-3.55 (m, 2H), 3.02-3.14 (m, 1H), 1.18-1.69 (m, 10H), 0.76 (s, br, 6H) |
| 23 | isobutyl | 4-(methylthio)benzyl | 4-chlorophenyl | 1 | white solid | 441.01 | 1.67 Method A | 441.2 | $^1$H NMR (DMSO-d$_6$) δ 7.79 (d, 2H, J = 8.0 Hz), 7.59, 7.51 (s, br, 1H), 7.31 (d, 2H, J = 8.0 Hz), 7.19 (d, 2H, J = 8.0 Hz), 7.03 (s, br, 1H), 4.68 (dd, 2H, J = 50 Hz, 15 Hz), 4.35 (t, 1H, J = 7.0 Hz), 3.32 (s, 3H), 1.24-1.35 (m, 3H), 0.81 (d, 3H J = 6.0 Hz), 0.51 (d, 3H, J = 6.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 24 | isobutyl | -(CH₂)₇-Br | 4-chlorophenyl | 1 | white solid | 467.86 | 1.75 Method A | 469.1 | ¹H NMR (DMSO-d₆) δ 7.83 (d, 2H, J = 8.0 Hz), 7.64 (d, 2H, J = 8.0 Hz), 7.42 (s, br, 1H), 7.01 (s, 1H), 4.25 (m, 1H), 3.35-3.51 (m, 3H), 3.08-3.14 (m, 1H), 1.19-1.82 (m, 11H), 0.86 (d, 6H, J = 6.0 Hz) |
| 25 | isobutyl | -(CH₂)₇-morpholinyl | 4-chlorophenyl | 3 | clear oil | 474.07 | 1.34 Method A | 474.4 | ¹H NMR (DMSO-d₆) δ 7.82 (d, 2H, J = 8.0 Hz), 7.64 (d, 2H, J = 8.0 Hz), 7.42 (s, br, 1H), 6.99 (s, 1H), 4.25 (m, 1H), 3.51-3.60 (s, br, 4H), 3.18-3.41 (m, 2H), 2.25-2.35 (s, br, 4H), 2.27 (m, 2H) 1.15-1.62 (m, 9H), 0.80 (d, 6H, J = 6.0 Hz) |
| 26 | isobutyl | -(CH₂)₇-piperidinyl | 4-chlorophenyl | 3 | clear oil | 472.09 | 1.27 Method A | 472 | ¹H NMR (DMSO-d₆) δ 7.83 (d, 2H, J = 8.0 Hz), 7.64 (d, 2H, J = 8.0 Hz), 7.42 (s, br, 1H), 7.00 (s, 1H), 4.23-4.26 (m, 1H), 3.22-3.45 (m, 1H), 3.11-3.14 (m, 1H), 2.16-2.28 (m, 5H), 1.19-1.52 (m,18H), 0.86 (m, 6H) |
| 27 | isobutyl | -(CH₂)₇-thiomorpholinyl | 4-chlorophenyl | 3 | clear oil | 490.13 | 1.21 Method A | 490 | ¹H NMR (DMSO-d₆) δ 7.83 (d, 2H, J = 8.0 Hz), 7.64 (d, 2H, J = 8.0 Hz), 7.44 (s, br, 1H), 7.06 (s, 1H), 4.21-4.25 (m, 1H), 3.55 (s, br, 4H), 3.19-3.40 (m, 4H), 2.43-2.57 (m, 8H), 2.23-2.30 (m, 2H), 1.18-1.59 (m, 9H), 0.82 (m, 6H) |
| 28 | isobutyl | -(CH₂)₅-morpholinyl | 4-chlorophenyl | 3 | clear oil | 446.01 | 1.08 Method A | 446.2 | ¹H NMR (DMSO-d₆) δ 7.84 (d, 2H, J = 8.0 Hz), 7.66 (d, 2H, J = 8.0 Hz), 7.49 (s, br, 1H), 7.02 (s, 1H), 4.23-4.26 (m, 1H), 3.94 (s, br, 2H), 3.71 (s, br, 2H), 3.52-3.57 (m, 1H), 3.14-3.17 (m, 1H), 3.06 (s, br, 4H), 1.17-1.65 (m,7H), 0.86 (m, 6H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 29 | isobutyl | 3-fluoro-4-hydroxybenzyl | 4-chlorophenyl | 1 | white solid | 428.91 | 1.51 Method A | 429.1 | ¹H NMR (CDCl₃) δ 7.69 (d, 2H, J = 9.0 Hz), 7.47 (d, 2H, J = 9.0 Hz), 7.13 (d, 1H, J = 11.2 Hz), 7.00 (d, 1H, J = 8.0 Hz), 6.88 (m, 1H), 6.27 (s, br, 1H), 5.49 (s, br, 1H), 5.24 (s, br, 1H), 4.40 (dd, 2H, J = 90 Hz, 18 Hz), 3.20 (m, 1H), 1.09-1.82 (m, 3H), 0.77 (d, 3H, J = 7.0 Hz), 0.68 (d, 3H, J = 7.0 Hz) |
| 30 | isobutyl | 4-tert-butylbenzyl | 4-trifluoromethylphenyl | 1 | white solid | 484.59 | 1.89 Method A | 485.0 | ¹H NMR (CDCl₃) δ 7.73 (d, 2H, J = 8.0 Hz), 7.65 (d, 2H, J = 8.0 Hz), 7.18-7.27 (m, 4H), 6.25 (s, br, 1H), 5.29 (s, br, 1H), 4.40-4.69 (m, 3H), 1.80-1.88 (m, 1H), 1.29 (s, 9H), 1.25-1.33 (m, 2H), 0.80 (d, 3H, J = 7.0 Hz), 0.69 (d, 3H, J = 7.0 Hz) |
| 31 | isobutyl | 4-tert-butylbenzyl | 4-methylphenyl | 1 | white solid | 430.61 | 1.82 Method A | 431.2 | ¹H NMR (CDCl₃) δ 7.60 (d, 2H, J = 8.2 Hz), 7.24-7.39 (m, 6H), 6.34 (s, br, 1H), 5.19 (s, br, 1H), 4.42-4.44 (m, 2H), 4.30 (t, 1H, J = 8 Hz), 2.41 (s, 3H), 1.74-1.83 (m, 1H), 1.28 (s, 9H), 1.25-1.33 (m, 1H), 0.93-1.01 (m, 1H), 0.72 (d, 3H, J = 7.0 Hz), 0.60 (d, 3H, J = 7.0 Hz) |
| 32 | isobutyl | 6-morpholinohexyl | 4-chlorophenyl | 3 | brown oil | 460.04 | 1.15 Method A | 460.2 | ¹H NMR (DMSO-d₆) δ 7.83 (d, 2H, J = 8.0 Hz), 7.64 (d, 2H, J = 8.0 Hz), 7.42 (s, br, 1H), 7.00 (s, 1H), 4.22-4.26 (m, 1H), 3.55 (s, br, 4H), 3.11-3.32 (m, 2H), 2.13-2.37 (m, 6H), 1.12-1.51 (m, 9H), 0.86 (m, 6H) |

TABLE 4-continued

| Ex. No. | R$^1$ | R$^2$ | R$^3$ | Reaction Scheme | Appearance | Calc. MW | Ret. Time/Method | M + H$^+$ | NMR Data |
|---|---|---|---|---|---|---|---|---|---|
| 33 | isobutyl | cyclohexylmethyl | 4-chlorophenyl | 1 | white solid | 400.97 | 1.85 Method A | 401 | $^1$H NMR (DMSO-d$_6$) δ 7.85 (d, 2H, J = 8.0 Hz), 7.65 (d, 2H, J = 8.0 Hz), 7.32 (s, br, 1H) 7.05 (s, br, 1H), 4.19 (t, 1H, J = 7.5 Hz), 2.99-3.02 (m, 1H), 1.07-1.65 (m, 14H), 0.78-0.84 (m, 7H) |
| 34 | isobutyl | thiomorpholinyl-hexyl | 4-chlorophenyl | 3 | clear Oil | 476.1 | 1.28 Method A | 476.1 | $^1$H NMR (CDCl$_3$) δ 7.76 (d, 2H, J = 8.0 Hz), 7.51 (d, 2H, J = 8.0 Hz), 6.55 (s, br, 1H), 5.41 (s, 1H), 4.17-4.20 (m, 1H), 3.26-3.38 (m, 1H), 3.13-3.17 (m, 1H), 2.62-2.92 (m, 8H), 2.32-2.36 (m, 2H), 1.85-1.87 (m, 1H), 1.25-1.47 (m, 7H), 0.96-0.99 (m, 1H), 0.75 (d, 3H, J = 6.6 Hz), 0.72 (d, 2H, J = 6.6 Hz) |
| 35 | isobutyl | thiomorpholinyl-pentyl | 4-chlorophenyl | 3 | clear oil | 462.08 | 1.31 Method A | 462.2 | $^1$H NMR (CDCl$_3$) δ 7.75 (d, 2H, J = 8.0 Hz), 7.52 (d, 2H, J = 8.0 Hz), 6.51 (s, br, 1H), 6.05 (s, 1H), 4.15-4.18 (m, 1H), 3.56-3.78 (m, 4H), 3.45-3.47 (m, 1H), 3.09-3.14 (m, 1H), 2.90-3.08 (m, 4H), 2.61-2.69 (m, 2H), 1.62-2.05 (m, 5H), 1.21-1.29 (m, 1H), 0.80-0.83 (m, 1H), 0.78 (d, 3H, J = 6.6 Hz), 0.71 (d, 2H, J = 6.6 Hz) |
| 36 | isobutyl | dimethylamino-pentyl | 4-chlorophenyl | 3 | clear oil | 418.0 | 1.25 Method A | 418.2 | $^1$H NMR (CDCl$_3$) δ 7.77 (d, 2H, J = 8.5 Hz), 7.51 (d, 2H, J = 8.5 Hz), 6.56 (s, br, 1H), 5.41 (s, 1H), 4.18-4.21 (m, 1H), 3.15-3.32 (m, 2H), 2.25-2.28 (m, 2H), 2.24 (s, 6H), 1.84-1.88 (m, 1H), 1.25-1.49 (m, 7H), 0.97-1.00 (m, 1H), 0.71-0.74 (m, 6H) |

TABLE 4-continued

| Ex. No. | R¹ | R² | R³ | Reaction Scheme | Appearance | Calc. MW | Ret. Time/Method | M+H⁺ | NMR Data |
|---|---|---|---|---|---|---|---|---|---|
| 37 |  |  |  | 1 | tan solid | 428.91 | 1.5 Method A | 429.1 | ¹H NMR (CDCl₃) δ 7.57 (d, 2H, J = 8.0 Hz), 7.38 (d, 2H, J = 9.0 Hz), 7.03-7.13 (m, 2H), 6.80 (t, 1H, J = 8.8 Hz), 6.17 (s, br, 1H), 5.39 (s, br, 1H), 4.48 (dd, 2H, J = 55 Hz,16 Hz), 3.84 (s, 3H), 3.75-3.84 (m, 1H), 1.11-1.30 (m, 1H), 0.91 (d, 3H, J = 7.0 Hz), 0.54 (d, 3H, J = 7.0 Hz) |
| 38 |  |  |  | 1 | white solid | 412.46 | 1.49 Method A | 413.2 | ¹H NMR (CDCl₃) δ 7.65-7.70 (m, 2H), 7.04-7.12 (m, 4H), 6.79 (t, 1H, J = 8.5 Hz), 6.21 (s, br, 1H), 5.27 (s, br, 1H), 4.48 (dd, 2H, J = 50 Hz,15 Hz), 3.86 (s, 3H), 3.79-3.85 (m, 1H), 2.16-2.22 (m, 1H), 0.90 (d, 3H, J = 7.0 Hz), 0.51 (d, 3H, J = 7.0 Hz) |
| 39 |  |  |  | 1 | white solid | 403.48 | 1.47 Method A | 404.2 | ¹H NMR (CDCl₃) δ 7.77-7.80 (m, 2H), 7.59 (d, 2H, J = 8.0 Hz), 7.49 (d, 2H, J = 8.0 Hz), 7.17-7.22 (m, 2H), 6.17 (s, br, 1H), 5.20 (s, br, 1H), 4.50 (dd, 2H, J = 60 Hz,17 Hz), 4.28 (t, 1H, J = 10 Hz), 1.74-1.83 (m, 1H), 1.25-1.33 (m, 1H), 0.99-1.10 (m, 1H), 0.77 (d, 3H, J = 7.0 Hz), 0.66 (d, 3H, J = 7.0 Hz) |
| 40 |  |  |  | 1 | white solid | 453.49 | 1.65 Method A | 454.1 | ¹H NMR (CDCl₃) δ 7.88 (d, 2H, J = 8.2 Hz), 7.78 (d,2H,J=8.5Hz), 7.59 (d, 2H, J = 8.5 Hz), 7.49 (d, 2H, J = 8.5 Hz), 6.10 (s, br, 1H), 5.19 (s, br, 1H),4.59 (dd, 2H, J = 50 Hz,16 Hz), 4.33 (t, 1H, J = 10 Hz), 1.76-1.81 (m, 1H), 1.25-1.35 (m, 1H), 1.02-1.07 (m, 1H), 0.78 (d, 3H, J = 7.0 Hz), 0.65 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 41 | isobutyl | 4-cyanobenzyl | 4-methylphenyl | 1 | white solid | 399.52 | 1.53 Method A | 400.2 | ¹H NMR (CDCl₃) δ 7.65 (d, 2H, J = 8.0 Hz), 7.58 (d, 2H, J = 8.2 Hz), 7.47 (d, 2H, J = 8.0 Hz),7.31 (d, 2H, J = 8.5 Hz), 6.24 (s, br, 1H), 5.16 (s, br, 1H), 4.50 (dd, 2H, J = 50 Hz,17 Hz), 4.27 (t, 1H, J = 10 Hz), 2.44 (s, 3H), 1.74-1.83 (m, 1H), 1.25-1.33 (m, 1H), 0.93-1.01 (m, 1H), 0.74 (d, 3H, J = 7.0 Hz), 0.63 (d, 3H, J = 7.0 Hz) |
| 42 | isobutyl | imidazolyl-hexyl | 4-chlorophenyl | 3 | clear oil | 441.0 | 1.27 Method A | 441.2 | ¹H NMR (CDCl₃) δ 7.74 (d, 2H, J = 8.2 Hz),7.67 (s, 1H), 7.50 (d, 2H, J = 8.2 Hz), 7.10 (s, 1H)) 6.93 (s,1H), 6.51 (s, br, 1H) 5.55 (s, br, 1H), 4.14-4.17 (m, 1H), 3.97 (t, 2H, J = 6.0 Hz), 3.29-3.35 (m, 1H), 3.09-3.14 (m, 1H), 1.62-1.66 (m, 3H), 1.55-1.62 (m, 2H), 1.25-1.29 (m, 3H), 0.80-0.83 (m, 1H), 0.74 (d,3H, J = 6.6 Hz), 0.71 (d, 2H, J = 6.6 Hz) |
| 43 | isobutyl | diethylaminohexyl | 4-chlorophenyl | 3 | clear oil | 446.06 | 1.29 Method A | 446.3 | ¹H NMR (CDCl₃) δ 7.76 (d, 2H, J = 8.0 Hz), 7.52 (d, 2H, J = 8.0 Hz), 6.61 (s, br, 1H) 5.45 (s, 1H), 4.15-4.18 (m, 1H), 3.09-3.24 (m, 2H), 2.50-2.58 (m, 4H), 2.31-2.39 (m, 2H), 1.92-1.99 (m, 1H, 1.15-1.59 (m, 8H), 1.00-1.04 (m, 7H), 0.71-0.74 (m, 6H) |

TABLE 4-continued

| Ex. No. | R¹ | R² | R³ | Reaction Scheme | Appear-ance | Calc. MW | Ret. Time/ Method | M + H⁺ | NMR Data |
|---|---|---|---|---|---|---|---|---|---|
| 44 | n-butyl | 3-fluoro-4-methoxybenzyl | 4-chlorophenyl | 1 | tan wax | 428.91 | 1.58 Method A | 429.1 | ¹H NMR (CDCl₃) δ 7.67 (d, 2H, J = 8.0 Hz), 7.45 (d, 2H, J = 9.0 Hz), 7.03-7.15 (m, 2H), 6.84 (t, 1H, J = 8.0 Hz), 6.25 (s, br, 1H), 5.19 (s, br, 1H), 4.45 (dd, 2H, J = 80 Hz, 18 Hz), 4.19-4.22 (m, 1H), 3.87 (s, 3H), 1.82-1.95 (m, 1H), 0.96-1.30 (m, 3H), 0.72-0.77 (m, 3H) |
| 45 | isobutyl | tetrahydroisoquinolinyl-alkyl | 4-chlorophenyl | 3 | clear oil | 506.11 | 1.39 Method A | 506.2 | ¹H NMR (CDCl₃) δ 7.75 (d, 2H, J = 8.0 Hz), 7.50 (d, 2H, J = 8.5 Hz), 7.01-7.13 (m, 4H), 6.55 (s, br, 1H), 5.39 (s, br, 1H), 4.18 (t, 1H, J = 6.0 Hz), 3.32-3.60 (m, 1H), 3.16-19 (m, 1H), 2.91 (s, br, 2H), 2.76 (s, br, 2H), 2.52 (s, br, 2H), 1.27-1.86 (m, 8H), 0.97-1.00 (m, 1H), 0.73 (m, 6H) |
| 46 | isobutyl | tert-butyl ester alkyl | 4-chlorophenyl | 1 | white solid | 418.94 | 2.7 Method A | 441 (M + Na⁺) | ¹H NMR (DMSO-d₆) δ 7.89 (d, 2H, J = 8.2 Hz), 7.65 (d, 2H, J = 8.4 Hz), 7.52 (s, br, 1H) 7.00 (s, br, 1H), 4.25 (dd, 2H, J = 80 Hz, 18 Hz), 4.10-4.13 (m, 1H), 2.59-2.60 (m, 1H), 1.35 (s, 9H), 1.32-1.35 (m, 2H), 0.860 (d, 3H, J = 6.0 Hz), 0.75 (d, 3H, J = 6.0 Hz) |
| 47 | isobutyl | 4-nitrobenzyl | 4-chlorophenyl | 1 | yellow solid | 439.92 | 1.69 Method A | 440.2 | ¹H NMR (CDCl₃) δ 8.17 (d, 2H, J = 7.0 Hz), 7.72 (d, 2H, J = 7.0 Hz), 7.54 (d, 1H, J = 8.8 Hz), 7.49 (d, 1H, J = 8.8 Hz), 6.14 (s, br, 1H), 5.18 (s, br, 1H), 4.60 (dd, 2H, J = 70 Hz, 18 Hz), 4.29-4.34 (m, 1H), 1.74-1.83 (m, 1H), 1.00-1.34 (m, 2H), 0.78 (d, 3H, J = 7.0 Hz), 0.67 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 48 | isobutyl | 4-aminobenzyl | 4-chlorophenyl | 4 | tan solid | 409.94 | 1.26 Method A | 410.1 | ¹H NMR (CDCl₃) δ 7.80 (d, 2H, J = 8.5 Hz), 7.63 (d, 2H, J = 8.5 Hz), 7.52 (s, br, 1H), 7.46 (d, 1H, J = 8.0 Hz), 7.26 (d, 1H, J = 8.0 Hz), 7.02 (s, br, 1H), 4.70 (dd, 2H, J = 50 Hz 18 Hz), 4.30-4.41 (m, 1H), 3.67 (s, br, 2H), 1.28-1.33 (m,3H), 0.86 (d, 3H, J = 7.0 Hz), 0.57 (d, 3H, J = 7.0 Hz) |
| 49 | isobutyl | morpholinopropyl | 4-chlorophenyl | 3 | tan foam | 431.99 | 1.19 Method A | 432 | ¹H NMR (DMSO-d₆) δ 7.81 (d, 2H, J = 8.0 Hz), 7.66 (d, 2H, J = 8.0 Hz), 7.45 (s, br, 1H), 7.02 (s, 1H), 4.27 (m, 1H), 3.56 (s, br, 4H), 3.55-3.57 (m, 1H), 3.08-3.14 (m, 1H), 2.22-2.32 (m, 6H), 1.79-1.82 (m, 11H), 1.17-1.62 (m, 4H), 0.86 (d, 6H, J = 6.0 Hz) |
| 50 | isobutyl | methyl 4-benzoate | 4-fluorophenyl | 1 | white solid | 436.51 | 1.58 Method A | 437.1 | ¹H NMR (CDCl₃) δ 7.95 (d, 2H, J = 8.0 Hz), 7.74-7.79 (m, 2H), 7.42 (d, 2H, J = 8.0 Hz), 7.14-7.19 (m, 2H) 6.24 (s, br, 1H), 5.20 (s, br, 1H),4.50 (dd, 2H, J = 50 Hz, 17 Hz), 4.12 (m, 1H), 3.91 (s, 3H), 1.75-1.82 (m, 1H), 1.25-1.31 (m, 1H), 1.05-1.12 (m, 1H), 0.75 (d, 3H, J = 7.0 Hz), 0.64 (d, 3H, J = 7.0 Hz) |
| 51 | isobutyl | 4-(methylamino)benzyl | 4-chlorophenyl | 4 | tan solid | 423.97 | 1.21 Method A | 424.1 | ¹H NMR (CDCl₃) δ 7.65 (d, 2H, J = 8.0 Hz), 7.58 (d, 2H, J = 8.2 Hz), 7.47 (d, 2H, J = 8.0 Hz), 7.31 (d, 2H, J = 8.5 Hz), 6.24 (s, br, 1H), 5.16 (s, br, 1H), 4.50 (dd, 2H, J = 50 Hz, 17 Hz), 4.27 (t, 1H, J = 10 Hz), 2.44 (s, 3H), 1.74-1.83 (m, 1H), 1.25-1.33 (m, 1H), 0.93-1.01 (m, 1H), 0.74 (d, 3H, J = 7.0 Hz), 0.63 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 52 | n-propyl | 4-CF₃-benzyl | 4-Cl-phenyl | 1 | white solid | 448.90 | 1.79 Method A | 449.0 | ¹H NMR (CDCl₃) δ 7.66 (d, 2H, J = 8.5 Hz), 7.43 (d, 2H, J = 8.5 Hz), 7.12 (d, 1H, J = 8.0 Hz), 6.49 (d, 1H, J = 8.0 Hz), 6.24 (s, br, 1H), 5.22 (s, br, 1H), 4.35 (dd, 2H, J = 50 Hz, 15 Hz), 4.22-4.27 (m, 1H), 2.04 (s, 3H), 1.27-1.89 (m, 3H), 0.74 (d, 3H, J = 7.0 Hz), 0.68 (d, 3H, J = 7.0 Hz) |
| 53 | iso-butyl | 2-OMe-benzyl | 4-Cl-phenyl | 1- Method A | white solid | 424.95 | 1.58 Method A | 425.2 | ¹H NMR (DMSO-d₆, 500 MHz) δ 7.82 (d, 2H, J = 8.2), 7.62 (d, 2H, J = 8.3), 7.44 (d, 2H, J = 7.1), 7.21 (t, 1H, J = 6.7), 6.97 (s, 1H), 6.92 (d, 2H, J = 6.9), 4.99 (d, 1H, J = 17), 4.40 (d, 1H, J = 17), 4.33 (br s, 1H), 3.76 (s, 3H), 1.20-1.40 (m, 3H), 0.79 (d, 3H, 5.2), 0.54 (d, 3H, J = 5.2) |
| 54 | n-propyl | 3-F-4-OMe-benzyl | 4-Cl-phenyl | 1- Method A | white solid | 400.86 | 1.81 min Method B | 398.94 (M − H⁻) | ¹H NMR (CDCl₃) δ 7.71 (d, 2H, J = 6.8 Hz), 7.48 (d, 2H, J = 6.8 Hz), 7.15 (d, 2H, J = 10 Hz), 7.02 (d, 2H, J = 8.0 Hz), 6.85 (t, 1H, J = 7.5 Hz), 6.19 (s, br, 1H), 5.13 (s, br, 1H), 4.31 (dd, 2H, J = 50 Hz, 15 Hz), 4.43-4.45 (m, 1H), 3.87 (s, 3H), 1.17 (d, 3H, J = 6.8 Hz) |
| 55 | iso-butyl | 4-OCF₃-benzyl | 4-Cl-phenyl | 1- Method A | white solid | 478.92 | 1.76 Method A | 479.1 | 7.81 (d, 2H, J = 8.5), 7.60 (d, 2H, J = 8.2), 7.54 (s, 1H), 7.51 (d, 2H, J = 8.5), 7.30 (d, 2H, J = 8.2), 7.04 (s, 1H), 4.83 (d, 1H, J = 17), 4.71 (s, 1H), 1.20-1.35 (m, 3H), 0.80 (d, 3H, J = 6.1), 0.47 (d, 3H, J = 6.2) |

TABLE 4-continued

| Ex. No. | R¹ | R² | R³ | Reaction Scheme | Appearance | Calc. MW | Ret. Time/Method | M+H⁺ | NMR Data |
|---|---|---|---|---|---|---|---|---|---|
| 56 | isobutyl | 4-tert-butylbenzyl | 4-fluorophenyl | 1-Method A | white solid | 434.58 | 1.95 min Method A | 435.24 | ¹H NMR (CDCl₃, 300 MHz) δ 7.67 (dd, 2H, J = 5.0, 8.9), 7.20-7.30 (m, 4H), 7.09 (dd, 2H, J = 8.6, 8.6), 6.28 (brs, 1H), 5.24 (brs, 1H), 4.44 (s, 2H), 4.34 (t, 1H, J = 7.8), 1.75-1.90 (m, 1H), 1.22-1.38 (m, 2H), 1.30 (s, 9H), 0.77 (d, 3H, J = 6.4), 0.67 (d, 3H, J = 6.4) |
| 57 | isobutyl | piperidinyl-alkyl | 4-chlorophenyl | 3 | brown oil | 458.07 | 2.16 Method C | 458.2 | ¹H NMR (CDCl₃, 300 MHz) δ 7.77 (dd, 2H, J = 1.6, 6.8), 7.53 (dd, 2H, J = 2.0, 6.7), 6.55 (s, 1H), 5.64 (s, 1H), 4.15 (dd, 1H, J = 5.6, 9.2), 3.57 (t, 2H, J = 12), 3.35-3.45 (m, 1H), 3.10-3.17 (m, 1H), 2.87-3.00 (m, 2H), 2.57-2.70 (m, 2H), 2.27-2.40 (m, 2H), 1.80-2.00 (m, 6H), 1.63-1.73 (m, 2H), 1.20-1.50 (m, 4H), 0.85-0.90 (m, 1H), 0.73 (d, 3H, J = 6.4), 0.70 (d, 3H, J = 6.9) |
| 58 | isobutyl | methyl ester alkyl | 4-chlorophenyl | 5 | colorless oil | 390.89 | 1.51 Method A | 391.2 | ¹H NMR (CDCl₃, 300 MHz) δ 7.91 (dd, 2H, J = 2.0, 6.8), 7.51 (dd, 2H, J = 2.2, 6.9), 7.06 (s, 1H), 5.33 (s, 1H), 4.13-4.25 (m, 2H), 4.03-4.15 (m, 3H), 1.77-1.85 (m, 1H), 1.35-1.45 (m, 1H), 1.30 (t, 3H, J = 7.1), 1.15-1.22 (m, 1H), 0.74 (d, 3H, J = 6.6), 0.71 (d, 3H, J = 6.5) |
| 59 | isobutyl | carboxylic acid alkyl | 4-chlorophenyl | 5 | white solid | 362.83 | 1.28 Method A | 363.1 | ¹H NMR (DMSO-d₆, 500 MHz) δ 7.90 (dd, 2H, J = 2.0, 6.8), 7.65 (dd, 2H, J = 2.0, 6.8), 7.60 (s, 1H), 7.06 (s, 1H), 4.32 (d, 1H, J = 18), 4.12 (t, 1H, J = 8.0), 4.02 (d, 1H, J = 18), 1.55-1.65 (m, 1H), 1.35-1.45 (m, 2H), 0.78 (d, 3H, J = 6.1), 0.73 (d, 3H, J = 6.1) |

TABLE 4-continued

Structure: H₂N-C(=O)-C(R¹)(NR²)-S(=O)₂-R³

| Ex. No. | R¹ | R² | R³ | Reaction Scheme | Appearance | Calc. MW | Ret. Time/Method | M+H+ | NMR Data |
|---|---|---|---|---|---|---|---|---|---|
| 60 | isobutyl | 4-methylbenzyl-CH₂ | 4-chlorophenyl | 1-solid support | white solid | 408.95 | 1.82 min Method B | 409.1 | $^1$H NMR (CDCl$_3$) δ 7.64 (d, 2H, J = 8.0 Hz), 7.44 (d, 2H, J = 8.0 Hz), 7.22 (d, 2H, J = 8.0 Hz), 7.08 (d, 2H, J = 8.0 Hz), 6.29 (s, br, 1H), 5.34 (s, br, 1H), 4.53 (d, 1H, J = 15.20 Hz), 4.34 (d, 1H, J = 15.20 Hz), 4.27 (t, 1H, J = 7.2 Hz), 2.32 (s, 3H), 1.84 (m, 1H), 1.30 (m, 1H), 1.21 (m, 1H), 0.75 (d, 3H, J = 6.8 Hz), 0.67 (d, 3H, J = 6.8 Hz) |
| 61 | isobutyl | 4-(methoxycarbonyl)benzyl-CH₂ | 4-chlorophenyl | 1-Method A | white solid | 452.96 | 1.85 min Method A | 453.08 | $^1$H NMR (CDCl$_3$, 300 MHz) δ 7.97 (dd, 2H, J = 1.7, 8.4), 7.68 (dd, 2H, J = 2.0, 8.7), 7.41-7.48 (m, 4H), 6.23 (brs, 1H), 5.16 (brs, 1H), 4.64 (d, 1H, J = 15.8), 4.47 (d, 1H, J = 15.9), 4.31 (t, 1H, J = 7.8), 3.92 (s, 3H), 1.76-1.83 (m, 1H), 1.26-1.35 (m, 1H), 1.08-1.13 (m, 1H), 0.76 (d, 3H, J = 6.0), 0.65 (d, 3H, J = 6.7) |
| 62 | isobutyl | 2,5-difluorobenzyl-CH₂ | 4-chlorophenyl | 1-solid support | white solid | 430.95 | 1.81 min Method B | 431.06 | $^1$H NMR (CDCl$_3$) δ 7.72 (d, 2H, J = 8.0 Hz), 7.49 (d, 2H, J = 8.0 Hz), 7.24 (m, 1H), 6.95 (m, 2H), 6.25 (d, br, 1H), 5.27 (s, br, 1H), 4.62 (d, 1H, J = 16.0 Hz), 4.45 (d, 1H, J = 16.0 Hz), 4.33 (t, 1H, J = 6.8 Hz), 1.84 (m, 1H), 1.30 (m, 1H), 1.21 (m, 1H), 0.78 (d, 3H, J = 6.8 Hz), 0.70 (d, 3H, J = 6.8 Hz) |
| 63 | isobutyl | biphenyl-CH₂ | 4-chlorophenyl | 1-solid support | pale yellow solid | 471.02 | 2.04 min Method B | 471.09 | $^1$H NMR (CDCl$_3$) δ 7.65 (d, 2H, J = 8.0 Hz), 7.58 (d, 2H, J = 8.0 Hz), 7.47 (m, 6H), 6.27 (s, br, 1H), 5.33 (s, br, 1H), 4.58 (d, 1H, J = 15.2 Hz), 4.45 (d, 1H, J = 15.2 Hz), 4.36 (t, 1H, J = 7.2 Hz), 1.84 (m, 1H), 1.30 (m, 1H), 1.21 (m, 1H), 0.78 (d, 3H, J = 6.8 Hz), 0.70 (d, 3H, J = 6.8 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 64 | isobutyl | prenyl | 4-chlorophenyl | 1-solid support | pale pink solid | 372.92 | 1.82 min Method B | 395.11 M + Na | ¹H NMR (CDCl₃) δ 7.65 (d, 2H, J = 8.0 Hz), 7.50 (d, 2H, J = 8.0 Hz), 6.75 (s, br, 1H), 6.70 (s, br, 1H), 5.04 (m, 1H), 4.32 (t, 1H, J = 7.2 Hz), 3.91 (d br, 2H, J = 7.0 Hz), 1.81 (m, 1H), 1.66 (s br, 6H), 1.30 (m, 1H), 1.21 (m, 1H), 0.77 (d, 3H, J = 6.5 Hz), 0.76 (d, 3H, J = 6.5 Hz) |
| 65 | isobutyl | 4-(dimethylamino)phenethyl | 4-chlorophenyl | 4 | white solid | 437.99 | 1.39 Method A | 438.1 | ¹H NMR (DMSO-d₆, 500 MHz) δ 7.74 (dd, 2H, J = 1.9, 6.7), 7.5 (dd, 2H, J = 1.9, 6.8), 7.43 (s, 1H), 7.16 (d, 2H, J = 8.6), 7.01 (s, 1H), 6.61 (d, 2H, J = 8.8), 4.59 (q, 2H, J = 16, 25), 4.34 (dd, 1H, J = 5.0, 9.3), 2.85 (s, 6H), 1.27-1.47 (m, 3H), 0.80 (d, 3H, J = 5.9), 0.52 (d, 3H, J = 6.1) |
| 66 | isobutyl | 4-(methylsulfonyl)phenethyl | 4-chlorophenyl | 1-Method A | white solid | 473.01 | 1.58 Method A | 437.0 | ¹H NMR (DMSO-d₆, 500 MHz) δ 7.87 (d, 2H, J = 8.2), 7.83 (d, 2H, J = 8.3), 7.64 (d, 2H, J = 8.5), 7.63 (d, 2H, J = 8.5), 7.59 (s, 1H), 7.08 (s, 1H), 4.92 (d, 1H, J = 17), 4.76 (d, 1H, J = 17), 4.39 (t, 1H, J = 6.9), 3.35 (brs, 1H), 1.20-1.40 (m, 3H), 0.81 (d, 3H, J = 6.2), 0.54 (d, 3H, J = 6.2) |
| 67 | isobutyl | butyl | 4-chlorophenyl | 1-Method A | colorless oil | 346.88 | 1.79 Method A | 347.1 | ¹H NMR (DMSO-d₆, 500 MHz) δ 7.83 (d, 2H, J = 8.8), 7.63 (d, 2H, J = 8.6), 7.41 (s, 1H), 7.0 (s, 1H), 4.25 (dd, 1H, J = 4.8, 8.9), 3.38-3.47 (m, 1H), 3.0-3.13 (m, 1H), 1.55-1.70 (m, 1H), 1.40-1.55 (m, 1H), 1.30-1.40 (m, 1H), 0.87 (t, 3H, J = 7.6), 0.73 (d, 3H, J = 6.4), 0.72 (d, 3H, J = 6.7) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 68 | isobutyl | thiomorpholinobutyl | 4-Cl-phenyl | 3 | white oil | 448.05 | 1.25 min Method C | 448.19 | $^1$H NMR (CDCl$_3$, 500 MHz), δ 7.76 (dd, 2H, J = 2.0, 6.7), 7.50 (dd, 2H, J = 2.0, 6.7), 6.51 (s, 1H), 5.45 (s, 1H), 4.20 (dd, 1H, J = 6.4, 8.2), 3.35-3.45 (m, 1H), 3.20-3.30 (m, 1H), 2.68 (brs, 8H), 2.35 (br s, 2H), 1.70-1.90 (m, 3H), 1.20-1.40 (m, 1H), 0.95-1.05 (m, 1H), 0.75 (d, 3H, J = 4.3), 0.73 (d, 3H, J = 4.4) |
| 69 | isobutyl | 4-carboxyphenylmethyl | 4-F-phenyl | 6 | white solid | 422.48 | 1.56 min Method A | 423.14 | $^1$H NMR (CDCl$_3$, 300 MHz) δ 7.89-7.93 (m, 4H), 7.84 (br s, 1H), 7.49 (d, 2H, J = 8.2), 7.24-7.29 (m, 2H), 6.58 (brs, 1H), 5.12 (d, 1H, J = 15.3), 4.23 (dd, 1H, J = 4.6, 9.7), 4.05 (d, 1H, J = 15.4), 2.04-2.14 (m, 1H), 1.23-1.32 (m, 1H), 0.79-0.88 (m, 1H), 0.72 (d, 3H, J = 6.6), 0.67 (d, 3H, J = 6.6) |
| 70 | propyl | 4-F-3-CF₃-phenylmethyl | 4-Cl-phenyl | 1-Method A | white solid | 466.89 | 1.77 min Method B | 467.03 | $^1$H NMR (CDCl$_3$) δ 7.65 (d, 2H, J = 6.8 Hz), 7.52-7.56 (m, 2H), 7.47 (d, 2H, J = 6.8 Hz), 7.11 (t, 1H, J = 8.5 Hz), 6.22 (s, br, 1H), 5.24 (s, br, 1H), 4.41 (dd, 2H, J = 50 Hz, 15 Hz), 4.28 (t, 1H, 7.5 Hz), 1.80-1.92 (m, 1H), 1.21-1.30 (m, 1H), 0.95-1.19 (m, 2H), 0.76 (t, 3H, J = 7.0 Hz) |
| 71 | propyl | 4-F-phenylmethyl | 4-Cl-phenyl | 1-Method A | white wax | 398.89 | 1.80 min Method B | 388.0 | $^1$H NMR (CDCl$_3$) δ 7.67 (d, 2H, J = 8.0 Hz) 7.54 (d, 2H, J = 8.0 Hz), 7.42-7.49 (m, 4H), 6.20 (s, br, 1H), 5.21 (s, br, 1H), 4.54 (dd, 2H, J = 50 Hz, 15 Hz), 4.25-4.29 (m, 1H), 1.82-1.95 (m, 1H), 1.26-1.33 (m, 1H), 0.98-1.12 (m, 2H), 0.75 (t, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 72 | (propyl) | 2-cyanobiphenyl-4-ylmethyl | 4-chlorophenyl | 1-Method A | white solid | 482.01 | 1.79 min Method B | 482.06 | ¹H NMR (CDCl₃) δ 7.76 (d, 1H, J = 7.5 Hz), 7.63-7.67 (m, 4H), 7.43-7.50 (m, 8H), 6.24 (s, br, 1H), 5.28 (s, br, 1H), 4.53 (dd, 2H, J = 50 Hz, 15 Hz), 4.27 (t, 1H, J = 7.3 Hz), 1.87-1.99 (m, 1H), 1.30-1.39 (m, 1H), 1.03-1.11 (m, 2H), 0.76 (t, 3H, J = 8.0 Hz) |
| 73 | (allyl) | 3-fluoro-4-methoxybenzyl | 4-chlorophenyl | 1-Method A | pale yellow solid | 426.90 | 1.86 min Method A | 427.09 | ¹H NMR (CDCl₃, 300 MHz) δ 7.69 (ddd, 2H, J = 2.0, 2.7, 8.7), 7.47 (dd, 2H, J = 2.0, 8.7), 7.15 (dd, 1H, J = 2.1, 12.0), 7.03 (d, 1H, J = 8.4), 6.84 (t, 1H, J = 8.5), 6.30 (br s, 1H), 5.25-5.30 (m, 2H), 4.96 (d, 1H, J = 1.4), 4.87 (dd, 1H, J = 1.4, 9.9), 4.57 (d, 1H, J = 15.4), 4.23-4.32 (m, 2H), 3.87 (s, 3H), 2.60-2.67 (m, 1H), 2.15-2.24 (m, 1H) |
| 74 | (allyl) | 4-(methoxycarbonyl)benzyl | 4-chlorophenyl | 1-Method A | colorless oil | 436.92 | 1.88 min Method A | 437.09 | ¹H NMR (CDCl₃, 300 MHz) δ 7.97 (dd 2H, J = 1.7, 8.3), 7.71 (dd, 2H, J = 2.0, 8.7), 7.43-7.50 (m, 4H), 6.26 (br s, 1H), 5.22-5.35 (m, 1H), 5.18 (br s, 1H), 4.84-4.96 (m, 2H), 4.69 (d, 1H, J = 15.8), 4.41 (d, 1H, J = 15.8), 4.31 (t, 1H, J = 7.5), 3.91 (s, 3H), 2.60-2.67 (m, 1H), 2.11-2.24 (m, 1H) |
| 75 | (allyl) | 4-cyanobenzyl | 4-chlorophenyl | 1-Method A | white solid | 403.89 | 1.63 min Method A | 404.03 | ¹H NMR (CDCl₃) δ 7.71 (ddd, 2H, J = 2.0, 2.6, 8.7), 7.60 (dd, 2H, J = 1.9, 8.3), 7.49-7.52 (m, 4H), 6.21 (br s, 1H), 5.22-5.33 (m, 1H), 5.17 (br s, 1H), 4.88-4.98 (m, 2H), 4.71 (d, 1H, J = 16.2), 4.40 (d, 1H, J = 16.1), 4.32 (t, 1H, J = 7.6), 2.54-2.63 (m, 1H), 2.09-2.19 (m, 1H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 76 | isobutyl | 4-(trifluoromethyl)benzyl | 4-chlorophenyl | 1-Method A | white solid | 446.88 | 2.04 min Method A | 447.05 | ¹H NMR (CDCl₃, 300 MHz) δ 7.67 (d, 2H, J = 8.6), 7.45-7.56 (m, 6H), 6.24 (br s, 1H), 5.25-5.39 (m, 1H), 5.19 (br s, 1H), 4.88-4.98 (m, 2H), 4.68 (d, 1H, J = 15.8), 4.42 (d, 1H, J = 15.81), 4.34 (t, 1H, J = 7.5), 2.58-2.68 (m, 1H), 2.13-2.23 (m, 1H) |
| 77 | n-propyl | 4-cyanobenzyl | 4-chlorophenyl | 1-Method A | white solid | 405.91 | 1.51 min Method B | 406.2 | ¹H NMR (CDCl₃) δ 7.70 (d, 2H, J = 8.0Hz) 7.68 (d, 2H, J = 8.0 Hz), 7.47-7.51 (m, 4H), 6.15 (s, br, 1H), 5.16 (s, br, 1H),4.53 (dd, 2H, J = 50 Hz, 15 Hz), 4.21-4.26 (m, 1H), 1.82-1.87 (m, 1H), 1.20-1.25 (m, 1H), 0.97-1.09 (m, 2H), 0.74 (t, 3H, J = 7.0 Hz) |
| 78 | isobutyl | 1-phenylethyl | 4-chlorophenyl | 1-solid support | white foam | 408.95 | 1.84 min Method B | 431.04 M + Na | ¹H NMR (CDCl₃) δ 7.83 (d, 2H, J = 8.0Hz), 7.52 (d, 2H, J = 8.0 Hz), 7.34-7.45 (m, 5H), 5.85 (s, br, 2H), 5.17 (q, 1H, 7.2 Hz), 3.78 (dd 1H, J = 8.4 Hz, 4 Hz), 2.36 (m, 1H), 1.62 (m, 1H), 1.50 (d, 3H, J = 7.2 Hz), 1.23 (m, 1H), 0.91 (d, 3H, J = 6.6 Hz), 0.84 (d, 3H, J = 6.6 Hz) |
| 79 | isobutyl | 2-phenylethyl | 4-chlorophenyl | 1-solid support | colorless syrup | 408.95 | 1.89 Method B | 431.04 M + Na | ¹H NMR (CDCl₃) δ 7.77 (d, 2H, J = 8.0Hz), 7.50 (d, 2H, J = 8.0 Hz), 7.17-7.32 (m, 5H), 6.67 (s, br, 1H), 6.15 (s, br, 1H), 5.17 (q, 1H, 7.2 Hz), 4.26 (dd 1H, J = 6.6 Hz), 3.48 (m, 1H), 3.37 (m, 1H), 2.97 (m, 1H), 2.90 (m, 1H), 1.92 (m, 1H), 1.33 (m, 1H), 1.10 (m, 1H), 0.76 (d, 3H, J = 6.6 Hz), 0.75 (d, 3H, J = 6.6 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 80 | isobutyl | (6-chloropyridin-3-yl)methyl | 4-chlorophenyl | 1- solid support | yellow solid | 430.36 | 1.64 min Method B | 430.02 | $^1$H NMR (CDCl$_3$) δ 8.34 (s, 1H), 7.67 (d, 1H, J = 6.8 Hz), 7.48 (d, 1H, J = 6.8 Hz), 7.25 (d, 1H, J = 6.8 Hz), 6.1 (br. S, 1H), 5.29 (br. s, 1H), 4.59 (d, 1H, J = 16 Hz), 4.39 (d, 1H, J = 16 Hz), 1.8 (m, 1H), 1.32 (m, 1H), 1.06 (m, 1H), 0.78 (d, 3H, J = 64 Hz), 0.68 (d, 3H, J = 6.4 Hz) |
| 81 | isobutyl | (5-chlorothiophen-2-yl)methyl | 4-chlorophenyl | 1- solid support | white solid | 435.39 | 1.87 Method B | 456.92 M + Na | $^1$H NMR (CDCl$_3$) δ 7.64 (d, 2H, J = 8.0 Hz), 7.50 (d, 2H, J = 8.0 Hz), 6.79 (d, 1H, J = 3.7 Hz), 6.72 (d, 1H, J = 3.7 Hz), 4.60 (d, 1H, J = 21.9), 4.56 (d, 1H, J = 21.9 Hz), 4.28 (t, 1H, J = 7.4 Hz), 1.86 (m, 1H), 1.33 (m, 1H), 1.25 (m, 1H), 0.76 (d, 3H, J = 6.5 Hz), 0.73 (d, 3H, J = 6.5 Hz) |
| 82 | isobutyl | cinnamyl | 4-chlorophenyl | 1- Method A | white solid | 420.96 | 1.97 Method A | 421.2 | $^1$H NMR (CDCl$_3$, 500 MHz) δ 7.77 (d, 2H, J = 8.6), 7.45 (d, 2H, J = 9.10), 7.26–7.35 (m, 5H), 6.54 (d, 1H, J = 16), 6.38 (brs, 1H), 6.00–6.07 (m, 1H), 5.34 (br s, 1H), 4.36 (t, 1H, J = 7.2), 4.02–4.15 (m, 2H), 1.83–1.92 (m, 1H), 1.35–1.43 (m, 1H), 1.25–1.32 (m, 1H), 0.79 (d, 3H, J = 6.7), 0.77 (d, 3H, J = 6.7) |
| 83 | isobutyl | 3-(dimethylamino)-3-oxopropyl | 4-chlorophenyl | 5 | white solid | 389.90 | 1.91 Method D | 390.2 | $^1$H NMR (DMSO-d$_6$, 500 MHz) δ 8.08 (br s, 1H), 7.97 (d, 2H, J = 8.7), 7.65 (d, 2H, J = 8.5), 7.01 (br s, 1H), 4.46 (d, 1H, J = 18), 4.22 (d, 1H, J = 18), 3.91 (t, 1H, J = 6.3), 3.00 (s, 3H), 2.85 (s, 3H), 1.40–1.50 (m, 2H), 1.30–1.40 (m, 1H), 0.85 (d, 3H, J = 6.1), 0.64 (d, 3H, J = 6.0) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 84 | isobutyl | CH₃NH-C(O)-CH₂- | 4-chlorophenyl | 5 | white solid | 375.88 | 1.38 Method A | 376.0 | ¹H NMR (CDCl₃, 500 MHz) δ 7.85 (dd, 2H, J = 1.8, 6.8), 7.50 (dd, 2H, J = 2.0, 6.8), 7.40 (br s, 1H), 6.37 (br s, 1H), 5.25 (br s, 1H), 4.26 (dd, 1H, J = 6.2, 8.6), 3.97 (d, 1H, J = 17), 3.85 (d, 1H, J = 17), 2.85 (d, 3H, J = 4.8), 1.75-1.85 (m, 1H), 1.40-1.48 (m, 1H), 0.88 (d, 3H, J = 6.4), 0.87 (d, 3H, J = 6.6) |
| 85 | isobutyl | thiomorpholinyl-C(O)-CH₂- | 4-chlorophenyl | 5 | white solid | 448.01 | 2.18 Method C | 448.1 | ¹H NMR (CDCl₃, 500 MHz) δ 8.10 (br s, 1H), 7.92 (d, 2H, J = 8.5), 7.50 (d, 2H, J = 8.5), 5.18 (br s, 1H), 4.35 (d, 1H, J = 17), 4.15 (t, 1H, J = 7.4), 3.97-4.05 (m, 1H), 3.95 (d, 1H, J = 17), 3.70-3.89 (m, 3H), 2.55-2.85 (m, 4H), 1.85-1.91 (m, 1H), 1.55-1.85 (m, 1H), 1.30-1.40 (m, 1H), 0.85 (d, 3H, J = 6.4), 0.83 (d, 3H, J = 6.4) |
| 86 | isobutyl | piperidinyl-C(O)-CH₂- | 4-chlorophenyl | 5 | white solid | 429.97 | 2.26 Method C | 430.2 | ¹H NMR (CDCl₃, 500 MHz) δ 8.59 (br s, 1H), 7.92 (d, 2H, J = 9.1), 7.47 (d, 2H, J = 8.6), 5.16 (br s, 1H), 4.42 (d, 1H, J = 17), 4.23 (dd, 1H, J = 5.6, 8.6), 3.87 (d, 1H, J = 17), 3.55-3.65 (m, 1H), 3.40-3.52 (m, 3H), 1.80-2.00 (m, 1H), 1.45-1.80 (m, 7H), 1.35-1.45 (m, 1H), 0.89 (d, 3H, J = 6.7), 0.86 (d, 3H, J = 6.5) |
| 87 | isobutyl | PhNH-C(O)-CH₂- | 4-chlorophenyl | 5 | white solid | 437.95 | 2.37 Method C | 438.2 | ¹H NMR (CDCl₃, 500 MHz) δ 8.95 (br s, 1H), 7.83 (d, 2H, J = 8.6), 7.47 (d, 2H, J = 8.1), 7.43 (d, 2H, J = 8.6), 7.33 (t, 2H, J = 8.1), 7.13 (t, 1H, J = 7.6), 6.65 (br s, 1H), 5.45 (br s, 1H), 4.40 (dd, 1H, J = 6.1, 8.6), 4.07 (d, 1H, J = 17), 4.03 (d, 1H, J = 17), 1.70-1.80 (m, 1H), 1.55-1.65 (m, 2H), 0.93 (d, 3H, J = 7.0), 0.90 (d, 3H, J = 6.4) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 88 | isobutyl | N-cyclopropyl propanamide | 4-chlorophenyl | 5 | white solid | 401.92 | 1.94 Method C | 402.2 | ¹H NMR (CDCl₃, 500 MHz) δ 7.85 (dd, 2H, J = 1.9, 8.9), 7.50 (dd, 2H, J = 2.0, 8.7), 7.40 (br s, 1H), 6.55 (br s, 1H), 6.30 (br s, 1H), 4.23 (dd, 1H, J = 2.9, 8.9), 3.92 (d, 1H, J = 17), 3.83 (d, 1H, J = 17), 2.68-2.73 (m, 1H), 1.75-1.83 (m, 1H), 1.50-1.57 (m, 1H), 1.40-1.49 (m, 1H), 0.88 (d, 3H, J = 6.4), 0.87 (d, 3H, J = 6.7), 0.80 (d, 2H, J = 7.0), 0.51 (t, 2H, J = 4.0) |
| 89 | isobutyl | 4-carboxyphenylmethyl | 4-chlorophenyl | 6 | white solid | 438.93 | 1.67 min Method A | 439.17 | ¹H NMR (CDCl₃, 500 MHz) δ 7.91 (d, 2H, J = 8.2), 7.81-7.84 (m, 3H), 7.56 (d, 2H, J = 8.6), 7.49 (d, 2H, J = 8.2), 6.55 (br s, 1H), 5.10 (d, 1H, J = 15.4), 4.23 (dd, 1H, J = 4.6, 9.7), 4.05 (d, 1H, J = 15.4), 2.04-2.14 (m, 1H), 1.20-1.31 (m, 1H), 0.80-0.89 (m, 1H), 0.74 (d, 3H, J = 6.6), 0.68 (d, 3H, J = 6.6) |
| 90 | allyl | 4-carboxyphenylmethyl | 4-chlorophenyl | 6 | white solid | 422.89 | 1.41 min Method A | 423.05 | ¹H NMR (DMSO-d₆, 300 MHz) δ 7.86 (d, 2H, J = 8.2), 7.85 (br s, 1H), 7.81 (d, 2H, J = 8.6), 7.61 (d, 2H, J = 8.6), 7.47 (d, 2H, J = 8.0), 7.10 (brs, 1H), 5.45-5.55 (m, 1H), 4.83-4.95 (m, 3H), 4.71 (d, 1H, J = 17.0), 4.47 (t, 1H, J = 7.4), 2.29-2.37 (m, 1H), 2.13-2.22 (m, 1H) |
| 91 | propyl | 4-(pyrrolidin-1-yl)phenylmethyl | 4-chlorophenyl | 2 | tan solid | 450.0 | 1.62 min Method B | 450.2 | ¹H NMR (CDCl₃) δ 7.67 (d, 2H, J = 7.0 Hz) 7.42 (d, 2H, J = 7.0 Hz), 7.17-7.26 (m, 2H), 6.49-6.58 (m, 2H), 6.18 (s, br, 1H), 5.11 (s, br, 1H), 4.33 (dd, 2H, J = 50 Hz, 15 Hz), 4.12-4.20 (m, 1H), 3.21-3.30 (m, 4H), 1.91-2.04 (m, 5H), 1.32-1.38 (m, 1H), 0.94-1.09 (m, 2H), 0.75 (t, 3H, J = 8.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 92 | isobutyl | tert-butyl piperidine-1-carboxylate ethyl | 4-chlorophenyl | 7 | white solid | 502.08 | 1.72 Method A | 502.1 | ¹H NMR (DMSO-d₆, 500 MHz) δ 7.86 (dd, 2H, J = 2.0, 6.8), 7.65 (dd, 2H, J = 2.0, 6.8), 7.37 (br s, 1H), 7.07 (br s, 1H), 4.19 (t, 1H, J = 7.6), 3.92 (br s, 2H), 3.35 (dd, 1H, J = 15, 6.8), 3.05 (dd, 1H, J = 15, 8.1), 1.85 (br s, 1H), 1.50-1.70 (m, 4H), 1.38 (s, 9H), 1.10-1.20 (m, 1H), 0.80-1.00 (m, 3H), 0.82 (d, 6H, J = 7.6) |
| 93 | isobutyl | 1,2,3,4-tetrahydroisoquinoline ethyl | 4-chlorophenyl | 5 | white solid | 478.01 | 1.60 Method A | 478.1 | ¹H NMR (DMSO-d₆, 500 MHz) δ 8.05 (s, 1H), 7.98 (d, 2H, J = 7.8), 7.65 (d, 2H, J = 7.8), 7.05 (s, 1H), 4.73 (s, 1H), 4.55-4.65 (m, 2H), 4.37 (t, 1H, J = 16), 3.95 (br s, 1H), 3.70 (br s, 2H), 2.90 (br s, 1H), 2.77 (br s, 1H), 1.00-1.55 (m, 4H), 0.70 (d, 6H, J = 4.1) |
| 94 | isobutyl | tert-butyl piperazine-1-carboxylate ethyl | 4-chlorophenyl | 5 | white solid | 530.20 | 1.59 Method A | 531.2 | ¹H NMR (DMSO-d₆, 500 MHz) δ 7.96 (d, 2H, J = 8.7), 7.65 (d, 2H, J = 8.6), 7.02 (s, 1H), 4.5 (d, 1H, J = 18), 4.27 (d, 2H, J = 18), 3.95 (br s, 1H) 3.35-3.50 (m, 8H), 1.41 (s, 9H), 0.74 (d, 3H, J = 6.5) 0.66 (d, 3H, J = 6.0) |
| 95 | isobutyl | (4-ethylphenyl)methanol | 4-chlorophenyl | 8 | white solid | 424.95 | 1.49 min Method A | 425.17 | ¹H NMR, 500 Hz, (CDCl₃) δ 7.68 (d, 2H, J = 8.0 Hz), 7.46 (d, 2H, J = 8.0 Hz), 7.33 (d, 2H, J = 8.0 Hz), 7.28 (d, 2H, J = 8.0 Hz), 6.26 (s, br, 1H), 5.35 (s, br, 1H), 4.67 (s, br, 2H), 4.56 (d, 1H, J_{ab} = 16 Hz), 4.36 (d, 1H, J_{ab} = 16 Hz), 4.26 (t, 1H, J = 7.6 Hz), 1.86-1.80 (m, 2H), 1.34-1.28 (m, 1H), 1.16-1.10 (m, 1H), 0.96 (d, 3H, J = 7.0 Hz), 0.93 (d, 3H, J = 7.0 Hz) |

TABLE 4-continued

[Structure: H2N-C(=O)-C(R1)(NR2)-S(=O)2-R3]

| Ex. No. | R1 | R2 | R3 | Reaction Scheme | Appearance | Calc. MW | Ret. Time/Method | M + H+ | NMR Data |
|---|---|---|---|---|---|---|---|---|---|
| 96 | isobutyl | 3-COOMe-benzyl | 4-Cl-phenyl | 1-Method A | white solid | 452.96 | 1.75 min Method A | 453.1 | $^1$H NMR (CDCl$_3$) δ 7.96-7.90 (m, 2H), 7.64 (A of ABq, 2H, J = 8.8 Hz), 7.56 (d, 1H, J = 7.5 Hz), 7.43 (B of ABq, 2H, J = 8.8 Hz), 7.37 (t, 1H, J = 7.5 Hz), 6.28 (bs, 1H), 5.25 (bs, 1H), 4.61 (A of ABq, 1H, J = 15.7 Hz), 4.48 (B of ABq, 1H, J = 15.7 Hz), 4.36 (t, 1H, J = 7.3 Hz), 3.91 (s, 3H), 1.86-1.76 (m, 1H), 1.39-1.30 (m, 1H), 1.23-1.13 (m, 1H), 0.78 (d, 3H, J = 6.6 Hz), 0.68 (d, 3H, J = 6.6 Hz) |
| 97 | cyclopropylmethyl | 4-CN-benzyl | 4-Cl-phenyl | 1-Method A | white solid | 417.92 | 1.53 min Method A | 418.11 | $^1$H NMR (CDCl$_3$, 300 MHz) δ 7.71 (d, 2H, J = 8.7), 7.60 (d, 2H, J = 8.4), 7.47-7.51 (m, 4H), 6.28 (br s, 1H), 5.17 (br s, 1H), 4.73 (d, 1H, J = 16.2), 4.41 (d, 1H, J = 15.9), 4.32 (dd, 1H, J = 1.5, 8.1), 1.65-1.82 (m, 1H), 1.14-1.30 (m, 1H), 0.27-0.40 (m, 2H), 0.12-0.22 (m, 1H), −0.18-0.05 (m, 2H) |
| 98 | cyclopropylmethyl | 4-CF3-benzyl | 4-Cl-phenyl | 1-Method A | white solid | 460.91 | 1.76 min Method A | 461.05 | $^1$H NMR (CDCl$_3$, 300 MHz) δ 7.67 (d, 2H, J = 8.4), 7.44-7.56 (m, 6H), 6.32 (br s, 1H), 5.20 (br s, 1H), 4.70 (d, 1H, J = 15.6), 4.43 (d, 1H, J = 15.6), 4.35 (t, 1H, J = 7.8), 1.70-1.84 (m, 1H), 1.26-1.32 (m, 1H), 0.32-0.40 (m, 2H), 0.16-0.24 (m, 1H), −0.14-0.00 (m, 2H) |
| 99 | cyclopropylmethyl | 4-COOMe-benzyl | 4-Cl-phenyl | 1-Method A | white solid | 450.94 | 1.63 min Method A | 451.06 | $^1$H NMR (CDCl$_3$, 300 MHz) δ 7.97 (d, 2H, J = 8.3), 7.70 (d, 2H, J = 8.7), 7.43-7.48 (m, 4H), 6.32 (br s, 1H), 5.15 (br s, 1H), 4.70 (d, 1H, J = 15.8), 4.43 (d, 1H, J = 15.8), 4.35 (t, 1H, J = 7.8), 3.91 (s, 3H), 1.70-1.82 (m, 1H), 1.23-1.35 (m, 1H), 0.32-0.40 (m, 2H), 0.10-0.21 (m, 1H), −0.25-−0.05 (m, 2H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 100 | isobutyl | 4-(2-(ethoxycarbonyl)propan-2-yl)benzyl | 4-chlorophenyl | 1-Method A | white solid | 509.06 | 1.94 min Method A | 509.2 | ¹H NMR (CDCl₃) δ 7.58 (A of ABq, 2H, J = 8.8 Hz), 7.40 (B of ABq, 2H, J = 8.8 Hz), 7.24 (bs, 4H), 6.20 (bs, 1H), 5.23 (bs, 1H), 4.45 (s, 2H), 4.36 (t, 1H, J = 7.3 Hz),4.12 (q, 2H, J = 7.2 Hz), 1.83-1.74 (m, 1H), 1.55 (s, 3H), 1.55 (s, 3H), 1.39-1.20 (m, 2H), 1.19 (t, 3H, J = 7.2 Hz), 0.78 (d, 3H, J = 6.6 Hz), 0.66 (d, 3H, J = 6.6 Hz) |
| 101 | isobutyl | 4-(morpholine-4-carbonyl)benzyl | 4-chlorophenyl | 6 | white solid | 508.04 | 1.48 min Method A | 508.22 | ¹H NMR (CDCl₃, 300 MHz) δ 7.68 (d, 2H, J = 8.6), 7.29-7.47 (m, 6H), 6.38 (br s, 1H), 5.75 (br s, 1H), 4.65 (d, 1H, J = 16.0), 4.42 (d, 1H, J = 16.0), 4.32 (t, 1H, J = 7.5), 3.30-3.85 (br m, 8H), 1.69-1.78 (m, 1H), 1.28-1.37 (m, 1H), 1.08-1.14 (m, 1H), 0.76 (d, 3H, J = 6.5), 0.63 (d, 3H, J = 6.6) |
| 102 | isobutyl | 4-(morpholine-4-carbonyl)benzyl | 4-fluorophenyl | 6 | white solid | 491.59 | 1.39 min Method A | 492.23 | ¹H NMR (CDCl₃, 300 MHz) δ 7.75-7.80 (m, 2H), 7.42 (d, 2H, J = 8.2), 7.33 (d, 2H, J = 8.2), 7.14-7.20 (m, 2H), 6.37 (br s, 1H), 5.64 (br s, 1H), 4.64 (d, 1H, J = 16.0), 4.44 (d, 1H, J = 16.0), 4.31 (t, 1H, J = 7.1), 3.20-3.85 (br m, 8H), 1.70-1.78 (m, 1H), 1.28-1.35 (m, 1H), 1.05-1.14 (m, 1H), 0.76 (d, 3H, J = 6.5), 0.63 (d, 3H, J = 6.6) |
| 103 | isobutyl | 4-(N-(2-morpholinoethyl)carbamoyl)benzyl | 4-chlorophenyl | 6 | colorless oil | 551.11 | 1.32 min Method A | 551.24 | ¹H NMR (CDCl₃, 300 MHz) δ 7.67-7.72 (m, 4H), 7.42-7.48 (m, 4H), 6.82 (br s, 1H), 6.25 (br s, 1H), 5.31 (br s, 1H), 4.65 (d, 1H, J = 15.9), 4.43 (d, 1H, J = 15.9), 4.30 (t, 1H, J = 7.9), 3.70-3.79 (m, 4H), 3.53-3.59 (m, 2H), 2.53-2.65 (m, 6H), 1.79-1.86 (m, 1H), 1.29-1.38 (m, 1H), 1.08-1.14 (m, 1H), 0.76 (d, 3H, J = 6.5), 0.65 (d, 3H, J = 6.6) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 104 | isobutyl | 4-((2-morpholinoethyl)carbamoyl)benzyl | 4-fluorophenyl | 6 | white solid | 534.66 | 1.22 min Method A | 535.28 | ¹H NMR (CDCl₃, 300 MHz) δ 7.75-7.80 (m, 2H), 7.71 (d, 2H, J = 8.2), 7.43 (d, 2H, J = 8.1), 7.14-7.20 (m, 2H), 6.81 (br s, 1H), 6.28 (br s, 1H), 5.31 (br s, 1H), 4.64 (d, 1H, J = 15.9), 4.44 (d, 1H, J = 15.9), 4.29 (t, 1H, J = 7.6), 3.70-3.79 (m, 4H), 3.53-3.59 (m, 2H), 2.52-2.63 (m, 6H), 1.77-1.85 (m, 1H), 1.29-1.38 (m, 1H), 1.06-1.13 (m, 1H), 0.75 (d, 3H, J = 6.5), 0.65 (d, 3H, J = 6.6) |
| 105 | isobutyl | 4-(4-(tert-butoxycarbonyl)piperazine-1-carbonyl)benzyl | 4-chlorophenyl | 6 | white solid | 607.17 | 1.70 min Method A | 607.29 | ¹H NMR (CDCl₃, 300 MHz) δ 7.69 (d, 2H, J = 8.6), 7.30-7.47 (m, 6H), 6.38 (br s, 1H), 5.75 (br s, 1H), 4.65 (d, 1H, J = 16.0), 4.43 (d, 1H, J = 16.0), 4.33 (t, 1H, J = 7.5), 3.30-3.85 (br m, 8H), 1.72-1.79 (m, 1H), 1.45 (s, 9H), 1.24-1.39 (m, 1H), 1.05-1.18 (m, 1H), 0.76 (d, 3H, J = 6.5), 0.62 (d, 3H, J = 6.6) |
| 106 | isobutyl | 4-(1,2,3,4-tetrahydroisoquinoline-2-carbonyl)benzyl | 4-chlorophenyl | 6 | white solid | 554.11 | 1.75 min Method A | 554.19 | ¹H NMR (CDCl₃, 300 MHz) δ 7.70 (ddd, 2H, J = 1.9, 2.4, 8.6), 7.47 (ddd, 2H, J = 2.0, 2.3, 8.7), 7.37-7.42 (m, 4H), 7.15-7.20 (m, 4H), 6.31 (br s, 1H), 5.60 (br s, 1H), 4.87 (br s, 1H), 4.65 (d, 1H, J = 15.9), 4.52 (br s, 1H), 4.47 (d, 1H, J = 15.9), 4.33 (t, 1H, J = 7.2), 4.05 (br s, 1H), 3.61 (br s, 1H), 2.85-3.01 (br m, 2H), 1.72-1.85 (m, 1H), 1.30-1.42 (m, 1H), 1.08-1.18 (m, 1H), 0.79 (d, 3H, J = 6.5), 0.66 (d, 3H, J = 6.6) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 107 | isobutyl | 3-fluoro-4-methoxybenzyl | 4-chlorophenyl | 1-Method A | clear wax | 456.97 | 1.60 min Method B | 455.1 (M − H⁻) | $^1$H NMR (CDCl$_3$) δ 7.61 (d, 2H, J = 8.0 Hz), 7.43 (d, 2H, J = 8.0 Hz), 6.82-7.10 (m, 3H), 6.21 (s, br, 1H), 5.15 (s, br, 1H), 4.35 (dd, 2H, J = 50 Hz, 15 Hz), 4.15-4.22 (m, 1H), 3.89 (s, br, 3H), 2.30-2.33 (m, 1H), 0.86-0.98 (m, 1H), 0.74 (s, 9H) |
| 108 | isobutyl | 4-cyanobenzyl | 4-chlorophenyl | 1-Method A | white solid | 433.96 | 1.58 min Method B | 432.14 (M − H⁻) | $^1$H NMR (CDCl$_3$) δ 7.67 (d, 2H, J = 8.0 Hz), 7.58 (d, 2H, J = 8.0 Hz), 7.45-7.49 (m, 4H), 6.19 (s, br, 1H), 5.15 (s, br, 1H), 4.55 (dd, 2H, J = 50 Hz, 15 Hz), 4.20-4.24 (m, 1H), 2.25-2.31 (m, 1H), 0.84-0.88 (m, 1H), 0.74 (s, 9H) |
| 109 | isobutyl | 4-trifluoromethylbenzyl | 4-chlorophenyl | 1-Method A | white solid | 476.95 | 1.62 min Method B | 475.12 (M − H⁻) | $^1$H NMR (CDCl$_3$) δ 7.61 (d, 2H, J = 8.0 Hz), 7.51 (d, 2H, J = 8.0 Hz), 7.40-7.44 (m, 4H), 6.20 (s, br, 1H), 5.21 (s, br, 1H), 4.51 (dd, 2H, J = 50 Hz, 15 Hz), 4.24-4.28 (m, 1H), 2.28-2.32 (m, 1H), 0.91-0.96 (m, 1H), 0.76 (s, 9H) |
| 110 | isobutyl | 4-(dimethylaminomethyl)benzyl | 4-chlorophenyl | 8 | tan solid | 452.02 | 1.25 min Method A | 452.23 | $^1$H NMR, 400 Hz, (CDCl$_3$) δ 7.94 (d, 2H, J = 8.0 Hz), 7.74 (d, 2H, J = 8.0 Hz), 7.63 (d, 2H, J = 8.0 Hz), 7.38 (d, 2H, J = 8.0 Hz), 6.27 (s, br, 1H), 5.40 (s,br, 1H), 4.52 (d, 1H, J$_{ab}$ = 16 Hz), 4.44 (d, 1H, J$_{ab}$ = 16 Hz), 3.28-3.23 (m, 3H), 2.17 (s, br, 6H), 1.95 (m, 1H), 1.55 (m, 2H), 0.96 (d, 3H, J = 7.0 Hz), 0.93 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 111 | isobutyl | 4-(trifluoromethoxy)benzyl amide | 4-chlorophenyl | 5 | white solid | 535.97 | 2.65 min Method C | 536.04 | $^1$H NMR (CDCl$_3$, 400 MHz) δ 7.80 (dd, 2H, J = 2.0, 9.0), 7.45 (dd, 2H, J = 2.0, 9.0), 7.32 (dd, 2H, J = 1.8, 9.0), 7.24 (br s, 1H), 7.17 (d, 2H, J = 9.0), 5.50 (br s, 1H), 4.43 (qd, 2H, J = 6.0, 15), 4.22 (t, 1H, J = 7.0), 4.05 (d, 1H, J = 17), 3.90 (d, 1H, J = 17), 1.70-1.80 (m, 1H), 1.42-1.55 (m, 1H), 1.32-1.41 (m, 1H), 0.83 (d, 6H, J = 7.9) |
| 112 | isobutyl | 2,5-difluorobenzyl amide | 4-chlorophenyl | 5 | white foam | 487.93 | 1.52 min Method A | 488.20 | $^1$H NMR (CDCl$_3$, 400 MHz) δ 7.77 (d, 2H, J = 8.3), 7.45 (d, 2H, J = 9.0), 7.30 (br s, 1H), 7.05-7.10 (m, 1H), 6.90-7.05 (m, 2H), 5.53 (br s, 1H), 4.39-4.50 (m, 2H), 4.24 (t, 1H, J = 7.1), 4.02 (d, 1H, J = 17), 3.90 (d, 2H, J = 17), 1.70-1.80 (m, 1H), 1.42-1.55 (m, 1H), 1.35-1.42 (m, 1H), 0.83 (d, 6H, J = 7.7) |
| 113 | isobutyl | tert-butyl amide | 4-chlorophenyl | 5 | white oily solid | 417.96 | 1.52 min Method A | 418.23 | $^1$H NMR (CDCl$_3$, 400 MHz) δ 7.92 (br s, 1H), 7.82 (d, 2H, J = 8.2), 7.47 (d, 2H, J = 8.2), 7.25 (br s, 1H), 6.23 (br s, 1H), 5.47 (br s, 1H), 4.25 (t, 1H, J = 7.2), 3.91 (d, 1H, J = 17), 3.75 (d, 1H, J = 17), 1.75-1.82 (m, 1H), 1.50-1.62 (m, 1H), 1.38-1.50 (m, 1H), 1.35 (s, 9H), 0.89 (d, 3H, J = 5.4), 0.87 (d, 3H, J = 5.6) |
| 114 | isobutyl | cyclohexylmethyl amide | 4-chlorophenyl | 5 | white solid | 458.02 | 1.62 min Method A | 458.26 | $^1$H NMR (CDCl$_3$, 400 MHz) δ 7.84 (dd, 2H, J = 2.0, 8.8), 7.68 (br s, 1H), 7.47 (dd, 2H, J = 2.0, 8.3), 6.62 (br t, 1H, J = 5.3), 5.45 (br s, 1H), 4.25 (dd, 1H, J = 2.3, 6.1), 3.98 (d, 1H, J = 17), 3.85 (d, 1H, J = 17), 3.03-3.15 (m, 2H), 1.86-1.92 (m, 1H), 1.40-1.85 (m, 7H), 1.05-1.35 (m, 4H), 0.90-0.99 (m, 2H), 0.88 (d, 3H, J = 6.6), 0.87 (d, 3H, J = 6.4) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 115 | isobutyl | pyridin-3-ylmethyl amide | 4-chlorophenyl | 5 | white solid | 452.96 | 1.14 min Method A | 453.22 | ¹H NMR (CDCl₃, 400 MHz) δ 8.53 (d, 2H, J = 5.2), 8.04 (t, 1H, J = 5.2), 7.80 (dd, 2H, J = 1.8, 8.5), 7.46 (dd, 2H, J = 1.8, 8.7), 7.33 (br s, 1H), 7.29 (d, 2H, J = 5.4), 5.78 (br s, 1H), 4.47 (qd, 2H, J = 6.0, 16), 4.21 (t, 1H, J = 7.4), 4.07 (d, 1H, J = 17), 3.92 (d, 1H, J = 17), 1.67-1.77(m, 1H), 1.30-1.47 (m, 2H), 0.81 (d, 3H, J = 6.5), 0.77 (d, 3H, J = 7.0) |
| 116 | isobutyl | 2-methoxyethyl ketone | 4-chlorophenyl | 5 | white foam | 419.93 | 1.29 Min Method A | 420.23 | ¹H NMR (CDCl₃, 400 MHz) δ 7.87 (dd, 2H, J = 2.0, 8.5), 7.85 (br s, 1H), 7.49 (dd, 2H, J = 2.1, 9.0), 6.73 (br s, 1H), 5.55 (br s, 1H), 4.22 (dd, 1H, J = 6.1, 8.3), 4.02 (d, 1H, J = 17), 3.87 (d, 1H, J = 17), 3.40-3.50 (m, 4H), 3.36 (s, 3H), 1.77-1.86 (m, 1H), 1.46-1.57 (m, 1H), 1.30-1.41 (m, 1H), 0.84 (d, 3H, J = 6.7), 0.83 (d, 3H, J = 6.5) |
| 117 | isobutyl | morpholinoethyl amide | 4-chlorophenyl | 5 | white foam | 475.01 | 1.16 min Method A | 475.26 | ¹H NMR (CDCl₃, 400 MHz) δ 7.85 (dd, 2H, J = 2.0, 8.5), 7.64 (br s, 1H), 7.47 (dd, 2H, J = 1.5, 7.1), 6.87 (br s, 1H), 5.55 (br s, 1H), 4.22 (dd, 1H, J = 6.2, 7.9), 4.00 (d, 1H, J = 17), 3.87 (d, 1H, J = 17), 3.72 (t, 1H, J = 4.2), 3.30-3.45 (m, 2H), 2.45-2.55 (m, 6H), 1.75-1.85 (m, 1H), 1.50-1.63 (m, 1H), 1.30-1.41 (m, 1H), 0.86 (d, 6H, J = 9.0) |

TABLE 4-continued

![Structure: H2N-C(=O)-C(R1)(NR2)-S(=O)2-R3]

| Ex. No. | R1 | R2 | R3 | Reaction Scheme | Appearance | Calc. MW | Ret. Time/Method | M + H+ | NMR Data |
|---|---|---|---|---|---|---|---|---|---|
| 118 | propyl | 4-Br-benzyl | 4-Cl-phenyl | 1-Method A | white solid | 459.79 | 1.62 min Method B | 461.1 | $^1$H NMR (CDCl$_3$) δ 7.67 (d, 2H, J = 7.0 Hz) 7.48 (d, 2H, J = 7.0 Hz), 7.41 (d, 2H, J = 6.5 Hz), 7.21 (d, 2H, J=6.5 Hz), 6.21 (s, br, 1H), 5.20 (s, br, 1H), 4.43 (dd, 2H, J = 50 Hz, 15 Hz), 4.12-4.24 (m, 1H), 1.88-1.90 (m, 1H), 1.24-1.29 (m, 1H), 0.98-1.08 (m, 2H), 0.74 (t, 3H, J = 7.0 Hz) |
| 119 | CH2-S-CH3 | 4-CN-benzyl | 4-Cl-phenyl | 1-Method A | yellow solid | 437.06 | 1.84 min Method F | (M + Na)+ 459.9 | $^1$H NMR (400 MHz, DMSO) δ 7.83 (d, 2H, J = 8.8), 7.80 (d, 2H, J = 8.3), 7.64 (d, 2H, J = 8.5), 7.59 (d, 2H, J = 8.6), 7.48 (s, 1H), 7.15 (s, 1H), 4.79 (ABq, 2H, Δv = 22.2, J$_{ab}$ = 17.4), 4.44 (dd, 1H, J = 8.0, 6.3), 2.21 (m, 2H), 1.84 (m, 1H), 1.81 (m, 3H), 1.53 (m, 1H) |
| 120 | CH2-S-CH3 | 4-CF3-benzyl | 4-Cl-phenyl | 1-Method A | white solid | 480.06 | 2.08 min Method F | (M + Na)+ 503.0 | $^1$H NMR (400 MHz, DMSO) δ 7.82 (d, 2H, J = 8.8), 7.68 (d, 2H, J = 8.6), 7.61 (m, 4H), 7.48 (s, 1H), 7.16 (s, 1H), 4.80 (ABq, 2H, Δv = 16.7, J$_{ab}$ = 17.0), 4.45 (dd, 1H, J = 8.2, 6.2), 2.22 (m, 2H), 1.82 (m, 1H), 1.78 (s, 3H), 1.61 (m, 1H) |
| 121 | isobutyl | morpholinopropyl-amide | 4-Cl-phenyl | 5 | white solid | 488.19 | 1.20 min Method A | 489.26 | $^1$H NMR (CDCl$_3$, 400 MHz) δ 7.95 (br s, 1H), 7.85 (dd, 2H, J = 2.5, 9.2), 7.70 (br s, 1H), 7.47 (dd, 2H, 2.0, 8.8), 5.42 (br s, 1H), 4.23 (dd, 1H, J = 6.3, 8.3), 3.94 (d, 1H, J = 17), 3.83 (d, 1H, J = 17), 3.73 (t, 4H, J = 4.7), 3.39-3.48 (m, 1H), 3.22-3.33 (m, 1H), 2.42-2.55 (m, 4H), 1.79-1.88 (m, 2H), 1.63-1.75 (m, 2H), 1.49-1.61 (m, 1H), 1.31-1.45 (m, 1H), 1.05-1.11 (m, 1H), 0.88 (d, 6H, J = 6.6) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 122 | isobutyl | -NHC(O)CH₂CH₂N(CH₃)₂ | 4-chlorophenylmethyl | 5 | white solid | 432.16 | 1.59 min Method C | 433.12 | ¹H NMR (CDCl₃, 400 MHz) δ 8.04 (br s, 1H), 7.88 (dd, 2H, J = 1.9, 6.9), 7.46 (dd, 2H, J = 1.8, 6.8), 6.93 (br s, 1H), 5.55 (br s, 1H), 4.20 (dd, 1H, J = 6.2, 8.3), 4.01 (d, 1H, J = 17), 3.80 (d, 1H, J = 17), 3.25-3.40 (m, 2H), 2.40-2.50 (m, 2H), 2.25 (s, 6H), 1.75-1.90 (m, 1H), 1.45-1.60 (m, 1H), 1.30-1.45 (m, 1H), 0.84 (d, 3H, J = 6.1), 0.82 (d, 3H, J = 6.4) |
| 123 | isobutyl | 4-(ethylaminocarbonyl)phenylmethyl | 4-chlorophenylmethyl | 6 | white solid | 466.00 | 1.49 min Method A | 466.17 | ¹H NMR (CDCl₃, 500 MHz) δ 7.68 (d, 4H, J = 8.6), 7.47 (ddd, 2H, J = 1.6, 2.4, 8.6), 7.41 (d, 2H, J = 8.2), 6.25 (br s, 1H), 6.12 (br s, 1H), 5.30 (br s, 1H), 4.63 (d, 1H, J = 15.8), 4.44 (d, 1H, J = 15.8), 4.30 (t, 1H, J = 6.8), 3.47-3.52 (m, 2H), 1.78-1.84 (m, 1H), 1.30-1.34 (m, 1H), 1.25 (t, 3H, J = 7.2), 1.08-1.13 (m, 1H), 0.76 (d, 3H, J = 6.6), 0.65 (d, 3H, J = 6.6) |
| 124 | isobutyl | 4-((4-fluorobenzyl)aminocarbonyl)phenylmethyl | 4-chlorophenylmethyl | 6 | colorless oil | 546.05 | 1.65 min Method A | 546.19 | ¹H NMR (CDCl₃, 500 MHz) δ 7.71 (d, 2H, J = 8.2), 7.67 (d, 2H, J = 8.6), 7.46 (d, 2H, J = 8.6), 7.41 (d, 2H, J = 8.0), 6.52 (br s, 1H), 6.24 (br s, 1H), 5.40 (br s, 1H), 4.63 (d, 1H, J = 15.9), 4.59 (d, 2H, J = 5.6), 4.42 (d, 1H, J = 15.9), 4.29 (t, 1H, J = 6.6), 1.78-1.84 (m, 1H), 1.29-1.34 (m, 1H), 1.25 (t, 3H, J = 7.2), 1.06-1.11 (m, 1H), 0.76 (d, 3H, J = 6.6), 0.66 (d, 3H, J = 6.6) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 125 | isobutyl | 4-(tert-butylcarbamoyl)benzyl | 4-chlorophenyl | 6 | colorless oil | 494.06 | 1.67 min Method A | 494.24 | ¹H NMR (CDCl₃, 500 MHz) δ 7.68 (dd, 2H, J = 1.7, 8.6), 7.63 (d, 2H, J = 8.2), 7.46 (d, 2H, J = 8.6), 7.39 (d, 2H, J = 8.2), 6.28 (br s, 1H), 5.94 (br s, 1H), 5.35 (br s, 1H), 4.63 (d, 1H, J = 15.8), 4.41 (d, 1H, J = 15.8), 4.29 (t, 1H, J = 6.6), 1.78-1.84(m, 1H), 1.46 (s, 9H), 1.29-1.34 (m, 1H), 1.25 (t, 3H), J = 7.2), 1.06-1.11 (m, 1H), 0.76 (d, 3H, J = 6.6), 0.66 (d, 3H, J = 6.6) |
| 126 | isobutyl | piperidin-4-ylmethyl | 4-chlorophenyl | 7 | white solid | 401.15 | 1.34 min Method A | 402.15 | ¹H NMR (DMSO-d₆, 500 MHz), δ 7.87 (d, 2H, J = 8.5), 7.66 (d, 2H, J = 8.6), 7.41 (s, 1H), 7.04 (s, 1H), 4.17 (t, 1H, J = 7.3), 3.40-3.50 (m, 1H), 3.20-3.25 (m, 1H), 3.03-3.10 (m, 1H), 2.65-2.80 (m, 2H), 1.85-2.00 (m, 1H), 1.20-1.85 (m, 2H), 1.45-1.60 (m, 4H), 1.30-1.40 (m, 1H), 1.10-1.30 (m, 4H), 0.75-0.90 (m, 1H), 0.82 (d, 3H, J = 7.3), 0.80 (d, 3H, J = 7.0) |
| 127 | isobutyl | 4-ethylbenzyl(diethylamino) | 4-chlorophenyl | 8 | white solid | 480.07 | 1.34 min Method A | 480.25 | ¹H NMR 400 MHz, (CDCl₃) δ 7.72 (d, 2H, J = 8.0 Hz), 7.60 (d, 2H, J = 8.0 Hz), 7.39-7.33 (m, 4H), 6.26 (s, br, 1H), 5.40 (s, br, 1H), 4.53 (d, 1H, J$_{ab}$ = 16 Hz), 4.42 (d, 1H, J$_{ab}$ = 16 Hz), 2.58 (q, 4H, J = 8.0 Hz), 1.94 (m, 1H), 1.59 (m, 2H), 1.06 (t, 6H, J = 8.0 Hz), 0.97 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 128 | isobutyl | N,N-diallyl-(4-ethylbenzyl)amine | 4-chlorophenyl | 8 | white solid | 504.1 | 1.32 min Method A | 504.25 | ¹H NMR 400 MHz, (CDCl₃) δ 7.69 (d, 2H, J = 8.0 Hz), 7.73 (d, 2H, J = 8.0 Hz), 7.48 (d, 2H, J = 8.0 Hz), 7.35 (d, 2H, J = 8.0 Hz), 6.25 (s, br, 1H), 5.35 (s, br, 1H), 4.52 (d, 1H, $J_{ab}$ = 16 Hz), 4.44 (d, 1H, $J_{ab}$ = 16 Hz), 3.35 (s, 2H), 3.47-3.42 (m, 1H), 3.01 (s, br, 1H), 1.90 (m, 1H), 1.63 (m, 2H) 0.97 (d, 3H, J = 7.0 Hz), 0.94 (d, 3H, J = 7.0 Hz) |
| 129 | isobutyl | N-benzyl-N-(4-ethylbenzyl)piperazine | 4-chlorophenyl | 8 | white solid | 583.2 | 1.26 min Method A | 583.40 | ¹H NMR 400 MHz, (CDCl₃) δ 7.72 (d, 2H, J = 8.0 Hz), 7.64 (d, 2H, J = 8.0 Hz), 7.37 (m, 4H), 7.21 (m, 5H), 6.35 (s, br, 1H), 5.87 (s, br, 1H), 4.72 (d, 1H, $J_{ab}$ = 16 Hz), 4.48 (d, 1H, $J_{ab}$ = 16 Hz), 3.55 (s, 3H), 3.52 (s, 3H), 3.74-3.43 (m, 1H), 2.45 (m, 8H), 1.59 (m, 2H), 0.98 (d, 3H, J = 7.0 Hz), 0.95 (d, 3H, J = 7.0 Hz) |
| 130 | isobutyl | 4-((4-ethylbenzyl)morpholine) | 4-chlorophenyl | 8 | amber glass | 496.06 | 1.32 min Method A | 496.25 | ¹H NMR 400 MHz, (CDCl₃) δ 7.68 (d, 2H, J = 8.0 Hz), 7.72 (d, 2H, J = 8.0 Hz), 7.40-7.36 (m, 4H), 6.35 (s, br, 1H), 5.37 (s, br, 1H), 4.59 (d, 1H, $J_{ab}$ = 16 Hz), 4.37 (d, 1H, $J_{ab}$ = 16 Hz), 3.7-3.5 (m, 4H), 3.48 (s, 3H), 3.46 (m, 4H), 2.23-2.1 (m, 4H), 1.85 (m, 1H), 1.55 (m, 2H), 0.98 (d, 3H, J = 7.0 Hz), 0.95 (d, 3H, J = 7.0 Hz) |
| 131 | isobutyl | 4-((4-ethylbenzyl)thiomorpholine) | 4-chlorophenyl | 8 | amber oil | 510.12 | 1.33 min Method A | 510.23 | ¹H NMR 400 MHz, (CDCl₃) δ 7.69 (d, 2H, J = 8.0 Hz), 7.65 (s, b, 4H), 7.37 (d, 2H, J = 8.0 Hz), 6.25 (s, b, 1H), 5.36 (s, b, 1H), 4.60 (d, 1H, $J_{ab}$ = 16 Hz), 4.38 (d, 1H, $J_{ab}$ = 16 Hz), 3.47-3.43 (m, 3H), 2.61 (m, 4H), 2.30 (m, 4H), 1.90 (m, 1H), 1.59 (m, 2H), 0.96 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 132 | isobutyl | 4-ethylbenzyl-(1-methylpiperidin-4-yl)methylamino | 4-chlorophenyl | 8 | amber glass | 535.15 | 1.24 min Method A | 535.32 | ¹H NMR 400 MHz, (CDCl₃) δ 8.02 (d, 2H, J = 8.0 Hz), 7.71 (d, 2H, J = 8.0 Hz), 7.40 (d, 2H, J = 8.0 Hz), 7.36 (d, 2H, J = 8.0 Hz), 6.27 (s, b, 1H), 5.40 (s, b, 1H), 4.52 (d, 1H, $J_{ab}$ = 16 Hz), 4.44 (d, 1H, $J_{ab}$ = 16 Hz), 3.61 (s, 2H), 3.45 (m, 1H), 2.72-2.63 (m, 3H), 2.41 (s, 3H), 2.32 (s, 3H), 2.05 (t, 4H, J = 12.0 Hz), 1.90 (m, 3H), 1.74-1.55 (m, 3H), 0.96 (d, 3H, J = 7.0 Hz), 0.93 (d, 3H, J = 7.0 Hz) |
| 133 | isobutyl | 4-ethylbenzyl-(1,2,3,4-tetrahydroisoquinolin-2-yl) | 4-chlorophenyl | 8 | amber glass | 540.13 | 1.28 min Method A | 540.34 | ¹H NMR 400 MHz, (CDCl₃) δ 7.72 (d, 2H, J = 8.0 Hz), 7.70 (d, 2H, J = 8.0 Hz), 7.52 (d, 2H, J = 8.0 Hz), 7.38 (d, 2H, J = 8.0 Hz), 7.24-7.14 (m, 3H), 6.88 (m, 1H), 6.25 (s, br, 1H), 5.39(s,br, 1H)>,4.62 (d, 1H. Iab= 16Hz), 4.40 (d, 1H, Jab= 16Hz), 3.45 (s, 2H), 3.46(m, 1H), 3.35-3.19 (m,2H), 3.93 (m, 1H), 2.71 (m, 1H), 2.61 (m, 1H), 2.49-2.43 (m, 2H), 1.89 (m, 1H), 1.67-1.54 (m, 2H), 0.97 (d, 3H, J = 7.0 Hz), 0.94 (d, 3H, J = 7.0 Hz) |
| 134 | isobutyl | 4-ethylbenzyl-(but-3-ynyl)methylamino | 4-chlorophenyl | 8 | white solid | 476.04 | 1.31 min Method A | 476.17 | ¹H NMR 400 MHz, (CDCl₃) δ 7.79 (d, 2H, J = 8.0 Hz), 7.65 (d, 2H, J = 8.0 Hz), 7.47 (d, 2H, J = 8.0 Hz), 7.37 (d, 2H, J = 8.0 Hz), 6.35 (s, br, 1H), 5.85 (s, br, 1H), 4.60 (s, 2H), 4.76 (d, 1H, $J_{ab}$ = 16 Hz), 4.30 (d, 1H, $J_{ab}$ = 16 Hz), 3.72 (s, br, 2H), 3.46 (m, 1H), 2.40 (s, br, 3H), 2.20 (s, 1H), 1.90 (m, 1H), 1.63 (m, 2H), 0.98 (d, 3H, J = 7.0 Hz), 0.95 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 135 | isobutyl | 4-ethylbenzyl-N(ethyl)-CH₂CH₂N(CH₃)₂ | 4-chlorophenyl | 8 | white solid | 532.14 | 1.34 min Method A | 532.32 | ¹H NMR 400 MHz, (CDCl₃) δ 7.69 (d, 2H, J = 8.0 Hz), 7.62 (d, 2H, J = 8.0 Hz), 7.37 (d, 2H, J = 8.0 Hz), 7.33 (d, 2H, J = 8.0 Hz), 6.27 (s, br, 1H), 5.40 (s, br, 1H), 4.59 (d, 1H, $J_{ab}$ = 16 Hz), 4.37 (d, 1H, $J_{ab}$ = 16 Hz), 3.53 (s, 3H), 3.44 (m, 1H), 2.79 (t, 2H, J = 8.0 Hz), 2.62 (q, 2H, J = 8.0 Hz), 2.41 (t, 2H, J = 8.0 Hz), 2.25 (s, 6H), 1.95-1.85 (m, 1H), 1.67-1.54 (m, 2H), 1.07 (t, 3H, J = 8.0 Hz), 0.98 (d, 3H, J = 7.0 Hz), 0.95 (d, 3H, J = 7.0 Hz) |
| 136 | isobutyl | 4-ethylbenzyl-N(ethyl)-CH₂CH₂N(ethyl)₂ | 4-chlorophenyl | 8 | white solid | 537.17 | 1.24 min Method A | 537.34 | ¹H NMR 400 MHz, (CDCl₃) δ 7.72 (d, 2H, J = 8.0 Hz), 7.64 (d, 2H, J = 8.0 Hz), 7.41-7.36 (m, 4H), 6.57 (s, br, 1H), 5.40 (s, br, 1H), 4.59 (d, 1H, $J_{ab}$ = 16 Hz), 4.37 (d, 1H, $J_{ab}$ = 16 Hz), 3.51 (s, 2H), 3.45 (m, 1H), 2.69 (t, 2H, J = 8.0 Hz), 2.62 (t, 2H, J = 8.0 Hz), 2.55 (q, 4H, J = 8.0 Hz), 2.35 (s, 3H), 1.89 (m, 1H), 1.60 (m, 2H), 1.00 (t, 6H, J = 8.0 Hz), 0.96 (d, 3H, J = 7.0 Hz), 0.94 (d, 3H, J = 7.0 Hz) |
| 137 | isobutyl | 4-ethylbenzyl-N(methyl)-CH₂CH₂N(CH₃)₂ | 4-chlorophenyl | 8 | white solid | 509.12 | 1.32 min Method A | 509.33 | ¹H NMR 400 MHz, (CDCl₃) δ 7.69 (d, 2H, J = 8.0 Hz), 8.01 (d, 2H, J = 8.0 Hz), 7.64 (d, 2H, J = 8.0 Hz), 7.40 (d, 2H, J = 8.0 Hz), 7.37 (d, 2H, J = 8.0 Hz), 6.27 (s, br, 1H), 5.39 (s, br, 1H), 4.58 (d, 1H, Jab = 16 Hz), 4.36 (d, 1H, Jab = 16 Hz) 3.51 (s, 2H), 3.45 (m, 1H), 2.66 (t, 2H, J = 8.0 Hz), 2.39 (t, 2H, J = 8.0 Hz), 2.35 (s, 3H), 2.25 (s, 6H), 1.90 (m, 1H), 1.59 (m, 2H), 0.97 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 138 | isobutyl | 4-ethylbenzyl(isobutyl)amine | 4-chlorophenyl | 8 | clear glass | 494.1 | 1.37 min Method A | 494.27 | ¹H NMR 400 MHz, (CDCl₃) δ 7.72 d, 2H, J = 8.0 Hz), 7.74 (d, 2H, J = 8.0 Hz), 7.52 (d, 2H, J = 8.0 Hz), 7.37 (d, 2H, J = 8.0 Hz), 6.26 (s, br, 1H), 5.39 (s, br, 1H), 4.55 (d, 1H, $J_{ab}$ = 16 Hz), 4.42 (d, 1H, $J_{ab}$ = 16 Hz), 3.70 (s, 3H), 3.46 (m, 1H), 2.38-2.35 (m,5H), 1.91 (m, 2H), 1.60 (m, 2H), 0.96 (d, 3H, J = 7.0 Hz), 0.90 (d, 3H, J = 7.0 Hz) |
| 139 | isobutyl | 4-ethylbenzyl(tert-butyl)amine | 4-chlorophenyl | 8 | white solid | 494.1 | 1.33 min Method A | 494.26 | ¹H NMR 400 MHz, (CDCl₃) δ 7.63 (d, 2H, J = 8.0 Hz), 7.73 (d, 2H, J = 8.0 Hz), 7.48 (d, 2H, J = 8.0 Hz), 7.37 (d, 2H, J = 8.0 Hz), 6.35 (s, br, 1H), 5.38 (s, br, 1H), 4.52 (d, 1H, $J_{ab}$ = 16 Hz), 4.44 (d, 1H, $J_{ab}$ = 16 Hz), 3.47-3.40 (m, 3H), 2.12 (s, 3H), 1.88 (m, 1H), 1.60 (m, 2H), 1.03 (s, 9H), 0.98 (d, 3H, J = 7.0 Hz), 0.95 (d, 3H, J = 7.0 Hz) |
| 140 | isobutyl | 4-ethylbenzyl-4-ethylpiperazine | 4-chlorophenyl | 8 | amber glass | 521.13 | 1.27 min Method A | 521.31 | ¹H NMR 400 MHz, (CDCl₃) δ 7.69 (d, 2H, J = 8.0 Hz), 7.65 (d, 2H, J = 8.0 Hz), 7.39-7.36 (m, 4H), 6.30 (s, br, 1H), 5.35 (s, br, 1H), 4.59 (d, 1H, $J_{ab}$ = 16 Hz), 4.37 (d, 1H, $J_{ab}$ = 16 Hz), 3.55 (s, 2H), 3.45 (m, 1H), 2.84 (m, 4H), 2.48 (q, 2H, J = 7.0 Hz), 2.28 (m, 4H), 1.88 (m, 1H), 1.60 (m, 2H), 1.20 (t, 3H, J = 7.0 Hz), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 141 | isobutyl | 4-ethylbenzyl / pyrrolidinylmethyl | 4-chlorophenyl | 8 | white solid | 478.06 | 1.31 min Method A | 478.22 | ¹H NMR 400 MHz, (CDCl₃) δ 7.72 (d, 2H J = 8.0 Hz), 7.71 (d, 2H, J = 8.0 Hz), 7.48 (d, 2H, J = 8.0 Hz), 7.38 (d, 2H, J = 8.0 Hz), 6.27 (s, br, 1H), 5.40 (s, br, 1H), 4.52 (d, 1H, J$_{ab}$ = 16 Hz), 4.43 (d, 1H, J$_{ab}$ = 16 Hz), 3.58 (s, br, 2H), 3.45 (m, 1H), 2.66 (m, 4H), 1.86 (m, 5H), 1.60 (m, 2H), 0.98 (d, 3H, J = 7.0 Hz), 0.95 (d, 3H, J = 7.0 Hz) |
| 142 | isobutyl | 4-ethylbenzyl / N-methoxy-N-methyl | 4-chlorophenyl | 8 | white foam | 468.02 | 1.58 min Method A | 468.25 | ¹H NMR 400 MHz, (CDCl₃) δ 7.69 (d, 2H, J = 8.0 Hz), 7.76 (d, 2H, J = 8.0 Hz), 7.75 (d, 2H, J = 8.0 Hz), 7.37 (d, 2H, J = 8.0 Hz), 6.25 (s, br, 1H), 5.38 (s, br, 1H), 4.76 (d, 1H, Jab = 16 Hz), 4.30 (d, 1H, Jab = 16 Hz), 3.75 (s, 2H), 3.45 (m, 1H), 3.36 (s, 3H), 2.61 (s, 3H), 1.88 (m, 1H), 1.59 (m, 2H), 0.98 (d, 3H, J = 7.0 Hz), 0.95 (d, 3H, J = 7.0 Hz) |
| 143 | isobutyl | 4-ethylbenzyl / N-(2-hydroxyethyl)-N-methyl | 4-chlorophenyl | 8 | white solid | 482.05 | 1.28 min Method A | 482.24 | ¹H NMR 400 MHz, (CDCl₃) δ 7.69 (d, 2H, J = 8.0 Hz), 7.72 (d, 2H, J = 8.0 Hz), 7.42-7.36 (m, 4H), 6.35 (s, br, 1H), 5.83 (s, br, 1H), 4.58 (d, 1H, J$_{ab}$ = 16Hz), 4.39 (d, 1H, J$_{ab}$ = 16 Hz), 3.52 (s, 1H), 3.50 (s, 2H), 3.48 (s, 1H), 3.45 (m, 1H), 2.55 (t, 2H, J = 8.0 Hz), 2.20 (s, 3H), 1.90 (m, 1H), 1.59 (m, 2H), 0.98 (d, 3H, J = 7.0 Hz), 0.95 (d, 3H, J = 7.0Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 144 | isobutyl | 4-ethylbenzyl-N(CH₂CH₂OH)₂ | 4-chlorophenyl | 8 | clear glass | 512.07 | 1.22 min Method A | 512.25 | ¹H NMR 400 MHz, (CDCl₃) δ 7.71 (d, 2H, J = 8.0 Hz), 7.74 (d, 2H, J = 8.0 Hz), 7.39 (d, 2H, J = 8.0 Hz), 7.31 (d, 2H, J = 8.0 Hz), 6.27 (s, br, 1H), 5.40 (s, br, 1H), 4.72 (d, 1H, $J_{ab}$ = 16 Hz), 4.39 (d, 1H, $J_{ab}$ = 16 Hz), 3.76 (t, 4H, J = 8.0 Hz), 3.45 (m, 1H), 3.38 (s, br, 2H), 3.15 (s, br, 2H), 3.76 (t, 4H, J = 8.0 Hz), 1.89 (m, 1H), 1.60 (m, 2H), 0.98 (d, 3H, J = 7.0 Hz), 0.95 (d, 3H, J = 7.0 Hz) |
| 145 | isobutyl | 4-ethylbenzyl-piperidine | 4-chlorophenyl | 8 | white solid | 492.09 | 1.31 min Method A | 492.21 | ¹H NMR 400 MHz, (CDCl₃) δ 7.63 (d, 2H, J = 8.0 Hz), 7.71 (d, 2H, J = 8.0 Hz), 7.47 (d, 2H, J = 8.0 Hz), 7.37 (d, 2H, J = 8.0 Hz), 6.26 (s, br, 1H), 5.39 (s, br, 1H), 4.52 (d, 1H, $J_{ab}$ = 16Hz), 4.43 (d, 1H, $J_{ab}$ = 16 Hz), 3.47-3.43 (m, 3H), 2.26 (m, 4H), 1.89 (m, 2H), 1.60 (m, 2H), 1.46-1.29 (m, 4H), 0.97 (d, 3H, J = 7.0 Hz), 0.94 (d, 3H, J = 7.0 Hz) |
| 146 | isobutyl | 4-ethylbenzyl-piperidine-3-carboxylic acid ethyl ester | 4-chlorophenyl | 8 | white solid | 564.15 | 1.33 min Method A | 564.24 | ¹H NMR 400 MHz, (CDCl₃) δ 7.69 (d, 2H, J = 8.0 Hz), 7.71 (d, 2H, J = 8.0 Hz), 7.48 (d, 2H, J = 8.0 Hz), 7.37 (d, 2H, J = 8.0 Hz), 6.35 (s, br, 1H), 5.40 (s, br, 1H), 4.72 (d, 1H, $J_{ab}$ = 16Hz), 4.48 (d, 1H, $J_{ab}$ = 16 Hz), 4.03 (q, 2H, J = 8.0 Hz), 3.47-3.42 (m, 3H), 3.21 (m, 1H), 2.62 (m, 1H), 2.63-2.36 (m, 3H), 2.06-1.95 (m, 1H), 1.93-1.80 (m, 3H), 1.67-1.50 (m, 3H), 1.13 (t, 3H, J = 8.0 Hz), 0.98 (d, 3H, J =.07 Hz), 0.95 (d, 3H, J = 7.0 Hz) |

TABLE 4-continued

| Ex. No. | R¹ | R² | R³ | Reaction Scheme | Appearance | Calc. MW | Ret. Time/Method | M+H+ | NMR Data |
|---|---|---|---|---|---|---|---|---|---|
| 147 | isobutyl | 4-ethylbenzyl-(4-benzylpiperidine) | 4-chlorophenyl | 8 | white solid | 582.21 | 1.46 min Method A | 582.41 | $^1$H NMR 400 MHz, (CDCl$_3$) δ 8.09 (d, 1H, J = 4.0 Hz), 8.02 (d, 2H, J = 8.0 Hz), 7.64 (d, 2H, J = 8.0 Hz), 7.41-7.36 (m, 5H), 6.72 (d, 1H, J = 12.0 Hz), 6.49 (t, 1H, J = 8.0 Hz), 6.35 (s, br, 1H), 5.87 (s, br, 1H), 4.80 (d, 1H, J$_{ab}$ = 16 Hz) 4.30 (d, 1H, J$_{ab}$ = 16 Hz), 3.84 (m, 4H), 3.55 (s, 2H), 3.46 (m, 1H), 2.57 (m, 4H), 1.89 (m, 1H), 1.60 (m, 2H), 0.98 (d, 3H, J = 7.0 Hz), 0.95 (d, 2H, J = 7.0 Hz) |
| 149 | isobutyl | 4-ethylbenzyl-N-benzyl | 4-chlorophenyl | 8 | white solid | 542.15 | 1.45 min Method A | 542.24 | $^1$H NMR 400 MHz, (CDCl$_3$) δ 7.70 (d, 2H, J = 8.0 Hz), 7.68 (d, 2H, J = 8.0 Hz), 7.47 (d, 2H, J = 8.0 Hz), 7.38 (d, 2H, J = 8.0 Hz), 7.29-7.16 (m, 5H), 6.28 (s, br, 1H), 5.38 (s, t, 1H), 4.52 (d, 1H, J$_{ab}$ = 16 Hz), 4.42 (d, 1H, J$_{ab}$ = 16 Hz), 3.54 (s, 2H), 3.45 (m, 1H), 2.62 (q, 2H, J = 7.0 Hz), 1.89 (m, 1H), 1.60 (m, 2H), 1.08 (t, 3H, J = 7.0 Hz), 0.98 (d, 3H, J = 7.0 Hz), 0.95 (d, 3H, J = 7.0 Hz) |
| 150 | isobutyl | 4-ethylbenzyl-N-methyl-benzyl | 4-chlorophenyl | 8 | amber film | 528.12 | 1.45 min Method A | 528.33 | $^1$H NMR 400 MHz, (CDCl$_3$) δ 7.72 (d, 2H, J = 8.0 Hz), 7.68 (d, 2H, J = 8.0 Hz), 7.54 (d, 2H, J = 8.0 Hz), 7.37 (d, 2H, J = 8.0 Hz), 7.35-7.29 (m, 5H), 6.27 (s, br, 1H), 5.37 (s, br, 1H), 4.52 (d, 1H, J$_{ab}$ = 16 Hz), 4.43 (d, 1H, J$_{ab}$ = 16 Hz), 3.55 (s, 2H), 3.45 (m, 1H), 2.17 (s, 3H), 1.89 (m, 1H), 1.60 (m, 2H), 0.98 (d, 3H, J = 7.0 Hz), 0.95 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 151 | isobutyl | N-methyl-N-(4-ethylbenzyl)-2-phenylethyl | 4-chlorophenyl | 8 | clear glass | 542.15 | 1.46 min Method A | 542.29 | ¹H NMR 400 MHz, (CDCl₃) δ 7.68 (d, 2H, J = 8.0 Hz), 7.64 (d, 2H, J = 8.0 Hz), 7.45 (d, 2H, J = 8.0 Hz), 7.39-7.26 (m, 4H), 6.97 (d, 1H, J = 8.0 Hz), 6.27 (s, br, 1H), 5.38 (s, br, 1H), 4.54 (d, 1H, $J_{ab}$ = 16 Hz), 4.44 (d, 1H, $J_{ab}$ = 16 Hz), 3.43 (s, 2H), 3.25 (t, 1H, J = 4.0 Hz), 2.77-2.69 (m, 4H), 2.40 (s, 3H), 1.94 (m, 1H), 1.60 (m, 2H) 0.97 (d, 2H, J = 7.0 Hz), 0.94 (d, 2H, J = 7.0 Hz) |
| 152 | isobutyl | N-methyl-piperazinyl-(4-ethylbenzyl) | 4-chlorophenyl | 8 | amber glass | 564.2 | 1.22 min Method A | 564.32 | ¹H NMR 400 MHz, (CDCl₃) δ 7.69 (d, 2H, J = 8.0 Hz), 7.59 (d, 2H, J = 8.0 Hz), 7.39-7.33 (m, 4H), 6.21 (s, br, 1H), 5.34 (s, br, 1H), 4.76 (d, 1H, $J_{ab}$ = 16 Hz), 4.31 (d, 1H, $J_{ab}$ = 16 Hz), 3.57 (s, 2H), 2.69-2.55 (m, 6H), 2.36-2.18 (m, 12H), 1.95 (m, 1H), 1.66-1.50 (m, 2H), 0.98 (d, 3H, J = 7.0 Hz), 0.94 (d, 3H, J = 7.0 Hz) |
| 153 | isobutyl | N-diethyl-propyl-amide | 4-chlorophenyl | 5 | white solid | 474.21 | 1.78 min Method C | 476.17 | ¹H NMR 400 MHz, (CDCl₃) δ 8.41 (br s, 2H), 7.85 (dd, 2H, J = 2.0, 6.8), 7.46 (dd, 2H, J = 2.0, 6.8), 5.46 (s, 1H), 4.21 (dd, 1H, J = 5.9, 8.8), 3.92 (d, 1H, J = 17), 3.77 (d, 1H, J = 17), 3.27-3.41 (m, 2H), 2.48-2.62 (m, 6H), 1.80-1.90 (m, 1H), 1.50-1.72 (m, 3H), 1.35-1.49 (m, 1H), 1.05 (t, 6H, J = 7.1), 0.87 (d, 3H, J = 6.4), 0.85 (d, 3H, J = 6.7) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 154 | isobutyl | ethyl piperidine-1-carboxylate (4-CH₂CH₂-piperidinyl with N-C(O)OEt) | 4-chlorophenyl | 5 | white solid | 516.18 | 1.53 min Method A | 517.30 | ¹H NMR 400 MHz, (CDCl₃) δ 7.83 (dd, 2H, J = 1.9, 6.8), 7.47 (dd, 2H, J = 2.0, 6.8), 7.31 (br s, 1H), 7.11 (br s, 1H), 5.57 (br s, 1H), 4.23 (dd, 1H, J = 6.8, 8.4), 4.00-4.15 (m, 2H), 3.95 (d, 1H, J = 17), 3.83 (d, 1H, J = 17), 2.93 (br s, 2H), 1.75-1.95 (m, 4H), 1.60-1.75 (1H, 1.25-1.55 (m, 1H), 1.25 (t, 5H, J = 7.7), 0.85 (d, 3H, J = 6.3), 0.83 (d, 3H, J = 6.3) |
| 155 | isobutyl | ethyl 2-(4-methylphenyl)propanoate (OEt ester) | 4-chlorophenyl | 1-Method A | white solid | 495.04 | 1.88 min Method A | 495.1 | ¹H NMR (CDCl₃) δ 7.62-7.59 (m, 2H), 7.43-7.39 (m, 2H), 7.28-7.25 (m, 2H), 7.22-7.19 (m, 2H), 6.22 (bs, 1H), 5.29 (bs, 1H), 4.53-4.43 (m, 2H), 4.42-4.37 (m, 1H), 4.16-4.07 (m, 2H), 1.82-1.73 (m, 1H), 1.48 (d, 3H, J = 7.3 Hz, isomer A), 1.47 (d, 3H, J = 7.3 Hz, isomer B), 1.36-1.22 (m, 2H), 1.21 (t, 3H, J = 7.1 Hz), 0.77 (d, 3H, J = 6.4 Hz, isomer A), 0.77 (d, 3H, J = 6.4 Hz, isomer B), 0.65 (d, 3H, J = 6.7 Hz, isomer A), 0.65 (d, 3H, J = 6.7 Hz, isomer B) |
| 156 | methyl | 4-(trifluoromethyl)benzyl | 4-chlorophenyl | 1-Method A | white solid | 434.07 | 1.57 min Method B | (M + H)⁺ 435.1 | ¹H NMR 400 MHz, (CDCl₃) δ 7.80 (d, 2H, J = 8.7), 7.66 (d, 2H, J = 8.3), 7.60 (m, 4H), 7.53 (s, 1H), 7.10 (s, 1H), 4.80 (ABq, 2H, Δν = 39.8, J_ab = 17.2), 4.30 (t, 1H, J = 7.5), 1.60 (m, 1H), 1.39 (m, 1H), 0.71 (t, 3H, J = 7.3) |
| 157 | methyl | 4-cyanobenzyl | 4-chlorophenyl | 1-Method A | white solid | 391.08 | 1.32 min Method B | (M + H)⁺ 392.1 | ¹H NMR 400 MHz, (CDCl₃) δ 7.81 (d, 2H, J = 8.7), 7.78 (d, 2H, J = 8.4), 7.62 (d, 2H, J = 8.7), 7.57 (d, 2H, J = 8.3), 7.52 (s, 1H), 7.09 (s, 1H), 4.80 (ABq, 2H, Δν = 45.0, J_ab = 17.6), 4.28 (t, 1H, J = 7.5,), 1.58 (m, 1H), 1.36 (m, 1H), 0.70 (t, 3H, J = 7.3) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 158 | isobutyl | 4-(cyclopropylaminocarbonyl)benzyl | 4-chlorophenyl | 6 | white solid | 478.01 | 1.53 min Method A | 478.17 | ¹H (CD₃OD, 300 MHz) δ 7.80 (ddd, 2H, J = 1.9, 2.4, 8.7), 7.73 (d, 2H, J = 8.3), 7.48-7.54 (m, 4H), 4.87 (m, 1H), 4.79 (d, 1H, J = 16.0), 4.49 (t, 1H, J = 6.2), 2.81-2.87 (m, 1H), 1.25-1.43 (m, 3H), 0.83 (d, 3H, J = 6.2), 0.77-0.83 (m, 2H), 0.63-0.66 (m, 2H), 0.57 (d, 3H, J = 6.1) |
| 159 | isobutyl | 4-(2-methoxyethylaminocarbonyl)benzyl | 4-chlorophenyl | 6 | white solid | 496.03 | 1.50 min Method A | 496.21 | ¹H HMR (CDCl₃, 300 MHz) δ 7.70 (d, 2H, J = 8.0), 7.68 (d, 2H, J = 8.6), 7.46 (d, 2H, J = 8.6), 7.41 (d, 2H, J = 8.0, 4.64 (d, 1H, J = 15.9), 4.43 (d, 1H, J = 15.9), 4.30 (t, 1H, J = 6.8), 3.63-3.66 (m, 2H), 3.55-3.58 (m, 2H), 3.39 (s, 3H), 1.76-1.84 (m, 1H), 1.28-1.34 (m, 1H), 1.05-1.11 (m, 1H), 0.75 (d, 3H, J = 6.5), 0.66 (d, 3H, J = 6.7) |
| 160 | isobutyl | 4-(4-(diethylamino)butylaminocarbonyl)benzyl | 4-chlorophenyl | 6 | white solid | 551.15 | 1.33 min Method A | 551.28 | ¹H HMR (CDCl₃, 500 MHz) δ 7.72 (d, 2H, J = 8.2), 7.67 (dd, 2H, J = 2.0, 8.7), 7.44 (dd, 2H, J = 1.8, 8.6), 7.39 (d, 2H, J = 8.2), 6.35 (br s, 1H), 5.46 (br s, 1H), 4.60 (d, 1H, J = 15.9), 4.50 (d, 1H, J = 15.9), 4.31 (t, 1H, J = 7.3), 3.54-3.57 (m, 2H), 2.56-2.64 (m, 6H), 1.72-1.80 (m, 3H), 1.28-1.34 (m, 1H), 1.13-1.16 (m, 1H), 1.03 (t, 6H, J = 7.2), 0.74 (d, 3H, J = 6.6), 0.61 (d, 3H, J = 6.6) |
| 161 | isobutyl | 4-(3-methylbutanoylamino)phenyl | 4-chlorophenyl | 9 | white solid | 494.06 | 1.51 min Method B | 494.2 | ¹H HMR (CDCl₃) δ 7.69 (d, 2H, J = 7.0 Hz), 7.45-7.47 (m, 4H), 7.30 (d, 2H, J = 8.0 Hz), 7.12 (s, br, 1H), 6.25 (s, br, 1H), 5.22 (s, br, 1H), 4.40 (dd, 2H, J = 50 Hz, 15 Hz), 4.25 (t, 1H, J = 7.4 Hz), 2.48-2.51 (m, 1H), 1.54-1.86 (m, 10H), 1.17-1.34 (m, 1H), 0.75 (d, 3H, J = 7.0 Hz), 0.67 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 162 | isobutyl | furan-2-carboxamide-phenylmethyl | 4-chlorophenyl | 9 | tan solid | 504.01 | 1.52 min Method B | 504.1 | ¹H HMR (CDCl₃) δ 8.10 (s, br, 1H), 7.67 (d, 2H, J = 7.0 Hz), 7.58 (d, 2H, J = 7.0 Hz), 7.23-7.49 (m, 6H), 6.54-6.57 (m, 1H), 6.27 (s, br, 1H), 5.50 (s, br, 1H), 4.51 (dd, 2H, J = 50 Hz, 15 Hz), 4.28 (t, 1H, J = 7.4 Hz), 1.78-1.85 (m, 1H), 1.12-1.32 (m, 2H), 0.75 (d, 3H, J = 7.0 Hz), 0.67 (d, 3H, J = 7.0 Hz) |
| 163 | isobutyl | acetamide-phenylmethyl | 4-chlorophenyl | 9 | white solid | 451.98 | 1.50 min Method B | 450.18 (M − H⁻) | ¹H HMR (CDCl₃) δ 7.67 (d, 2H, J = 8.0 Hz), 7.28-7.46 (m, 6H), 7.12 (s, br, 1H), 6.24 (s, br, 1H), 5.19 (s, br, 1H), 4.48 (dd, 2H, J = 50 Hz, 15 Hz), 4.27 (t, 1H, J = 7.0 Hz), 2.18 (s, 3H), 1.80-2.01 (m, 1H), 1.12-1.32 (m, 2H), 0.75 (d, 3H, J = 7.0 Hz), 0.67 (d, 3H, J = 7.0 Hz) |
| 164 | isobutyl | N-methyl-N-(3-cyanopropyl)-aminomethyl-phenylmethyl | 4-chlorophenyl | 8 | white solid | 491.06 | 1.31 min Method A | 491.24 | ¹H HMR, 400 MHz, (CDCl₃) δ 7.69 (d, 2H, J = 8.0 Hz), 7.64 (d, 2H, J = 8.0 Hz), 7.51 (d, 2H, J = 8.0 Hz), 7.37 (d, 2H, J = 8.0 Hz), 6.25 (s, br, 1H), 5.35 (s, br, 1H), 4.39 (d, 1H, $J_{ab}$ = 16 Hz), 4.36 (d, 1H, $J_{ab}$ = 16 Hz), 3.62 (s, 2H), 3.25 (t, 1H, J = 6.0 Hz), 2.55-2.48 (m, 7H), 1.94 (m, 1H), 1.60 (m, 2H), 0.97 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 165 | isobutyl | 4-ethylbenzyl-(cyclopropylmethylpropyl)amino | 4-chlorophenyl | 8 | white solid | 520.14 | 1.40 min Method A | 520.32 | ¹H HMR, 400 Hz, (CDCl₃) δ 7.72 (d, 2H, J = 8.0 Hz), 7.66 (d, 2H, J = 8.0 Hz), 7.51 (d, 2H, J = 8.0 Hz), 7.37 (d, 2H, J = 8.0 Hz), 6.28 (s, br, 1H), 5.39 (s, br, 1H), 4.52 (d, 1H, $J_{ab}$ = 16 Hz), 4.43 (d, 1H, $J_{ab}$ = 16 Hz), 3.57 (s, 2H), 3.25 (t, 1H, J = 6.0 Hz), 2.59 (t, 2H, J = 8.0 Hz), 2.30 (d, 2H, J = 6.0 Hz), 2.01-1.90 (m, 1H), 1.68-1.49 (m, 4H), 1.02 (m, 1H), 0.98 (d, 3H, J = 7.0 Hz), 0.94 (d, 3H, J = 7.0 Hz), 0.89 (t, 3H, J = 8.0 Hz), 0.44-0.31 (m, 4H) |
| 166 | isobutyl | 4-ethylbenzyl-(3-methylpiperidinyl) | 4-chlorophenyl | 8 | clear glass | 506.11 | 1.41 min Method A | 506.31 | ¹H HMR, 400 Hz, (CDCl₃) δ 7.73 (d, 2H, J = 8.0 Hz), 7.65 (d, 2H, J = 8.0 Hz), 7.44 (d, 2H, J = 8.0 Hz), 7.38 (d, 2H, J = 8.0 Hz), 6.27 (s, br, 1H), 5.39 (s, br, 1H), 4.56 (d, 1H, $J_{ab}$ = 16 Hz), 4.42 (d, 1H, $J_{ab}$ = 16 Hz), 3.45 (d, 1H, Jab = 12 Hz), 3.28 (d, 1H, $J_{ab}$ = 12 Hz), 3.25 (t, 1H, J = 6.0 Hz), 2.75 (m, 4H), 2.0-1.53 (m, 7H), 1.35 (m, 1H), 1.17 (m, 1H), 0.97 (d, 3H, J = 7.0 Hz), 0.94 (d, 3H, J = 7.0 Hz), 0.87 (m, 3H) |
| 167 | isobutyl | 4-ethylbenzyl-(4-methylpiperidinyl) | 4-chlorophenyl | 8 | clear glass | 506.11 | 1.42 min Method A | 506.30 | ¹H HMR, 400 Hz, (CDCl₃) δ 7.71 (d, 2H, J = 8.0 Hz), 7.65 (d, 2H, J = 8.0 Hz), 7.43 (d, 2H, J = 8.0 Hz), 7.37 (d, 2H, J = 8.0 Hz), 6.26 (s, br, 1H), 5.40 (s, br, 1H), 4.56 (d, 1H, $J_{ab}$ = 16 Hz), 4.42 (d, 1H, $J_{ab}$ = 16 Hz), 3.48 (s, 2H), 3.25 (t, 1H, J = 6.0 Hz), 2.56-2.42 (m, 4H), 1.93 (m, 1H), 1.89-1.48 (m, 6H), 1.34 (m, 1H), 0.98-0.93 (m, 9H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 168 | isobutyl | 4-ethylbenzyl-(decahydroquinolin-1-yl)methyl | 4-chlorophenyl | 8 | clear glass | 546.18 | 1.46 min Method A | 546.35 | ¹H HMR, 400 Hz, (CDCl₃) δ 7.72 (d, 2H, J = 8.0 Hz), 7.65 (d, 2H, J = 8.0 Hz), 7.42 (d, 2H, J = 8.0 Hz), 7.38 (d, 2H, J = 8.0 Hz), 6.27 (s, br, 1H), 5.40 (s, br, 1H), 4.52 (d, 1H, J$_{ab}$ = 16 Hz), 4.43 (d, 1H, J$_{ab}$ = 16 Hz), 3.45 (d, 1H, J$_{ab}$ = 12 Hz), 3.28 (d, 1H, J$_{ab}$ = 12 Hz), 3.25 (t, 1H, J = 6.0 Hz), 2.87 (m, 1H), 2.70-2.56 (m, 3H), 2.39 (m, 1H), 2.31-2.19 (m, 4H), 1.95 (m, 1H), 1.77 (m, 1H), 1.68-1.59 (m,2H), 1.54-1.44 (m, 4H), 1.28 (m, 2H), 0.98 (d, 3H, J = 7.0 Hz), 0.94 (d, 2H, J = 7.0 Hz) |
| 169 | isobutyl | 4-ethylbenzyl-(diisopropylamino)methyl | 4-chlorophenyl | 8 | clear glass | 508.13 | 1.39 min Method A | 502.28 | ¹H HMR, 400 Hz, (CDCl₃) δ 7.70 (d, 2H, J = 8.0 Hz), 7.68 (d, 2H, J = 8.0 Hz), 7.55 (d, 2H, J = 8.0 Hz), 7.38 (d, 2H, J = 8.0 Hz), 6.28 (s, br, 1H),5.37 (s, br, 1H), 4.57 (d, 1H J$_{ab}$ = 16 Hz), 4.36 (d, 1H, J$_{ab}$ = 16 Hz), 3.38 (s, 2H), 3.25 (t, 1H, J = 6.0 Hz), 2.83 (m, 2H), 1.92 (m, 1H), 1.60 (m, 2H), 0.98 (d, 3H, J = 7.0 Hz), 0.94 (d, 3H, J = 7.0 Hz), 0.84 (s, 6H), 0.82 (s, 6H) |
| 170 | isobutyl | 4-ethylbenzyl-(N-methyl-N-butyl)amino | 4-chlorophenyl | 8 | clear glass | 494.1 | 1.34 min Method A | 494.26 | ¹H HMR, 400 Hz, (CDCl₃) δ 7.69 (d, 2H, J = 8.0 Hz), 7.67 (d, 2H, J = 8.0 Hz), 7.44 (d, 2H, J = 8.0 Hz), 7.38 (d, 2H, J = 8.0 Hz), 6.27 (s, br, 1H), 5.39 (s, br, 1H), 4.52 (d, 1H, J$_{ab}$ = 16 Hz), 4.44 (d, 1H, J$_{ab}$ = 16 Hz), 3.40 (s, 2H), 3.25 (t, 1H, J = 6.0 Hz), 2.39 (s, 3H), 1.94 (m, 1H), 1.68-1.50 (m, 2H), 1.43 (m, 2H), 1.30 (m, 2H), 0.98 (d, 3H, J = 7.0 Hz), 0.94 (d, 3H, J = 7.0 Hz), 0.86 (t, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 171 | isobutyl | 4-ethylbenzyl-N-ethyl-propyl | 4-chlorophenyl | 8 | clear glass | 508.13 | 1.40 min Method A | 508.27 | ¹H HMR, 400 Hz, (CDCl₃) δ 7.69 (d, 2H, J = 8.0 Hz), 7.64 (d, 2H, J = 8.0 Hz), 7.4-7.33 (m, 4H), 6.25 (s, br, 1H), 5.35 (s, br, 1H), 4.52 (d, 1H, $J_{ab}$ = 16 Hz), 4.43 (d, 1H, $J_{ab}$ = 16 Hz), 3.46 (s, 2H), 3.25 (t, 1H, J = 6.0 Hz), 2.62 (t, 2H, J = 6.0 Hz), 2.52 (q, 2H, J = 7.0 Hz), 1.94 (m, 1H), 1.68-1.45 (m, 4H), 1.29 (m, 2H), 1.02 (t, 3H, J = 7.0 Hz), 0.98 (d, 3H, J = 7.0 Hz), 0.94 (d, 3H, J = 7.0 Hz), 0.88 (t, 3H, J = 7.0 Hz) |
| 172 | isobutyl | 4-ethylbenzyl-piperidin-4-yl | 4-chlorophenyl | 8 | amber glass | 575.22 | 1.34 min Method A | 575.32 | ¹H HMR, 400 Hz, (CDCl₃) δ 7.72 (d, 2H, J = 8.0 Hz), 7.59 (d, 2H, J = 8.0 Hz), 7.39-7.33 (m, 4H), 6.25 (s, br, 1H), 5.36 (s, br, 1H), 4.53 (d, 1H, $J_{ab}$ = 16 Hz), 4.39 (d, 1H, $J_{ab}$ = 16 Hz), 3.57 (s, 2H), 3.25 (t, 1H, J = 6.0 Hz), 2.62-2.32 (m, 9H), 1.94 (m, 1H), 1.68-1.50 (m, 2H), 1.48-1.20 (m, 12H), 0.98 (d, 3H, J = 7.0 Hz), 0.94 (d, 3H, J = 7.0 Hz) |
| 173 | cyclopropylmethyl | 4-carboxybenzyl | 4-chlorophenyl | 6 | white solid | 436.92 | 1.52 min Method A | 437.16 | ¹H HMR (DMSO-d₆, 300 MHz) δ 7.85 (d, 2H, J = 8.4), 7.82 (dd, 2H, J = 1.8, 8.7), 7.61 (dd, 2H, J = 1.8, 8.7), 7.54 (br s, 1H), 7.47 (d, 2H, J = 8.4), 7.09 (br s, 1H), 4.85 (d, 1H, J = 17.4), 4.69 (d, 1H, J = 17.1), 4.42 (t, 1H, J = 7.2), 1.40-1.48 (m, 1H), 1.27-1.34 (m, 1H), 0.42-0.47 (m, 1H), 0.25-0.30 (m, 2H), 0.00-0.03 (m, 1H), −0.10−0.07 (m, 1H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 174 | CH₂-O-C(CH₃)₃ | 4-CF₃-phenyl-CH₂ | 4-Cl-phenyl | 1-Method A | off-white solid | 492.11 | 2.13 min Method D | M + Na 514.95 | ¹H HMR (DMSO) δ 7.76 (d, 2H, J = 6.8 Hz), 7.61 (m, 6H), 7.44 (s, br, 1H), 7.13 (s, br, 1H), 4.78 (dd, 2H, J = 5.2 Hz, 16 Hz), 4.58 (t, 1H, J = 8.0 Hz), 3.47 (d, 2H, J = 6.0 Hz), 0.88 (s, 9H) |
| 175 | CH₂-O-C(CH₃)₃ | 4-CN-phenyl-CH₂ | 4-Cl-phenyl | 1-Method A | white solid | 449.12 | 1.94 min Method D | M + Na 471.97 | ¹H HMR (DMSO) δ 7.77 (m, 4H), 7.60 (m, 4H), 7.45 (s, br, 1H), 7.12 (s, br, 1H), 4.78 (dd, 2H, J = 5.6 Hz, 20 Hz), 4.57 (t, 1H, J = 8.0 Hz), 3.47 (d, 2H, J = 6.0 Hz), 0.88 (s, 9H) |
| 176 | isobutyl | 3-OCF₃-phenyl-CH₂ | 4-Cl-phenyl | 1-solid support | | 478.90 | 1.86 Method B | 479.02 | |
| 177 | isobutyl | 2-CH₃,4-F-phenyl-CH₂ | 4-Cl-phenyl | 1-solid support | | 426.90 | 1.82 Method B | M + Na 449.02 | |

TABLE 4-continued

| Ex. No. | R¹ | R² | R³ | Reaction Scheme | Appearance | Calc. MW | Ret. Time/Method | M+H⁺ | NMR Data |
|---|---|---|---|---|---|---|---|---|---|
| 178 | isobutyl | 2-cyano biphenyl | 4-chlorophenyl | 1-solid support | | 496.00 | 1.81 Method B | 496.06 | |
| 179 | isobutyl | 2-fluorophenyl | 4-chlorophenyl | 1-solid support | | 412.90 | 1.72 Method B | 413.04 | |
| 180 | isobutyl | 2,5-dimethylphenyl | 4-chlorophenyl | 1-solid support | | 423.00 | 1.86 Method B | 445.02 M+Na | |
| 181 | isobutyl | 4-benzyloxyphenyl | 4-chlorophenyl | 1-solid support | | 501.10 | 1.94 Method B | 523.04 M+Na | |
| 182 | isobutyl | 3,5-dimethylisoxazol-4-yl | 4-chlorophenyl | 1-solid support | | 413.90 | 1.53 Method B | 414.05 | |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 183 | isobutyl | 3,5-dimethylphenyl-CH₂ | 4-Cl-phenyl | 1-solid support | | 423.00 | 1.88 Method B | 423.08 | |
| 184 | isobutyl | 4-HO-3-(propanoyl)phenyl-CH₂ | 4-Cl-phenyl | 1-solid support | | 467.00 | 1.60 Method B | 467.06 | |
| 185 | isobutyl | 3-(2-F-phenoxy)phenyl-CH₂ | 4-Cl-phenyl | 1-solid support | | 505.00 | 1.89 Method B | 505.07 | |
| 186 | isobutyl | 2-(F₃CO)phenyl-CH₂ | 4-Cl-phenyl | 1-solid support | | 478.90 | 1.84 Method B | 479.02 | |
| 187 | isobutyl | 3-(4-F-phenoxy)phenyl-CH₂ | 4-Cl-phenyl | 1-solid support | | 505.00 | 1.93 Method B | 505.06 | |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 188 | isobutyl | 3-chlorobenzyl | 4-chlorophenyl | 1-solid support | | 429.40 | 1.80 Method B | 450.90 M + Na | |
| 189 | isobutyl | 4-ethylbenzyl | 4-chlorophenyl | 1-solid support | | 423.00 | 1.89 Method B | 423.09 | |
| 190 | isobutyl | 4,4-dimethyl-2-pentenyl | 4-chlorophenyl | 1-solid support | | 425.00 | 1.92 Method B | 425.11 | |
| 191 | isobutyl | 3-phenoxybenzyl | 4-chlorophenyl | 1-solid support | | 487.00 | 1.91 Method B | 487.04 | |
| 192 | isobutyl | 4-isopropylbenzyl | 4-chlorophenyl | 1-solid support | | 437.00 | 1.95 Method B | 459.05 M + Na | |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 193 | isobutyl | pentenyl | 4-chlorobenzyl | 1-solid support | | 358.90 | 1.67 Method B | 381.07 M + Na | |
| 194 | isobutyl | 4-bromobenzyl | 4-chlorobenzyl | 1-solid support | | 473.80 | 1.86 Method B | 472.9 | |
| 195 | isobutyl | 2,4-difluorobenzyl | 4-chlorobenzyl | 1-solid support | | 430.9 | 1.75 Method B | 431.04 | |
| 196 | isobutyl | chloropentenyl | 4-chlorobenzyl | 1-solid support | | 379.30 | 1.65 Method B | 400.98 | |
| 197 | isobutyl | 4-vinylbenzyl | 4-chlorobenzyl | 1-solid support | | 421.00 | 1.82 Method B | 443.06 M + Na | |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 198 | isobutyl | (Z)-3-chloroallyl | 4-chlorophenyl | 1-solid support | | 379.30 | 1.64 Method B | 400.99 | |
| 199 | isobutyl | 4-(SCF₃)benzyl | 4-chlorophenyl | 1-solid support | | 495.00 | 1.95 Method B | 494.98 | |
| 200 | isobutyl | 4-(tert-pentyl)benzyl | 4-chlorophenyl | 1-solid support | | 465.10 | 2.05 Method B | 487.10 M + Na | |
| 201 | isobutyl | 3-MeO-4-COOMe-benzyl | 4-chlorophenyl | 1-solid support | | 483.00 | 1.72 Method B | 483.04 | |
| 202 | isobutyl | 3,5-dichlorobenzyl | 4-chlorophenyl | 1-solid support | | 463.80 | 1.91 Method B | 486.96 M + Na | |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 203 | isobutyl | 3,4-difluorophenethyl | 4-chlorophenyl | 1-solid support | | 430.90 | 1.77 Method B | 431.04 | |
| 204 | isobutyl | 3-methylphenethyl | 4-chlorophenyl | 1-solid support | | 409.00 | 1.79 Method B | 409.07 | |
| 205 | isobutyl | 2-(trifluoromethoxy)phenethyl | 4-chlorophenyl | 1-solid support | | 462.90 | 1.81 Method B | 463.04 | |
| 206 | isobutyl | 3,4-dimethylphenethyl | 4-chlorophenyl | 1-solid support | | 423.00 | 1.86 Method B | 423.10 | |
| 207 | isobutyl | 4-bromo-2-fluorophenethyl | 4-chlorophenyl | 1-solid support | | 491.80 | 1.88 Method B | 492.91 | |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 208 | isobutyl | 2-methylphenethyl | 4-chlorophenylmethyl | 1-solid support | | 409.00 | 1.78 Method B | 431.04 M + Na | |
| 209 | isobutyl | 3-cyanophenethyl | 4-chlorophenylmethyl | 1-solid support | | 419.9 | 1.58 Method B | 442.04 M + Na | |
| 210 | isobutyl | allyl | 4-chlorophenylmethyl | 1-solid support | | 344.90 | 1.56 Method B | 367.05 M + Na | |
| 211 | isobutyl | 4-fluoro-2-trifluoromethoxyphenethyl | 4-chlorophenylmethyl | 1-solid support | | 480.90 | 1.87 Method B | 481.02 | |
| 212 | isobutyl | 3,5-difluorophenethyl | 4-chlorophenylmethyl | 1-solid support | | 430.90 | 1.76 Method B | 453.02 | |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 213 | isobutyl | 3,5-dimethoxybenzyl | 4-chlorophenyl | 1-solid support | | 455.00 | 1.71 Method B | 455.07 | |
| 214 | isobutyl | 4-(phenoxycarbonyl)benzyl | 4-chlorophenyl | 1-solid support | | 515.00 | 1.91 Method B | 515.09 | |
| 215 | isobutyl | 3-chloro-2-fluorobenzyl | 4-chlorophenyl | 1-solid support | | 447.40 | 1.82 Method B | 468.99 M + Na | |
| 216 | isobutyl | 2-fluoro-5-(trifluoromethyl)benzyl | 4-chlorophenyl | 1-solid support | | 480.90 | 1.80 Method B | 481.00 | |
| 217 | isobutyl | (E)-5-methoxypent-2-enyl | 4-chlorophenyl | 1-solid support | | 402.90 | 1.600 Method B | 403.12 | |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 218 | isobutyl | 2-Cl-phenyl | 4-Cl-phenyl | 1-solid support | | 429.40 | 1.78 Method B | 429.04 | |
| 219 | isobutyl | 2,4,5-triF-phenyl | 4-Cl-phenyl | 1-solid support | | 448.90 | 1.78 Method B | 471.00 | |
| 220 | isobutyl | 2,3-diF-phenyl | 4-Cl-phenyl | 1-solid support | | 430.90 | 1.75 Method B | 453.03 | |
| 221 | isobutyl | 3-CF₃-5-F-phenyl | 4-Cl-phenyl | 1-solid support | | 480.90 | 1.85 Method B | 503.00 M + Na | |
| 222 | isobutyl | 2-naphthyl | 4-Cl-phenyl | 1-solid support | | 445.00 | 1.87 Method B | 467.06 M + Na | |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 223 | isobutyl | 2-acetoxybenzyl | 4-chlorophenyl | 1-solid support | | 453.00 | 1.62 Method B | 453.03 | |
| 224 | isobutyl | 4-acetoxybenzyl | 4-chlorophenyl | 1-solid support | | 453.00 | 1.63 Method B | 453.05 | |
| 225 | isobutyl | (2-methylthiazol-4-yl)methyl | 4-chlorophenyl | 1-solid support | | 416.00 | 1.53 Method B | 416.04 | |
| 226 | isobutyl | (thiazol-4-yl)methyl | 4-chlorophenyl | 1-solid support | | 401.90 | 1.45 Method B | 401.96 | |
| 227 | isobutyl | (pyridin-4-yl)methyl | 4-chlorophenyl | 1-solid support | | 395.90 | 1.12 Method B | 396.01 | |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 228 | isobutyl | methallyl | 4-Cl-phenyl | 1-solid support | | 358.90 | 1.62 Method B | 381.01 M + Na | |
| 229 | isobutyl | 4-OMe-3-Me-benzyl | 4-Cl-phenyl | 1-solid support | | 439.00 | 1.80 Method B | 460.97 M + Na | |
| 230 | isobutyl | 2-OMe-benzyl | 4-Cl-phenyl | 1-solid support | | 424.90 | 1.72 Method B | 425.03 | |
| 231 | isobutyl | 2,5-diCl-benzyl | 4-Cl-phenyl | 1-solid support | | 463.80 | 1.85 Method B | 464.90 | |
| 232 | isobutyl | 5-(ethoxycarbonyl)furan-2-ylmethyl | 4-Cl-phenyl | 1-solid support | | 456.90 | 1.64 Method B | 456.02 | |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 233 | isobutyl | 2-F, 5-Cl phenyl | 4-Cl phenyl | 1-solid support | | 447.40 | 1.78 Method B | 468.92 M + Na | |
| 234 | n-butyl | 4-CN phenyl | 4-Cl phenyl | 1-Method A | white solid | 419.11 | 1.91 min Method F | (M + Na)⁺ 442.0 | ¹H HMR (400 MHz, DMSO) δ 7.82 (d, 2H, J = 8.7), 7.80 (d, 2H, J = 8.4), 7.62 (d, 2H, J = 8.7), 7.59 (d, 2H, J = 8.3), 7.51 (s, 1H), 7.07 (s, 1H), 4.81 (ABq, 2H, Δν = 38.0, J$_{ab}$ = 17.5), 4.31 (t, 1H, J = 6.7), 1.54 (m, 1H), 1.29 (m, 1H), 1.03 (m, 3H), 0.85 (m, 1H), 0.66 (t, 3H, J = 6.9) |
| 235 | n-butyl | 4-CF₃ phenyl | 4-Cl phenyl | 1-Method A | white solid | 462.10 | 2.13 min Method F | (M + Na)⁺ 485.0 | ¹H HMR (400 MHz, DMSO) δ 7.81 (d, 2H, J = 8.7), 7.69 (d, 2H, J = 8.3), 7.61 (m, 4H), 7.51 (s, 1H), 7.07 (s, 1H), 4.82 (ABq, 2H, Δν = 31.9, J$_{ab}$ = 17.1), 4.32 (t, 1H, J = 8.3), 1.53 (m, 1H), 1.31 (m, 1H), 1.05 (m, 3H), 0.88 (m, 1H), 0.63 (t, 3H, J = 6.8) |
| 236 | isobutyl | 3,5-bis(CF₃) phenyl | 4-Cl phenyl | 1-solid support | white solid | 530.92 | 1.92 Method B | 530.99 | |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 237 | isobutyl | ethyl methacrylate group | 4-Cl-phenyl | 1-solid support | white solid | 416.93 | 1.61 Method B | 417.07 | |
| 238 | isobutyl | 4-(1-carboxyethyl)benzyl | 4-Cl-phenyl | 1-solid support | white solid | 466.99 | 1.62 Method B | 467.06 | |
| 239 | isobutyl | 2-chloroallyl ethyl | 4-Cl-phenyl | 1-solid support | white solid | 379.13 | 1.62 | 400.98 M + Na | |
| 240 | isobutyl | 3-pyridylmethyl | 4-Cl-phenyl | 1-solid support | white solid | 395.91 | 1.13 | 396.01 | |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 241 | isobutyl | N-(4-ethylbenzyl)-N-heptyl | 4-chlorophenyl | 8 | amber glass | 592.29 | 1.69 min Method A | 592.39 | ¹H HMR, 400 Hz, (CDCl₃) δ 7.72 (d, 2H, J = 8.0 Hz), 7.65 (d, 2H, J = 8.0 Hz), 7.43 (d, 2H, J = 8.0 Hz), 7.37 (d, 2H, J = 8.0 Hz), 6.27 (s, br, 1H), 5.40 (s, br, 1H), 4.56 (d, 1H, $J_{ab}$ = 16 Hz), 4.40 (d, 1H, $J_{ab}$ = 16 Hz), 3.56 (s, 2H), 3.25 (t, 1H, J = 6.0 Hz), 2.40 (t, 4H, J = 6.0 Hz), 1.95 (m, 1H), 1.68-1.52 (m, 2H), 1.42 (q, 4H, J = 6.0 Hz), 1.28-1.22 (m, 12H), 0.98 (d, 3H, J = 7.0 Hz), 0.88 (t, 6H, J = 6.0 Hz) |
| 242 | isobutyl | N-(4-ethylbenzyl)-N-nonyl | 4-chlorophenyl | 8 | amber glass | 648.4 | 1.88 min Method A | 648.43 | ¹H HMR, 400 Hz, (CDCl₃) δ 7.71 (d, 2H, J = 8.0 Hz), 7.64 (d, 2H, J = 8.0 Hz), 7.43 (d, 2H, J = 8.0 Hz), 7.37 (d, 2H, J = 8.0 Hz), 6.27 (s br, 1H), 5.40 (s, br, 1H), 4.56 (d, 1H, $J_{ab}$ = 16 Hz), 4.40 (d, 1H, $J_{ab}$ = 16 Hz), 3.56 (s, 2H), 3.25 (t, 1H, J = 6.0 Hz), 2.47 (t, 4H, J = 6.0 Hz), 1.95 (m, 1H), 1.68-1.50 (m, 2H), 1.43-1.14 (m, 14H), 0.98 (d, 3H, J = 7.0 Hz), 0.94 (d, 3H, J = 7.0 Hz), 0.88 (t, 6H, J = 6.0 Hz) |
| 243 | isobutyl | N-(4-ethylbenzyl)-N-(ethoxycarbonylmethyl) | 4-chlorophenyl | 9 | clear glass | 524.08 | 1.35 min Method A | 542.25 | ¹H HMR, 400 Hz, (CDCl₃) δ 7.69 (d, 2H, J = 8.0 Hz), 7.64 (d, 2H, J = 8.0 Hz), 7.50 (d, 2H, J = 8.0 Hz), 7.38 (d, 2H, J = 8.0 Hz), 6.25 (s, br, 1H), 5.34 (s, br, 1H), 4.70 (d, 1H, $J_{ab}$ = 16 Hz), 4.48 (d, 1H, $J_{ab}$ = 16 Hz), 4.24-4.08 (m, 4H), 3.42 (s, 2H), 3.25 (t, 1H, J = 6 Hz), 2.51 (s, 3H), 1.94 (M, 1H), 1.68-1.54 (m, 2H), 1.22 (t, 3H, J = 6.0 Hz), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 244 | isobutyl | 4-(morpholinopropylaminocarbonyl)benzyl | 4-chlorophenyl | 6 | white solid | 565.14 | 1.29 min Method B | 564.99 | ¹H NMR (CDCl₃, 300 MHz,) δ 8.12 (br s, 1H), 7.77 (d, 2H, J = 8.8), 7.70 (d, 2H, J = 8.6), 7.47 (d, 2H, J = 8.4), 7.45 (d, 2H, J = 8.0), 6.25 (br s, 1H), 5.31 (br s, 1H), 4.66 (d, 1H, J = 15.7), 4.38 (d, 1H, J = 15.8), 4.27 (t, 1H, J = 7.1), 3.51-3.89 (m, 4H), 2.35-2.74 (m, 4H), 1.78-1.88 (m, 2H), 1.40-1.65 (m, 4H), 1.24-1.32 (m, 2H), 1.03-1.10 (m, 1H), 0.74 (d, 3H, J = 6.5), 0.65 (d, 3H, J = 6.6) |
| 245 | isobutyl | 4-carbamoylbenzyl | 4-chlorophenyl | 6 | white solid | 437.95 | 1.36 min Method B | 438.20 | ¹H NMR (CDCl₃, 300 MHz) δ 7.72 (dd, 2H, J = 1.9, 8.7), 7.69 (dd, 2H, J = 1.8, 8.7), 7.44 (d, 2H, J = 8.6), 6.21 (br s, 1H), 5.98 (br s, 1H), 5.88 (br s, 1H), 5.39 (br s, 1H), 4.66 (d, 1H, J = 15.7), 4.41 (d, 1H, J = 15.9), 4.29 (t, 1H, J = 6.5), 1.77-1.87 (m, 1H), 1.25-1.36 (m, 1H), 1.03-1.11 (m, 1H), 0.75 (d, 3H, J = 6.6), 0.65 (d, 3H, J = 6.6) |
| 246 | isobutyl | 4-(piperidinoethylaminocarbonyl)benzyl | 4-chlorophenyl | 6 | white solid | 549.14 | 1.34 min Method B | 549.00 | ¹H NMR (CDCl₃, 300 MHz) δ 7.82 (d, 2H, J = 7.8), 7.67 (dd, 2H, J = 2.0, 8.7), 7.40-7.46 (m, 5H), 6.22 (br s, 1H), 5.23 (br s, 1H), 4.61 (d, 1H, J = 15.9), 4.42 (d, 1H, J = 15.7), 4.28 (t, 1H, J = 7.2), 3.60-3.69 (m, 2H), 2.45-2.83 (m, 6H), 1.40-1.85 (m, 7H), 1.24-1.35 (m, 1H), 1.05-1.14 (m, 1H), 0.75 (d, 3H, J = 6.5), 0.66 (d, 3H, J = 6.6) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 247 | isobutyl | 4-(thiomorpholine-4-carbonyl)benzyl | 4-chlorophenyl | 6 | white solid | 524.11 | 1.61 min Method B | 523.94 | ¹H NMR (CDCl₃, 300 MHz) δ 7.68 (d, 2H, J = 8.4), 7.46 (d, 2H, J = 8.4), 7.39 (d, 2H, J = 8.1), 7.29 (d, 2H, J = 8.1), 6.20 (br s, 1H), 5.24 (br s, 1H), 4.60 (d, 1H, J = 15.8), 4.44 (d, 1H, J = 15.9), 4.30 (t, 1H, J = 6.9), 3.70-4.05 (br m, 4H), 2.45-2.60 (m, 4H), 1.73-1.80 (m, 1H), 1.28-1.35 (m, 1H), 1.05-1.14 (m, 1H), 0.76 (d, 3H, J = 6.5), 0.66 (d, 3H, J = 6.6) |
| 248 | n-propyl | 4-morpholinobenzyl | 4-chlorophenyl | 2 | red solid | 466.00 | 1.48 min Method B | 466.2 | ¹H NMR (CDCl₃) δ 7.65 (d, 2H, J = 7.0 Hz), 7.41 (d, 2H, J = 7.0 Hz), 7.20 (d, 2H, J = 8.8 Hz), 6.79 (d, 2H, J = 8.8 Hz), 6.23 (s, br, 1H), 5.20 (s, br, 1H), 4.32 (dd, 2H, J = 50 Hz, 15 Hz), 4.19-4.27 (m, 1H), 3.84-3.87 (m, 4H), 3.12-3.16 (m, 4H), 1.91-1.95 (m, 1H), 1.35-1.39 (m, 1H), 0.92-1.06 (m, 2H), 0.74 (t, 3H, J = 8.0 Hz) |
| 249 | n-propyl | 4-(4-methylpiperazin-1-yl)benzyl | 4-chlorophenyl | 2 | yellow solid | 479.05 | 1.18 min Method B | 479.02 | ¹H NMR (CDCl₃) δ 7.63 (d, 2H, J = 8.0 Hz), 7.40 (d, 2H, J = 8.0 Hz), 7.19 (d, 2H, J = 8.8 Hz), 6.78 (d, 2H, J = 8.8 Hz), 6.25 (s, br, 1H), 5.21 (s, br, 1H), 4.36 (dd, 2H, J = 50 Hz, 15 Hz), 4.20-4.27 (m, 1H), 3.28-3.35 (m, 4H), 2.69-2.76 (m, 4H), 2.48 (s, 3H), 1.93-1.97 (m, 1H), 1.35-1.39 (m, 1H), 0.90-1.07 (m, 2H), 0.72 (t, 3H, J = 8.0 Hz) |
| 250 | n-propyl | 4-(2,5-dimethylpyrrol-1-yl)benzyl | 4-chlorophenyl | 2 | tan solid | 474.03 | 1.92 min Method B | 474.2 | ¹H NMR (CDCl₃) δ 7.68 (d, 2H, J = 8.8 Hz), 7.43-7.45 (m, 4H), 7.12 (d, 2H, J = 8.8 Hz), 6.78 (d, 2H, J = 8.8 Hz), 6.19 (s, br, 1H), 5.18 (s, br, 1H), 4.56 (dd, 2H, J = 50 Hz, 15 Hz), 4.21-4.30 (m, 1H), 2.01 (s, 6H), 1.93-1.97 (m, 1H), 1.35-1.39 (m, 1H), 0.90-1.07 (m, 2H), 0.72 (t, 3H, J = 8.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 251 | isobutyl | 4-(N-methoxy-N-methylcarbamoyl)benzyl | 4-chlorophenyl | 6 | white solid | 482.00 | 2.01 min Method B | 479.07 | ¹H NMR (CDCl₃, 300 MHz) δ 7.67 (ddd, 2H, J = 1.9, 2.4, 8.7), 7.58 (d, 2H, J = 8.1), 7.43 (ddd, 2H, J = 1.5, 2.4, 8.7), 7.37 (d, 2H, J = 8.2), 6.30 (br s, 1H), 5.70 (bs, 1H), 4.62 (d, 1H, J = 15.9), 4.32 (t, 1H, J = 7.3), 3.51 (s, 3H), 3.32 (s, 3H), 1.73-1.80 (m, 1H), 1.28-1.35 (m, 1H), 1.05-1.14 (m, 1H), 0.74 (d, 3H, J = 6.5), 0.61 (d, 3H, J = 6.6) |
| 252 | isobutyl | 2-(ethoxycarbonyl)benzyl | 4-chlorophenyl | 1-Method A | white solid | 466.98 | 1.92 min Method A | 467.2 | ¹H NMR (CDCl₃) δ 7.92 (d, 1H, J = 8.0 Hz), 7.79 (A of ABq, 2H, J = 8.8 Hz), 7.72 (d, 1H, J = 7.7 Hz), 7.50 (B of ABq, 2H, J = 8.8 Hz), 7.31 (t, 1H, J = 7.7 Hz), 6.29 (bs, 1H), 5.21 (bs, 1H), 5.02 (s, 2H), 4.35 (q, 2H, J = 7.0 Hz), 4.27 (dd, 1H, J = 8.6, 5.5 Hz), 1.88-1.78 (m, 1H), 1.39 (t, 3H, J = 7.0 Hz), 1.37-1.29 (m, 1H), 1.02-0.93 (m, 1H), 0.75 (d, 3H, J = 6.6 Hz), 0.66 (d, 3H, J = 6.6 Hz) |
| 253 | isobutyl | 3-(ethoxycarbonyl)benzyl | 4-chlorophenyl | 1-Method A | white solid | 481.01 | 1.81 min Method A | 481.2 | ¹H NMR (CDCl₃) δ 7.67 (A of ABq, 2H, J = 8.8 Hz), 7.44 (B of ABq, 2H, J = 8.8 Hz), 7.27-7.15 (m, 3H), 6.24 (bs, 1H), 5.26 (bs, 1H), 4.55 (A of ABq, 1H, J = 15.4 Hz), 4.39 (B of ABq, 1H, J = 15.4 Hz), 4.29 (t, 1H, J = 7.0 Hz), 4.15 (q, 2H, J = 7.2 Hz), 1.87-1.78 (m, 1H), 1.37-1.29 (m, 1H), 1.26 (t, 3H, J = 7.2 Hz), 1.24-1.13 (m, 1H), 0.76 (d, 3H, J = 6.2 Hz), 0.67 (d, 3H, J = 6.6 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 254 | isobutyl | (6-(dimethylamino)pyridin-3-yl)methyl | 4-chlorophenyl | 10 | white solid | 438.98 | 1.20 Method B | 439.05 | ¹H NMR (CDCl₃) TFA salt: δ 8.04 (s, 1H), 8.03 (d, 1H, J = 9.80 Hz), 7.76 (d, 2H, J = 7.6 Hz), 7.54 (d, 2H, J = 7.6 Hz), 6.83 (d, 1H, J = 9.8 Hz), 6.62 (br s, 1H), 6.40 (br s, 1H), 4.64 (d, 1H, J = 15.9 Hz), 4.29 (m, 1H), 4.18 (d, 1H, J = 15.9 Hz), 3.30 (s, 6H), 1.84 (m, 1H), 1.29 (m, 1H), 0.93 (m, 1H), 0.77 (d, 3H, J = 6.5 Hz), 0.72 (d, 3H, J = 6.5 Hz) |
| 255 | isobutyl | 4-(allyloxy)benzyl | 4-chlorophenyl | 1-Method A | light orange residue | 450.14 | 2.02 min Method E | 450.98 | ¹H NMR (DMSO) δ 7.78 (d, 2H, J = 8.4 Hz), 7.58 (d, 2H, J = 8.8 Hz), 7.47 (s, br, 1H), 7.29 (d, 2H, J = 8.8 Hz), 7.00 (s br, 1H), 6.87 (d, 2H, J = 8.8 Hz), 6.03 (m, 1H), 5.32 (dd, 2H, J = 12 Hz, 56 Hz), 4.63 (m, 4H), 5.32 (dd, 2H, J = 12 Hz, 56 Hz), 4.35 (m, 1H), 1.33 (m, 3H), 0.80 (d, 3H, J = 6.0 Hz), 0.50 (d, 3H, J = 6.0 Hz), |
| 256 | isobutyl | (1-(phenethylcarbamoyl)piperidin-4-yl)methyl | 4-chlorophenyl | 7 | white solid | 548.22 | 1.87 min Method A | 549.00 | ¹H NMR (CDCl₃, 500 MHz), δ 7.71 (d, 2H, J = 8.6), 7.71 (d, 2H, J = 8.9), 7.15-7.35 (m, 5H), 6.64 (s, 1H), 5.86 (s, 1H), 4.15 (dd, 1H, J = 5.2, 9.5), 3.88 (d, 1H, J = 13), 3.76 (d, 1H, J = 13), 3.46 (t, 2H, J = 6.7), 3.21-3.29 (m, 1H), 2.97 (dd, 1H, J = 4.6, 14), 2.65-2.85 (m, 4H), 1.75-1.95 (m, 3H), 1.00-1.30 (m, 5H), 0.75-0.80 (m, 1H), 0.72 (d, 3H, J = 6.7), 0.67 (d, 3H, J = 6.7) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 257 | isobutyl | piperidine-1-carboxamide, N-phenyl | 4-chlorophenyl | 7 | white solid | 520.19 | 1.74 min Method A | 521.31 | ¹H NMR (CDCl₃, 500 MHz) δ 7.72 (d, 2H, J = 8.8), 7.51 (d, 2H, J = 8.8), 7.33 (d, 2H, J = 7.6), 7.28 (d, 2H, J = 7.6), 7.03 (t, 1H, J = 7.3), 6.67 (s, 1H), 5.42 (s, 1H), 3.97-4.22 (m, 3H), 3.27-3.35 (m, 1H), 2.78-3.02 (m, 3H), 1.83-1.99 (m, 3H), 1.09-1.42 (m, 4H), 0.75-0.82 (m, 1H), 0.74 (d, 3H, J = 6.4), 0.67 (d, 3H, J = 6.7) |
| 258 | isobutyl | piperidine-1-carboxamide, N-cyclohexyl | 4-chlorophenyl | 7 | white solid | 526.24 | 1.81 min Method A | 527.34 | ¹H NMR (CDCl₃, 500 MHz) δ 7.73 (d, 2H, J = 8.9), 7.51 (d, 2H, J = 8.9), 6.65 (s, 1H), 5.37 (s, 1H), 4.15 (dd, 1H, J = 5.1, 6.5), 3.92 (d, 1H, J = 12), 3.82 (d, 1H, J = 14), 3.57-3.67 (m, 1H), 3.26 (dd, 1H, J = 10, 14), 2.98 (dd, 1H, J = 4.5, 14), 2.74 (q, 2H, J = 12, 24), 1.80-1.97 (m, 5H), 1.64-1.72 (m, 3H), 1.00-1.43 (m, 10H), 0.75-0.82 (m, 1H), 0.73 (d, 3H, J = 6.4), 0.67 (d, 3H, 6.7) |
| 259 | isobutyl | piperidine-1-carboxamide, N-(1-phenylethyl) | 4-chlorophenyl | 7 | white solid | 548.22 | 1.78 min Method A | 549.32 | ¹H NMR (CDCl₃, 500 MHz) δ 7.71 (d, 2H, J = 8.2), 7.50 (d, 2H, J = 8.5), 7.30 (d, 4H, J = 4.3), 7.20-7.25 (m, 1H), 6.65 (s, 1H), 5.74 (s, 1H), 4.99 (t, 1H, J = 7.02), 4.70-4.77 (m, 1H), 4.10-4.25 (m, 1H), 4.00 (d, 1H, J = 13), 3.90 (d, 1H, J = 13), 3.15-3.35 (m, 1H), 2.90-3.00 (m, 1H), 2.60-2.75 (m, 2H), 1.50-1.95 (m, 5H), 1.46 (d, 3H, J = 6.7), 1.00-1.30 (m, 2H), 0.75-0.83 (m, 1H), 0.73 (d, 3H, J = 6.4), 0.67 (d, 3H, J = 6.4) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 260 | isobutyl | 4-(trifluoromethyl)phenyl-NHC(O)-piperidin-4-yl | 4-chlorophenyl | 7 | white solid | 588.18 | 1.90 min Method A | 589.25 | ¹H NMR (CDCl₃, 500 MHz) δ 7.73 (d, 2H, J = 8.9), 7.62 (d, 4H, J = 8.6), 7.45 (d, 2H, J = 8.5), 6.67 (s, 1H), 6.52 (s, 1H), 4.45 (s, 1H), 4.16 (dd, 1H, J = 5.2, 9.8), 4.12 (d, 1H, J = 12), 4.03 (d, 1H, J = 14), 3.80 (dd, 1H, J = 10, 14), 3.00 (dd, 1H, J = 4.5, 14), 2.84-2.92 (m, 2H), 1.85-2.00 (m, 3H), 1.69 (d, 1H, J = 12), 1.10-1.35 (m, 3H), 0.75-0.82 (m, 1H), 0.74 (d, 3H, J = 6.7), 0.68 (d, 3H, J = 6.7) |
| 261 | isobutyl | 3-chlorophenyl-NHC(O)-piperidin-4-yl | 4-chlorophenyl | 7 | white solid | 554.14 | 1.86 min Method A | 555.24 | ¹H NMR (CDCl₃, 500 MHz) δ 7.73 (d, 2H, J = 8.6), 7.52 (d, 2H, J = 8.9), 7.45 (s, 1H), 7.18 (d, 2H, J = 6.7), 6.95-7.02 (m, 1H), 6.65 (s, 1H), 6.50 (s, 1H), 5.50 (s, 1H), 4.16 (dd, 1H, J = 5.2, 9.5), 4.08 (d, 1H, J = 15), 3.99 (d, 1H, J = 14), 3.30 (dd, 1H, J = 10, 15), 2.99 (dd, 1H, J = 4.5, 15), 2.80-2.92 (m, 2H), 1.80-2.00 (m, 3H), 1.67 (d, 1H, J = 13), 1.05-1.40 (m, 4H), 0.75-0.80 (m, 1H), 0.74 (d, 3H, J = 6.7), 0.68 (d, 3H, J = 6.7) |
| 262 | isobutyl | 4-(ethoxycarbonyl)phenyl-NHC(O)-piperidin-4-yl | 4-chlorophenyl | 7 | white solid | 592.21 | 1.86 min Method A | 593.30 | ¹H NMR (CDCl₃, 500 MHz) δ 7.96 (d, 2H, J = 8.9), 7.73 (d, 2H, J = 8.9), 7.51 (d, J = 8.6), 7.42 (d, 2H, J = 8.6), 6.65 (s, 2H), 5.45 (s, 1H), 4.83 (q, 2H, J = 7.0), 4.16 (dd, 1H, J = 5.2, 9.8), 4.11 (d, 1H, J = 13), 4.03 (d, 1H, J = 13), 3.30 (dd, 1H, J = 10, 14), 3.00 (dd, 1H, J = 4.2, 14), 2.81-2.95 (m, 2H), 1.84-2.01 (m, 3H), 1.68 (d, 1H, J = 13), 1.37 (t, 3H, J = 7.3), 1.08-1.34 (m, 4H), 0.76-0.82 (m, 1H), 0.74 (d, 3H, J = 6.7), 0.68 (d, 3H, J = 6.7) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 263 | isobutyl | ethyl (piperidine-1-carbonyl)glycinate | 4-chlorophenyl | 7 | white solid | 530.20 | 2.18 min Method C | 531.11 | ¹H NMR (CDCl₃, 500 MHz) δ 7.73 (d, 2H, J = 8.5), 7.51 (d, 2H, J = 8.6), 6.67 (s, 1H), 5.41 (s, 1H), 4.97 (s, 1H), 4.20 (q, 2H, J = 7.0), 4.15 (dd, 1H, J = 5.1, 9.5), 3.90-4.04 (m, 4H), 3.26 (dd, 1H, J = 10, 14), 2.99 (dd, 1H, J = 4.5, 14), 2.70-2.82 (m, 2H), 1.80-1.95 (m, 3H), 1.28 (t, 3H, J = 7.3), 1.05-1.25 (m, 3H), 0.75-0.80 (m, 1H), 0.72 (d, 3H, J = 6.7), 0.67 (d, 3H, J = 6.4) |
| 264 | isobutyl | 4-(tetrazol-5-yl)benzyl | 4-chlorophenyl | 1-Method A | white solid | 462.96 | 1.47 Method B | 462.98 | ¹H NMR (CDCl₃) δ 7.81 (d, 2H, J = 8.4 Hz), 7.75 (d, 2H, J = 8.0 Hz), 7.55 (d, 2H, J = 8.4 Hz), 7.5 (d, 2H, J = 8.0 Hz), 6.86 (s, 1H), 6.44 (s, 1H), 4.96 (d, 1H, J = 15.6 Hz), 4.36 (dd, 1H, J = 5.6 Hz, 6.0 Hz), 1.99 (m, 1H), 1.29 (m, 1H), 1.06 (m, 1H), 0.77 (d, 3H, J = 6.8 Hz), 0.74 (d, 3H, J = 6.8 Hz) |
| 265 | isobutyl | ethyl 4-benzylphenylacetate | 4-chlorophenyl | 1-Method A | white solid | 481.01 | 1.81 min Method A | 481.3 | ¹H NMR (CDCl₃) δ 7.61 (A of ABq, 2H, J = 8.8 Hz), 7.42 (B of ABq, 2H, J = 8.8 Hz), 7.27 (A of ABq, 2H, J = 8.4 Hz), 7.19 (B of ABq, 2H, J = 8.4 Hz), 6.21 (bs, 1H), 5.19 (bs, 1H), 4.52 (A of ABq, 1H, J = 15.5 Hz, 1H), 4.39 (B of ABq, 1H, J = 15.5 Hz, 1H), 4.30 (t, 1H, J = 7.3 Hz), 4.14 (q, 2H, J = 7.1 Hz), 3.58 (s, 2H), 1.86-1.76 (m, 1H), 1.36-1.27 (m, 1H), 1.14 (t, 3H, J = 7.1 Hz), 1.23-1.13 (m, 1H), 0.76 (d, 3H, J = 6.2 Hz), 0.66 (d, 3H, J = 6.6 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 266 | isobutyl | 4-(4-ethylbenzyl)-1-(pyridin-4-yl)piperazine | 4-chlorophenyl | 8 | white foam | 570.16 | 1.17 min Method A | 570.39 | $^1$H NMR, 400 Hz, (CDCl$_3$) δ 8.21 (d, 2H, J = 4.0 Hz), 8.02 (d, 2H, J = 8.0 Hz), 7.59 (d, 2H, J = 8.0 Hz), 7.39-7.33 (m, 4H), 6.83 (d, 2H, J = 4.0 Hz), 6.23 (s, br, 1H), 5.34 (s, br, 1H), 4.60 (d, 1H, J$_{ab}$ = 16 Hz), 4.39 (d, 1H, J$_{ab}$ = 16 Hz), 3.57 (s, 2H), 3.27-3.15 (m, 5H), 2.58-2.45 (m, 4H), 1.94 (m, 1H), 1.60 (m, 2H), 0.98 (d, 3H, J = 7.0 Hz), 0.94 (d, 3H, J = 7.0 Hz) |
| 267 | isobutyl | 1-(4-ethylbenzyl)-3-hydroxypiperidine | 4-chlorophenyl | 8 | white foam | 508.08 | 1.28 min Method A | 508.21 | $^1$H NMR, 400 Hz, (CDCl$_3$) δ 7.69 (d, 2H, J = 8.0 Hz), 7.63 (d, 2H, J = 8.0 Hz), 7.43-7.36 (m, 4H), 6.27 (s, br, 1H), 5.39 (s, br, 1H), 4.59 (d, 1H, J$_{ab}$ = 16 Hz), 4.36 (d, 1H, J$_{ab}$ = 16 Hz), 2.83 (m, 1H), 2.41 (m, 2H), 2.18 (m, 1H), 1.95 (m, 1H), 1.85 (m, 1H), 1.76-1.52 (m, 5H), 0.98 (d, 3H, J = 7.0 Hz), 0.94 (d, 3H, J = 7.0 Hz) |
| 268 | isobutyl | 1-(4-ethylbenzyl)-4-hydroxypiperidine | 4-chlorophenyl | 8 | white foam | 508.08 | 1.26 min Method A | 508.18 | $^1$H NMR, 400 Hz, (CDCl$_3$) δ 7.72 (d, 2H, J = 8.0 Hz), 7.65 (d, 2H, J = 8.0 Hz), 7.45 (d, 2H, J = 8.0 Hz), 7.38 (d, 2H, J = 8.0 Hz), 6.27 (s, br, 1H), 5.39 (s, br, 1H), 4.59 (d, 1H, J$_{ab}$ = 16 Hz), 4.36 (d, 1H, J$_{ab}$ = 16 Hz), 3.77 (m, 1H), 3.47 (s, 2H), 3.25 (t, 1H, J = 6.0 Hz), 2.80 (m, 4H), 1.95 (m, 1H), 1.77-1.50 (m, 6H), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 269 | isobutyl | 4-ethylbenzyl-NH- | 4-chlorophenyl | 8 | white foam | 437.99 | 1.28 min Method A | 438.16 | ¹H NMR, 400 Hz, (CDCl₃) δ 7.71 (d, 2H, J = 8.0 Hz), 7.66 (d, 2H, J = 8.0 Hz), 7.43 (d, 2H, J = 8.0 Hz), 7.37 (d, 2H, J = 8.0 Hz), 6.35 (s, br, 1H), 5.87 (s, br, 1H), 4.76 (d, 1H, $J_{ab}$ = 16 Hz), 4.30 (d, 1H, $J_{ab}$ = 16.0 Hz), 3.54 (s, 5H), 3.25 (t, 1H, J = 6.0 Hz), 1.94 (m, 1H), 1.60 (m, 2H), 1.18 (s, br, NH), 0.98 (d, 3H, J = 7.0 Hz), 0.94 (d, 3H, J = 7.0 Hz) |
| 270 | isobutyl | 4-ethylbenzyl-NH-CH₂CH₂-OH | 4-chlorophenyl | 8 | white foam | 468.02 | 1.28 min Method A | 468.16 | ¹H NMR, 400 Hz, (CDCl₃) δ 7.72 (d, 2H, J = 8.0 Hz), 7.67 (d, 2H, J = 8.0 Hz), 7.38 (d, 2H, J = 8.0 Hz), 7.33 (d, 2H, J = 8.0 Hz), 6.35 (s, br, 1H), 5.85 (s, br, 1H), 4.24-4.12 (m, 4H), 3.67 (s, 2H), 3.24 (t, 1H, J = 6.0 Hz), 3.06 (t, 2H, J = 6.0 Hz), 2.60 (s, br, NH), 1.95 (m, 1H), 1.68-1.52 (m, 2H), 0.98 (d, 3H, J = 7.0 Hz), 0.94 (d, 3H, J = 7.0 Hz) |
| 271 | isobutyl | 4-ethylbenzyl-NH-CH₂CH₂-OCH₃ | 4-chlorophenyl | 8 | clear glass | 482.05 | 1.31 min Method A | 482.18 | ¹H NMR, 400 Hz, (CDCl₃) δ 7.79 (d, 2H, J = 8.0 Hz), 7.69 (d, 2H, J = 8.0 Hz), 7.38 (d, 2H, J = 8.0 Hz), 7.33 (d, 2H, J = 8.0 Hz), 6.35 (s, br, 1H), 5.85 (s, br, 1H), 4.60 (d, 1H, $J_{ab}$ = 16 Hz), 4.43 (d, 1H, $J_{ab}$ = 16 Hz), 3.67 (s, 2H), 3.61 (t, 2H, J = 6.0 Hz), 3.35 (s, 3H), 3.29-3.24 (m, 3H), 1.94 (m, 1H), 1.62 (m, 2H), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 272 | isobutyl | N,N-dimethylaminoacetyl-N-methyl-(4-methylbenzyl) | 4-chlorophenyl | 9 | white solid | 523.1 | 1.30 min Method A | 523.40 | ¹H NMR, 400 Hz, (CDCl₃) δ 8.02 (d, 2H, J = 8.0 Hz), 7.71 (d, 2H, J = 8.0 Hz), 7.37 (d, 2H, J = 8.0 Hz), 7.28 (d, 2H, J = 8.0 Hz), 6.23 (s, br, 1H), 5.51 (s, br, 1H), 4.46 (s, 2H), 4.70 (d, 1H, $J_{ab}$ = 16 Hz), 4.33 (d, 1H, $J_{ab}$ = 16 Hz), 3.25 (t, 1H, J = 6.0 Hz), 2.69 (s, 3H), 2.63 (s, 2H), 2.20 (s, 6H), 1.95 (m, 1H), 1.60 (m, 2H), 0.98 (d, 3H, J = 7.0 Hz), 0.94 (d, 3H, J = 7.0 Hz) |
| 273 | isobutyl | 4-acetylbenzyl | 4-chlorophenyl | 16 | white solid | 436.96 | 1.43 min Method B | 437.13 | ¹H NMR (CDCl₃, 300 MHz) δ 7.87 (d, 2H, J = 8.4), 7.67 (dd, 2H, J = 1.8, 8.7), 7.42-7.46 (m, 4H), 6.21 (br s, 1H), 5.28 (br s, 1H), 4.64 (d, 1H, J = 15.9), 4.45 (d, 1H, J = 15.9), 4.31 (t, 1H, J = 6.6), 2.58 (s, 3H), 1.73-1.80 (m, 1H), 1.25-1.35 (m, 1H), 1.05-1.14 (m, 1H), 0.74 (d, 3H, J = 6.5), 0.65 (d, 3H, J = 6.6) |
| 274 | isobutyl | 3-piperidinopropanoyl-(4-methylanilide) | 4-chlorophenyl | 17 | yellow foam | 549.14 | 1.38 min Method A | 549.16 | ¹H NMR, 400 Hz, (CDCl₃) δ 7.69 (d, 2H, J = 8.0 Hz), 7.63 (d, 2H, J = 8.0 Hz), 7.38 (d, 2H, J = 8.0 Hz), 7.23 (d, 2H, J = 8.0 Hz), 6.25 (s, br, 1H), 5.35 (s, br, 1H), 4.75 (d, 1H, $J_{ab}$ = 16 Hz), 4.38 (d, 1H, $J_{ab}$ = 16 Hz), 3.25 (t, 1H, J = 6.0 Hz), 2.65 (t, 2H, J = 6.0 Hz), 2.56-2.44 (m, 8H), 1.95 (m, 1H), 1.68-1.45 (m, 8H), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 275 | isobutyl | 4-ethylphenyl-NH-C(O)-CH₂CH₂-N(4-methylpiperazinyl) | 4-chlorophenyl | 17 | clear glass | 564.15 | 1.21 min Method A | 564.32 | ¹H NMR, 400 Hz, (CDCl₃) δ 9.30 (s, 1H, NH), 8.02 (d, 2H, J = 8.0 Hz), 7.61 (d, 2H, J = 8.0 Hz), 7.36 (d, 2H, J = 8.0 Hz), 7.23 (d, 2H, J = 8.0 Hz), 6.25 (s, br, 1H), 5.33 (s, br, 1H), 4.72 (d, 1H, J$_{ab}$ = 16 Hz), 4.48 (d, 1H, J$_{ab}$ = 16 Hz), 3.25 (t, 1H, J = 6.0 Hz), 2.65-2.38 (m, 12H), 2.28 (s, 2H), 1.95 (m, 1H), 1.59 (m, 2H), 0.98 (d, 3H, J = 7.0 Hz), 0.94 (d, 3H, J = 7.0 Hz) |
| 276 | isobutyl | 4-ethylphenyl-NH-C(O)-CH₂CH₂-N(CH₃)₂ | 4-chlorophenyl | 17 | tan foam | 509.07 | 1.33 min Method A | 509.17 | ¹H NMR, 400 Hz, (CDCl₃) δ 9.31 (s, 1H, NH), 8.02 (d, 2H, J = 8.0 Hz), 7.63 (d, 2H, J = 8.0 Hz), 7.36 (d, 2H, J = 8.0 Hz), 7.23 (d, 2H, J = 8.0 Hz), 6.25 (s, br, 1H), 5.34 (s, br, 1H), 4.71 (d, 1H, J$_{ab}$ = 16 Hz), 4.48 (d, 1H, J$_{ab}$ = 16 Hz), 3.25 (t, 1H, J = 6.0 Hz), 2.66 (t, 2H, J = 8.0 Hz), 2.56 (t, 2H, J = 8.0 Hz), 2.38 (s, 6H), 1.95 (m, 1H), 1.60 (m, 2H), 0.98 (d, 3H, J = 7.0 Hz), 0.94 (d, 3H, J = 7.0 Hz) |
| 277 | isobutyl | 4-ethylphenyl-NH-C(O)-(3-pyridyl) | 4-chlorophenyl | 9 | tan foam | 515.04 | 1.47 min Method A | 515.13 | ¹H NMR, 400 Hz, (CDCl₃) δ 8.95 (s, br, NH), 8.67 (d, 1H, J = 8.0 Hz), 8.17 (d, 1H, J = 8.0 Hz), 8.02 (d, 2H, J = 8.0 Hz), 7.77 (d, 2H, J = 8.0 Hz), 7.57 (m, 4H), 7.38 (d, 2H, J = 8.0 Hz), 6.27 (s, br, 1H), 5.39 (s, br, 1H), 4.72 (d, 1H, J$_{ab}$ = 16 Hz), 4.30 (d, 1H, J$_{ab}$ = 16 Hz), 3.25 (t, 1H, J = 6.0 Hz), 1.95 (m, 1H), 1.60 (m, 2H), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 278 | isobutyl | 4-[(pyridin-4-yl)carbonyl]piperidin-4-ylmethyl | 4-chlorophenyl | 7 | white solid | 507.06 | 2.44 min Method C | 509.20 | ¹H NMR (CDCl₃, 500 MHz) δ 8.66 (br s, 2H), 7.80 (d, 1H, J = 8.6), 7.73 (d, 2H, J = 8.5), 7.51 (d, 2H, J = 7.6), 7.41 (br s, 1H), 6.64 (br s, 1H), 5.35 (br s, 1H), 4.70 (br s, 1H), 4.10 (br s, 1H), 3.71 (br s, 1H), 3.33 (br s, 1H), 3.02 (dd, 2H, J = 4.8, 16), 2.70-2.85 (br s, 1H), 1.50-2.09 (m, 5H), 1.18-1.33 (m, 4H), 0.73 (d, 3H, J = 6.7), 0.68 (d, 3H, J = 6.5). |
| 279 | isobutyl | 4-[(4-dimethylaminophenyl)carbonyl]piperidin-4-ylmethyl | 4-chlorophenyl | 7 | white solid | 549.14 | 2.76 min Method C | 549.07 | ¹H NMR (CDCl₃, 500 MHz) δ 7.74 (dd, 2H, J = 1.7, 6.7), 7.51 (dd, 2H, J = 2.2, 6.9), 7.34 (d, 2H, J = 8.0), 6.70 (br s, 1H), 6.60 (br s, 1H), 5.30 (br s, 1H), 4.13 (dd, 1H, J = 5.5, 10), 3.35 (dd, 1H, J = 11, 14), 3.00 (s, 6H), 2.85 (s, 2H), 1.80-2.00 (m, 3H), 1.50-1.70 (m, 1H), 1.10-1.30 (m, 4H), 0.80-0.90 (m, 1H), 0.745 (d, 3H, J = 6.7), 0.67 (d, 3H, J = 6.5) |
| 280 | isobutyl | 4-[(4-trifluoromethylphenyl)carbonyl]piperidin-4-ylmethyl | 4-chlorophenyl | 7 | white solid | 574.07 | 3.03 Method C | 574.03 | ¹H NMR (CDCl₃, 500 MHz) δ 7.73 (d, 2H, J = 8.2), 7.65 (d, 2H, J = 7.9), 7.51 (d, 2H, J = 8.9), 7.48 (d, 2H, J = 7.6), 6.65 (br s, 1H), 5.45 (br s, 1H), 4.71 (br s, 1H), 4.13 (br s, 1H), 3.65 (br s, 1H), 3.30 (br s, 1H), 2.97 (d, 2H J = 12), 2.65-2.86 (m, 1H), 1.45-2.07 (m, 6H), 0.98-1.85 (m, 3H), 0.73 (br, s, 3H), 0.67 (br, s, 3H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 281 | isobutyl | piperidine-4-methyl N-(but-2-enoyl) | 4-chlorophenyl | 7 | white solid | 470.04 | 2.78 min Method C | 470.03 | ¹H NMR (CDCl₃, 500 MHz) δ 7.72 (d, 2H, J = 8.5), 7.50 (d, 2H, J = 8.6), 6.78-6.90 (m, 1H), 6.55-6.65 (m, 1H), 6.23 (dd, 1H, J = 1.5, 15), 5.33-5.60 (m, 1H), 4.50-4.75 (m, 1H), 4.09-4.20 (m, 1H), 3.90-4.05 (m, 1H), 2.80-3.25 (m, 3H), 2.40-2.75 (m, 1H), 1.50-2.00 (m, 8H), 1.00-1.40 (m, 3H), 0.73 (br, s, 3H), 0.67 (br, s, 3H) |
| 282 | isobutyl | piperidine-4-methyl N-benzoyl | 4-chlorophenyl | 7 | white solid | 506.07 | 2.86 min Method C | 508.03 | ¹H NMR (CDCl₃, 500 MHz) δ 7.73 (d, 2H, J = 8.5), 7.51 (d, 2H, J = 8.5), 7.38 (br s, 4H), 6.65 (br s, 1H), 5.35 (bns, 1H), 4.71 (br s, 1H), 4.14 (br s, 1H), 3.76 (br s, 1H), 3.30 (br s, 1H), 2.60-3.05 (m, 3H), 0.99-2.05 (m, 10H), 0.73 (d, 3H, J = 7.8), 0.67 (d, 3H, J = 7.8) |
| 283 | isobutyl | piperidine-4-methyl N-(4-cyanobenzyl) | 4-chlorophenyl | 7 | white solid | 517.09 | 1.34 min Method A | 517.19 | ¹H NMR (CDCl₃, 500 MHz) δ 7.72 (d, 2H, J = 8.5), 7.50-7.65 (m, 2H), 7.50 (d, 2H, J = 7.0), 7.35-7.45 (m, 2H), 6.67 (s, 1H), 5.32 (s, 1H), 4.14 (dd, 1H, J = 5.0, 9.0), 3.52 (br s, 1H), 3.28 (t, 1H, J = 14), 2.97 (dd, 1H, J = 3.5, 14), 2.82 (br s, 1H), 1.00-2.00 (m, 10H), 0.71 (d, 3H, J = 6.5), 0.66 (d, 3H, J = 6.5) |
| 284 | isobutyl | piperidine-4-methyl N-[2-(4-methoxyphenyl)acetyl] | 4-chlorophenyl | 7 | white solid | 550.12 | 2.87 min Method C | 550.06 | ¹H NMR (CDCl₃, 500 MHz) δ 7.72 (d, 2H, J = 8.6), 7.50 (d, 2H, J = 8.5), 7.13 (d, 2H, J = 8.5), 6.85 (br s, 2H), 6.63 (d, 1H, J = 33), 5.41 (br s, 1H), 4.62 (t, 1H, J = 14), 4.10-4.17 (m, 1H), 3.75-3.90 (m, 4H), 3.65 (s, 3H), 3.14-3.30 (m, 1H), 2.80-2.95 (m, 2H), 2.43-2.60 (m, 1H), 1.45-2.00 (m, 4H), 1.15-1.30 (m, 2H), 0.71 (dd, 3H, J = 7.6, 8.4), 0.65 (dd, 3H, J = 6.0, 8.0) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 285 | isobutyl | 6-chloropyridin-3-yl carbonyl piperidinyl ethyl | 4-chlorophenyl | 7 | white solid | 541.50 | 2.76 min Method C | 540.98 | ¹H NMR (CDCl₃, 500 MHz) δ 8.43 (s, 1H), 7.73 (d, 2H, J = 8.5), 7.70 (d, 1H, J = 2.4, 8.4), 7.51 (d, 2H, J = 8.6), 7.87 (d, 1H, J = 8.2), 6.63 (br s, 1H), 5.35 (br s, 1H), 4.68 (br s, 1H), 4.15 (dd, 1H, J = 4.9, 9.8), 3.71 (br s, 1H), 3.31 (br s, 1H), 3.00 (dd, 2H, J = 4.8, 14), 2.65-2.86 (m, 2H, J = 4.8, 14), 1.77-2.07 (m, 3H), 1.6-1.76 (m, 1H), 1.00-1.86 (m, 3H), 0.85-0.93 (m, 1H), 0.73 (d, 3H, J = 6.7), 0.67 (d, 3H, J = 6.7) |
| 286 | isobutyl | 4-cyanophenyl ketone piperidinyl ethyl | 4-chlorophenyl | 7 | white solid | 545.11 | 1.36 min Method A | 545.16 | ¹H NMR (CDCl₃, 500 MHz) δ 8.11 (d, 2H, J = 8.6), 7.75 (d, 2H, J = 8.6), 7.73 (d, 2H, J = 8.9), 7.50 (d, 2H, J = 8.9), 6.65 (br s, 1H), 5.38 (br s, 1H), 4.14 (dd, 1H, J = 5.5, 9.5), 3.80 (brs, 1H), 3.27 (dd, 1H, J = 10, 14), 2.97 (dd, 2H, J = 4.6, 14), 1.17-2.00 (m, 11H), 0.75-0.81 (m, 1H), 0.73 (d, 3H, J = 6.4), 0.67 (d, 3H, J = 6.7) |
| 287 | isobutyl | 4-(2-hydroxypropan-2-yl)phenyl methyl | 4-chlorophenyl | 12 | white solid | 453.01 | 1.81 min Method A | 453.16 | ¹H NMR (CDCl₃, 300 MHz) δ 7.61 (d, 2H, J = 8.7), 7.40 (d, 2H, J = 8.7), 7.37 (d, 2H, J = 8.4), 7.26 (d, 2H, J = 8.4), 6.28 (br s, 1H), 5.25 (br s, 1H), 4.49 (d, 1H, J = 15.9), 4.41 (d, 1H, J = 15.9), 4.33 (t, 1H, J = 6.6), 1.73-1.80 (m, 1H), 1.55 (s, 6H), 1.28-1.35 (m, 1H), 1.20-1.25 (m, 1H), 0.77 (d, 3H, J = 6.5), 0.66 (d, 3H, J = 6.6) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 288 | isobutyl | (pyridin-3-ylmethyl)piperidin-4-ylmethyl | 4-chlorophenyl | 7 | white solid | 493.07 | 1.25 min Method A | 493.23 | ¹H NMR (CDCl₃, 500 MHz) δ 8.51 (s, 2H), 7.73 (d, 2H, J = 8.5), 7.50 (d, 2H, J = 8.5), 6.67 (s, 1H), 5.83 (s, 1H), 4.15 (dd, 1H, J = 5.2, 8.9), 3.50 (br s, 2H), 3.25 (dd, 1H, J = 8.5, 14), 2.75-3.05 (m, 3H), 1.60-2.10 (m, 6H), 1.10-1.40 (m, 4H), 0.75-0.85 (m, 1H), 0.72 (d, 3H, J = 6.4), 0.67 (d, 3H, J = 6.7) |
| 289 | n-propyl | 4-(3-(dimethylamino)pyrrolidin-1-yl)phenyl methyl | 4-chlorophenyl | 2 | yellow solid | 493.07 | 0.93 min Method B | 493.2 | ¹H NMR (CDCl₃) δ 7.67 (d, 2H, J = 7.0 Hz), 7.44 (d, 2H, J = 7.0 Hz), 7.19 (d, 2H, J = 8.0 Hz), 6.46 (d, 2H, J = 8.0 Hz), 6.21 (s, br, 1H), 5.17 (s, br, 1H), 4.31 (dd, 2H J = 50 Hz, 15 Hz), 4.15-4.22 (m, 1H), 3.84-3.87 (m, 4H), 3.91-3.99 (m, 1H), 3.51-3.54 (m, 3H), 3.22-3.26 (m, 1H), 2.75 (s, 3H), 2.23-2.36 (m, 3H), 1.91-1.98 (m, 1H), 1.32-1.40 (m, 1H), 0.81-1.04 (m, 2H), 0.73 (t, 3H, 7.2 Hz) |
| 290 | n-propyl | 4-(piperidin-1-yl)phenylmethyl | 4-chlorophenyl | 2 | tan solid | 464.03 | 1.16 min Method B | 464.2 | ¹H NMR (CDCl₃) δ 7.62 (d, 2H, J = 8.8 Hz), 7.40 (d, 2H, J = 8.0 Hz), 7.11-7.20 (m, 2H), 6.79-6.88 (m, 2H), 6.20 (s, br, 1H), 5.13 (s, br, 1H), 4.30 (dd, 2H, J = 50 Hz, 15 Hz), 4.13-4.21 (m, 1H), 3.10-3.19 (m, 4H), 1.92-1.95 (m, 1H), 1.39-1.90 (m, 8H), 1.22-1.26 (m, 1H), 0.97-1.05 (m, 2H), 0.73 (t, 3H, J = 8.0 Hz) |
| 291 | isobutyl | 4-(2-(piperidin-1-yl)ethoxy)phenylmethyl | 4-chlorophenyl | 11 | orange solid | 522.11 | 1.52 min Method E | 522.1 | ¹H NMR (DMSO) δ 7.78 (d, 2H, J = 8.4 Hz), 7.58 (d, 2H, J = 8.8 Hz), 7.47 (s, br, 1H), 7.27 (d, 2H, J = 8.4 Hz), 7.00 (s br, 1H), 6.85 (d, 2H, J = 8.8 Hz), 4.63 (dd, 2H, J = 16 Hz, 38 Hz), 4.34 (m, 1H), 4.03 (s, 2H), 2.63 (m, 2H), 2.42 (m, 3H), 1.39 (m, 10H), 0.80 (d, 3H, J = 6.0 Hz), 0.50 (d, 3H, J = 6.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 292 | isobutyl | 4-(2-(dimethylamino)ethoxy)benzyl | 4-chlorophenyl | 11 | white solid | 481.18 | 1.46 min Method E | 482.06 | ¹H NMR (DMSO) δ 7.79 (d, 2H, J = 8.8 Hz), 7.60 (d, 2H, J = 8.8 Hz), 7.49 (s, br, 1H), 7.35 (d, 2H, J = 8.4 Hz), 7.01 (s, br, 1H), 6.94 (d, 2H, J = 8.8 Hz), 4.68 (dd, 2H, J = 16 Hz, 53 Hz), 4.35 (m, 1H), 4.28 (t, 2H, J = 4.8 Hz), 3.34 (m, 2H), 2.86 (s, 6H), 1.33 (m, 3H), 0.80 (d, 3H, J = 6.0 Hz), 0.50 (d, 3H, J = 6.0 Hz) |
| 293 | isobutyl | 4-(2-(diethylamino)ethoxy)benzyl | 4-chlorophenyl | 11 | white residue | 509.21 | 1.52 min Method E | M + Na 532.03 | ¹H NMR (DMSO) δ 7.79 (d, 2H, J = 8.4 Hz), 7.60 (d, 2H, J = 8.4 Hz), 7.48 (s, br, 1H), 7.35 (d, 2H J = 8.8 Hz), 7.01 (s br, 1H), 6.94 (d, 2H, J = 8.8 Hz), 4.68 (dd, 2H, J = 17 Hz, 54 Hz), 4.35 (m, 1H), 4.28 (t, 2H, J = 4.8 Hz), 3.51 (m, 3H), 3.21 (m, 3H), 1.29 (m, 9H), 0.80 (d, 3H, J = 6.0 Hz), 0.50 (d, 3H, J = 6.0 Hz) |
| 294 | isobutyl | 4-(2-(N-methyl-N-phenylamino)ethoxy)benzyl | 4-chlorophenyl | 11 | light brown solid | 544.12 | 1.78 min Method E | 544.13 | ¹H NMR (DMSO) δ 7.78 (d, 2H, J = 8.9 Hz), 7.57 (d, 2H, J = 8.0 Hz), 7.45 (s, br, 1H), 7.27 (d, 2H, J = 8.0 Hz), 7.17 (t, 2H, J = 8.9 Hz) 7.00 (s br, 1H), 6.84 (d, 2H, J = 8.0 Hz), 6.75 (d, 2H, J = 8.0 Hz), 6.62 (t, 1H, J = 8.0 Hz), 4.65 (dd, 2H, J = 17 Hz, 41 Hz), 4.34 (m, 1H), 4.10 (t, 2H, J = 5.5 Hz), 3.71 (t, 2H, J = 7.9 Hz), 2.96 (m, 3H), 1.32 (m, 3H), 0.79 (d, 3H, J = 6.0 Hz), 0.49 (d, 3H, J = 6.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 295 | isobutyl | 4-(2-(N-benzyl-N-methylamino)ethoxy)benzyl | 4-chlorophenyl | 11 | white powder | 558.14 | 1.62 min Method E | 558.10 | ¹H NMR (DMSO) δ 7.80 (d, 2H, J = 8.6 Hz), 7.60 (d, 2H, J = 8.6 Hz), 7.54 (m, 2H), 7.49 (m, 4H), 7.34 (d, 2H, J = 8.6 Hz) 7.01 (s br, 1H), 6.93 (d, 2H, J = 8.6 Hz), 4.68 (dd, 2H, J = 17.0 Hz, 54 Hz), 4.47 (m, 1H), 4.36 (m, 4 Hz), 3.50 (m, 2H), 2.80 (s, 3H), 1.34 (m, 3H), 0.80 (d, 3H, J = 6.0 Hz), 0.51 (d, 3H, J = 6.0 Hz) |
| 296 | isobutyl | 4-(2-(pyrrolidin-1-yl)ethoxy)benzyl | 4-chlorophenyl | 11 | white powder | 508.08 | 1.49 min Method E | 508.07 | ¹H NMR (DMSO) δ 7.79 (d, 2H, J = 8.6 Hz), 7.61 (d, 2H, J = 8.6 Hz), 7.49 (s, br, 1H), 7.35 (d, 2H, J = 8.6 Hz), 7.00 (s br, 1H), 6.94 (d, 2H, J = 8.6 Hz), 4.68 (dd, 2H, J = 17.0 Hz, 53 Hz), 4.35 (m, 1H), 4.27 (m, 2H), 3.59 (m, 4H), 3.13 (m, 2H), 2.03 (m, 2H), 1.89 (m, 2H), 1.34 (m, 3H), 0.80 (d, 3H, J = 6.0 Hz), 0.52 (d, 3H, J = 6.0 Hz) |
| 297 | isobutyl | 4-(2-(morpholin-4-yl)ethoxy)benzyl | 4-chlorophenyl | 11 | off white solid | 524.08 | 1.46 min Method E | 524.09 | ¹H NMR (DMSO) δ 7.78 (d, 2H, J = 8.9 Hz), 7.57 (d, 2H, J = 8.0 Hz), 7.45 (s, br, 1H), 7.27 (d, 2H, J = 8.0 Hz), 7.17 (t, 2H, J = 8.9 Hz) 7.00 (s br, 1H), 6.84 (d, 2H, J = 8.0 Hz), 6.75 (d, 2H, J = 8.0 Hz), 6.62 (t, 1H, J = 8.0 Hz), 4.65 (dd, 2H, J = 17 Hz, 41 Hz), 4.34 (m, 1H), 4.10 (t, 2H, J = 5.5 Hz), 3.71 (t, 2H, J = 7.9 Hz), 2.96 (m, 3H), 1.32 (m, 3H), 0.79 (d, 3H, J = 6.0 Hz), 0.49 (d, 3H, J = 6.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 298 | isobutyl | 4-(2-(thiomorpholin-4-yl)ethoxy)benzyl | 4-chlorophenyl | 11 | white solid | 540.15 | 1.52 min Method E | 540.06 | ¹H NMR (DMSO) δ 7.80 (d, 2H, J = 8.8 Hz), 7.60 (d, 2H, J = 8.0 Hz), 7.48 (s, br, 1H), 7.35 (d, 2H, J = 8.8 Hz),7.01 (s br, 1H) 6.95 (d, 2H, J = 8.8 Hz),4.68 (dd, 2H, J = 16.4 Hz, 55 Hz), 4.34 (m, 3H), 3.79 (m, 2H), 3.58 (m, 2H), 3.27 (m, 2H), 3.02 (m, 2H), 2.89 (m, 2H), 1.34 (m, 3H), 0.80 (d, 3H, J = 6.0 Hz), 0.52 (d, 3H, J = 6.0 Hz) |
| 299 | isobutyl | 4-(2-(4-methylpiperazin-1-yl)ethoxy)benzyl | 4-chlorophenyl | 11 | light orange solid | 537.13 | 1.43 min Method E | 537.13 | ¹H NMR (DMSO) δ 7.79 (d, 2H, J = 8.8 Hz), 7.59 (d, 2H, J = 8.0 Hz), 7.48 (s br, 1H), 7.31 (d, 2H, J = 8.8 Hz), 7.00 (s br, 1H) 6.88 (d, 2H, J = 8.8 Hz), 4.66 (dd, 2H, J = 16.4 Hz, 49 Hz), 4.35 (m, 1H), 4.11 (m, 2H), 3.18 (m, 9H), 2.78 (m, 3H), 2.63 (m, 1H), 1.34 (m, 3H), 0.80 (d, 3H, J = 6.0 Hz), 0.51 (d, 3H, J = 6.0 Hz) |
| 300 | propyl | 4-(4-(dimethylamino)piperidin-1-yl)benzyl | 4-chlorophenyl | 2 | tan solid | 507.10 | 1.19 min Method B | 507.2 | ¹H NMR (CDCl₃) δ 7.63 (d, 2H, J = 8.0 Hz), 7.41 (d, 2H, J = 8.0 Hz), 7.13-7.24 (m, 2H), 6.74-6.80 (m, 2H), 6.23 (s, br, 1H), 5.13 (s,br, 1H), 4.37 (dd, 2H, J = 50 Hz, 15 Hz), 4.11-4.19 (m, 1H), 3.77-3.81 (m, 1H), 3.44 (s, 6H), 3.06-3.13 (m, 8H), 1.93-1.96 (m, 1H), 1.25-1.29 (m, 1H), 0.95-1.09 (m, 2H), 0.71 (t, 3H, J = 8.0 Hz) |

TABLE 4-continued

| Ex. No. | R¹ | R² | R³ | Reaction Scheme | Appearance | Calc. MW | Ret. Time/Method | M+H⁺ | NMR Data |
|---|---|---|---|---|---|---|---|---|---|
| 301 | isobutyl | 4-(2-(pyrrolidin-1-yl)pyridin-4-yl)ethyl | 4-chlorophenyl | 10 | yellow foam | 465.02 | 1.22 Method B | 465.25 | ¹H NMR (CDCl₃) TFA salt: δ 8.07 (s, 1H), 7.91 (d, 1H, J = 9.6 Hz), 7.74 (d, 2H, J = 6.8 Hz), 7.52 (d, 2H, J = 6.8 Hz), 6.64 (d, 1H, J = 9.6 Hz), 6.36 (s, 1H), 5.77 (s, 1H), 4.52 (d, 1H, J = 16.0 Hz), 4.28 (dd, 1H, J = 5.6 Hz, 6.0 Hz), 4.21 (d, 1H, J = 16.0 Hz), 3.62 (m, 4H), 2.13 (m, 4H), 1.84 (m, 1H), 1.32 (m, 1H), 0.96 (m, 1H), 0.79 (d, 3H, J = 6.8 Hz), 0.72 (d, 3H, J = 6.8 Hz) |
| 302 | isobutyl | 4-(2-(piperidin-1-yl)pyridin-4-yl)ethyl | 4-chlorophenyl | 10 | yellow foam | 479.05 | 1.28 Method B | 479.06 | ¹H NMR (CDCl₃) TFA salt: δ 8.01 (s, 1H), 7.95 (d, 1H, J = 9.6 Hz), 7.75 (d, 2H, J = 8.0 Hz), 7.50 (d, 2H, J = 8.4 Hz), 6.88 (d, 1H, J = 9.6 Hz), 6.43 (s, 1H), 6.04 (s, 1H), 4.53 (d, 1H, J = 16.0 Hz), 4.28 (dd, 1H, J = 5.6 Hz, 6.0 Hz), 4.20 (d, 1H, J = 16.0 Hz), 3.65 (m, 4H), 1.82 (m, 1H), 1.74 (m, 6H), 1.31 (m, 1H), 0.95 (m, 1H), 0.78 (d, 3H, J = 6.4 Hz), 0.71 (d, 3H, J = 6.4 Hz) |
| 303 | isobutyl | 4-(2-morpholinopyridin-4-yl)ethyl | 4-chlorophenyl | 10 | white solid | 481.02 | 1.16 Method B | 481.05 | ¹H NMR (CDCl₃) TFA salt: δ 8.25 (s, 1H), 8.06 (d, 1H, J = 9.6 Hz), 7.74 (d, 2H, J = 8.0 Hz), 7.54 (d, 2H, J = 8.0 Hz), 6.91 (d, 1H, J = 9.6 Hz), 6.55 (s, 1H), 6.28 (s, 1H), 4.61 (d, 1H, J = 16.0 Hz), 4.28 (dd, 1H, J = 5.2 Hz, 6.2 Hz), 4.21 (d, 1H, J = 16.0 Hz), 3.87 (m, 4H), 3.67 (m, 4H), 1.84 (m, 1H), 1.27 (m, 1H), 0.93 (m, 1H), 0.76 (d, 3H, J = 6.4 Hz), 0.72 (d, 3H, J = 6.4 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 304 | isobutyl | 5-(2,5-dimethylpyrrolidin-1-yl)pyridin-2-yl-ethyl | 4-chlorophenyl | 10 | brown solid | 493.07 | 1.357 Method B | 493.04 | ¹H NMR (CDCl₃) TFA salt: δ 8.04 (s, 1H), 7.93 (d, 1H, J = 9.2 Hz), 7.73 (d, 2H, J = 8.0 Hz), 7.50 (d, 2H, J = 8.0 Hz), 6.69 (d, 1H, J = 9.2 Hz), 6.38 (s, 1H), 5.98 (s, 1H), 4.50 (d, 1H, J = 16.0 Hz), 4.30 (dd, 1H, J = 5.6 Hz, 6.0 Hz), 4.22 (d, 1H, J = 16.0 Hz), 4.20 (m, 2H), 3.87 (m, 4H), 2.24 (m, 2H), 1.90 (m, 2H), 1.84 (m, 1H), 1.36 (d, 3H, J = 2.0 Hz), 1.34 (d, 3H, J = 2.0 Hz), 1.32 (m, 1H), 0.98 (m, 1H), 0.79 (d, 3H, J = 6.4 Hz), 0.72 (d, 3H, J = 6.4 Hz) |
| 305 | isobutyl | 2-(piperidin-1-yl)ethyl-piperidin-4-yl | 4-chlorophenyl | 7 | white solid | 513 | 1.03 min Method A | 513.36 | ¹H NMR (CDCl₃, 500 MHz) δ 7.72 (d, 2H, J = 8.5), 7.50 (d, 2H, J = 7.0), 6.65 (s, 1H), 6.35 (s, 1H), 4.14 (dd, 1H, J = 5.5, 9.0), 3.25 (dd, 1H, J = 10, 14), 1.35-2.95 (m, 24H), 1.15-1.30 (m, 3H), 0.72 (d, 3H, J = 6.5), 0.67 (d, 3H, J = 6.7) |
| 306 | isobutyl | 2-(dimethylamino)acetyl-piperidin-4-yl | 4-chlorophenyl | 7 | white solid | 487 | 1.43 min Method A | 487.019 | ¹H NMR (CDCl₃, 300 MHz) δ 7.72 (d, 2H, J = 8.4), 7.51 (d, 2H, J = 8.7), 6.67 (d, 1H, J = 24.3), 5.40 (d, 1H, J = 12, 6), 4.54 (br s, 1H), 3.90-4.20 (m, 4H), 3.40-3.55 (m, 2H), 3.05-3.35 (m, 2H), 2.85-3.05 (m, 2H), 2.40-2.60 (m, 1H), 2.35 (d, 6H, J = 8.1), 0.60-1.95 (m, 11H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 307 | isobutyl | 4-(dimethylamino)cyclohexylmethyl | 4-chlorophenyl | 1-Method A | clear oil | 444.03 | 1.28 min Method B | 444.04 | ¹H NMR (CDCl₃) δ 7.72 (d, J = 6.8 Hz, 2H), 7.52 (d, J = 6.8 Hz, 2H), 6.75 (s, br, 1H), 5.79 (s, br, 1H), 4.14 (dd, J = 9.6 Hz, 4.8 Hz, 1H), 3.23 (del, J=14.4Hz, 10.0 Hz, 1H), 3.12 (m, 1H), 2.92 (dd, J = 14.4 Hz, 4.8 Hz, 1H), 2.77 (m, 6H), 2.09 (m, 2H), 1.83 (m, 1H), 1.71 (m, 1H), 0.75-1.52 (m, 8H), 0.73 (d, J = 6.8 Hz, 3H), 0.67 (d, J = 6.8 Hz, 3H) |
| 308 | isobutyl | N-(4-ethylphenyl)-2-(dimethylamino)acetamide | 4-chlorophenyl | 23 | tan foam | 495.04 | 1.31 min Method A | 495.14 | ¹H NMR, 400 Hz, (CDCl₃) δ 8.85 (s, 1H, NH), 8.02 (d, 2H, J = 8.0 Hz), 7.75 (d, 2H, J = 8.0 Hz), 7.38 (d, 2H, J = 8.0 Hz), 7.29 (d, 2H, J = 8.0 Hz), 6.23 (s, br, 1H), 5.39 (s, br, 1H), 4.62 (m, 4H), 3.25 (t, 1H, J = 6.0 Hz), 2.95 (s, 6H), 1.95 (m, 1H), 1.60 (m, 2H), 0.98 (d, 3H, J = 7.0 Hz), 0.94 (d, 3H, J = 7.0 Hz) |
| 309 | 4-chlorophenyl | N-(4-ethylphenyl)-2-(piperidin-1-yl)acetamide | 4-chlorophenyl | 23 | tan foam | 535.11 | 1.34 min Method A | 535.29 | ¹H NMR, 400 Hz, (CDCl₃) δ 8.85 (s, 1H, NH), 8.02 (d, 2H, J = 8.0 Hz), 7.78 (d, 2H, J = 8.0 Hz), 7.38 (d, 2H, J = 8.0 Hz), 7.30 (d, 2H, J = 8.0 Hz), 6.25 (s, br, 1H), 5.36 (s, br, 1H), 4.62 (m,4H), 3.25 (t, 1H, J = 6.0 Hz), 2.42 (m, 4H), 1.95 (m, 1H), 1.68-1.38 (m, 8H), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appear-ance | Calc. MW | Ret. Time/ Method | M + H⁺ | NMR Data |
|---|---|---|---|---|---|---|---|---|---|
| 310 | isobutyl | 4-methylpiperazinyl-acetamide-(4-ethylphenyl) | 4-chlorophenyl | 23 | tan foam | 550.12 | 1.24 min Method A | 550.25 | ¹H NMR, 400 Hz, (CDCl₃) δ 8.83 (s, 1H, NH), 8.02 (d, 2H, J=8.0Hz), 7.78 (d, 2H, J = 8.0 Hz), 7.38 (d, 2H, J = 8.0 Hz), 7.30 (d, 2H, J = 8.0 Hz), 6.20 (s, br, 1H), 5.39 (s, br, 1H), 4.71 (d, 1H, $J_{ab}$ = 16 Hz), 4.48 (d, 1H, $J_{ab}$ = 16 Hz), 4.26 (s, 2H), 3.25 (m, 1H), 2.67 (m, 8H), 2.40 (s, 3H), 1.95 (m, 1H), 1.60 (m, 2H), 0.98 (d, 3H, J = 7.0 Hz), 0.94 (d, 3H, J = 7.0 Hz) |
| 311 | isobutyl | benzylpiperidinyl | 4-chlorophenyl | 7 | white solid | 492.09 | 2.30 min Method C | 492.16 | ¹H NMR (CDCl₃, 300 MHz) δ 7.73 (d, 2H, J = 8.4), 7.48 (d, 2H, J = 8.4), 7.15-7.38 (m, 5H), 6.67 (s, 1H), 5.37 (s, 1H), 4.14 (dd, 1H, J = 5.4, 9.0), 3.47 (s, 2H), 3.24 (dd, 1H, J = 10, 14), 2.75-3.05 (m, 3H), 1.45-2.05 (m, 10H), 0.75-0.90 (m, 1H), 0.71 (d, 3H, J = 6.6), 0.65 (d, 3H, J = 6.6) |
| 312 | isobutyl | diethylamino-propanoyl-piperidinyl | 4-chlorophenyl | 7 | white solid | 529.15 | 2.27 min Method C | 529.16 | ¹H NMR (CDCl₃, 300 MHz) δ 7.73 (d, 2H, J = 8.7), 7.50 (d, 2H, J = 8.7), 6.65 (d, 1H, J = 5.1), 4.55 (br s, 1H), 4.05-4.30 (m, 1), 3.57-3.95 (m, 1H), 3.10-3.40 (m, 1H), 2.40-3.00 (m, 12H), 1.70-2.00 (m, 3H), 0.90-1.30 (m, 10H), 0.60-0.75 (m, 6H) |
| 313 | isobutyl | Boc-N-methylglycyl-piperidinyl | 4-chlorophenyl | 7 | white solid | 573.16 | 1.78 min Method A | 573.18 | ¹H NMR (CDCl₃, 300 MHz) δ 7.72 (d, 2H, J = 7.8), 7.50 (d, 2H, J = 14), 5.35 (s, 1H), 6.65 (d, 1H, J = 14), 5.35 (s, 1H), 4.45-4.65 (m, 1H), 3.67-4.25 (m, 3H), 3.35-3.60 (m, 3H), 3.10-3.25 (m, 1H), 2.80-3.10 (m, 2H), 2.90 (s, 3H), 0.95-2.00 (m, 7H), 1.46 (s, 9H), 0.73 (br, s, 3H), 0.67 (br, s, 3H) |

TABLE 4-continued

| Ex. No. | R¹ | R² | R³ | Reaction Scheme | Appearance | Calc. MW | Ret. Time/Method | M+H⁺ | NMR Data |
|---|---|---|---|---|---|---|---|---|---|
| 314 | isobutyl | (1H-benzimidazol-2-ylmethyl)-piperidin-4-ylmethyl | 4-chlorophenyl | 7 | white solid | 532.11 | 1.47 min Method A | 532.19 | ¹H NMR (CDCl₃, 300 MHz) δ 7.74 (d, 2H, J = 8.8), 7.50 (d, 3H, 8.8), 7.17-7.27 (m, 3H), 6.63 (s, 1H), 5.60 (s, 1H), 4.13 (dd, 1H, J = 5.5, 9.2), 3.80 (s, 2H), 3.28 (dd, 1H, J = 9.5, 15), 2.80-305 (m, 3H), 1.50-2.25 (m, 6H), 1.15-1.45 (m, 5H), 0.72 (d, 3H, J = 6.6), 0.66 (d, 3H, J = 6.6) |
| 315 | isobutyl | (1-isopropylpiperidin-4-yl)methyl | 4-chlorophenyl | 7 | white solid | 444.04 | 2.11 min Method C | 444.13 | ¹H NMR (CDCl₃, 300 MHz) δ 7.73 (d, 2H, J = 8.7), 7.48 (d, 2H, J = 8.4), 6.69 (br s, 1H), 5.45 (br s, 1H), 4.14 (dd, 1H, J = 10, 15), 3.15-3.35 (m, 1H), 2.90-3.05 (m, 1H), 2.75-2.90 (m, 1H), 2.60-2.75 (m, 1H), 1.50-2.25 (m, 6H), 1.05-1.40 (m, 3H), 1.00 (d, 6H, J = 11), 0.75-0.90 (m, 1H), 0.71 (d, 3H, J = 10), 0.66 (d, 3H, J = 10) |
| 316 | isobutyl | N-(4-ethylphenyl)isonicotinamide | 4-chlorophenyl | 9 | yellow foam | 515.04 | 1.50 min Method A | 515.08 | ¹H NMR, 400 Hz, (CDCl₃) δ 9.97 (s, 1H, NH), 8.82 (d, 2H, J = 4.0 Hz), 8.02 (d, 2H, J = 8.0 Hz), 7.76 (d, 2H, J = 8.0 Hz), 7.73 (d, 2H, J = 4.0 Hz), 7.46 (d, 2H, J = 8.0 Hz), 7.38 (d, 2H, J = 8.0 Hz), 6.27 (s, br, 1H), 5.39 (s, br, 1H), 4.72 (d, 1H, J ab = 16 Hz), 4.30 (d, 1H, J ab = 16 Hz), 4.26 (s, 2H), 3.25 (t, 1H, J = 6.0 Hz), 1.95 (m, 1H), 1.60 (m, 2H), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 317 | n-butyl | 3-fluoro-4-(piperidin-1-yl)benzyl | 4-chlorophenyl | 2 | dark wax | 482.02 | 1.42 min Method B | 482.01 | ¹H NMR (CDCl₃) δ 7.63 (d, 2H, J = 8.2 Hz), 7.42 (d, 2H, J = 8.2 Hz), 6.71-7.08 (m, 3H), 6.20 (s, br, 1H), 5.15 (s, br, 1H), 4.27 (dd, 2H, J = 50 Hz, 15 Hz), 4.23- (t, 1H, J = 7.0 Hz), 2.99-3.10 (m, 4H), 1.92-1.95 (m, 1H), 1.53-1.59 (m, 2H), 1.41-1.90 (m, 4H), 1.21-1.24 (m, 1H), 0.98-1.08 (m, 2H), 0.74 (t, 3H, J = 8.0 Hz) |
| 318 | isobutyl | 3-fluoro-4-(morpholin-4-yl)benzyl | 4-chlorophenyl | 2 | dark solid | 498.02 | 1.68 min Method B | 498.2 | ¹H NMR (CDCl₃) δ 7.66 (d, 2H, J = 8.0 Hz), 7.42 (d, 2H, J = 8.0 Hz), 6.84-7.02 (m, 3H), 6.20 (s, br, 1H), 5.22 (s, br, 1H), 4.34 (dd, 2H, J = 50 Hz, 15 Hz), 4.19-4.25 (m, 1H), 3.84-3.86 (m, 4H), 3.15-3.17 (m, 1H), 3.03-3.06 (m, 4H), 1.31-1.77 (m, 2H), 0.95 (d, 3H, J = 7.0 Hz), 0.83 (d, 3H, J = 7.0 Hz) |
| 319 | isobutyl | N-(4-ethylphenyl)pyridine-2-carboxamide | 4-chlorophenyl | 9 | tan foam | 515.04 | 1.77 min Method A | 515.15 | ¹H NMR, 400 Hz, (CDCl₃) δ 9.90 (s, 1H, NH), 8.51 (d, 1H, J = 4.0 Hz), 8.11 (d, 2H, J = 8.0 Hz), 8.01 (d, 2H, J = 8.0 Hz), 7.78 (m, 3H), 7.59 (d, 2H, J = 8.0 Hz), 7.38 (d, 2H, J = 8.0 Hz), 7.32 (t, 1H, J = 4.0 Hz), 6.27 (s, br, 1H), 5.38 (s, br, 1H), 4.71 (d, 1H, J$_{ab}$ = 16 Hz), 4.3l (d, 1H, J$_{ab}$ = 16 Hz), 3.25 (t, 1H, J = 6.0 Hz), 1.95 (m, 1H), 1.60 (m, 2H), 0.98 (d, 3H, J = 7.0 Hz), 0.94 (d, 3H, J = 7.0 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 320 | isobutyl | 2-fluoro-4-(4-methylpiperazin-1-yl)phenyl | 4-chlorophenyl | 2 | tan solid | 511.06 | 1.12 min Method B | 511.2 | ¹H NMR (DMSO-d₆) δ 7.78 (d, 2H, J = 8.2 Hz), 7.55 (d, 2H, J = 8.2 Hz), 7.02-7.14 (m, 3H), 6.80 (s, br, 1H), 4.82 (s, br, 1H), 3.58-4.63 (m, 2H), 4.32-4.38 (m, 1H), 3.42-3.56 (m, 4H), 3.16-3.21 (m, 1H), 2.84 (s, 3H), 2.49-2.51 (m, 4H), 1.85 (s, 3H), 1.76-1.82 (m, 1H), 1.21-1.33 (m, 2H), 0.82 (d, 3H, J = 7.0 Hz), 0.56 (d, 3H, J = 7.0 Hz) |
| 321 | isobutyl | (tetrahydrofuran-2-yl)methyl-piperidinyl | 4-chlorophenyl | 7 | white solid | 486.08 | 2.22 min Method C | 486.12 | ¹H NMR (CDCl₃, 300 MHz) δ 7.73 (d, 2H, J = 8.5), 7.49 (d, 2H, J = 8.6), 6.67 (s, 1H), 5.35 (s, 1H), 4.15 (dd, 1H, J = 5.8, 9.2), 4.05 (br s, 1H), 3.85 (dd, 1H, J = 7.0, 15), 3.73 (dd, 1H, J = 7.3, 15), 3.20-3.29 (m, 1H, 2.95-3.05 (m, 3H), 2.43-2.51 (br s, 2H), 1.20-2.10 (m, 14H), 0.80-0.90 (m, 1H), 0.72 (d, 3H, J = 6.7), 0.67 (d, 3H, J = 6.7) |
| 322 | isobutyl | 1-(2-fluoroethyl)piperidin-4-ylmethyl | 4-chlorophenyl | 7 | white solid | 448.00 | 1.34 min Method A | 448.24 | ¹H NMR (CDCl₃, 300 MHz) δ 7.73 (d, 2H, J = 8.7), 7.48 (d, 2H, J = 8.7), 6.67 (s, 1H), 5.43 (s, 1H), 4.60 (d, 1H, J = 5.1), 4.45 (d, 1H, J = 4.8), 4.15 (dd, 1H, J = 5.6, 9.0), 3.25 (dd, 1H, J = 10, 15), 2.85-3.05 (m, 3H), 2.70 (t, 1H, J = 5.0), 2.67 (t, 1H, J = 4.7), 1.50-2.15 (m, 6H), 1.10-1.40 (3H), 0.75-0.90 (m, 1H), 0.71 (d, 3H, J = 6.3), 0.66 (d, 3H, J = 6.7) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 323 | isobutyl | 4-(N-methylacetamido)benzyl | 4-chlorophenyl | 9 | tan solid | 465.14 | 1.52 min Method B | 466.1 | $^1$H NMR (CDCl$_3$) δ 7.68 (d, 2H, J = 8.4 Hz), 7.46 (d, 2H, J = 8.4 Hz), 7.43 (d, 2H, J = 8.0 Hz), 7.10 (d, 2H, J = 8.0 Hz), 6.19 (s, br, 1H), 5.16 (s, br, 1H), 4.44 (dd, 2H, J = 50 Hz, 15 Hz), 4.31-4.35 (m, 1H), 3.23 (s, 3H), 1.85 (s, 3H), 1.76-1.82 (m, 1H), 1.14-1.35 (m, 2H), 0.78 (d, 3H, J = 7.0 Hz), 0.65 (d, 3H, J = 7.0 Hz) |
| 324 | isobutyl | 4-(N,N-dimethylcarbamoyl)piperidinylmethyl | 4-chlorophenyl | 7 | white powder | 473.04 | 1.54 mins Method A | 473.17 | $^1$H NMR (CDCl$_3$, 300 MHz) δ 7.73 (d, 2H, J = 8.1), 7.50 (d, 2H, J = 8.1), 6.67 (s, 1H), 5.85 (s, 1H), 4.15 (dd, 1H, J = 5.1, 9.2), 3.65 (d, 2H, J = 10), 3.26 (dd, 1H, J = 9.9, 15), 2.97 (dd, 1H, J = 4.4, 14), 2.60-2.85 (m, 3H), 2.80 (s, 6H), 1.75-1.95 (m, 3H), 1.05-1.30 (m, 3H), 0.72 (d, 3H, J = 6.2), 0.65 (d, 3H, J = 6.6) |
| 325 | isobutyl | 4-(pyridine-4-carbonyl)piperidinylmethyl | 4-chlorophenyl | 7 | white solid | 507.06 | 1.41 min Method A | 507.20 | $^1$H NMR (CDCl$_3$, 300 MHz) δ 8.64 (s, 2H), 7.72 (d, 3H, J = 8.4), 7.50 (d, 2H, J = 8.8), 7.35 (dd, 1H, J = 4.8, 7.7), 6.63 (s, 1H), 5.39 (br s, 1H), 4.69 (br s, 1H), 4.05-4.20 (m, 1H), 3.72 (brs, 1H), 3.25 (m, 1H), 2.50-3.200 (m, 3H), 1.50-2.10 (m, 5H), 1.00-1.40 (m, 3H), 0.72 (d, 3H, J = 6.6), 0.66 (d, 3H, J = 6.6) |
| 326 | n-propyl | 4-cyano-3-fluorobenzyl | 4-chlorophenyl | 1-Method A | white solid | 423.90 | 1.55 min Method B | 424.11 | $^1$H NMR (CDCl$_3$) δ 7.69-7.71 (m, 3H), 7.48-7.56 (m, 4H), 6.11 (s, br, 1H), 5.22 (s, br, 1H), 4.57 (dd, 2H, J = 50 Hz, 15 Hz), 4.22-4.26 (m, 1H), 1.80-1.83 (m, 1H), 0.99-1.23 (m, 3H), 0.74 (t, 3H, J = 8.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 327 | CH₂CH₂CF₃ | 4-CN-phenyl-CH₂CH₂- | 4-Cl-phenyl- | 1-Method A | white solid | 459.06 | 1.57 min Method G | (M + Na)⁺ 481.9 | ¹H NMR (400 MHz, DMSO) δ 7.84 (d, 2H, J = 8.8), 7.80 (d, 2H, J = 8.6), 7.65 (d, 2H, J = 8.7), 7.59 (d, 2H, J = 8.3,), 7.47 (s, 1H),7.25 (s, 1H) 4.79 (ABq, 2H, Δν = 5.1, J$_{ab}$ = 17.4), 4.43 (dd, 1H, J = 8.5, 6.6), 2.05 (m, 2H), 1.82 (m, 1H), 1.49 (m, 1H) |
| 328 | CH₂CH₂CF₃ | 4-CF₃-phenyl-CH₂CH₂- | 4-Cl-phenyl- | 1-Method A | white solid | 502.06 | 1.83 min Method G | (M + H)⁺ 502.9 | ¹H NMR (400 MHz, DMSO) δ 7.84 (d, 2H, J = 8.8), 7.68 (d, 2H, J = 8.0), 7.65-7.60 (m, 4H), 7.47 (s, 1H), 7.26 (s, 1H) 4.79 (s, 2H), 4.45 (dd, 1H, J = 8.8, 6.1), 2.03 (m, 2H), 1.82 (m, 1H), 1.52 (m, 1H) |
| 329 | CH₂CH₂CF₃ | 4-CO₂CH₃-phenyl-CH₂CH₂- | 4-Cl-phenyl- | 1-Method A | white solid | 492.07 | 2.39 min Method G | (M + H)⁺ 492.9 | ¹H NMR (400 MHz, DMSO) δ 7.91 (d, 2H, J = 8.3), 7.85 (d, 2H, J = 8.8), 7.64 (d, 2H, J = 8.6), 7.54 (d, 2H, J = 8.3), 7.43 (s, 1H), 7.23 (s, 1H) 4.79 (ABq, 2H, Δν = 3.4, J$_{ab}$ = 17.2), 4.42 (dd, 1H, J = 8.5, 6.1), 3.85 (s, 3H), 2.02 (m, 2H), 1.80 (m, 1H), 1.52 (m, 1H) |
| 330 | CH₂CH₂CH₂CF₃ | 4-CN-phenyl-CH₂CH₂- | 4-Cl-phenyl- | 1-Method A | white solid | 473.08 | 1.60 Method G | (M + Na)⁺ 495.9 | ¹H NMR (400 MHz, DMSO) δ 7.83 (d, 2H, J = 8.8), 7.80 (d, 2H, J = 8.3), 7.63 (d, 2H, J = 8.6), 7.59 (d, 2H, J = 8.3), 7.50 (s, 1H), 7.13 (s, 1H) 4.83 (ABq, 2H, Δν = 36.2, J$_{ab}$ = 17.6), 4.37 (dd, 1H, J = 8.5, 6.3), 2.09 (m, 1H), 1.88 (m, 1H), 1.64 (m, 1H), 1.45 (m, 1H), 1.27 (m, 2H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 331 | (CH₂CH₂CH₂CF₃ group) | 4-CF₃-phenyl-CH₂ | 4-Cl-phenyl | 1-Method A | white solid | 516.07 | 1.84 Method G | (M + H)⁺ 516.9 | ¹H NMR (400 MHz, DMSO) δ 7.82 (d, 2H, J = 8.8), 7.69-7.60 (m, 6H), 7.49 (s, 1H), 7.13 (s, 1H) 4.85 (ABq, 2H, Δν = 27.9, J$_{ab}$ = 17.1), 4.38 (dd, 1H, J = 9.0, 5.9), 2.05 (m, 1H), 1.75 (m, 1H), 1.65 (m, 1H), 1.46 (m, 1H), 1.27 (m, 2H) |
| 332 | 4-Cl-phenyl-CH₂ | CH₂CF₃ | 4-Cl-phenyl | 1-Method A | white solid | 506.09 | 1.67 Method G | (M + H)⁺ 506.9 | ¹H NMR (400 MHz, DMSO) δ 7.90 (d, 2H, J = 8.6), 7.83 (d, 2H, J = 8.8), 7.62 (d, 2H, J = 8.8), 7.54 (d, 2H, J = 8.3), 7.47 (s, 1H), 7.11 (s, 1H) 4.84 (ABq, 2H, Δν = 36.3, J$_{ab}$ = 17.4), 4.36 (dd, 1H, J = 8.6, 6.1), 3.85 (s, 3H), 2.04 (m, 1H), 1.82 (m, 1H), 1.62 (m, 1H), 1.45 (m, 1H), 1.26 (m, 2H) |
| 333 | CH₂CH₂CH₂F | 4-CN-phenyl-CH₂ | 4-Cl-phenyl | 19 | white solid | 437.10 | 1.48 Method G | (M + Na)⁺ 459.9 | ¹H NMR (400 MHz, DMSO) δ 7.82 (d, 2H, J = 8.8), 7.79 (d, 2H, J = 8.5), 7.63 (d, 2H, J = 8.8), 7.58 (d, 2H, J = 8.3), 7.52 (s, 1H), 7.09 (s, 1H) 4.82 (ABq, 2H, Δν = 37.2, J$_{ab}$ = 17.6), 4.34 (dd, 1H, J = 8.0, 6.6), 4.25 (dt, 2H, J$_d$ = 47.2, J$_t$ = 5.7), 1.58 (m, 1H), 1.49-1.12 (m, 5H) |
| 334 | CH₂CH₂CH₂F | 4-CF₃-phenyl-CH₂ | 4-Cl-phenyl | 19 | white solid | 480.09 | 1.76 Method G | (M + Na)⁺ 502.9 | ¹H NMR (400 MHz, DMSO) δ 7.80 (d, 2H, J = 8.6), 7.67 (d, 2H, J = 8.6), 7.60 (m, 4H), 7.52 (s, 1H), 7.09 (s, 1H), 4.83 (ABq, 2H, Δν = 30.1, J$_{ab}$ = 17.4), 4.36 (dd, 1H, J = 8.6, 6.2), 4.22 (dt, 2H, J$_d$ = 47.5, J$_t$ = 6.4), 1.61 (m, 1H), 1.48-1.11 (m, 5H) |

TABLE 4-continued

| Ex. No. | R¹ | R² | R³ | Reaction Scheme | Appearance | Calc. MW | Ret. Time/Method | M+H+ | NMR Data |
|---|---|---|---|---|---|---|---|---|---|
| 335 | (CH₂)₃F chain | 4-(CO₂CH₃)-benzyl | 4-Cl-phenyl | 19 | white solid | 470.11 | 1.58 Method G | (M+H)+ 471.0 | ¹H NMR (400 MHz, DMSO) δ 7.90 (d, 2H, J = 8.3), 7.82 (d, 2H, J = 8.8), 7.62 (d, 2H, J = 8.8), 7.53 (d, 2H, J = 8.4), 7.50 (s, 1H), 7.07 (s, 1H), 4.82 (ABq, 2H, Δν = 39.4, J$_{ab}$ = 17.4), 4.34 (dd, 1H, J = 8.3, 6.6), 4.22 (dt, 2H, J$_d$ = 41.6, J$_t$ = 6.1), 3.85 (s, 3H), 1.58 (m, 1H), 1.46-1.12 (m, 5H) |
| 336 | (CH₂)₃F chain | 4-CN-benzyl | 4-Cl-phenyl | 19 | white solid | 423.08 | 1.43 Method G | (M+H)+ 423.9 | ¹H NMR (400 MHz, DMSO) δ 7.82 (d, 2H, J = 8.8), 7.78 (d, 2H, J = 8.3), 7.63 (d, 2H, J = 6.8), 7.57 (d, 2H, J = 8.6), 7.53 (s, 1H), 7.14 (s, 1H), 4.81 (ABq, 2H, Δν = 36.2, J$_{ab}$ = 17.6), 4.38 (t, 1H, J = 7.6), 4.27 (m, 1H), 4.15 (m, 1H), 1.64 (m, 1H), 1.54-1.36 (m, 3H) |
| 337 | (CH₂)₃F chain | 4-CF₃-benzyl | 4-Cl-phenyl | 19 | white solid | 466.07 | 1.72 Method G | (M+Na)+ 489.0 | ¹H NMR (400 MHz, DMSO) δ 7.80 (d, 2H, J = 8.8), 7.66 (d, 2H, J = 8.1), 7.62-7.57 (m, 4H), 7.54 (s, 1H), 7.15 (s, 1H), 4.81 (ABq, 2H, Δν = 29.1, J$_{ab}$ = 17.1), 4.40 (t, 1H, J = 6.9), 4.25 (m, 1H), 4.13 (m, 1H), 1.67 (m, 1H), 1.55-1.39 (m, 3H) |
| 338 | (CH₂)₃F chain | 4-(CO₂CH₃)-benzyl | 4-Cl-phenyl | 19 | yellow solid | 456.09 | 1.54 Method G | (M+H)+ 457.0 | ¹H NMR (400 MHz, DMSO) δ 7.90 (d, 2H, J = 8.3), 7.83 (d, 2H, J = 8.8), 7.62 (d, 2H, J = 8.8), 7.52 (d, 2H, J = 8.3), 7.50 (s, 1H), 7.11 (s, 1H), 4.82 (ABq, 2H, Δν = 54.5, J$_{ab}$ = 17.3), 4.37 (t, 1H, J = 8.0), 4.28-4.03 (m, 2H), 3.85 (s, 3H), 1.64 (m, 1H), 1.53-1.36 (m, 3H) |

TABLE 4-continued

| Ex. No. | R¹ | R² | R³ | Reaction Scheme | Appearance | Calc. MW | Ret. Time/Method | M+H⁺ | NMR Data |
|---|---|---|---|---|---|---|---|---|---|
| 339 | (fluoroethyl) | 4-(trifluoromethyl)phenyl-CH₂ | 4-chlorophenyl-CH₂ | 19 | white solid | 452.86 | 1.85 min Method A | 452.91 | ¹H NMR (CDCl₃, 300 MHz) δ 7.70 (d, 2H, J = 8.7), 7.54 (d, 2H, J = 8.4), 7.42-7.49 (m, 4H), 6.31 (br s, 1H), 5.23 (br s, 1H), 4.58-4.63 (m, 2H), 4.33-4.41 (m, 2H), 4.19 (t, 1H, J = 4.5), 2.18-2.37 (m, 1H), 1.54-1.66 (m, 1H) |
| 340 | (fluoroethyl) | 4-(methoxycarbonyl)phenyl-CH₂ | isobutyl | 19 | white solid | 442.89 | 1.68 min Method A | 442.90 | ¹H NMR (CDCl₃, 300 MHz) δ 7.96 (d, 2H, J = 8.4), 7.72 (d, 2H, J = 8.7), 7.48 (d, 2H, J = 8.7), 7.39 (d, 2H, J = 8.4), 6.32 (br s, 1H), 5.18 (br s, 1H), 4.54-4.63 (m, 2H), 4.30-4.42 (m, 2H), 4.16 (t, 1H, J = 4.5), 3.90 (s, 3H), 2.18-2.37 (m, 1H), 1.54-1.66 (m, 1H) |
| 341 | (fluoroethyl) | 4-cyanophenyl-CH₂ | 4-chlorophenyl-CH₂ | 19 | white solid | 409.87 | 1.57 min Method A | 410.07 | ¹H NMR (CDCl₃, 300 MHz) δ 7.72 (dd, 2H, J = 1.8, 8.7), 7.59 (d, 2H, J = 8.1), 7.50 (dd, 2H, J = 2.1, 8.7), 7.46 (d, 2H, J = 8.1), 6.30 (br s, 1H), 5.21 (br s, 1H), 4.56-4.68 (m, 2H), 4.31-4.37 (m, 2H), 4.18 (t, 1H, J = 4.8), 2.17-2.37 (m, 1H), 1.48-1.64 (m, 1H) |
| 342 | (difluoropropyl) | 4-(trifluoromethyl)phenyl-CH₂ | 4-chlorophenyl-CH₂ | 19 | white solid | 470.85 | 1.88 min Method A | 470.89 | ¹H NMR (CDCl₃, 300 MHz) δ 7.70 (d, 2H, J = 8.7), 7.56 (d, 2H, J = 8.4), 7.51 (d, 2H, J = 8.4), 7.43 (d, 2H, J = 8.1), 6.32 (br s, 1H), 5.75 (tm, 1H, J_{H-F} = 57), 5.34 (br s, 1H), 4.52-4.63 (m, 2H), 4.32 (d, 1H, J = 15.6), 2.51-2.66 (m, 1H), 1.54-1.69 (m, 1H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 343 | CH₂CHF₂ group | methyl 4-benzoate group | 4-chlorophenyl | 19 | white solid | 460.88 | 1.74 min Method A | 461.07 | ¹H NMR (CDCl₃, 300 MHz) δ 7.97 (dd, 2H, J = 2.0, 8.4), 7.72 (d, 2H, J = 8.7), 7.51 (d, 2H, J = 8.7), 7.38 (d, 2H, J = 8.4), 6.32 (br s, 1H), 5.75 (tm, 1H, $J_{H-F}$ = 57), 5.18 (br s, 1H), 4.60 (d, 1H, J = 15.6), 4.50-4.55 (m, 1H), 4.32 (d, 1H, J = 15.6), 3.91 (s, 3H), 2.51-2.66 (m, 1H), 1.54-1.69 (m, 1H) |
| 344 | CH₂CHF₂ group | 4-cyanophenyl | 4-chlorophenyl | 19 | white solid | 427.85 | 1.62 min Method A | 428.06 | ¹H NMR (CDCl₃, 300 MHz) δ 7.70 (d, 2H, J = 8.7), 7.61 (d, 2H, J = 8.1), 7.53 (d, 2H, J = 8.7), 7.45 (d, 2H, J = 7.8), 6.32 (br s, 1H), 5.71 (tm, 1H, $J_{H-F}$ = 57), 5.21 (br s, 1H), 4.64 (d, 1H, J = 15.6), 4.51-4.55 (m, 1H), 4.28 (d, 1H, J = 15.6), 2.48-2.60 (m, 1H), 1.54-1.69 (m, 1H) |
| 345 | CH₂CH₂CF₃ group | 4-trifluoromethylphenyl | 4-chlorophenyl | 1-Method A sep cond 1 | white solid | 502.87 | 1.99 min Method E | 503.02 | ¹H NMR (DMSO) δ 7.83 (d, 2H, J = 8.8 Hz), 7.64 (m, 6H), 7.46 (s br, 1H), 7.25 (s br, 1H) 4.79 (s, 2H), 4.44 (m, 1H), 2.03 (m, 2H), 1.83 (m, 1H), 1.50 (m, 1H) |
| 346 | CH₂CH₂CF₃ group | 4-cyanophenyl | 4-chlorophenyl | 1-Method A sep cond 2 | white solid | 459.88 | 1.76 min Mehtod E | 460.13 | ¹H NMR (DMSO) δ 7.84 (d, 2H, J = 8.0 Hz), 7.80 (d, 2H, J = 7.7 Hz), 7.65 (d, 2H, J = 8.2 Hz), 7.59 (d, 2H J = 7.7 Hz), 7.47 (s br, 1H), 7.25 (s br, 1H), 4.78 (AB, 2H, Δν = 5 Hz, $J_{ab}$ = 17 Hz), 4.43 (m, 1H), 2.05 (m, 2H), 1.83 (m, 1H), 1.48 (m, 1H) |

TABLE 4-continued

| Ex. No. | R¹ | R² | R³ | Reaction Scheme | Appearance | Calc. MW | Ret. Time/ Method | M+H⁺ | NMR Data |
|---|---|---|---|---|---|---|---|---|---|
| 347 | (3-fluoropropyl) | 4-cyanobenzyl | 4-chlorophenyl | 1-Method A, sep cond 3 | yellow waxy solid | 437.92 | 1.67 min Method E | 438.22 | ¹H NMR (DMSO) δ 7.81 (m, 4H) 7.61 (m, 4H), 7.53 (s br, 1H), 7.09 (s br, 1H), 4.81 (AB, 2H, Δν = 5 Hz, $J_{ab}$ = 17 Hz), 4.33 (m, 2H), 4.19 (t, 1H, J = 6.0 Hz), 1.44 (m, 6H) |
| 348 | (3-fluoropropyl) | 4-trifluoromethylbenzyl | 4-chlorophenyl | 1-Method A, sep cond 3 | white powder | 480.91 | 1.94 min Method E | M + Na 503.14 | ¹H NMR (DMSO) δ 7.99 (d, 2H, J = 8.8 Hz), 7.82 (m, 6H), 7.70 (s br, 1H), 7.27 (s br, 1H), 5.00 (m, 2H), 4.51 (m, 2H), 4.33 (m, 1H) 1.77 (m, 1H), 1.47 (m, 6H) |
| 349 | (2-fluoro-2-methylpropyl) | 4-(methoxycarbonyl)benzyl | 4-chlorophenyl | 1-Method A | white powder | 470.94 | 1.59 min Method B | 493.17 M + Na+ | ¹H NMR (CDCl₃) δ 7.94 (d, J = 8.0 Hz, 2H), 7.72 (d, J = 6.8 Hz, 2H), 7.46 (d, J = 6.8 Hz, 2H), 7.38 (d, J = 8.0 Hz, 2H), 6.25 (s, br, 1H), 5.26 (s, br, 1H), 4.37-4.62 (m, 3H), 3.90 (s, 3H), 2.45 (m, 1H), 1.45 (m, 1H), 1.27 (d, J = 21.2 Hz, 3H), 1.17 (d, J = 21.6 Hz, 3H) |
| 350 | (3,3-difluoropropyl) | 4-trifluoromethylbenzyl | 4-chlorophenyl | 22 | white solid | 484.88 | 1.93 min Method E | 485.09 | ¹H NMR (DMSO) δ 7.81 (d, 2H, J = 8.8 Hz), 7.63 (m, 6H), 7.51 (s br, 1H), 7.21 (s br, 1H), 5.85 (t, 1H, 56 Hz), 4.81(AB2, 2H, Δν = 5 Hz, $J_{ab}$ = 15 Hz), 4.42 (t, 1H, J = 8.0 Hz), 1.49 (m, 4H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 351 | (CH₂C(CH₃)₂CH₂F) | 4-CN-phenyl-CH₂CH₂- | 4-Cl-phenyl | 1-Method A | white solid | 437.92 | 1.49 min Method B | 460.13 M + Na+ | ¹H NMR (CDCl₃) δ 7.72 (d, J=6.8 Hz, 2H), 7.58 (d, J = 8.4 Hz, 2H), 7.48 (d, J = 8.4 Hz, 2H), 7.45 (d, J = 6.8 Hz, 2H), 6.25 (s, br, 1H), 5.28 (s, br, 1H), 4.32-4.64 (m, 3H), 2.45 (m, 1H), 1.38 (m, 1H), 1.24 (d, J = 21.2 Hz, 3H), 1.21 (d, J = 22 Hz, 3H), |
| 352 | (CH₂C(CH₃)₂CH₂F) | 4-CF₃-phenyl-CH₂CH₂- | 4-Cl-phenyl | 1-Method A | white solid | 480.91 | 1.76 min Method B | 503.12 M + Na+ | ¹H NMR (CDCl₃) δ 7.69 (d, J = 84 Hz, 2H), 7.52 (d, J = 8.0 Hz, 2H), 7.45 (d, J = 8.4 Hz, 2H), 7.43 (d, J = 8.0 Hz, 2H), 6.30 (s, br, 1H), 5.44 (s, br, 1H), 4.34-4.66 (m, 3H), 2.49 (m, 1H), 1.46 (m, 1H), 1.26 (d, J = 21.6 Hz, 3H), 1.22 (d, J = 21.6 Hz, 3H), |
| 353 | (CH₂CH₂CH₂F) | 4-CF₃-phenyl-CH₂CH₂- | 4-Cl-phenyl | 18 | white solid | 466.89 | 1.41 min Method B | 466.16 | ¹H NMR (CDCl₃) δ 7.66 (d, 2H, J = 8.4 Hz) 7.45-7.55 (m, 6H), 6.17 (s, br, 1H), 5.19 (s, br, 1H), 4.53 (dd, 2H, J = 50 Hz, 15 Hz), 4.34-4.37 (m, 2H), 4.22-4.25 (m, 1H), 2.00-2.05 (m, 1H), 1.43-1.49 (m, 3H) |
| 354 | (CH₂CH₂CH₂F) | 4-CN-phenyl-CH₂CH₂- | 4-Cl-phenyl | 18 | white solid | 423.90 | 1.54 min Method B | 421.1 | ¹H NMR (DMSO-d₆) δ 7.86 (d, 2H, J = 8.0 Hz) 7.48-7.75 (m, 6H), 6.56 (s, br, 1H), 5.69 (s, br, 1H), 4.72 (dd, 2H, J = 42 Hz, 16 Hz), 4.51-4.55 (m, 3H), 1.43-2.07 (m, 4H) |
| 355 | (CH₂CH₂CF₃) | 4-(morpholinoethoxy)-3-fluoro-phenyl-CH₂- | 4-Cl-phenyl | 11 | yellow solid | 582.02 | 1.47 min Method E | 582.22 | ¹H NMR (DMSO) δ 7.81 (d, 2H, J = 8.8 Hz), 7.63 (d, 2H, J = 8.5 Hz), 7.43 (s br, 1H), 7.24 (m, 4H), 4.64 (s, 2H), 4.42 (m, 3H), 3.99 (m, 2H), 3.62 (m, 6H), 3.23 (m, 2H), 1.85 (m, 4H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 356 | CH₂CH₂CF₃ branched | 4-(2-(4-methylpiperazin-1-yl)ethoxy)-3-fluorobenzyl | 4-Cl-phenyl | 11 | brown solid | 595.06 | 1.42 min Method E | 595.23 | ¹H NMR (DMSO) δ 7.80 (d, 2H, J = 8.8 Hz), 7.63 (d, 2H, J = 8.5 Hz), 7.42 (s br, 1H), 7.17 (m, 4H), 4.62 (s, 2H),4.41 (m, 1H), 4.18 (m, 2H), 3.96 (s, 1H), 3.39 (m, 2H), 3.05 (m, 7H), 2.78 (s, 3H), 1.97 (m, 3H), 1.58 (m, 1H) |
| 357 | CH₂C(CH₃)₂F | 4-CN-benzyl | 4-Cl-phenyl | 21 | white solid | 437.10 | 1.50 Method G | (M + Na)⁺ 460.2 | ¹H NMR (400 MHz, DMSO) δ 7.83 (d, 2H, J = 8.5), 7.75 (d, 2H, J = 8.3), 7.68 (s, 1H), 7.64 (d, 2H, J = 8.6), 7.49 (d, 2H, J = 8.1), 7.20 (s, 1H), 4.67 (ABq, 2H, Δν = 28.3, J$_{ab}$ = 17.3), 4.54 (dd, 1H, J = 9.3, 3.2), 2.23 (m, 1H), 1.42 (m, 1H), 1.25 (d, 3H, J = 21.6), 1.21 (d, 3H, J = 21.7) |
| 358 | CH₂C(CH₃)₂F | 4-CF₃-benzyl | 4-Cl-phenyl | 21 | white solid | 480.09 | 1.76 Method G | (M + Na)⁺ | ¹H NMR (400 MHz, DMSO) δ 7.80 (d, 2H, J = 8.6), 7.69 (s, 1H), 7.61 (m, 4H), 7.50 (d, 2H, J = 8.1), 7.22 (s, 1H), 4.68 (ABq, 2H, Δν = 2.7, J$_{ab}$ =17.1), 4.57 (dd, 1H, J = 9.1, 3.0), 2.26 (m, 1H), 1.47 (m, 1H), 1.24 (d, 3H, J = 21.5), 1.22 (d, 3H, J = 21.5) |
| 359 | CH₂C(CH₃)₂F | 4-CO₂CH₃-benzyl | 4-Cl-phenyl | 21 | white solid | 470.11 | 1.62 Method G | (M + Na)⁺ 493.2 | ¹H NMR (400 MHz, DMSO) δ 7.86 (d, 2H, J = 8.3), 7.83 (d, 2H, J = 8.8), 7.63 (m, 3H), 7.44 (d, 2H, J = 8.3), 7.18 (s, 1H), 4.67 (ABq, 2H, Δν = 10.3, J$_{ab}$ =17.1), 4.53 (dd, 1H, J = 9.3, 2.9), 3.85 (s, 3H), 2.22 (m, 1H), 1.46 (m, 1H), 1.22 (d, 3H, J = 21.5), 1.19 (d, 3H, J = 21.6) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 360 | -CH₂CH₂F | 4-cyanobenzyl | 4-chlorophenyl | 18 | white solid | 409.87 | 1.53 min Method B | 407.99 (M − H)⁻ | ¹H NMR (CDCl₃) δ 7.72 (d, 2H, J = 8.4 Hz) 7.58 (d, 2H, J = 8.4 Hz), 7.50 (d, 2H, J = 8.4 Hz), 7.45 (d, 2H, J = 8.4 Hz), 6.29 (s, br, 1H), 5.21 (s, br, 1H), 4.19-4.67 (m, 5H), 2.17-2.28 (m, 1H), 1.49-1.61 (m, 1H) |
| 361 | -CH₂CH₂F | 4-trifluoromethylbenzyl | 4-chlorophenyl | 18 | white solid | 452.86 | 1.56 min Method B | 452.85 | ¹H NMR (CDCl₃) δ 7.69 (d, 2H, J = 8.4 Hz) 7.56 (d, 2H, J = 8.4 Hz), 7.49 (d, 2H, J = 8.4 Hz), 7.43 (d, 2H, J = 8.4 Hz), 6.31 (s, br, 1H), 5.24 (s, br, 1H), 4.19-4.62 (m, 5H), 2.16-2.30 (m, 1H), 1.56-1.63 (m, 1H) |
| 362 | -CH₂CH₂CH₂F | 4-(CO₂Me)benzyl | 4-chlorophenyl | 18 | white solid | 456.93 | 1.86 min Method B | 457.16 | ¹H NMR (CDCl₃, 300 MHz) δ 7.96 (d, 2H, J = 8.4), 7.69 (dd, 2H, J = 1.8, 8.4), 7.47 (ddd, 2H, J = 1.5, 2.1, 8.7), 7.42 (d, 2H, J = 8.4), 6.19 (br s, 1H), 5.18 (br s, 1H), 4.64 (d, 1H, J = 15.6), 4.42 (d, 1H, J = 15.9), 4.30-4.35 (m, 2H), 4.18 (t, 1H, J = 3.6), 3.90 (s, 3H), 1.89-2.08 (m, 1H), 1.38-1.50 (m, 3H) |
| 363 | -CH₂CH₂CH₂F | 4-(2-hydroxypropan-2-yl)benzyl | 4-chlorophenyl | 18 | white solid | 456.97 | 1.80 min Method B | 454.98 (neg. ion) | ¹H NMR (CDCl₃, 300 MHz) δ 7.64 (d, 2H, J = 8.7), 7.42 (d, 2H, J = 8.7), 7.38 (d, 2H, J = 8.4), 7.26 (d, 2H, J = 8.4), 6.19 (br, 1H), 5.28 (br s, 1H), 4.51 (d, 1H, J = 15.6), 4.39 (d, 1H, J = 15.3), 4.30-4.35 (m, 2H), 4.18 (t, 1H, J = 3.6), 1.92-2.08 (m, 1H), 1.55 (s, 6H), 1.35-1.50 (m, 3H) |

TABLE 4-continued

| Ex. No. | R[1] | R[2] | R[3] | Reaction Scheme | Appearance | Calc. MW | Ret. Time/ Method | M+H+ | NMR Data |
|---|---|---|---|---|---|---|---|---|---|
| 364 | (CH2)3F chain | 4-CO2H-benzyl | 4-chlorophenyl | 18 | white solid | 442.90 | 1.73 min Method B | 443.12 | 1H NMR (CDCl3, 300 MHz) δ 7.81 (d, 2H, J = 8.4), 7.59 (dd, 2H, J = 1.8, 8.4), 7.29-7.33 (m, 4H), 6.76 (br, 1H), 5.80 (brs, 1H), 4.62 (d, 1H, J = 16.2), 4.44 (d, 1H, J = 16.2), 4.31 (t, 1H, J = 6.9), 3.85-4.10 (m, 2H), 1.70-1.85 (m, 1H), 1.30-1.48 (m, 3H) |
| 365 | CH2CH2CF3 | morpholinoethoxy-fluorophenyl-methyl | 4-chlorophenyl | 11 | off-white solid | 585.02 | 1.47 min Method E | 582.18 | 1H NMR (DMSO) δ 7.80 (m, 2H), 7.62 (m, 2H), 7.42 (m, 1H), 7.18 (m, 4H), 4.62 (m, 3H), 4.42 (m, 1H), 4.14 (m, 1H), 4.00 (m, 3H), 3.58 (m, 4H), 2.93 (m, 1H), 2.70 (m, 2H), 2.01 (m, 2H), 1.85 (m, 1H), 1.59 (m, 1H) |
| 366 | CH2CH2CF3 | N-methylpiperazino-ethoxy-fluorophenyl-methyl | 4-chlorophenyl | 11, sep cond 4 | yellow | 595.06 | 1.43 min Method E | 595.19 | 1H NMR (CDCl3) δ 7.72 (d, 2H, J = 8.7 Hz), 7.52 (d, 2H, J = 8.8 Hz), 7.14 (m, 1H), 7.01 (m, 1H), 6.87 (m, 1H), 6.24 (s br, 1H), 5.36 (m, 1H), 4.51 (m, 1H), 4.28 (m, 4H), 3.23 (m, 9H), 2.77 (m, 3H), 1.94 (m, 3H), 1.40 (m, 1H) |
| 367 | CH2CH2CF3 | N-methylpiperazino-ethoxy-fluorophenyl-methyl | 4-chlorophenyl | 11, sep cond 4 | white solid | 595.06 | 1.42 min Method E | 595.20 | 1H NMR (DMSO) δ 7.80 (m, 2H), 7.62 (m, 2H), 7.42 (s br, 1H), 7.18 (m, 4H), 4.61 (m, 2H), 4.42 (m, 1H), 4.14 (m, 1H), 3.72 (m, 1H), 3.57 (m, 1H), 3.32 (s, 3H), 2.75 (m, 6H), 2.27 (m, 2H), 1.97 (m, 3H), 1.60 (m, 1H) |
| 368 | (CH2)3F chain | morpholinoethoxy-fluorophenyl-methyl | 4-chlorophenyl | 11, sep cond 4 | dark yellow solid | 546.04 | 1.55 min Method E | 546.20 | 1H NMR (CDCl3) δ 7.77 (d, 2H, J = 8.5 Hz), 7.61 (d, 2H, J = 8.5 Hz), 7.53 (m, 1H), 7.19 (m, 4H), 4.67 (ABq, 2H, Δν = 35, Jab = 16 Hz), 4.30 (m, 6H), 4.01 (m, 4H), 3.48 (m, 1H), 1.68 (m, 1H), 1.49 (m, 4H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 369 | (CH2)3F chain | 4-(2-(4-methylpiperazin-1-yl)ethoxy)-3-fluorobenzyl | 4-chlorophenyl | 11, sep cond 4 | orange-yellow solid | 559.08 | 1.29 min Method E | 559.22 | ¹H NMR (DMSO) δ 7.77 (d, 2H, J = 8.3 Hz), 7.60 (d, 2H, J = 8.3 Hz), 7.50 (s br, 1H), 7.16 (m, 4H), 4.65 (ABq, 2H, Δν = 20, $J_{ab}$ = 16 Hz), 4.33 (m, 2H), 4.18 (m, 4H), 3.17 (m, 7H), 2.78 (s, 3H), 1.67 (m, 1H), 1.50 (m, 5H) |
| 370 | (CH2)3F chain | 4-(2-morpholinoethoxy)benzyl | 4-chlorophenyl | 11, sep cond 4 | yellow solid | 528.05 | 1.32 min Method E | 528.17 | ¹H NMR (DMSO) δ 7.74 (d, 2H, J = 8.3 Hz), 7.60 (d, 2H, J = 8.3 Hz), 7.44 (s br, 1H), 7.35 (d, 2H, J = 8.5 Hz), 7.08 (s br, 1H), 6.95 (d, 2H, J = 8.5 Hz), 4.68 (ABq, 2H, Δν = 24, $J_{ab}$ = 16 Hz), 3.77 (m, 13H), 1.66 (m, 1H), 1.45 (m, 5H) |
| 371 | (CH2)3F chain | 4-(2-(4-methylpiperazin-1-yl)ethoxy)benzyl | 4-chlorophenyl | 11, sep cond 4 | light-orange solid | 541.09 | 1.26 min Method E | 541.24 | ¹H NMR (DMSO) δ 7.77 (d, 2H, J = 8.3 Hz), 7.59 (d, 2H, J = 8.3 Hz), 7.43 (s br, 1H), 7.31 (d, 2H, J = 8.5 Hz), 7.08 (s br, 1H), 6.87 (d, 2H, J = 8.8 Hz), 4.66 (ABq, 2H, Δν = 16, $J_{ab}$ = 16 Hz), 4.22 (m, 5H), 3.17 (m, 8H), 2.77 (m, 3H), 1.65 (m, 1H), 1.46 (m, 5H) |
| 372 | (CH2)3F chain | 4-((4-methylpiperazin-1-yl)methyl)-ethylbenzyl | 4-chlorophenyl | 18, 8 | amber glass | 511.05 | 1.09 min Method A | 511.21 | ¹H NMR 400 Hz, (CDCl₃) δ 7.66 (d, 2H, J = 8.0 Hz), 7.43 (d, 2H, J = 8.0 Hz), 7.26 (d, 2H, J = 8.0 Hz), 7.21 (d, 2H, J = 8.0 Hz), 6.25 (s. br, 1H), 5.45 (s, br, 1H), 4.52 (d, 1H, $J_{ab}$ = 12.0 Hz), 4.38 (d, 1H, $J_{ab}$ = 12.0 Hz), 4.29 (m, 2H), 4.18 (t, 1H, J = 6.0 Hz), 3.72 (m, 1H), 3.47 (s, 2H), 2.29 (s, 3H), 2.0 (m, 2H), 1.83 (m, 2H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 373 | (CH₂)₃F chain | 4-(morpholinomethyl)phenyl | 4-chlorophenyl | 18, 8 | amber glass | 498.01 | 1.40 min Method A | 498.20 | ¹H NMR 400 Hz, (CDCl₃) δ 7.66 (d, 2H, J = 8.0 Hz), 7.44 (d, 2H, J = 8.0 Hz), 7.27 (d, 2H, J = 8.0 Hz), 7.22 (d, 2H, J = 8.0 Hz), 6.24 (s, br, 1H), 5.42 (s,br, 1H), 4.52 (d, 1H, $J_{ab}$ = 2.0 Hz), 4.38 (d, 1H, $J_{ab}$ = 12.0 Hz), 4.29 (m, 2H), 4.18 (m, 1H), 3.68 (t, 4H, J = 4.0 Hz), 3.45 (s, 2H), 2.40 (s, br, 4H), 1.99 (m, 1H), 1.45 (m, 3H) |
| 374 | (CH₂)₃F chain | 2-fluoro-4-ethyl-benzyl-(4-methylpiperazinyl) | 4-chlorophenyl | 18, 8 | amber glass | 529.08 | 1.17 min Method A | 529.22 | ¹H NMR 400 Hz, (CDCl₃) δ 7.68 (d, 2H, J = 8.0 Hz), 7.46 (d, 2H, J = 8.0 Hz), 7.25 (t, 1H, J = 6.0 Hz), 7.05 (t, 1H, J = 6.0 Hz), 6.28 (s, br, 1H), 5.49 (s, br, 1H), 4.54 (d, 1H, $J_{ab}$ = 12.0 Hz), 4.33 (m, 2H), 4.22 (m, 1H), 3.57 (s, 2H), 2.32 (s, 3H), 2.01 (m, 1H), 1.44 (m, 2H) |
| 375 | (CH₂)₃F chain | 2-fluoro-4-ethyl-benzyl-morpholino | 4-chlorophenyl | 18, 8 | amber glass | 516.00 | 1.10 min Method A | 516.17 | ¹H NMR 400 Hz, (CDCl₃) δ 7.68 (d, 2H, J = 8.0 Hz), 7.45 (d, 2H, J = 8.0 Hz), 7.28 (t, 1H, J = 6.0 Hz), 7.06 (t, 2H, J = 6.0 Hz), 6.24 (s, br, 1H), 5.40 (s, br, 1H), 4.53 (d, 1H, $J_{ab}$ = 12.0 Hz), 4.36 (d, 1H, $J_{ab}$ = 12.0 Hz), 4.34 (m, 2H), 4.21 (m, 1H), 3.69 (t, 4H, J = 4.0 Hz), 3.53 (s, 2H), 2.44 (s, br, 3H), 2.0 (m, 1H), 1.45 (m, 2H) |
| 376 | CH₂F chain | 4-(1,2,4-triazol-1-yl)phenethyl | 4-chlorophenyl | 18 | white solid | 451.91 | 1.39 min Method B | 451.90 | ¹H NMR (CDCl₃) δ 8.55 (s, 1H) 8.09 (s, 1H), 7.75 (d, 2H, J = 8.0 Hz) 7.62 (d, 2H, J = 8.4 Hz), 7.47-7.51 (m, 4H), 6.36 (s, br, 1H), 5.28 (s, br, 1H), 4.31-4.62 (m, 5H), 2.16-2.30 (m, 1H), 1.56-1.66 (m, 1H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 377 | CHF₂-CH₂-CH₂- (gem-difluoro propyl) | 4-cyanobenzyl | 4-chlorophenyl | 22 | white solid | 441.89 | 1.65 min Method E | M+Na 464.01 | ¹H NMR (CDCl₃) δ 7.69 (d, 2H, J = 8.3 Hz), 7.60 (d, 2H, J = 8.3 Hz), 7.49 (m, 4H), 6.18 (s br, 1H), 5.67 (tt, 1H, J = 56 Hz, 4.0 Hz), 5.22 (s br, 1H), 4.52 (AB2, 2H, Δν = 16, J_ab = 100 Hz), 4.34 (m, 1H), 2.03 (m, 1H), 1.68 (m, 1H), 1.38 (m, 1H), 0.86 (m, 1H) |
| 378 | 2-fluoroethyl | 4-(pyrazol-1-yl)benzyl | 4-chlorophenyl | 18 | white solid | 450.92 | 1.52 min Method B | 450.91 | ¹H NMR (CDCl₃) δ 7.91 (s, 1H), 7.71 (m, 3H) 7.63 (d, 2H, J = 8.4 Hz), 7.50 (d, 2H, J = 8.4 Hz), 7.41 (d, 2H, J = 8.4 Hz), 6.47 (s, 1H), 6.34 (s, br, 1H), 5.18 (s, br, 1H), 4.30-4.60 (m, 5H), 2.14-2.29 (m, 1H), 1.56-1.66 (m, 1H) |
| 379 | 2-fluoroethyl | 4-(1,2,3-thiadiazol-4-yl)benzyl | 4-chlorophenyl | 18 | white solid | 468.96 | 1.53 min Method B | 469.04 | ¹H NMR (CDCl₃) δ 8.64 (s, 1H), 7.98 (d, 2H, J = 8.4 Hz), 7.75 (d, 2H, J = 8.4 Hz), 7.45-7.50 (m, 4H), 6.35 (s, br, 1H), 5.20 (s, br, 1H), 4.22-4.64 (m, 5H), 2.20-2.35 (m, 1H), 1.54-1.62 (m, 1H) |
| 380 | 3-fluoropropyl | 4-(pyrazol-1-yl)benzyl | 4-chlorophenyl | 18 | white solid | 464.95 | 1.54 min Method B | 464.99 | ¹H NMR (CDCl₃) δ 8.54 (s, 1H), 8.10 (s, 1H), 7.73 (d, 2H, J = 8.4 Hz), 7.62 (d, 2H, J = 8.4 Hz), 7.48-7.52 (m, 5H), 6.22 (s, br, 1H), 5.18 (s, br, 1H), 4.32-4.69 (m, 5H), 2.09-2.19 (m, 1H), 1.44-1.61 (m, 3H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 381 | (CH₂CH₂CH₂F) | (4-(1H-1,2,4-triazol-1-yl)benzyl) | (4-chlorophenyl) | 18 | white solid | 465.94 | 1.49 min Method B | 465.96 | ¹H NMR (CDCl₃) δ 8.55 (s, 1H), 8.09 (s, 1H), 7.73 (d, 2H, J = 8.4 Hz), 7.62 (d, 2H, J = 8.4 Hz), 7.47-7.51 (m, 4H) 6.36 (s, br, 1H), 5.28 (s, br, 1H), 4.31-4.66 (m, 5H), 2.10-2.39 (m, 1H), 1.56-1.66 (m, 3H) |
| 382 | (CH₂CH₂CF₃) | (4-(1H-1,2,4-triazol-1-yl)benzyl) | (4-chlorophenyl) | 1- Method A | white solid | 501.92 | 1.53 min Method B | 502.1 | ¹H NMR (CDCl₃) δ 8.56 (s, 1H), 8.10 (s, 1H), 7.72 (d, 2H, J = 8.4 Hz), 7.64 (d, 2H, J = 8.4 Hz), 7.49-7.52 (m, 4H), 6.23 (s, br, 1H), 5.22 (s, br, 1H), 4.32-4.64 (m, 3H), 1.44-2.20 (m, 4H) |
| 383 | (CH₂CH₂CF₃) | (4-(1H-pyrazol-1-yl)benzyl) | (4-chlorophenyl) | 1- Method A | white solid | 500.93 | 1.66 min Method B | 501.13 | ¹H NMR (CDCl₃) δ 7.91 (s, 1H), 7.41-7.78 (m, 9H), 6.47 (s, 1H), 6.23 (s,br, 1H), 5.27 (s, br, 1H), 4.30-4.59 (m, 3H), 1.47-2.21 (m, 4H) |
| 384 | (CH₂CH₂CH₂F) | (4-(2-morpholinoethoxy)-3-fluorobenzyl) | (4-chlorophenyl) | 18, 11 | beige solid | 532.01 | 1.36 min Method E | 532.18 | ¹H NMR (DMSO) δ 7.80 (d, 2H, J = 8.3 Hz), 7.61 (d, 2H, J = 8.3 Hz), 7.56 (s br, 1H),7.23 (s br, 1H), 7.19 (m, 3H), 4.64 (ABq, 2H, Δν = 16, J$_{ab}$ = 16 Hz), 4.51 (t, 1H, J = 8.0 Hz), 4.42 (m, 2H), 4.03 (m, 12H), 2.02 (m, 1H), 1.82 (m, 1H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 385 | (CH₂CH₂F) | 2-F-4-(2-(4-methylpiperazin-1-yl)ethoxy)benzyl | 4-chlorophenyl | 18, 11 | pale orange solid | 545.05 | 1.32 min Method E | 545.25 | ¹H NMR (DMSO) δ 7.79 (d, 2H, J = 8.3 Hz), 7.60 (d, 2H, J = 8.3 Hz), 7.54 (s br, 1H), 7.14 (m, 5H), 4.62 (ABq, 2H, Δν = 8.0 Hz, J_ab = 16 Hz), 4.51 (t, 1H, J = 8.0 Hz), 4.24 (m, 5H), 3.17 (m, 8H), 2.78 (m, 3H), 2.02 (m, 1H), 1.81 (m, 1H) |
| 386 | (CH₂CH₂F) | 4-(2-morpholinoethoxy)benzyl | 4-chlorophenyl | 18, 11 | yellow residue | 514.02 | 1.33 min Method E | 514.20 | ¹H NMR (DMSO) δ 7.80 (d, 2H, J = 8.3 Hz), 7.61 (d, 2H, J = 8.3 Hz), 7.48 (s br, 1H), 7.33 (d, 2H, J = 8.3 Hz), 7.15 (s br, 1H), 6.95 (d, 2H, J = 8.3 Hz), 4.65 (ABq, 2H, Δν = 8.0 Hz, J_ab = 16 Hz), 3.86 (m, 15H), 2.03 (m, 1H), 1.79 (m, 1H) |
| 387 | (CMe₂CH₂F) | 4-(2-(4-methylpiperazin-1-yl)ethoxy)benzyl | 4-chlorophenyl | 18, 11 | orange solid | 527.06 | 1.28 min Method E | 527.20 | ¹H NMR (DMSO) δ 7.79 (d, 2H, J = 8.3 Hz), 7.60 (d, 2H, J = 8.3 Hz), 7.47 (s br, 1H), 7.30 (d, 2H, J = 8.3 Hz), 7.15 (s br, 1H), 6.89 (d, 2H, J = 8.3 Hz), 4.63 (ABq, 2H, Δν = 8.0 Hz, J_ab = 16 Hz), 4.48 (t, 1H, J = 8.0 Hz), 4.15 (m, 4H), 3.24 (m, 10H), 2.79 (m, 3H), 2.03 (m, 1H), 1.80 (m, 1H) |
| 388 | (CMe₂CH₂F) | 2-F-4-(2-morpholinoethoxy)benzyl | 4-chlorophenyl | 18, 11 | tan solid | 560.06 | 1.65 min Method E | 559.14 | ¹H NMR (DMSO) δ 7.76 (d, 2H, J = 8.3 Hz), 7.59 (m, 3H), 7.21 (s, br, 1H), 7.08 (s br, 1H), 7.04 (m, 2H), 4.53 (m, 5H), 3.92 (m, 4H), 3.45 (m, 6H), 2.25 (m, 1H), 1.54 (m, 1H), 1.25 (d, 3H, J = 20 Hz), 1.22 (d, 3H, J = 20 Hz) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 389 | CH2CHF2 | 4-(pyrazol-1-yl)benzyl | 4-chlorophenyl | 18 | yellow solid | 478.91 | 1.55 min Method B | 491.04 (M + Na) | ¹H NMR (CDCl₃) δ 7.92 (s, 1H), 7.72-7.76 (m, 3H), 7.65 (d, 2H, J = 8.4 Hz) 7.52 (d, 2H, J = 8.4 Hz), 7.40 (d, 2H, J = 8.4 Hz) 6.47 (s, 1H), 6.30 (s, br, 1H), 5.21 (s, br, 1H), 4.27-4.57 (m, 3H), 2.51-2.60 (m, 1H), 1.53-1.65 (m, 2H) |
| 390 | CH2CHF2 | 4-(1,2,4-triazol-1-yl)benzyl | 4-chlorophenyl | 18 | white solid | 469.90 | 1.48 min Method B | 470.1 | ¹H NMR (CDCl₃) δ (s, 1H), 7.40-7.76 (m, 9H), 6.50 (s, 1H), 6.27 (s, br, 1H), 5.22 (s, br, 1H), 4.25-4.55 (m, 3H), 2.49-2.58 (m, 1H), 1.51-1.62 (m, 2H) |
| 391 | CH2CH2CH2F | 4-(N-ethylcarbamoyl)benzyl | 4-chlorophenyl | 18, 6 | white solid | 469.97 | 1.59 min Method A | 470.09 | ¹H NMR (MeOD, 400 MHz) δ 7.77 (ddd, 2H, J = 2.0, 2.4, 8.8), 7.71 (d, 2H, J = 8.4), 7.51 (ddd, 2H, J = 2.0, 2.4, 8.8), 7.48 (d, 2H, J = 8.0), 4.80 (d, 1H, J = 16.4), 4.72 (d, 1H, J = 16.4), 4.47 (t, 1H, J = 7.2), 4.05-4.28 (m, 2H), 3.38 (q, 2H, J = 7.2), 1.70-1.85 (m, 1H), 1.30-1.48 (m, 3H), 1.20 (t, 3H, J = 7.2) |
| 392 | CH2CH2CH2F | 4-(N-(2-methoxyethyl)carbamoyl)benzyl | 4-chlorophenyl | 18, 6 | white solid | 500.00 | 1.57 min Method A | 500.10 | ¹H NMR (MeOD, 400 MHz) δ 7.72-7.81 (m, 4H), 7.48-7.52 (m, 4H), 4.80 (d,1H, J =16.4), 4.72 (d, 1H, J = 16.4), 4.47 (t, 1H, J = 7.2), 4.05-4.28 (m, 2H), 3.54 (s, 3H), 3.25-2.36 (m, 4H), 1.70-1.85 (m, 1H), 1.30-1.48 (m, 3H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 393 | (CH₂)₃F | N-methyl-N-ethyl-4-benzamide | 4-chlorophenyl | 18, 6 | white solid | 484.00 | 1.65 min Method A | 484.12 | ¹H NMR (MeOD, 400 MHz) δ 7.79 (d, 2H, J = 8.8), 7.50-7.54 (m, 4H), 7.29-7.33 (m, 2H), 4.79 (d, 1H, J = 16.4), 4.72 (d, 1H, J = 16.4), 4.47 (t, 1H, J = 7.2), 4.05-4.28 (m, 2H), 3.52-3.56 (m, 2H), 3.03 and 2.94 (2s, 3H), 1.70-1.85 (m, 1H), 1.30-1.48 (m, 3H), 1.15-1.25 (m, 3H) |
| 394 | (CH₂)₃F | N-(pyridin-2-ylmethyl)-4-benzamide | 4-chlorophenyl | 18, 6 | white solid | 533.03 | 1.36 min Method A | 533.15 | ¹H NMR (MeOD, 400 MHz) δ 8.48 (d, 1H, J = 4.8), 7.76-7.82 (m, 5H), 7.50-7.53 (m, 4H), 7.41 (d, 1H, J = 8.0), 7.28-7.30 (m, 1H), 4.82 (d, 1H, J = 16.0), 4.72 (d, 1H, J = 16.4), 4.67 (s, 2H), 4.48 (t, 1H, J = 7.2), 4.05-4.28 (m, 2H), 1.70-1.85 (m, 1H), 1.30-1.48 (m, 3H) |
| 395 | (CH₂)₂F | 2-fluoro-4-(morpholinomethyl)phenyl | 4-chlorophenyl | 18, 8 | amber glass | 501.98 | 1.17 min Method A | 502.25 | ¹H NMR, 400 Hz, (CDCl₃) δ 7.77 (d, 2H, J = 8.0 Hz), 7.51 (d, 2H, J = 8.0 Hz), 7.42 (t, 1H, J = 6.0 Hz), 7.26 (d, 1H, J = 6.0 Hz), 7.14 (d, 1H, J = 6.0 Hz), 6.35 (s, br, 1H), 6.07 (s, br, 1H), 4.82 (d, 1H, J_{ab} = 12.0 Hz), 4.35 (m, 1H), 4.19 (m, 5H), 3.59 (s, br, 4H), 3.48 (d, br, 1H), 2.90 (d, br, 1H), 2.20 (m, 1H), 1.50 (m, 1H) |
| 396 | (CH₂)₂F | 2-fluoro-4-((4-methylpiperazin-1-yl)methyl)phenyl | 4-chlorophenyl | 18, 8 | amber glass | 515.02 | 1.21 min Method A | 515.27 | ¹H NMR, 400 Hz, (CDCl₃) δ 7.76 (d, 2H, J = 8.0 Hz), 7.50 (d, 2H, J = 8.0 Hz), 7.32 (m, 1H), 7.19 (d, 1H, J = 8.0 Hz), 7.07 (d, 1H, J = 8.0 Hz), 6.35 (s, br, 1H), 5.67 (s, br, 1H), 4.86 (d, 1H, J_{ab} = 12.0 Hz), 4.70 (s, 2H), 4.56 (m, 2H), 4.17 (m, 6H), 2.80 (s, 3H), 2.22 (m, 1H), 1.54 (m, 1H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 397 | (2-fluoroethyl) | (4-ethylbenzyl)morpholine | 4-chlorophenyl | 18, 8 | amber glass | 483.98 | 1.21 min Method A | 483.98 | ¹H NMR, 400 Hz, (CDCl₃) δ 7.77 (d, 2H, J = 8.0 Hz), 7.51 (d, 2H, J = 8.0 Hz), 7.41 (d, 2H, J = 8.0 Hz), 7.31 (d, 2H, J = 8.0 Hz), 6.34 (s, br, 1H), 6.05 (s, br, 1H), 4.83 (d, 1H, J$_{ab}$ = 12.0 Hz), 4.51 (m, 1H), 4.20 (m, 4H), 3.94 (m, 5H), 3.51 (d, 1H, J = 12.0 Hz), 3.40 (d, 1H, J = 6.0 Hz), 2.76 (t, 1H, J = 6.0 Hz), 2.89 (t, 1H, J = 6.0 Hz), 2.20 (m, 1H), 1.51 (m, 1H) |
| 398 | (2-fluoroethyl) | (4-ethylbenzyl)-4-methylpiperazine | 4-chlorophenyl | 18, 8 | amber glass | 497.03 | 1.16 min Method A | 498.74 | ¹H NMR, 400 Hz, (CDCl₃) δ 7.76 (d, 2H, J = 8.0 Hz), 7.51 (d, 2H, J = 8.0 Hz), 7.37 (d, 2H, J = 8.0 Hz), 7.27 (d, 2H, J = 8.0 Hz), 6.31 (s, br, 1H), 5.80 (s, br, 1H), 4.82 (d, 1H, J$_{ab}$ = 12.0 Hz), 4.55 (m, 2H), 4.16 (m, 5H), 3.82 (d, 1H), 2.78 (s, 3H), 2.21 (m, 1H), 1.52 (m, 1H) |
| 399 | (2,2-dimethyl-2-fluoroethyl) | 2-(2-fluoro-4-substituted-phenoxy)ethyl-4-methylpiperazine | 4-chlorophenyl | 20, 11 | colorless residue | 573.11 | 1.63 min Method E | | ¹H NMR (DMSO) δ 7.76 (d, 2H, J = 8.3 Hz), 7.59 (m, 3H), 7.20 (s br, 1H), 7.08 (s br, 1H), 7.03 (m, 2H), 4.53 (m, 11H), 3.92 (m, 4H), 3.45 (m, 3H), 2.24 (m, 1H), 1.54 (m, 1H), 1.25 (d, 3H, J = 20 Hz), 1.22 (d, 3H, J = 20 Hz) |
| 400 | (3,3,3-trifluoropropyl) | 2-(4-substituted-phenoxy)ethyl morpholine | 4-chlorophenyl | 11 | light yellow solid | 564.03 | 1.51 min Method E | 564.19 | ¹H NMR (DMSO) δ 7.81 (d, 2H, J = 8.3 Hz), 7.63 (d, 2H, J = 8.3 Hz), 7.36 (m, 3H), 7.20 (s br, 1H), 6.96 (d, 2H, J = 8.0 Hz), 4.64 (s, 2H), 4.37 (m, 3H), 4.00 (m, 2H), 3.61 (m, 6H), 3.21 (m, 2H), 1.97 (m, 2H), 1.82 (m, 1H), 1.60 (m, 1H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 401 | (CH₂CH(CF₃)—, wavy bond) | 4-(2-(4-methylpiperazin-1-yl)ethoxy)benzyl | 4-chlorophenyl | 11 | pale orange solid | 577.07 | 1.47 min Method E | 577.20 | ¹H NMR (DMSO) δ 7.80 (d, 2H, J = 8.0 Hz), 7.62 (d, 2H, J = 8.0 Hz), 7.33 (m, 3H), 7.20 (s br, 1H), 6.89 (d, 2H, J = 8.0 Hz), 4.63 (s, 2H), 4.39 (m, 1H), 4.10 (m, 2H), 3.25 (m, 10H), 2.77 (s, 3H), 1.89 (m, 2H), 1.81 (m, 1H), 1.60 (m, 1H) |
| 402 | CH₂C(CH₃)₂F | 4-(2-morpholinoethoxy)benzyl | 4-chlorophenyl | 20, 11 | pale yellow residue | 542.07 | 1.51 min Method E | 542.21 | ¹H NMR (DMSO) δ 7.77 (d, 2H, J = 8.0 Hz), 7.59 (d, 2H, J = 8.0 Hz), 7.55 (s br, 1H), 7.26 (d, 2H, J = 8.0 Hz), 7.15 (s br, 1H), 6.90 (d, 2H, J = 8.0 Hz), 4.52 (m, 2H), 4.32 (m, 2H), 4.00 (m, 2H), 3.71 (m, 2H), 3.38 (m, 7H), 2.23 (m, 1H), 1.55 (m, 1H), 1.23 (d, 3H, J = 20 Hz), 1.21 (d, 3H, J = 20 Hz) |
| 403 | CH₂C(CH₃)₂F | 4-(2-(4-methylpiperazin-1-yl)ethoxy)benzyl | 4-chlorophenyl | 20, 11 | light orange solid | 555.12 | 1.45 min Method E | 555.27 | ¹H NMR (DMSO) δ 7.76 (d, 2H, J = 8.0 Hz), 7.58 (d, 2H, J = 8.0 Hz), 7.54 (s br, 1H), 7.22 (d, 2H, J = 8.0 Hz), 7.16 (s br, 1H), 6.84 (d, 2H, J = 8.0 Hz), 4.52 (m, 2H), 4.13 (m, 2H), 3.25 (m, 11H), 2.79 (m, 3H), 2.20 (m, 1H), 1.56 (m, 1H), 1.23 (d, 3H, J = 20 Hz), 1.20 (d, 3H, J = 20 Hz) |
| 404 | CH₂CH(CH₃)F | 4-(2-morpholinoethoxy)benzyl | 4-chlorophenyl | 18, 11 | pale yellow residue | 532.01 | 1.43 min Method E | 532.18 | ¹H NMR (DMSO) δ 7.81 (d, 2H, J = 8.0 Hz), 7.62 (d, 2H, J = 8.0 Hz), 7.48 (s br, 1H), 7.34 (d, 2H, J = 8.0 Hz), 7.25 (s br, 1H), 6.96 (d, 2H, J = 8.0 Hz), 5.72 (tt, 1H, J = 8.0 Hz, 56 Hz), 4.61 (s, 2H), 4.52 (t, 1H, J = 8.0 Hz), 4.33 (t, 2H, J = 8.0 Hz), 3.96 (m, 2H), 3.56 (m, 2H), 3.22 (m, 2H), 2.24 (m, 1H), 1.95 (m, 1H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 405 | CHF₂-CH₂- | 4-methylpiperazinyl-ethoxy-phenyl | 4-chlorophenyl | 18, 11 | pale yellow solid | 545.05 | 1.37 min Method E | 545.19 | ¹H NMR (DMSO) δ 7.81 (d, 2H, J = 8.0 Hz), 7.61 (d, 2H, J = 8.0 Hz), 7.46 (s br, 1H), 7.30 (d, 2H, J = 8.0 Hz), 7.25 (s br, 1H), 6.89 (d, 2H, J = 8.0 Hz), 5.64 (m, 1H), 4.60 (s, 2H), 4.52 (t, 1H, J = 8.0 Hz), 4.11 (m, 2H), 3.17 (m, 10H), 2.77 (m, 3H), 2.24 (m, 1H), 1.96 (m, 1H) |
| 406 | CHF₂-CH₂- | morpholinyl-ethoxy-fluorophenyl | 4-chlorophenyl | 18, 11 | yellow residue | 550.00 | 1.43 min Method E | 550.16 | ¹H NMR (DMSO) δ 7.80 (d, 2H, J = 8.0 Hz), 7.62 (d, 2H, J = 8.0 Hz), 7.56 (s br, 1H), 7.23 (m, 4H), 5.80 (tt, 1H, J = 4.0 Hz, 56 Hz), 3.93 (m, 15H), 2.29 (m, 1H), 1.99 (m, 1H) |
| 407 | CHF₂-CH₂- | 4-methylpiperazinyl-ethoxy-fluorophenyl | 4-chlorophenyl | 18, 11 | orange solid | 563.04 | 1.37 min Method E | 563.21 | ¹H NMR (DMSO) δ 7.80 (d, 2H, J = 8.0 Hz), 7.62 (d, 2H, J = 8.0 Hz), 7.55 (s br, 1H), 7.29 (s br, 1H), 7.15 (m, 3H), 5.78 (tt, 1H, J = 4.0 Hz, 56 Hz), 4.56 (m, 3H), 4.21 (m, 2H), 3.22 (m, 10H), 2.79 (m, 3H), 2.30 (m, 1H), 1.97 (m, 1H) |
| 408 | CH₂F-CH₂-CH₂- | 6-(dimethylamino)pyridin-3-yl | 4-chlorophenyl | 18, 10, sep cond 5 | clear oil | 442.94 | 0.993 min Method B | 443.19 | ¹H NMR (CDCl₃) δ 8.07 (s, 1H), 7.67 (d, J = 6.8 Hz, 2H), 7.55 (d, J = 8.8 Hz, 1H), 7.44 (d, J = 6.8 Hz, 2H), 6.47 (d, J = 8.8 Hz, 1H), 6.30 (s, br, 1H), 5.45 (s, br, 1H), 4.20-4.46 (m, 5H), 3.12 (s, 6H), 1.22-1.85 (m, 4H) |
| 409 | CH₂F-CH₂-CH₂- | 6-(dimethylamino)pyridin-3-yl | 4-chlorophenyl | 18, 10, sep cond 5 | clear oil | 442.94 | 0.993 min Method B | 443.19 | ¹H NMR (CDCl₃) δ 8.07 (s, 1H), 7.67 (d, J = 6.8 Hz, 2H), 7.55 (d, J = 8.8 Hz, 1H), 7.44 (d, J = 6.8 Hz, 2H), 6.47 (d, J = 8.8 Hz, 1H), 6.30 (s, br, 1H), 5.45 (s, br, 1H), 4.20-4.46 (m, 5H), 3.12 (s, 6H), 1.22-1.85 (m, 4H) |

TABLE 4-continued

| Ex. No. | R¹ | R² | R³ | Reaction Scheme | Appearance | Calc. MW | Ret. Time/Method | M+H⁺ | NMR Data |
|---|---|---|---|---|---|---|---|---|---|
| 410 | CH₂C(CH₃)₂CH₂F | 4-(morpholinomethyl)phenyl-ethyl | 4-chlorophenyl | 20, 8 | amber glass | 512.04 | 1.44 min Method B | 512.20 | ¹H NMR, 400 Hz, (CDCl₃) δ 7.69 (d, 2H, J = 8.0 Hz), 7.42 (d, 2H, J = 8.0 Hz), 7.22 (dd, 4H, J = 8.0 Hz), 6.27 (s, br, 1H), 5.26 (s, br, 1H), 4.58 (d, 1H), 4.43 (d, 1H, $J_{ab}$ = 16.0 Hz), 4.36 (d, 1H, $J_{ab}$ = 16.0 Hz), 3.68 (m, 6H), 3.46 (s, 2H), 2.45 (m, 6H), 1.53 (m, 1H), 1.26 (d, 3H, J = 20.0 Hz), 1.17 (d, 3H, J = 20.0 Hz) |
| 411 | CH₂C(CH₃)₂CH₂F | 4-((4-methylpiperazin-1-yl)methyl)phenyl-ethyl | 4-chlorophenyl | 20, 8 | amber glass | 525.08 | 1.38 min Method B | 525.24 | ¹H NMR, 400 Hz, (CDCl₃) δ 7.69 (d, 2H, J = 8.0 Hz), 7.42 (d, 2H, J = 8.0 Hz), 7.22 (dd, 4H, J = 8.0 Hz), 6.26 (s, br, 1H), 5.24 (s, br, 1H), 4.57 (m, 1H), 4.43 (d, 1H, $J_{ab}$ = 16.0 Hz), 4.35 (d, 1H, $J_{ab}$ = 16.0 Hz), 3.48 (s, 2H), 2.47 (m, 7H), 2.30 (s, 3H), 1.26 (d, 3H, J = 22.0 Hz), 1.18 (d, 3H, J = 22.0 Hz) |
| 412 | CH₂CHF₂ | 4-cyanobenzyl | 4-chlorophenyl | 18 | white solid | 427.87 | 1.39 min Method B | 428.13 | ¹H NMR (CDCl₃, 400 MHz) δ 7.72 (dd, 2H, J = 2.0, 8.8), 7.61 (d, 2H, J = 8.4), 7.53 (dd, 2H, J = 2.0, 8.4), 7.45 (d, 2H, J = 8.0), 6.32 (br s, 1H), 5.73 (tm, 1H, $J_{HF}$ = 57), 5.22 (br s, 1H), 4.64 (d, 1H, J = 16.4), 4.50-4.60 (m, 1H, J = 16.4), 2.42-2.60 (m, 1H), 1.50-1.63 (m, 1H) |
| 413 | CH₂CHF₂ | 4-(trifluoromethyl)benzyl | 4-chlorophenyl | 18 | white solid | 470.86 | 1.69 min Method B | 471.13 | ¹H NMR (CDCl₃, 400 MHz) δ 7.69 (dd, 2H, J = 1.6, 8.8), 7.56 (d, 2H, J = 8.4), 7.51 (ddd, 2H, J = 2.0, 2.4, 8.4), 7.43 (d, 2H, J = 8.4), 6.32 (br s, 1H), 5.75 (tm, 1H, $J_{HF}$ = 57), 5.25 (br s, 1H), 4.60 (d, 1H, J = 15.6), 4.50-4.60 (m, 1H), 4.32 (d, 1H, J = 15.6), 2.50-2.60 (m, 1H), 1.55-1.70 (m, 1H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 414 | 4-Cl-phenyl | 4-(5-methyl-1,3,4-oxadiazol-2-yl)benzyl | 4-Cl-phenyl | 18, 13 | white solid | 480.95 | 1.41 min Method B | 481.22 | $^1$H NMR (CDCl$_3$, 400 MHz) δ 7.96 (d, 2H, J = 8.4), 7.70 (d, 2H, J = 8.4), 7.47-7.50 (m, 4H), 6.22 (brs, 1H), 5.18 (brs, 1H), 4.66 (d, 1H, J = 15.6), 4.43 (d, 1H, J = 15.6), 4.30-4.35 (m, 2H), 4.19-4.21 (m, 1H), 2.61 (s, 3H), 1.93-2.08 (m, 1H), 1.38-1.50 (m, 3H) |
| 415 | 2-fluoroethyl | 4-(6-dimethylaminopyridin-3-yl)benzyl | 4-Cl-phenyl | 18, 10 | white foam | 428.92 | 1.34 Method B | 429.18 | $^1$H NMR (CDCl$_3$) TFA salt δ 8.10 (s, 1H), 8.04 (d, 1H, J = 9.2 Hz), 7.76 (d, 2H, J = 6.8 Hz), 7.52 (d, 2H, J = 6.8 Hz), 6.80 (d, 2H, J = 9.2 Hz), 6.46 (s, 1H), 6.00 (s, 1H), 4.60 (d, 1H, J = 15.6 Hz), 4.54 (dd, 1H, J = 5.2 Hz, 6.2 Hz), 4.30 (m, 1H), 4.18 (m, 1H), 4.07 (d, 1H, J = 15.6 Hz), 3.29 (s, 6H), 2.25 (m, 1H), 1.55 (m, 1H) |
| 416 | isobutyl | 4-(trifluoromethyl)benzyl | 6-Cl-pyridin-3-yl | 1-Method A | off-white solid | 463.91 | 1.50 min Method B | 464.11 | $^1$H NMR (CDCl$_3$, 300 MHz) δ 8.72 (d, 1H, J = 2.4), 7.82 (dd, 1H, J = 2.7, 8.4), 7.55 (d, 2H, J = 8.1), 7.47 (d, 2H, J = 8.1), 7.37 (d, 1H, J = 8.4), 5.97 (brs, 1H), 5.26 (brs, 1H), 4.62 (d, 1H, J = 16.2), 4.54 (d, 1H, J = 15.9), 4.44 (t, 1H, J = 7.5), 1.70-1.77 (m, 1H), 1.35-1.43 (m, 1H), 1.21-1.31 (m, 1H), 0.85 (d, 3H, J = 6.3), 0.67 (d, 3H, J = 6.6) |
| 417 | isobutyl | 4-(methoxycarbonyl)benzyl | 6-Cl-pyridin-3-yl | 1-Method A | white solid | 453.95 | 1.37 min Method B | 545.14 | $^1$H NMR (CDCl$_3$, 300 MHz) δ 8.71 (d, 1H, J = 3.0), 7.96 (d, 2H, J = 8.1), 7.85 (dd, 1H, J = 2.4, 8.4), 7.37-7.43 (m, 3H), 5.99 (brs, 1H), 5.24 (brs, 1H), 4.61 (d, 1H, J = 15.9), 4.53 (d, 1H, J = 15.9), 4.41 (t, 1H, J = 7.2), 3.91 (s, 3H), 1.70-1.76 (m, 1H), 1.35-1.43 (m, 1H), 1.21-1.31 (m, 1H), 0.82 (d, 3H, J = 6.6), 0.66 (d, 3H, J = 6.6) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 418 | isobutyl | 4-cyanobenzyl | 6-chloropyridin-3-yl | 1-Method A | white solid | 420.92 | 1.64 min Method A | 421.15 | ¹H NMR (CDCl₃, 300 MHz) δ 8.74 (d, 1H, J = 2.4), 7.90 (dd, 1H, J = 2.4, 8.4), 7.61 (d, 2H, J = 8.4), 7.50 (d, 2H, J = 8.4), 7.44 (d, 1H, J = 8.4), 5.92 (br s, 1H), 5.22 (br s, 1H), 4.65 (d, 1H, J = 16.5), 4.52 (d, 1H, J = 16.5), 4.40 (t, 1H, J = 7.5), 1.65-1.74 (m, 1H), 1.33-1.40 (m, 1H), 1.18-1.25 (m, 1H), 0.83 (d, 3H, J = 6.6), 0.66 (d, 3H, J = 6.6) |
| 419 | isobutyl | (4-methylpiperazin-1-yl)carbonyl-piperidin-4-ylmethyl | 4-chlorophenyl | 7 | white solid | 528.12 | 1.35 min Method A | 528.26 | ¹H NMR (CDCl₃, 500 MHz) δ 7.72 (d, 2H, J = 8.6), 7.51 (d, 2H, J = 8.8), 6.65 (s, 1H), 5.35 (s, 1H), 4.14 (dd, 1H, J = 5.1, 9.5), 3.63-3.75 (m, 2H), 3.35-3.55 (m, 3H), 3.25 (dd, 1H, J = 9.8, 14), 2.98 (dd, 1H, J = 4.5, 14), 2.35-2.87 (m, 8H), 1.77-1.92 (m, 3H), 1.59 (d, 2H, J = 13), 1.05-1.30 (m, 1H), 0.75-0.80 (m, 1H), 0.72 (d, 3H, J = 6.4), 0.67 (d, 3H, J = 6.7) |
| 420 | isobutyl | morpholin-4-ylcarbonyl-piperidin-4-ylmethyl | 4-chlorophenyl | 7 | white solid | 515.08 | 1.56 min Method A | 515.33 | ¹H NMR (CDCl₃, 500 MHz) δ 7.71 (d, 2H, J = 8.5), 7.50 (d, 2H, J = 8.5), 6.65 (s, 1H), 5.47 (s, 1H), 4.13 (dd, 1H, J = 5.2, 9.2), 3.60-3.75 (m, 6H), 3.15-3.30 (m, 6H), 2.97 (dd, 1H, J = 4.6, 14), 2.71 (dd, 2H, J = 14, 25), 1.75-1.92 (m, 3H), 1.67 (d, 1H, J = 12), 1.05-1.30 (m, 3H), 0.75-0.81 (m, 1H), 0.71 (d, 3H, J = 6.7), 0.65 (d, 3H, J = 6.7) |
| 421 | isobutyl | methoxycarbonyl-piperidin-4-ylmethyl | 4-chlorophenyl | 7 | white solid | 460.00 | 1.68 min Method A | 460.17 | ¹H NMR (CDCl₃, 500 MHz) δ 7.73 (d, 2H, J = 8.5), 7.50 (d, 2H, J = 8.6), 6.65 (s, 1H), 5.35 (s, 1H), 4.15 (dd, 1H, J = 5.2, 9.5), 3.67 (s, 3H), 3.25 (t, 1H, J = 10), 3.97 (dd, 1H, J = 4.8, 14), 2.61-2.80 (m, 2H), 1.74-1.94 (m, 3H), 0.89-1.40 (m, 4H), 0.75-0.80 (m, 1H), 0.72 (d, 3H, J = 6.4), 0.67 (m, 3H, J = 6.7) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 422 | isobutyl | 3-fluoro-4-bromobenzyl | 4-chlorophenyl | 1- Method A | tan solid | 491.81 | 1.84 min Method B | 491.04 | ¹H NMR (CDCl₃) δ 7.71 (d, 2H, J = 8.0 Hz), 7.50-7.58 (m, 2H), 7.41 (d, 2H, J = 8.0 Hz), 7.17-7.22 (m, 1H), 6.23 (s, br, 1H), 5.25 (s, br, 1H), 4.41 (dd, 2H, J = 50 Hz, 15 Hz), 4.31-4.35 (m, 1H), 1.80-1.86 (m, 1H), 1.41-1.44 (m, 1H), 1.11-1.15 (m, 1H), 0.81 (d, 3H, J = 7.0 Hz), 0.71 (d, 3H, J = 7.0 Hz) |
| 423 | sec-butyl | 4-CO₂CH₃-benzyl | 4-chlorophenyl | 1- Method A | white solid | 424.09 | 1.54 min Method F | (M + H)⁺ 425.1 | ¹H NMR (400 MHz, DMSO) δ 7.90 (d, 2H, J = 8.1), 7.82 (d, 2H, J = 8.5), 7.61 (d, 2H, J = 8.5), 7.52 (d, 2H, J = 8.1), 7.49 (s, 1H), 7.07 (s, 1H), 4.81 (ABq, 2H, Δν = 45.3, J_ab = 17.3), 4.27 (t, 1H, J = 7.3), 3.85 (s, 3H), 1.55 (m, 1H), 1.38 (m, 1H), 0.68 (t, 3H, J = 7.3) |
| 424 | sec-butyl | 4-CO₂CH₃-benzyl | 4-chlorophenyl | 1- Method A | white solid | 452.12 | 1.69 min Method F | (M + H)⁺ 453.1 | ¹H NMR (400 MHz, DMSO) δ 7.90 (d, 2H, J = 8.3), 7.83 (d, 2H, J = 8.8), 7.62 (d, 2H, J = 8.8), 7.54 (d, 2H, J = 8.3), 7.48 (s, 1H), 7.04 (s, 1H), 4.82 (ABq, 2H, Δν = 41.3, J_ab = 17.3), 4.31 (t, 1H, J = 8.1), 3.85 (s, 3H), 1.52 (m, 1H), 1.29 (m, 1H), 1.04 (m, 3H), 0.90 (m, 1H), 0.63 (t, 3H, J = 7.3) |
| 425 | isobutyl | 4-(pyrazol-1-yl)benzyl | 4-chlorophenyl | 1- Method A | pale yellow solid | 460.99 | 1.48 min Method B | 460.13 | ¹H NMR (CDCl₃, 400 MHz) δ 7.91 (d, 1H, J = 1.5), 7.67-7.72 (m, 3H), 7.62 (d, 2H, J = 8.7), 7.42-7.48 (m, 4H), 6.46 (t, 1H, J = 2.1), 6.24 (br s, 1H), 5.21 (br s, 1H), 4.62 (d, 1H, J = 15.3), 4.42 (d, 1H, J = 15.6), 4.29 (t, 1H, J = 6.9), 1.80-1.88 (m, 1H), 1.28-1.40 (m, 1H), 1.12-1.21 (m, 1H), 0.75 (d, 3H, J = 6.6), 0.66 (d, 3H, J = 6.6) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 426 | isobutyl | 4-(1H-1,2,4-triazol-1-yl)phenyl-CH₂ | 4-chlorophenyl | 1-Method A | white solid | 461.97 | 1.39 min Method B | 462.18 | ¹H NMR (CDCl₃, 300 MHz) δ 8.54 (s, 1H), 8.10 (s, 1H), 7.71 (d, 2H, J = 8.4), 7.61 (d, 2H, J = 8.4), 7.46-7.52 (m, 4H), 6.23 (br s, 1H), 5.19 (br s, 1H), 4.66 (d, 1H, J = 15.9), 4.42 (d, 1H, J = 15.9), 4.30 (t, 1H, J = 6.9), 1.79-1.89 (m, 1H), 1.30-1.38 (m, 1H), 1.07-1.14 (m, 1H), 0.76 (d, 3H, J = 6.6), 0.66 (d, 3H, J = 6.6) |
| 427 | isobutyl | 3-fluoro-4-(2-morpholinoethoxy)benzyl | 4-chlorophenyl | 11 | pale yellow solid | 542.07 | 1.48 min Method E | 542.25 | ¹H NMR (CDCl₃) δ 7.71 (d, 2H, J = 8.00 Hz), 7.49 (d, 2H, J = 8.0 Hz), 7.16 (d, 1H, J = 12.0 Hz), 7.05 (d, 1H, J = 8.0 Hz), 6.86 (t, 1H, J = 8.0 Hz), 6.40 (s, br, 1H), 5.87 (s br, 1H), 4.42 (ABq, 2H, Δν = 16, J$_{ab}$ = 164 Hz), 4.49 (d, 2H, J = 4.0 Hz), 4.27 (t, 1H, J = 8.0 Hz), 4.04 (m, 4H), 3.69 (m, 2H), 3.51 (m, 2H), 3.10 (m, 2H), 1.83 (m, 1H), 1.29 (m, 1H), 1.07 (m, 1H), 0.75 (d, 3H, J = 8.0 Hz), 0.68 (d, 3H, J = 8.0 Hz) |
| 428 | isobutyl | 3-fluoro-4-(2-(4-methylpiperazin-1-yl)ethoxy)benzyl | 4-chlorophenyl | 11 | yellow solid | 555.12 | 1.41 min Method E | 555.28 | ¹H NMR (CDCl₃) δ 7.71 (d, 2H, J = 8.00 Hz), 7.50 (d, 2H, J = 8.0 Hz), 7.16 (d, 1H, J = 12.0 Hz), 7.05 (d, 1H, J = 8.0 Hz), 6.87 (t, 1H, J = 8.0 Hz), 6.38 (s, br, 1H), 5.91 (s br, 1H), 4.41 (AB₂, 2H, Δν = 16, J$_{ab}$ = 176 Hz), 4.45 (m, 2H), 4.27 (t, 1H, J = 8.0 Hz), 3.81 (m, 4H), 3.67 (m, 4H), 3.48 (m, 1H), 2.89 (s, 3H), 1.83 (m, 1H), 1.29 (m, 1H), 1.05 (m, 1H), 0.75 (d, 3H, J = 8.0 Hz), 0.68 (d, 3H, J = 8.0 Hz) |

TABLE 4-continued

| Ex. No. | R[1] | R[2] | R[3] | Reaction Scheme | Appearance | Calc. MW | Ret. Time/Method | M+H[+] | NMR Data |
|---|---|---|---|---|---|---|---|---|---|
| 429 | isobutyl | piperidine-thiomorpholine acetyl | 4-chlorophenyl | 7 | white solid | 545.17 | 1.84 min Method C | 545.36 | $^1$H NMR (CDCl₃, 500 MHz) δ 7.73 (d, 2H, J = 9.0), 7.51 (d, 2H, J = 8.0), 6.65 (2 s, 1H), 5.40 (s, 1H), 4.54 (t, 1H, J = 13), 3.85-4.20 (m, 2H), 2.40-3.50 (m, 12H), 1.75-2.00 (m, 3H), 0.92-1.20 (m, 1H), 0.73 (d, 3H, J = 5.8, 6.1), 0.67 (d, 3H, J = 6.1, 6.4) |
| 430 | isobutyl | piperidine-piperidine propanoyl | 4-chlorophenyl | 7 | white solid | 541.16 | 1.43 min Method A | 541.24 | $^1$H NMR (CDCl₃, 500 MHz) δ 7.71 (d, 2H, J = 6.4), 7.50 (d, 2H, J = 8.2), 6.65 (d, 1H, J = 41), 5.44 (s, 1H), 4.55 (t, 1H, J = 13), 4.15 (br s, 1H), 3.95 (br s, 1H), 3.15-3.35 (m, 1H), 2.90-3.00 (m, 2H), 2.60-2.70 (m, 2H), 2.50-2.57 (m, 2H), 2.35-2.50 (m, 6H), 1.85-2.00 (m, 3H), 1.35-1.75 (m, 3H), 1.00-1.30 (m, 5H), 0.90-1.00 (m, 1H), 0.72 (dd, 3H, J = 7.0, 7.3), 0.66 (dd, 3H, J = 5.1, 6.4) |
| 431 | isobutyl | piperidine-morpholine acetyl | 4-chlorophenyl | 7 | white solid | 529.10 | 1.38 min Method A | 529.27 | $^1$H NMR (CDCl₃, 500 MHz) δ 7.72 (d, 2H, 8.5), 7.51 (d, 2H, J = 8.9), 6.65 (d, 1H, J = 32), 5.43 (s, 1H), 4.55 (t, 1H, J = 13), 4.14 (dd, 1H, J = 4.8, 9.5), 3.88 (br s, 4H), 3.21-3.84 (m, 2H), 2.90-3.05 (m, 3H), 2.47-2.67 (m, 1H), 1.80-2.05 (m, 3H), 1.40-1.75 (m, 6H), 1.00-1.35 (m, 4H), 0.73 (dd, 3H, J = 3.4, 6.4), 0.67 (dd, 3H, J = 2.7, 6.7) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 432 | isobutyl | piperidine-CH₂-C(=O)-CH₂-OMe | 4-chlorophenyl | 7 | white solid | 474.02 | 1.55 min Method A | 474.28 | ¹H NMR (CDCl₃, 500 MHz) δ 7.72 (d, 2H, J = 7.6), 7.50 (d, 2H, J = 8.6), 6.65 (d, 1H, J = 40), 5.46 (s, 1H), 4.56 (t, 1H, J = 13) 4.00-4.20 (m, 2H), 3.80-3.90 (m, 1H), 3.40 (s, 3H), 3.20-3.35 (m, 1H), 2.85-3.05 (m, 2H), 2.40-2.65 (m, 1H), 1.50-2.00 (m, 5H), 1.00-1.45 (m, 2H), 0.83-0.90 (m, 1H), 0.72 (dd, 3H, J = 6.7, 8.2), 0.67 (dd, 3H, J = 5.8, 6.4) |
| 433 | isobutyl | 4-(2-fluoropropan-2-yl)phenyl | 4-chlorophenyl | 1-Method A | white solid | 455.00 | 1.83 min Method B | 454.15 | ¹H NMR (CDCl₃, 300 Hz) δ 7.61 (dd, 2H, J = 1.8, 8.7), 7.40 (ddd, 2H, J = 2.1, 2.4, 8.7), 7.26 (d, 4H, J = 7.2), 6.25 (br s, 1H), 5.19 (br s, 1H), 4.51 (d, 1H, J = 15.6), 4.43 (d, 1H, J = 15.6), 4.34 (t, 1H, J = 7.2), 1.75-1.85 (m, 1H), 1.69 (s, 3H), 1.62 (s, 3H), 1.22-1.35 (m, 2H), 0.78 (d, 3H, J = 6.3), 0.66 (d, 3H, J = 6.3) |
| 434 | isobutyl | piperidine-CH₂-C(=O)-N-methylpiperazine | 4-chlorophenyl | 7 | white solid | 542.15 | 1.73 min Method C | 542.46 | ¹H NMR (CDCl₃, 500 MHz) δ 7.72 (d, 2H, J = 8.5), 7.51 (d, 2H, J = 8.5), 6.65 (d, 1H, J = 39), 5.42 (s, 1H), 4.55 (t, 1H, J = 14), 4.00-4.17 (m, 2H), 3.05-3.33 (m, 3H), 2.85-3.05 (m, 2H), 2.40-2.70 (m, 8H), 2.32 (s, 3H), 1.55-2.10 (m, 6H), 1.00-1.30 (m, 6H), 0.72 (t, 3H, J = 6.7, 6.7), 0.67 (t, 3H, J = 6.1, 6.4) |
| 435 | isobutyl | piperidine-C(=O)-isoxazole | 4-chlorophenyl | 7 | white solid | 497.02 | 1.70 min Method A | 479.19 | ¹H NMR (CDCl₃, 500 MHz) δ 8.31 (s, 1H), 7.76 (d, 2H, J = 8.9), 7.56 (d, 2H, J = 8.5), 6.74 (s, 1H), 4.81 (t, 1H, J = 7.6), 4.71 (br s, 1H), 4.20 (br s, 1H), 3.13 (t, 2H, J = 8.6), 2.70-2.95 (m, 2H), 2.05-2.20 (m, 1H), 1.85-2.00 (m, 2H), 1.55-1.85 (m, 4H), 1.10-1.35 (m, 3H), 1.00 (d, 3H, J = 6.4), 0.97 (d, 3H, J = 6.7), 0.87 (t, 1H, J = 7.0) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 436 | isobutyl | 4-(5-methyl-1,3,4-oxadiazol-2-yl)benzyl | 4-chlorophenyl | 13 | white solid | 476.99 | 1.76 min Method B | 477.22 | ¹H NMR (CDCl₃, 300 MHz) δ 7.94 (dd, 2H, J = 1.8, 8.4), 7.69 (dd, 2H, J = 1.8, 8.7), 7.45-7.50 (m, 4H), 6.23 (br s, 1H), 5.19 (br s, 1H), 4.65 (d, 1H, J = 15.9), 4.46 (d, 1H, J = 15.9), 4.31 (dd, 1H, J = 6.6, 7.8), 2.61 (s, 3H), 1.75-1.85 (m, 1H), 1.28-1.35 (m, 1H), 1.08-1.15 (m, 1H), 0.76 (d, 3H, J = 6.6), 0.64 (d, 3H, J = 6.6) |
| 437 | isobutyl | 4-(3-methyl-1,2,4-oxadiazol-5-yl)benzyl | 4-chlorophenyl | 14 | pale yellow solid | 476.99 | 1.92 min Method B | 477.18 | ¹H NMR (CDCl₃, 300 MHz) δ 8.04 (d, 2H, J = 8.4), 7.70 (dd, 2H, J = 1.8, 8.4), 7.45-7.52 (m, 4H), 6.23 (br s, 1H), 5.19 (br s, 1H), 4.67 (d, 1H, J = 16.2), 4.47 (d, 1H, J = 15.9), 4.31 (t, 1H, J = 7.2), 2.47 (s, 3H), 1.75-1.85 (m, 1H), 1.28-1.35 (m, 1H), 1.08-1.15 (m, 1H), 0.76 (d, 3H, J = 6.6), 0.64 (d, 3H, J = 6.6) |
| 438 | isobutyl | 4-(N-ethyl-N-methylcarbamoyl)benzyl | 4-chlorophenyl | 6 | white solid | 480.03 | 1.81 min Method B | 480.26 | ¹H NMR (CDCl₃, 300 MHz) δ 7.67 (d, 2H, J = 8.7), 7.45 (d, 2H, J = 8.7), 7.38 (d, 2H, J = 8.1), 7.32 (d, 2H, J = 7.5), 6.23 (br s, 1H), 5.19 (br s, 1H), 4.59 (d, 1H, J = 16.2), 4.45 (d, 1H, J = 15.9), 4.30 (t, 1H, J = 6.9), 3.47-3.56 (br m, 1H), 3.15-3.35 (br m, 1H), 2.81-3.09 (br m, 3H), 1.75-1.85 (m, 1H), 1.05-1.40 (m, 5H), 0.76 (d, 3H, J = 6.6), 0.65 (d, 3H, J = 6.6) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 439 | isobutyl | 4-(pyridin-2-ylmethylcarbamoyl)benzyl | 4-chlorophenyl | 6 | white solid | 529.06 | 1.60 min Method B | 529.25 | ¹H NMR (CDCl₃, 300 MHz) δ 8.57 (d, 1H, J = 4.8), 7.80 (d, 2H, J = 8.4), 7.70-7.73 (m, 2H), 7.67 (d, 2H, J = 8.4), 7.45 (d, 2H, J = 8.4), 7.42 (d, 2H, J = 7.8), 7.36 (d, 1H, J = 7.8), 7.28 (br s, 1H), 6.23 (br s, 1H), 5.22 (br s, 1H), 4.77 (d, 2H, J = 4.8), 4.63 (d, 1H, J = 15.9), 4.44 (d, 1H, J = 15.9), 4.29 (t, 1H, J = 7.2), 1.73-1.85 (m, 1H), 1.25-1.38 (m, 1H), 1.06-1.14 (m, 1H), 0.75 (d, 3H, J = 6.3), 0.65 (d, 3H, J = 6.6) |
| 440 | isobutyl | 2-fluoro-4-ethyl-benzyl morpholine | 4-chlorophenyl | 8 | amber glass | 512.04 | 1.36 min Method A | 512.24 | ¹H NMR 400 Hz (CDCl₃) δ 7.70 (d, 2H, J = 8.0 Hz), 7.74 (d, 2H, J = 8.0 Hz), 7.31 (d, 2H, J = 6 Hz), 7.08 (d, 2H, J = 8.0 Hz), 6.25 (s, br, 1H), 5.41 (s, br, 1H), 4.56 (d, 1H, J$_{ab}$ = 12 Hz), 4.43 (d, 1H, J$_{ab}$ = 12 Hz), 4.35 (t, 1H, J = 6.0 Hz), 3.72 (t, 4H, J = 4.0 Hz), 3.56 (s, 2H), 2.48 (t, 4H, J = 41.0 Hz), 1.79 (m, 1H), 1.36 (m, 1H), 1.18 (m, 1H), 0.79 (d, 3H, J = 6.0 Hz), 0.69 (d, 3H, J = 6.0 Hz) |
| 441 | isobutyl | 2-fluoro-4-ethyl-benzyl N-methylpiperazine | 4-chlorophenyl | 8 | amber glass | 525.08 | 1.35 min Method A | 525.23 | ¹H NMR 400 Hz (CDCl₃) δ 7.69 (d, 2H, J = 8.0 Hz), 7.47 (d, 2H, J = 8.0 Hz), 7.28 (t, 1H, J = 6.0 Hz), 7.07 (dd, 2H, J = 8.0 Hz), 6.29 (s, br, 1H), 5.55 (s, br, 1H), 4.46 (d, 1H, J$_{ab}$ = 14.0 Hz), 4.41 (d, 1H, J$_{ab}$ = 14.0 Hz), 4.34 (t, 1H, J = 6.0 Hz), 3.58 (s, 2H), 2.33 (s, 3H), 1.78 (m, 1H), 1.18 (m, 1H), 0.79 (d, 3H, J = 6.0 Hz), 0.68 (d, 3H, J = 6.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 442 | isobutyl | methyl 2-fluoro-4-ethylbenzoate | 4-chlorophenyl | 1-Method A | amber glass | 470.94 | 1.74 min Method A | 471.12 | ¹H NMR 400 Hz (CDCl₃) δ 7.78 (t, 1H, J = 6.0 Hz), 7.72 (d, 2H, J = 8.0 Hz), 7.51 (d, 2H, J = 8.0 Hz), 7.19 (m, 2H), 6.21 (s, br, 1H), 5.37 (s, br, 1H), 4.64 (d, 1H, $J_{ab}$ = 14.0 Hz), 4.47 (d, 1H, $J_{ab}$ = 14.0 Hz), 4.34 (t, 1H, J = 6.0 Hz), 3.95 (s, 3H), 1.80 (m, 1H), 1.37 (m, 1H), 1.01 (m, 1H), 0.80 (d, 3H, J = 6.0 Hz), 0.69 (d, 3H, J = 6.0 Hz) |
| 443 | 2-hydroxy-2-methylpropyl | 4-cyanobenzyl | 4-chlorophenyl | 21 | white solid | 435.10 | 1.40 min Method D | (M + Na)⁺ 458.2 | ¹H NMR (400 MHz, DMSO) δ 7.84 (d, 2H, J = 8.6), 7.76 (d, 2H, J = 8.3), 7.62 (d, 2H, J = 8.8), 7.51 (d, 2H, J = 8.3), 7.40 (s, 1H), 7.11 (s, 1H), 4.63 (ABq, 2H, Δν = 5.9, $J_{ab}$ = 17.6, 4.56 (dd, 1H, J = 8.3, 2.5), 4.54 (s, 1H), 1.95 (dd, 1H, J = 13.7, 8.6), 1.26 (dd, 1H, J = 13.6, 2.4), 1.04 (s, 3H), 0.99 (s, 3H) |
| 444 | isobutyl | 2-(2,2-difluoroethyl)piperidin-4-yl)methyl | 4-chlorophenyl | 7 | clear oil | 465.17 | 1.38 min Method A | 466.20 | ¹H NMR (CDCl₃, 500 MHz) δ 7.73 (d, 2H, J = 8.8), 7.50 (d, 2H, J = 8.9), 6.67 (s, 1H), 5.37 (s, 1H), 4.14 (dd, 1H, J = 5.5, 9.5), 3.25 (dd, 1H, J = 10, 14), 2.97 (dd, 1H, J = 4.5, 14), 2.87-2.95 (m, 2H), 2.65-2.75 (m, 2H), 2.07-2.23 (m, 2H), 1.83-1.90 (m, 1H), 1.50-1.82 (m, 4H), 1.15-1.40 (m, 3H), 0.77-0.85 (m, 1H), 0.72 (d, 3H, J = 6.7), 0.66 (d, 3H, J = 6.4) |
| 445 | isobutyl | 2-fluoro-4-ethylbenzoic acid | 4-chlorophenyl | 6 | amber glass | 456.92 | 1.62 min Method A | 457.32 | ¹H NMR 400 Hz (CDCl₃) δ 7.77 (d, 2H, J = 6.0 Hz), 7.68 (t, 1H, J = 6.0 Hz), 7.64 (d, 2H, J = 8.0 Hz), 7.39 (m, 3H), 6.21 (s, br, 1H), 5.35 (s, br, 1H), 4.67 (d, 1H, $J_{ab}$ = 14.0 Hz), 4.38 (d, 1H, $J_{ab}$ = 14.0 Hz), 3.44 (m, 1H), 1.88 (m, 1H), 1.59 (m, 2H), 0.79 (d, 3H, J = 6.0 Hz), 0.69 (d, 3H, J = 6.0 Hz) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 446 | (methallyl) | 4-CN-benzyl-CH₂ | 4-Cl-phenyl | 18 | off-white solid | 417.09 | 1.53 min Method F | (M + Na)⁺ 418.2 | ¹H NMR (400 MHz, DMSO) δ 7.82 (d, 2H, J = 8.8), 7.74 (d, 2H, J = 8.5), 7.63 (d, 2H, J = 8.8), 7.62 (s, 1H), 7.53 (d, 2H, J = 8.5), 7.09 (s, 1H), 4.80 (ABq, 2H, Δν = 17.9, J$_{ab}$ = 17.8), 4.70 (s, 1H), 4.62 (t, 1H, J = 7.6), 4.60 (s, 1H), 2.34 (dd, 1H, J = 14.4, 7.1), 2.02 (dd, 1H, J = 14.6, 7.3), 1.57 (s, 3H) |
| 447 | (methallyl) | 4-pyrazolyl-phenyl-CH₂ | 4-Cl-phenyl | 18 | off-white solid | 458.12 | 1.59 min Method G | (M + Na)⁺ 459.2 | ¹H NMR (400 MHz, DMSO) δ 8.45 (d, 1H, J = 2.2), 7.82 (d, 2H, J = 8.6), 7.72 (m, 3H), 7.60 (d, 2H, J = 8.8), 7.57 (s, 1H), 7.44 (d, 2H, J = 8.5), 7.09 (s, 1H), 6.54 (t, 1H, J = 2.0), 4.74 (ABq, 2H, Δν = 25.5, J$_{ab}$ = 16.8), 4.71 (s, 1H), 4.61 (m, 2H), 2.37 (dd, 1H, J = 14.2, 7.1) 2.08 (dd, 1H, J = 14.7, 7.6), 1.57 (s, 3H) |
| 448 | F-CH₂CH₂ | 4-CO₂Me-phenyl-CH₂ | 4-Cl-phenyl | 18 | off-white solid | 442.90 | 1.74 min Method A | 443.05 | ¹H NMR (CDCl₃, 400 MHz) δ 7.96 (d, 2H, J = 8.2), 7.72 (d, 2H, J = 8.0), 7.48 (d, 2H, J = 8.0), 7.39 (d, 2H, J = 8.0), 6.33 (br s, 1H), 5.20 (br s, 1H), 4.55-4.62 (m, 2H), 4.39 (d, 1H, J = 15.4), 4.28-4.32 (m, 1H), 4.17-4.21 (m, 1H), 3.90 (s, 3H), 2.17-2.35 (m, 1H), 1.56-1.65 (m, 1H) |
| 449 | F-CH₂CH₂ | 4-(2-hydroxypropan-2-yl)-phenyl-CH₂ | 4-Cl-phenyl | 18, 12 | yellow foam | 442.94 | 1.65 min Method A | 442.11 | ¹H NMR (CDCl₃, 400 MHz) δ 7.67 (ddd, 2H, J = 2.0, 2.6, 8.8), 7.42 (ddd, 2H, J = 2.0, 2.3, 8.8), 7.39 (d, 2H, J = 8.2), 7.24 (d, 2H, J = 8.2), 6.34 (br s, 1H), 5.35 (br s, 1H), 4.56 (dd, 1H, J = 5.8, 8.5), 4.48 (d, 1H, J = 15.5), 4.35 (d, 1H, J = 15.5), 4.30-4.33 (m, 1H), 4.18-4.22 (m, 1H), 2.23-2.39 (m, 1H), 1.56-1.670 (m, 2H), 1.57 (s, 6H) |

TABLE 4-continued

| Ex. No. | R¹ | R² | R³ | Reaction Scheme | Appearance | Calc. MW | Ret. Time/Method | M+H⁺ | NMR Data |
|---|---|---|---|---|---|---|---|---|---|
| 450 | (2-fluoroethyl) | 4-(5-methyl-1,3,4-oxadiazol-2-yl)benzyl | 4-chlorophenyl | 18, 13 | white solid | 466.92 | 1.61 min Method A | 467.18 | ¹H NMR (CDCl₃, 400 MHz) δ 7.96 (ddd, 2H, J = 1.7, 2.0, 8.4), 7.73 (ddd, 2H, J = 1.9, 2.5, 8.7), 7.49 (ddd, 2H, J = 2.0, 2.3, 8.7), 7.46 (d, 2H, J = 8.6), 6.34 (br s, 1H), 5.21 (br s, 1H), 4.64 (d, 1H, J = 15.4), 4.57-4.60 (m, 1H), 4.39 (d, 1H, J = 16.1), 4.30-4.32 (m, 1H), 4.18-4.21 (m, 1H), 2.61 (s, 3H), 2.18-2.36 (m, 1H), 1.55-1.66 (m, 1H) |
| 451 | (3-fluoropropyl) | 4-(2-morpholinoacetyl)piperidin-1-ylmethyl | 4-chlorophenyl | 18, 7 | clear oil | 533.07 | 1.71 min Method A | 533.22 | ¹H NMR (CDCl₃, 400 MHz) δ 7.73 (d, 2H, J = 8.6), 7.51 (d, 2H, J = 8.8), 6.67 (s, 1H), 5.51 (s, 1H), 4.14-4.52 (m, 4H), 3.76-3.95 (m, 2H), 3.50-3.72 (m, 1H), 3.19-3.27 (m, 1H), 2.86-3.07 (m, 1H), 2.56-2.80 (m, 2H), 1.70-1.99 (m, 7H), 1.36-1.63 (m, 10H) |
| 452 | (3-fluoropropyl) | 4-(cyclohexylcarbamoyl)piperidin-1-ylmethyl | 4-chlorophenyl | 18, 7 | clear oil | 517.07 | 2.53 min Method A | 517.32 | ¹H NMR (CDCl₃, 400 MHz) δ 7.74 (d, 2H, J = 8.6), 7.50 (d, 2H, J = 8.5), 6.70 (s, 1H), 5.60 (s, 1H), 4.50 (dd, 1H, J = 4.9, 9.8), 4.22-4.31 (m, 2H), 3.81-4.00 (m, 5H), 3.53-3.66 (m, 2H), 3.40-3.50 (m, 1H), 3.13-3.25 (m, 3H), 2.89 (dd, 1H, J = 4.6, 14), 2.62-2.77 (m, 3H), 1.50-1.95 (m, 6H), 1.01-1.45 (m, 5H) |
| 453 | (4-fluorobutyl) | 4-(cyclohexylcarbamoyl)piperidin-1-ylmethyl | 4-chlorophenyl | 18, 7 | clear oil | 531.09 | 2.27 min Method A | 531.36 | ¹H NMR (CDCl₃, 400 MHz) δ 7.73 (d, 2H, J = 8.6), 7.51 (d, 2H, J = 8.6), 6.65 (d, 1H, J = 28), 5.47 (s, 1H), 4.50-4.63 (m, 1H), 4.20-4.45 (m, 1H), 4.05-4.15 (m, 2H), 3.55-3.65 (m, 2H), 3.05-3.35 (m, 6H), 2.85-3.00 (m, 3H), 2.55-2.35 (m, 2H), 1.50-2.00 (m, 6H), 1.00-1.45 (m, 7H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 454 | ![R1: CH2CH2CF3] | ![R2: 4-(morpholinomethyl)-phenethyl] | ![R3: 4-chlorophenyl] | 8 | amber glass | 533.99 | 1.40 min Method A | 534.27 | ¹H NMR 400 Hz (CDCl₃) δ 7.78 (d, 2H, J = 8.0 Hz), 7.39 (m, 6H), 6.34 (s, br, 1H), 5.80 (s, br, 1H), 4.72 (d, 1H, $J_{ab}$ = 14.0 Hz), 4.16 (m, 1H), 4.34 (d, 1H, Jab = 14.0 Hz), 3.60 (m, 4H), 3.84 (s, 2H), 2.62 (m, 2H), 2.25 (m, 4H) |
| 455 | ![R1: CH2CHF2] | ![R2: 4-(morpholinomethyl)-phenethyl] | ![R3: 4-chlorophenyl] | 18, 8 | amber glass | 501.98 | 1.27 min Method A | 502.24 | ¹H NMR 400 Hz (CDCl₃) δ 7.79 (d, 2H, J = 8.0 Hz), 7.39 (m, 6H), 6.33 (s, br, 1H), 5.80 (s, br, 1H), 4.68 (d, 1H, $J_{ab}$ = 14.0 Hz), 4.22 (d, 1H, $J_{ab}$ = 14.0 Hz), 3.55 (s, 2H), 2.62 (m, 2H), 2.43 (m, 8H), 2.30 (s, 3H) |
| 456 | ![R1: CH2CHF2] | ![R2: 4-(4-methylpiperazin-1-ylmethyl)benzyl] | ![R3: 4-chlorophenyl] | 18, 8 | amber glass | 515.02 | 1.22 min Method A | 515.31 | ¹H NMR 400 Hz (CDCl₃) δ 7.79 (d, 2H, J = 8.0 Hz), 7.52 (d, 2H), 7.39 (m, 4H), 6.34 (s, br, 1H), 5.78 (s, br, 1H), 5.72 (t, 1H, J = 54.0 Hz), 4.68 (d, 1H, $J_{ab}$ = 14.0 Hz), 4.34 (d, 1H, $J_{ab}$ = 14.0 Hz), 3.88 (m, 1H), 3.56 (m, 4H), 2.49 (m, 2H), 2.26 (m, 4H) |
| 457 | ![R1: CH2CH2CF3] | ![R2: 4-(4-methylpiperazin-1-ylmethyl)benzyl] | ![R3: 4-chlorophenyl] | 8 | amber glass | 547.03 | 1.26 min Method A | 547.20 | ¹H NMR 400 Hz (CDCl₃) δ 7.78 (d, 2H, J = 8.0 Hz), 7.50 (d, 2H, J = 8.0 Hz), 7.41 (m, 4H), 6.35 (s, br, 1H), 5.80 (s, br, 1H), 5.72 (t, 1H, J = 54.0 Hz), 4.68 (d, 1H, $J_{ab}$ = 14.0 Hz), 4.35 (d, 1H, $J_{ab}$ = 14.0 Hz), 3.87 (m, 1H), 3.55 (s, 2H), 2.44 (m, 10H), 2.30 (s, 3H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 458 | CH₂CHF₂ group | 5-(dimethylamino)pyridin-2-yl-CH₂CH₂ | 4-chlorophenyl | 18, 1- Method B | white foam | 446.91 | 1.01 Method B | 447.13 | ¹H NMR (CDCl₃) TFA salt δ 8.14 (s, 1H), 7.98 (d, 1H, J = 9.6 Hz), 7.76 (d, 2H, J = 6.8 Hz), 7.55 (d, 2H, J = 6.8 Hz), 6.81 (d, 2H, J = 9.6 Hz), 6.45 (s, 1H), 6.10 (s, 1H), 5.70(t, 1H, J = 110.0 Hz), 4.60 (d, 1H, J = 16.0 Hz), 4.51 (m, 1H), 4.06 (d, 1H, J = 16 Hz), 3.30 (s, 6H), 2.55 (m, 1H), 1.60 (m, 1H) |
| 459 | neopentyl-CHF group | 5-(dimethylamino)pyridin-2-yl-CH₂CH₂ | 4-chlorophenyl | 18, 1- Method B | white foam | 456.97 | 1.14 Method B | 457.23 | ¹H NMR (CDCl₃) TFA salt δ 8.11 (s, 1H), 7.95 (d, 1H, J = 9.6 Hz), 7.77 (d, 2H, J = 6.8 Hz), 7.51 (d, 2H, J = 6.8 Hz), 6.76 (d, 2H, J = 9.6 Hz), 6.34 (s, 1H), 6.02 (s, 1H), 4.58 (d br., 1H, J = 8.4 Hz), 4.46 (d, 1H, J = 16.0 Hz), 4.06 (d, 1H, J = 16 Hz), 3.29 (s, 6H), 2.50 (m, 1H), 1.39 (m, 1H), 1.25 (d, 3H, J = 22.0 Hz), 1.17 (d, 3H, J = 22.0 Hz) |
| 460 | CH₂CH₂CF₃ | 5-(dimethylamino)pyridin-2-yl-CH₂CH₂ | 4-chlorophenyl | 1- Method B | light yellow gummy solid | 478.92 | 1.89 min 3 × 50 mm ODS-A C-18 column, 4 mL/min, 0-100% MeOH/ H₂O 0.1% TFA 4 min gradient | 479.21 | ¹H NMR (CDCl₃) δ 8.09 (s, 1H), 8.01 (d, 1H, J = 9.2 Hz), 7.75 (d, 2H, J = 8.4 Hz), 7.53 (d, 2H, J = 8.4 Hz), 6.82 (d, 1H, J = 9.2 Hz), 6.62 (s, br, 1H), 6.12 (s, br, 1H), 4.18-4.58 (m, 3H), 3.30 (s, 6H), 2.15 (m, 1H), 2.05 (m, 1H), 1.85 (m, 1H), 1.40 (m, 1H) |
| 461 | CH₂CHF₂ | 6-chloropyridin-3-yl-CH₂CH₂ | 4-chlorophenyl | 18 | clear oil | 438.28 | 1.41 min Method B | 438.01 | ¹H NMR (CDCl₃) δ 8.33 (s, 1H), 7.73 (d, 1H, J = 8.4 Hz), 7.71 (d, 2H, J = 8.8 Hz), 7.51 (d, 2H, J = 8.8 Hz), 7.27 (d, 1H, J = 8.4 Hz), 6.56 (s, br, 1H), 6.11 (s, br, 1H), 5.69 (m, 1H), 4.21-4.62 (m, 3H), 2.52 (m, 1H), 1.63 (m, 1H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 462 | (CH₂CH₂CF₃) | (6-chloropyridin-3-yl)methyl | 4-chlorophenyl | 1 | white solid | 470.30 | 1.53 min Method B | 470.02 | ¹H NMR (CDCl₃) δ 8.38 (s, 1H), 7.79 (d, 1H, J = 8.0 Hz), 7.68 (d, 2H, J = 8.4 Hz), 7.50 (d, 2H, J = 8.4 Hz), 7.31 (d, 1H, J = 8.0 Hz), 6.57 (s, br, 1H), 6.25 (s, br, 1H), 4.29-4.64 (m, 3H), 2.12 (m, 1H), 1.98 (m, 1H), 1.81 (m, 1H), 1.43 (m, 1H) |
| 463 | (3-fluoropyrrolidinyl) | (6-chloropyridin-3-yl)methyl | 4-chlorophenyl | 18 | clear oil | 434.32 | 1.43 min Method B | 434.13 | ¹H NMR (CDCl₃) δ 8.37 (s, 1H), 7.70 (d, 1H, J = 8.8 Hz), 7.68 (d, 1H, J = 8.8 Hz), 7.67 (d, 2H, J = 6.8 Hz), 7.48 (d, 2H, J = 6.8 Hz), 6.25 (s, br, 1H), 5.31 (s.br, 1H), 4.34-4.62 (m, 5H), 1.35-2.05 (m, 4H) |
| 464 | (CH₂CH₂F) | 1-(2,2-difluoroethyl)piperidin-4-ylmethyl | 4-chlorophenyl | 18, 7 | clear oil | 469.14 | 1.14 min Method A | 470.17 | ¹H NMR (CDCl₃, 400 MHz) δ 7.73 (d, 2H, J = 8.8), 6.65 (s, 1H), 5.39 (s, 1H), 4.05-4.35 (m, 2H), 3.25 (dd, 1H, J = 10, 14), 2.85-3.04 (m, 3H), 2.65-2.85 (m, 2H), 2.09-2.29 (m, 2H), 1.93-2.10 (m, 1H), 1.83-1.91 (m, 10H) |
| 465 | isobutyl | 4-(5-methyl-1,2,4-oxadiazol-3-yl)phenyl | 4-chlorophenyl | 15 | white solid | 476.99 | 1.91 min Method A | 477.13 | ¹H NMR (CDCl₃, 500 MHz) δ 7.98 (d, 2H, J = 8.2), 7.68 (d, 2H, J = 8.9), 7.45 (d, 4H, J = 8.5), 6.21 (s, 1H), 5.19 (s, 1H), 4.62 (d, 1H, J = 15), 4.48 (d, 1H, J = 16), 4.31 (t, 1H, J = 7.0), 2.65 (s, 3H), 1.75-1.85 (m, 1H), 1.20-1.35 (m, 4H), 1.10-1.17 (m, 1H), 0.85-0.90 (m, 1H), 0.75 (d, 3H, J = 6.7), 0.64 (d, 3H, J = 6.4) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 466 | CH₂CH₂CF₃ | 5-(morpholin-4-yl)pyridin-2-yl-ethyl | 4-chlorophenyl | 1-Method B | clear gummy solid | 520.96 | 1.17 min Method B | 521.19 | ¹H NMR (CDCl₃) δ 8.16 (s, 1H), 8.06 (d, 1H, J = 9.2 Hz), 7.75 (d, 2H, J = 8.4 Hz), 7.50 (d, 2H, J = 8.4 Hz), 7.31 (d, 1H, J = 9.2 Hz), 6.67 (s, br, 1H), 6.20 (s, br, 1H), 4.19-4.60 (m, 3H), 3.87 (m, 4H), 3.69 (m, 4H), 2.14 (m, 1H), 1.98 (m, 1H), 1.83 (m, 1H), 1.38 (m, 1H) |
| 467 | CH₂CH₂F | 5-(morpholin-4-yl)pyridin-2-yl-ethyl | 4-chlorophenyl | 18, 1-Method B | clear gummy solid | 470.95 | 0.983 min Method B | 471.19 | ¹H NMR (CDCl₃) δ 8.15 (s, 1H), 8.10 (d, 1H, J = 9.2 Hz), 7.77 (d, 2H, J = 8.4 Hz), 7.53 (d, 2H, J = 8.4 Hz), 6.93 (d, 1H, J = 9.2 Hz), 6.65 (s, br, 1H), 6.22 (s, br, 1H), 4.09-4.67 (m, 5H), 3.87 (m,4H), 3.68 (m, 4H), 2.25 (m, 1H), 1.63 (m, 1H) |
| 468 | CH₂C(CH₃)₂F | 5-(morpholin-4-yl)pyridin-2-yl-ethyl | 4-chlorophenyl | 1-Method B | clear gummy solid | 499.01 | 1.153 min Method B | 499.23 | ¹H NMR (CDCl₃) δ 8.12 (s, 1H), 8.07 (d, 1H, J = 9.2 Hz), 7.78 (d, 2H, J = 8.4 Hz), 7.52 (d, 2H, J = 8.4 Hz), 6.91 (d, 1H, J = 9.2 Hz), 6.63 (s, br, 1H), 6.19 (s, br, 1H), 4.07-4.62 (m, 3H), 3.86 (m, 4H), 3.68 (m, 4H), 2.46 (m, 1H), 1.31 (m, 1H), 1.25 (d, 3H, J = 21.6), 1.17 (d, 3H, J = 21.6) |
| 469 | CH₂CH(CH₃)₂ | 3-(4-ethylphenyl)-5-(chloromethyl)-1,2,4-oxadiazole | 4-chlorophenyl | 15 | white solid | 511.43 | 1.90 min Method C | 511.13 | ¹H NMR (CDCl₃, 400 MHz) δ 8.01 (d, 2H, J = 8.3), 7.69 (d, 2H, J = 8.8), 7.43-7.51 (m, 4H), 6.20 (s, 1H), 5.15 (s, 1H), 4.74 (s, 2H), 4.63 (d, 1H, J = 15), 4.47 (d, 1H, J = 16), 4.31 (t, 1H, J = 6.8), 1.74-1.87 (m, 1H), 1.04-1.88 (m, 4H), 0.82-0.94 (m, 1H), 0.76 (d, 3H, J = 6.6), 0.65 (d, 3H, J = 6.6) |

TABLE 4-continued

| Ex. No. | R[1] | R[2] | R[3] | Reaction Scheme | Appearance | Calc. MW | Ret. Time/ Method | M + H[+] | NMR Data |
|---|---|---|---|---|---|---|---|---|---|
| 470 | (2-fluoroethyl) | 4-(3-(trimethylsilyl)propoxycarbonyl)benzyl | 4-chlorophenyl | 1 | white solid | 529.11 | 2.17 min Method D | 529.11 | $^1$H NMR (CDCl$_3$, 400 MHz) δ 7.95 (d, 2H, J = 8.4), 7.71 (dd, 2H, J = 1.6, 8.4), 7.48 (dd, 2H, J = 2.4, 8.8), 7.38 (dd, 2H, J = 2.4, 8.8), 6.31 (br s, 1H), 5.22 (br s, 1H), 4.60 (d, 1H, J = 15.6), 4.55-4.58 (m, 1H), 4.38-4.42 (m, 3H), 4.29-4.32 (m, 1H), 4.17-4.21 (m, 1H), 2.18-2.32 (m, 2H), 1.12 (dd, 2H, J = 6.8, 8.4), 0.08 (s, 9H) |
| 471 | isobutyl | 4-(5-(chloromethyl)-1,2,4-oxadiazol-3-yl)benzyl | 4-chlorophenyl | 15, 23 | white solid | 510.14 | 1.86 min Method A | 511.13 | $^1$H NMR (CDCl$_3$, 400 MHz) δ 8.01 (d, 2H, J = 8.4), 7.69 (d, 2H, J = 8.8), 7.47 (d, 2H, J = 8.0), 7.46 (d, 2H, J = 8.8), 6.20 (br s, 1H), 5.20 (br s, 1H), 4.74 (s, 2H), 4.64 (d, 1H, J = 15), 4.49 (d, 1H, J = 15), 4.31 (t, 1H, J = 7.0), 1.73-1.87 (m, 1H), 1.20-1.37 (m, 1H), 1.07-1.17 (m, 1H), 0.76 (d, 3H, J = 6.6), 0.65 (d, 3H, 6.6) |
| 472 | isobutyl | 4-(5-((dimethylamino)methyl)-1,2,4-oxadiazol-3-yl)benzyl | 4-chlorophenyl | 15, 8 | white solid | 519.17 | 1.42 min Method A | 520.18 | $^1$H NMR (CDCl$_3$, 400 MHz) δ 8.02 (d, 2H, J = 7.6), 7.71 (d, 2H, J = 8.4), 7.52 (d, 2H, J = 8.0), 7.48 (d, 2H, J = 8.4), 6.23 (br s, 1H), 5.17 (br s, 1H), 4.70 (d, 1H, J = 16), 4.44 (d, 1H, J = 16), 4.31 (t, 1H, J = 6.4), 3.70 (s, 2H), 3.02 (s, 6H), 1.75-1.90 (m, 1H), 1.00-1.40 (m, 2H), 0.76 (d, 3H, J = 6.8), 0.66 (d, 3H, J = 6.4) |
| 473 | (2-fluoro-1-fluoromethylethyl) | 4-(methoxycarbonyl)benzyl | 4-chlorophenyl | 1 | off-white foam | 460.89 | 2.11 min Method A | 461.08 | $^1$H NMR (CDCl$_3$, 300 MHz) δ 7.97 (d, 2H, J = 8.4), 7.72 (d, 2H, J = 8.4), 7.51 (dd, 2H, J = 2.0, 8.4), 7.38 (d, 2H, J = 8.0), 6.32 (br s, 1H), 5.71 (tm, 1H, J$_{HF}$ = 55), 5.19 (br s, 1H), 4.60 (d, 1H, J = 15.6), 4.49-4.53 (m, 1H), 4.33 (d, 1H, J = 15.6), 3.91 (s, 3H), 2.42-2.68 (m, 1H), 1.54-1.65 (m, 1H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 474 | CH₂CHF₂ | 4-tBu(F)-benzyl | 4-Cl-phenyl | 1 | pale yellow foam | 462.92 | 2.24 min Method A | 485.07 (M + Na⁺) | ¹H NMR (CDCl₃, 400 MHz) δ 7.67 (d, 2H, J = 8.4), 7.47 (d, 2H, J = 8.8), 7.25-7.29 (m, 4H), 6.33 (br s, 1H), 5.72 (tm, 1H, $J_{H-F}$=57), 5.23 (br s, 1H), 4.49-4.53 (m, 1H), 4.46 (d, 1H, J = 15.6), 4.34 (d, 1H, J = 15.0), 2.52-2.60 (m, 1H), 1.55-1.65 (m, 1H), 1.68 (s, 3H), 1.63 (s, 3H) |
| 475 | CH₂CHF₂ | 5-Me-oxadiazolyl-phenyl | 4-Cl-phenyl | 1, 13 | white foam | 484.91 | 1.67 min Method D | 485.07 | ¹H NMR (CDCl₃, 400 MHz) δ 7.97 (d, 2H, J = 8.0), 7.73 (dd, 2H, J = 2.0, 8.8), 7.52 (dd, 2H, J = 2.0, 8.8), 7.45 (d, 2H, J = 8.4), 6.34 (br s, 1H), 5.73 (tm, 1H, $J_{H-F}$=57), 5.20 (br s, 1H), 4.63 (d, 1H, J = 15.6), 4.52-4.55 (m, 1H), 4.32 (d, 1H, J = 15.6), 2.61 (s, 3H), 2.55-2.60 (m, 1H), 1.61-1.65 (m, 1H) |
| 476 | CH₂CHF₂ | 4-(2-hydroxyprop-2-yl)-benzyl | 4-Cl-phenyl | 1, 12 | white foam | 460.93 | 1.72 min Method D | 483.07 (M + Na⁺) | ¹H NMR (CDCl₃, 400 MHz) δ 7.68 (dd, 2H, J = 2.0, 8.8), 7.48 (dd, 2H, J = 8.4), 7.41 (d, 2H, J = 8.4), 7.23 (d, 2H, J = 8.8), 6.30 (br s, 1H), 5.73 (tm, 1H, $J_{H-F}$=57), 5.18 (br s, 1H), 4.48-4.52 (m, 1H), 4.44 (d, 1H, J = 15.2), 4.34 (d, 1H, J = 15.2), 2.50-2.65 (m, 1H), 1.61-1.70 (m, 1H), 1.56 (s, 6H) |
| 477 | CH₂CH₂F | 4-(2,2-difluoroethyl)-piperidinyl-methyl | 4-Cl-phenyl | 7 | clear oil | 455.93 | 0.99 min Method A | 456.20 | ¹H NMR (CDCl₃, 400 MHz) δ 7.72-7.86 (m, 2H), 7.45-7.52 (m, 2H), 6.70 (br s, 1H), 5.44 (br s, 1H), 4.46-4.57 (m, 2H), 4.00-4.37 (m, 2H), 3.24 (dd, 1H, J = 4.4, 9.8), 2.70-3.15 (m, 6H), 2.15-2.34 (m, 2H), 1.80-1.93 (m, 2H), 1.54-1.63 (m, 2H), 1.25-1.35 (m, 2H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 478 | CH₂CH₂F | piperidine-N-C(O)CH₂-morpholine | 4-Cl-phenyl | 7 | clear oil | 519.04 | 1.12 min Method A | 519.23 | ¹H NMR (CDCl₃, 400 MHz) δ 7.71-7.84 (m, 2H), 7.39-7.55 (m, 2H), 6.70 (br m, 1H), 5.87 (br m, 1H), 4.88 (m, 1H), 4.50 (d, 1H, J = 9.5), 4.21-4.31 (m, 2H), 4.11-4.20 (m, 2H), 3.80-3.87 (m, 2H), 3.69-3.77 (m, 2H), 3.31-3.50 (m, 2H), 3.00-3.21 (m, 2H), 2.80-3.95 (m, 2H), 2.10-2.50 (m, 4H), 1.85-1.95 (m, 2H), 1.73 (d, 2H, J = 8.5), 1.40-1.50 (m, 2H) |
| 479 | CH₂CHF₂ | piperidine-N-C(O)NH-cyclohexyl | 4-Cl-phenyl | 7 | clear oil | 535.06 | 1.72 min Method A | 535.18 | ¹H NMR (CDCl₃, 400 MHz) δ 7.73 (d, 2H, J = 8.6), 7.53 (d, 2H, J = 8.6), 6.70 (br s, 1H), 5.70 (m, 1H, J_HF = 50), 5.55 (br s, 1H), 4.46 (dd, 1H, J = 3, 8, 10), 3.80-4.00 (m, 3H), 3.50-3.70 (m, 1H), 3.15-3.30 (m, 1H), 2.80-3.95 (m, 1H), 2.60-2.80 (m, 2H), 2.40-2.60 (m, 1H), 1.05-2.00 (m, 16H) |
| 480 | CH₂CH₂F | 4-(2-fluoroisopropyl)benzyl | 4-Cl-phenyl | 1 | off-white foam | 444.93 | 1.89 min Method D | 467.09 (M + Na⁺) | ¹H NMR (CDCl₃, 400 MHz) δ 7.66 (ddd, 2H, J = 2.0, 2.4, 8.8), 7.44 (ddd, 2H, J = 2.0, 2.4, 8.8), 7.25-7.31 (m, 4H), 6.30 (br s, 1H), 5.22 (br s, 1H), 4.56-4.60 (m, 1H), 4.47 (d, 1H, J = 15.6), 4.39 (d, 1H, J = 16.0), 4.32-4.36 (m, 1H), 4.20-4.24 (m, 1H), 2.23-2.39 (m, 1H), 1.70-1.85 (m, 1H), 1.65-1.68 (m, 3H), 1.53 (s, 3H) |
| 481 | CH₂CH₂F | 4-carboxybenzyl | 4-Cl-phenyl | 6 | white solid | 428.87 | 1.58 min Method D | 429.04 | ¹H NMR (CD₃OD, 400 MHz) δ 7.92 (d, 2H, J = 8.4), 7.79 (ddd, 2H, J = 2.0, 2.4, 8.8), 7.52 (ddd, 2H, J = 2.0, 2.8, 8.8), 7.47 (d, 2H, J = 8.0), 4.80 (d, 1H, J = 16), 4.66 (d, 1H, J = 14.5), 4.64 (t, 1H, J = 7.6), 4.10-4.33 (m, 2H), 2.05-2.12 (m, 1H), 1.72-1.80 (m, 1H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 482 | CHF₂-CH₂- | 4-(CH₂)-benzoic acid | 4-chlorophenyl-CH₂- | 6 | yellow solid | 446.86 | 1.39 min Method B | 447.06 | ¹H NMR (CDCl₃, 400 MHz) δ 7.89 (d, 2H, J = 8.0), 7.66 (dd, 2H, J = 2.0, 8.0), 7.41 (dd, 2H, J = 2.0, 8.4), 7.31 (d, 2H, J = 8.0), 6.61 (br s, 1H), 5.90 (br s, 1H), 5.76 (tm, 1H, J$_{H-F}$ = 57), 4.56 (d, 1H, J = 16.0), 4.49-4.52 (m, 1H), 4.36 (d, 1H, J = 12.0), 2.50-2.65 (m, 1H), 1.61-1.70 (m, 1H) |
| 483 | FCH₂-CH₂- | 4-(CH₂)-N-ethylbenzamide | 4-chlorophenyl-CH₂- | 6 | white solid | 455.94 | 1.34 min Method B | 488.11 (M + Na⁺) | ¹H NMR (CDCl₃, 400 MHz) δ 7.72 (d, 2H, J = 8.0), 7.68 (d, 2H, J = 8.0), 7.49 (ddd, 2H, J = 2.0, 2.4, 8.4), 7.38 (d, 2H, J = 8.0), 6.32 (br s, 1H), 6.06 (br s, 1H), 5.19 (br s, 1H), 4.59 (d, 1H, J = 15.0), 4.56-4.60 (m, 1H), 4.37 (d, 1H, J = 15.0), 4.29-4.32 (m, 1H), 4.16-4.19 (m, 1H), 3.45-3.49 (m, 2H), 2.15-2.30 (m, 1H), 1.50-1.65 (m, 1H), 1.25 (t, 3H, J = 8.0) |
| 484 | FCH₂-CH₂- | 4-(CH₂)-N-methyl-N-ethylbenzamide | 4-chlorophenyl-CH₂- | 6 | white solid | 469.97 | 1.40 min Method B | 470.15 | ¹H NMR (CDCl₃, 400 MHz) δ 7.72 (d, 2H, J = 8.0), 7.48 (d, 2H, J = 8.0), 7.30-7.36 (m, 4H), 6.30 (br s, 1H), 5.26 (br s, 1H), 4.54-4.58 (m, 2H), 4.38 (d, 1H, J = 15.2), 4.29-4.32 (m, 1H), 4.18-4.22 (m, 1H), 3.55-3.59 (m, 1H), 3.22-3.27 (m, 1H), 2.90 and 3.05 (2 s, 3H), 2.20-2.33 (m, 1H), 1.50-1.65 (m, 1H), 1.08-1.30 (m, 3H) |
| 485 | CHF₂-CH₂- | 4-(CH₂)-N-ethylbenzamide | 4-chlorophenyl-CH₂- | 6 | white solid | 473.93 | 1.33 min Method B | 474.11 | ¹H NMR (CDCl₃, 400 MHz) δ 7.72 (d, 2H, J = 8.8), 7.70 (d, 2H, J = 8.4), 7.51 (d, 2H, J = 8.8), 7.38 (d, 2H, J = 8.0), 6.31 (br s, 1H), 6.05 (br s, 1H), 5.72 (tm, 1H, J$_{H-F}$ = 57), 5.20 (br s, 1H), 4.59 (d, 1H, J = 15.6), 4.49-4.52 (m, 1H), 4.31 (d, 1H, J = 15.6), 3.46-3.53 (m, 2H), 2.45-2.65 (m, 1H), 1.57-1.65 (m, 1H), 1.25 (t, 3H, J = 7.2) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 486 | CH₂CHF₂ group | 4-(pyridin-2-ylmethylcarbamoyl)benzyl | 4-chlorophenyl | 6 | white solid | 536.99 | 1.13 min Method B | 537.17 | ¹H NMR (CDCl₃, 400 MHz) δ 8.57 (d, 1H, J = 4.8), 7.83 (d, 2H, J = 8.4), 7.71-7.78 (m, 3H), 7.71 (br s, 1H), 7.52 (dd, 2H, J = 1.6, 8.8), 7.40 (d, 2H, J = 8.0), 7.30-7.35 (m, 1H), 7.23-7.28 (m, 1H), 6.32 (br s, 1H), 5.72 (tm, 1H, $J_{HF}$ =57), 5.25 (br s, 1H), 4.75 (d, 2H, J = 4.8), 4.59 (d, 1H, J = 15.6), 4.49-4.53 (m, 1H), 4.33 (d, 1H, J = 15.6), 2.48-2.65 (m, 1H), 1.58-1.65 (m, 1H) |
| 487 | CH₂CH₂F group | 4-(pyridin-2-ylmethylcarbamoyl)benzyl | 4-chlorophenyl | 6 | white solid | 519.00 | 1.10 min Method B | 519.35 | ¹H NMR (CDCl₃, 400 MHz) δ 8.58 (d, 1H, J = 4.4), 7.92 (d, 2H, J = 8.4), 7.71-7.78 (m, 4H), 7.48 (dd, 2H, J = 2.0, 8.8), 7.39-7.44 (m, 3H), 7.24-7.30 (m, 1H), 6.28 (br s, 1H), 5.20 (br s, 1H), 4.78 (d, 2H, J = 4.8), 4.55-4.61 (m, 2H), 4.39 (d, 1H, J = 15.6), 4.29-4.32 (m, 1H), 4.17-4.21 (m, 1H), 2.20-2.33 (m, 1H), 1.50-1.65 (m, 1H) |
| 488 | CH₂CHF₂ group | 4-(N-ethyl-N-methylcarbamoyl)benzyl | 4-chlorophenyl | 6 | white solid | 487.96 | 1.63 min Method D | 488.34 | ¹H NMR (CDCl₃, 400 MHz) δ 7.72 (dd, 2H, J = 2.0, 8.8), 7.51 (dd, 2H, J = 2.0, 8.4), 7.50 (s, 4H), 6.30 (br s, 1H), 5.72 (tm, 1H, $J_{HF}$ =57), 5.24 (br s, 1H), 4.55 (d, 1H, J = 15.5), 4.49-4.52 (m, 1H), 4.33 (d, 1H, J = 15.5), 3.57 (br s, 1H), 3.23 (br s, 1H), 2.90 and 3.05 (2 s, 3H), 2.48-2.62 (m, 1H), 1.57-1.72 (m, 1H), 1.08-1.30 (m, 3H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 489 | CHF-CH₂F group | 4-(2-methoxyethylaminocarbonyl)benzyl | 4-chlorophenyl | 6 | off-white solid | 503.96 | 1.40 min Method A | 504.41 | ¹H NMR (CDCl₃, 400 MHz) δ 7.72 (d, 4H, J = 8.4), 7.52 (d, 2H, J = 8.8), 7.38 (d, 2H, J = 8.4), 6.49 (br s, 1H), 6.31 (br s, 1H),5.72 (tm, 1H, $J_{H-F}$ = 57), 5.19 (br s, 1H), 4.59 (d, 1H, J = 15.0), 4.48-4.52 (m, 1H),4.31 (d, 1H, J = 15.6), 3.62-3.68 (m, 2H), 3.53-3.59 (m, 2H), 3.39 (s, 3H), 2.48-2.62 (m, 1H), 1.57-1.72 (m, 1H) |
| 490 | CH₂-CH₂F group | 4-(2-methoxyethylaminocarbonyl)benzyl | 4-chlorophenyl | 6 | white solid | 485.97 | 1.27 min Method B | 486.14 | ¹H NMR (CDCl₃, 300 MHz) δ 7.69-7.74 (m, 4H), 7.51 (dd, 2H, J = 1.8, 8.4), 7.38 (d, 2H, J = 8.1), 6.48 (br s, 1H), 6.32 (br s, 1H), 5.19 (br s, 1H), 4.54-4.62 (m, 2H), 4.30-4.41 (m, 2H), 4.13-4.19 (m, 1H), 3.61-3.67 (m, 2H), 3.53-3.59 (m, 2H), 3.39 (s, 3H), 2.48-2.62 (m, 1H), 1.57-1.72 (m, 1H) |
| 491 | CHF-CH₂F group | 4-(3-methyl-1,2,4-oxadiazol-5-yl)benzyl | 4-chlorophenyl | 14 | off-white solid | 484.91 | 1.54 min Method B | 485.12 | ¹H NMR (CDCl₃, 400 MHz) δ 8.06 (d, 2H, J = 8.4), 7.74 (d, 2H, J = 8.8), 7.53 (d, 2H, J = 8.8), 7.48 (d, 2H, J = 8.4), 6.34 (br s, 1H), 5.72 (tm, 1H, $J_{H-F}$ = 57), 5.20 (br s, 1H), 4.65 (d, 1H, J = 15.4), 4.51-4.56 (m, 1H), 4.33 (d, 1H, J = 15.8), 2.48-2.65 (m, 1H), 2.47 (s, 3H), 1.57-1.65 (m, 1H) |
| 492 | CH₂-CH₂F group | 4-(3-methyl-1,2,4-oxadiazol-5-yl)benzyl | 4-chlorophenyl | 14 | off-white solid | 466.92 | 1.65 min Method A | 467.19 | ¹H NMR (CDCl₃, 400 MHz) δ 8.04 (d,2H, J = 8.0), 7.74 (dd, 2H, J = 1.6, 8.4), 7.48-7.51 (m, 4H), 6.32 (br s, 1H), 5.17 (br s, 1H), 4.65 (d, 1H, J = 16.0), 4.56-4.60 (m, 1H), 4.40 (d, 1H, J = 16.0), 4.29-4.32 (m, 1H), 4.18-4.21 (m, 1H), 2.47 (s, 3H), 2.18-2.38 (m, 1H), 1.50-1.65 (m, 1H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 493 | F₃C-(propyl) | 4-(carboxy)benzyl | 4-chlorophenyl | 6 | white solid | 478.88 | 1.59 min Method A | 479.15 | ¹H NMR (DMSO-d₆, 400 MHz) δ 7.88 (d, 2H, J = 8.0), 7.85 (d, 2H, J = 8.8), 7.63 (d, 2H, J = 8.8), 7.51 (d, 2H, J = 8.0), 7.42 (br s, 1H), 7.24 (br s, 1H), 4.77 (d, 2H, J = 2.0), 4.40-4.44 (m, 1H), 1.97-2.05 (m, 2H), 1.75-1.84 (m, 1H), 1.42-1.50 (m, 1H) |
| 494 | F₃C-(propyl) | 4-(methoxycarbonyl)benzyl | 4-chlorophenyl | 1 | white solid | 492.91 | 1.66 min Method A | 493.11 | ¹H NMR (CDCl₃, 400 MHz) δ 7.97 (d, 2H, J = 8.4), 7.69 (dd, 2H, J = 1.6, 8.4), 7.50 (dd, 2H, J = 2.0, 8.4), 7.40 (d, 2H, J = 8.4), 6.22 (br s, 1H), 5.19 (br s, 1H), 4.58 (d, 1H, J = 16.0), 4.43 (d, 1H, J = 15.6), 4.31-4.35 (m, 1H), 3.91 (s, 3H), 2.08-2.20 (m, 1H), 1.88-2.03 (m, 1H), 1.69-1.82 (m, 1H), 1.38-1.47 (m, 1H) |
| 495 | F₃C-(propyl) | 4-(N,N-ethylmethylcarbamoyl)benzyl | 4-chlorophenyl | 6 | off-white solid | 519.97 | 1.48 min Method B | 520.21 | ¹H NMR (CDCl₃, 400 MHz) δ 7.70 (d, 2H, J = 8.4), 7.50 (d, 2H, J = 8.8), 7.37 (d, 2H, J = 8.4), 7.33 (d, 2H, J = 8.0), 6.20 (br s, 1H), 5.26 (br s, 1H), 4.45-4.52 (m, 2H), 4.33 (t, 1H, J = 7.2), 3.61-3.70 (m, 1H), 3.22-3.27 (m, 1H), 2.90 and 3.06 (2 s, 3H), 2.05-2.18 (m, 1H), 1.90-2.03 (m, 1H), 1.69-1.82 (m, 1H), 1.38-1.47 (m, 1H), 1.11-1.28 (m, 3H) |
| 496 | F₃C-(propyl) | 4-(N-(pyridin-2-ylmethyl)carbamoyl)benzyl | 4-chlorophenyl | 6 | off-white solid | 569.01 | 1.21 min Method B | 569.16 | ¹H NMR (CDCl₃, 400 MHz) δ 8.57 (d, 1H, J = 4.8), 7.82 (d, 2H, J = 8.4), 7.68-7.72 (m, 4H), 7.50 (d, 2H, J = 8.8), 7.42 (d, 2H, J = 8.4), 7.35 (d, 1H, J = 8.0), 7.24 (br s, 1H), 6.24 (br s, 1H), 5.26 (d, 1H), 4.76 (d, 2H, J = 4.8), 4.58 (d, 1H, J = 15.6), 4.41 (d, 1H, J = 15.6), 4.31-4.35 (m, 1H), 2.10-2.19 (m, 1H), 1.90-2.03 (m, 1H), 1.69-1.82 (m, 1H), 1.38-1.47 (m, 1H) |

TABLE 4-continued

| Ex. No. | R¹ | R² | R³ | Reaction Scheme | Appearance | Calc. MW | Ret. Time/ Method | M + H⁺ | NMR Data |
|---|---|---|---|---|---|---|---|---|---|
| 497 | F₃C-CH₂CH₂- | 4-(2-methoxyethylaminocarbonyl)phenyl-CH₂CH₂- | 4-Cl-C₆H₄- | 6 | white solid | 535.97 | 1.53 min Method A | 536.16 | ¹H NMR (CDCl₃, 400 MHz) δ 7.72 (d, 2H, J = 8.0), 7.69 (d, 2H, J = 8.4), 7.50 (d, 2H, J = 8.4), 7.40 (d, 2H, J = 8.4), 6.48 (br s, 1H), 6.22 (br s, 1H), 5.20 (br s, 1H), 4.57 (d, 1H, J = 15.6), 4.41 (d, 1H, J = 15.6), 4.30-4.34 (m, 1H), 3.63-3.67 (m, 2H), 3.55-3.57 (m, 2H), 3.39 (s, 3H), 2.10-2.20 (m, 1H), 1.88-2.03 (m, 1H), 1.69-1.82 (m, 1H), 1.38-1.47 (m, 1H) |
| 498 | F₃C-CH₂CH₂- | 4-(ethylaminocarbonyl)phenyl-CH₂CH₂- | 4-Cl-C₆H₄- | 6 | white solid | 505.95 | 1.55 min Method A | 506.10 | ¹H NMR (CDCl₃, 400 MHz) δ 7.69 (dd, 2H, J = 1.6, 8.4), 7.50 (d, 2H, J = 8.4), 7.39 (d, 2H, J = 8.0), 7.25-7.28 (m, 2H), 6.22 (br s, 1H), 6.03 (br s, 1H), 5.19 (br s, 1H), 4.57 (d, 1H, J = 15.6), 4.41 (d, 1H, J = 15.6), 4.30-4.33 (m, 1H), 3.48-3.53 (m, 2H), 2.10-2.20 (m, 1H), 1.88-2.03 (m, 1H), 1.69-1.82 (m, 1H), 1.38-1.47 (m, 1H), 1.25 (t, 3H, J = 7.2) |
| 499 | F₃C-CH₂CH₂- | 4-(3-methyl-1,2,4-oxadiazol-5-yl)phenyl-CH₂CH₂- | 4-Cl-C₆H₄- | 1 | off-white foam | 494.94 | 1.74 min Method B | 475.27 (M - HF + H+) | ¹H NMR (CDCl₃, 500 MHz) δ 7.65 (dd, 2H, J = 2.0, 8.5), 7.46 (ddd, 2H, J = 2.0, 2.5, 7.5), 7.25-7.31 (m, 4H), 6.18 (br s, 1H), 5.24 (br s, 1H), 4.47 (d, 1H, J = 15.5), 4.41 (d, 1H, J = 15.0), 4.35 (t, 1H, J = 7.7), 2.08-2.20 (m, 1H), 1.88-2.03 (m, 1H), 1.69-1.82 (m, 1H), 1.68 (s, 3H), 1.63 (s, 3H), 1.38-1.47 (m, 1H) |

TABLE 4-continued

| Ex. No. | R¹ | R² | R³ | Reaction Scheme | Appearance | Calc. MW | Ret. Time/Method | M + H⁺ | NMR Data |
|---|---|---|---|---|---|---|---|---|---|
| 500 | F₃C-propyl | 4-(2-fluoropropan-2-yl)benzyl | 4-chlorophenyl | 1 | off-white foam | 494.94 | 1.74 min Method B | 475.27 (M-HF +H+) | ¹H NMR (CDCl₃, 500 MHz) δ 7.65 (dd, 2H, J = 2.0, 8.5), 7.46 (ddd, 2H, J = 2.0, 2.5, 7.5), 7.25-7.31 (m, 4H, ), 5.24 (br s, 1H), 4.47 (d, 1H, J = 15.5), 4.41 (d, 1H, J = 15.0), 4.35 (t, 1H, J = 7.7), 2.0-2.20 (m, 1H), 1.88-2.03 (m, 1H), 1.69-1.82 (m, 1H), 1.68 (s, 3H), 1.63 (s, 3H), 1.38-1.47 (m, 1H) |
| 501 | F₃C-propyl | 4-(2-hydroxypropan-2-yl)benzyl | 4-chlorophenyl | 12 | off-white solid | 492.95 | 2.20 min Method A | 475.96 (−H₂O) 492.01 (neg ion) | ¹H NMR (CDCl₃, 500 MHz) δ 7.65 (d, 2H, J = 8.8), 7.46 (d, 2H, J = 8.4), 7.40 (d, 2H, J = 8.4), 7.25-7.27 (m, 2H), 6.19 (br s, 1H), 5.23 (br s, 1H), 4.46 (d, 1H, J = 15.4), 4.41 (d, 1H, J = 15.4), 4.34 (t, 1H, J = 7.6), 2.08-2.20 (m, 1H), 1.88-2.03 (m, 1H), 1.69-1.82 (m, 1H), 1.56 (s, 3H), 1.54 (s, 3H), 1.38-1.47 (m, 1H) |

Method A=4.6×33 mm ODS-A C-18 column, 5 mL/min, 10:90:0.1 (MeOH/H₂O/TFA) to 90:10:0.1 (MeOH/H₂O/TFA), 2 min gradient Method B=3×50 mm ODS-A C-18 column, 5 mL/min, 10:90:0.1 (MeOH/H₂O/TFA) to 90:10:0.1 (MeOH/H₂O/TFA), 2 min gradient Method C=3×50 mm ODS-A C-18 column, 5 mL/min, 10:90:0.1 (MeOH/H₂O/TFA) to 90:10:0.1 (MeOH/H₂O/TFA), 3 min gradient Method D=4.6×50 mm PHENOMENEX® Luna C-18 S5 column, 5 mL/min, 0-100% MeOH/H₂O, 0.1% TFA, 2 min gradient Method E=4.6×50 mm XTERRA® C-18 S5 column, 5 mL/min, 0-100% MeOH/H₂O, 0.1% TFA, 2 min gradient Method F=4.6×50 mm PHENOMENEX® Luna C-18 S5 column, 5 mL/min, 10:90:0.1 (MeOH/H₂O/TFA) to 90:10:0.1 (MeOH/H₂O/TFA), 2 min gradient Method G=3.0×50 mm XTERRA® C-18 S7 column, 5 mL/min, 10:90:0.1 (MeOH/H₂O/TFA) to 90:10:0.1 (MeOH/H₂O/TFA), 2 min gradient

What is claimed is:

1. A compound of formula I; or an optical isomer thereof

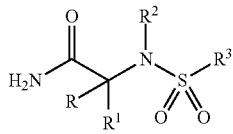

I wherein:
R¹ is a straight-chain $C_{1-6}$ alkyl optionally substituted with halogen;
R is hydrogen;
R² is

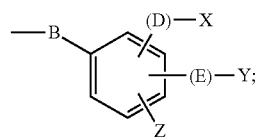

D and E are a direct bond;
Z is halogen;
X is hydrogen;
Y is a heterocyclic group, in which said heterocyclic group is oxadiazolyl, wherein said heterocyclic group is optionally substituted with $C_{1-4}$alkyl;
B is a straight-chain $C_{1-6}$alkyl; and
R³ is phenyl optionally substituted with halogen,
or a non-toxic pharmaceutically acceptable salt thereof.

2. A method for the treatment of disorders responsive to the inhibition of β-amyloid peptide production in a mammal in need thereof, which comprises administering to said mammal a therapeutically effective amount of a compound of claim 1.

3. A method of claim 2 wherein said disorder is Alzheimer's Disease and Down's Syndrome.

* * * * *